(12) United States Patent
Connor

(10) Patent No.: US 10,602,965 B2
(45) Date of Patent: Mar. 31, 2020

(54) WEARABLE DEFORMABLE CONDUCTIVE SENSORS FOR HUMAN MOTION CAPTURE INCLUDING TRANS-JOINT PITCH, YAW, AND ROLL

(71) Applicant: Robert A. Connor, Burnsville, MN (US)

(72) Inventor: Robert A. Connor, Burnsville, MN (US)

(73) Assignee: Medibotics, St. Paul, MN (US)

( * ) Notice: Subject to any disclaimer, the term of this patent is extended or adjusted under 35 U.S.C. 154(b) by 81 days.

(21) Appl. No.: 16/010,448

(22) Filed: Jun. 16, 2018

(65) Prior Publication Data

US 2018/0303383 A1    Oct. 25, 2018

Related U.S. Application Data

(63) Continuation-in-part of application No. 15/702,081, filed on Sep. 12, 2017, and a continuation-in-part of application No. 15/227,254, filed on Aug. 3, 2016, now Pat. No. 10,321,873, and a continuation-in-part of application No. 15/130,995, filed on Apr. 17, 2016, now Pat. No. 9,891,718, said application No. 15/227,254 is a continuation-in-part of application No. 15/079,447, filed on Mar. 24, 2016, now Pat. No. 10,234,934, which is a continuation-in-part of
(Continued)

(51) Int. Cl.
*A61B 5/11* (2006.01)
*A61B 5/00* (2006.01)
*G01B 7/16* (2006.01)

(52) U.S. Cl.
CPC .......... *A61B 5/1126* (2013.01); *A61B 5/4528* (2013.01); *A61B 5/6804* (2013.01); *G01B 7/18* (2013.01); *G01B 7/22* (2013.01); *A61B 2503/10* (2013.01); *A61B 2562/0261* (2013.01)

(58) Field of Classification Search
CPC ....... A61B 5/11; A61B 5/1116; A61B 5/1121; A61B 5/1126; A61B 5/4528; A61B 5/6801; A61B 5/6804; A61B 5/6806; A61B 2562/0261; A61B 2562/0295; A61B 2562/046; G06F 3/011; G06F 3/014; G06F 3/03; G01B 7/18; G01B 7/22
USPC ................................................ 73/849, 865.4
See application file for complete search history.

(56) References Cited

U.S. PATENT DOCUMENTS 3,711,627 A   1/1973   Maringulov
3,974,491 A   8/1976   Sipe
(Continued)

OTHER PUBLICATIONS

"Wearable Conductive Fiber Sensors for Multi-Axis Human Joint Angle Measurement," Peter Gibbs and Harry Asada, Mar. 2, 2005. (Year: 2005).*

*Primary Examiner* — Benjamin R Schmitt

(57) ABSTRACT

This invention comprises wearable deformable electromagnetic energy pathways which enable ambulatory (camera-free) three-dimensional human body motion capture including trans joint pitch, yaw, and roll. It can be embodied in a plurality of elongate electrically-conductive strips which diverge as they span a body joint in a proximal to distal manner and pairs of electromagnetic energy emitters and receivers which are in electromagnetic communication with the strips. In an example, conductive-fluid-filled lumens can be used instead of electrically-conductive strips.

1 Claim, 35 Drawing Sheets

Related U.S. Application Data application No. 14/463,741, filed on Aug. 20, 2014, now Pat. No. 9,588,582, said application No. 15/079,447 is a continuation-in-part of application No. 14/664,832, filed on Mar. 21, 2015, now Pat. No. 9,582,072, which is a continuation-in-part of application No. 14/463,741, filed on Aug. 20, 2014, now Pat. No. 9,588,582, said application No. 15/227,254 is a continuation-in-part of application No. 14/736,652, filed on Jun. 11, 2015, now abandoned, which is a continuation-in-part of application No. 14/664,832, filed on Mar. 21, 2015, now Pat. No. 9,582,072, said application No. 15/227,254 is a continuation-in-part of application No. 14/664,832, filed on Mar. 21, 2015, now Pat. No. 9,582,072, which is a continuation-in-part of application No. 14/463,741, filed on Aug. 20, 2014, now Pat. No. 9,588,582, said application No. 15/702,081 is a continuation-in-part of application No. 14/795,373, filed on Jul. 9, 2015, now abandoned, which is a continuation-in-part of application No. 14/736,652, filed on Jun. 11, 2015, now abandoned, which is a continuation-in-part of application No. 14/664,832, filed on Mar. 21, 2015, now Pat. No. 9,582,072, application No. 16/010,448, which is a continuation-in-part of application No. 15/227,254, filed on Aug. 3, 2016, now Pat. No. 10,321,873, and a continuation-in-part of application No. 15/130,995, filed on Apr. 17, 2016, now Pat. No. 9,891,718, said application No. 15/227,254 is a continuation-in-part of application No. 15/079,447, filed on Mar. 24, 2016, now Pat. No. 10,234,934, which is a continuation-in-part of application No. 14/463,741, filed on Aug. 20, 2014, now Pat. No. 9,588,582, said application No. 15/079,447 is a continuation-in-part of application No. 14/664,832, filed on Mar. 21, 2015, now Pat. No. 9,582,072, which is a continuation-in-part of application No. 14/463,741, filed on Aug. 20, 2014, now Pat. No. 9,588,582, and a continuation-in-part of application No. 14/736,652, filed on Jun. 11, 2015, now abandoned, which is a continuation-in-part of application No. 14/664,832, filed on Mar. 21, 2015, now Pat. No. 9,582,072, said application No. 15/227,254 is a continuation-in-part of application No. 14/664,832, filed on Mar. 21, 2015, now Pat. No. 9,582,072, which is a continuation-in-part of application No. 14/463,741, filed on Aug. 20, 2014, now Pat. No. 9,588,582.

(60) Provisional application No. 62/683,237, filed on Jun. 11, 2018, provisional application No. 62/538,793, filed on Jul. 30, 2017, provisional application No. 62/449,735, filed on Jan. 24, 2017, provisional application No. 62/357,957, filed on Jul. 2, 2016, provisional application No. 62/150,886, filed on Apr. 22, 2015, provisional application No. 61/878,893, filed on Sep. 17, 2013, provisional application No. 61/976,650, filed on Apr. 8, 2014, provisional application No. 62/014,747, filed on Jun. 20, 2014, provisional application No. 62/100,217, filed on Jan. 6, 2015, provisional application No. 62/065,032, filed on Oct. 17, 2014, provisional application No. 62/086,053, filed on Dec. 1, 2014, provisional application No. 62/182,473, filed on Jun. 20, 2015, provisional application No. 62/187,906, filed on Jul. 2, 2015, provisional application No. 62/538,793, filed on Jul. 30, 2017.

(56) References Cited

U.S. PATENT DOCUMENTS

| | | | |
|---|---|---|---|
| 4,542,291 | A | 9/1985 | Zimmerman |
| 5,012,819 | A | 5/1991 | Marras et al. |
| 5,086,785 | A | 2/1992 | Gentile et al. |
| 5,184,009 | A | 2/1993 | Wright et al. |
| 5,184,319 | A | 2/1993 | Kramer |
| 5,280,265 | A | 1/1994 | Kramer et al. |
| 5,316,017 | A | 5/1994 | Edwards et al. |
| 5,337,758 | A | 8/1994 | Moore et al. |
| 5,375,610 | A | 12/1994 | LaCourse et al. |
| 5,442,729 | A | 8/1995 | Kramer et al. |
| 5,474,088 | A | 12/1995 | Zaharkin et al. |
| 5,516,249 | A | 5/1996 | Brimhall |
| 5,533,531 | A | 7/1996 | Edwards et al. |
| 5,592,401 | A | 1/1997 | Kramer |
| 5,615,132 | A | 3/1997 | Horton et al. |
| 5,640,971 | A | 6/1997 | Martin |
| 5,656,904 | A | 8/1997 | Lander |
| 5,676,157 | A | 10/1997 | Kramer |
| 5,694,497 | A | 12/1997 | Sansone |
| 5,813,406 | A | 9/1998 | Kramer et al. |
| 5,819,206 | A | 10/1998 | Horton et al. |
| 5,915,673 | A | 6/1999 | Kazerooni |
| 5,930,741 | A | 7/1999 | Kramer |
| 5,961,541 | A | 10/1999 | Ferrati |
| 5,980,472 | A | 11/1999 | Seyl |
| 5,989,700 | A | 11/1999 | Krivopal |
| 6,003,340 | A | 12/1999 | Borak et al. |
| 6,005,548 | A | 12/1999 | Latypov et al. |
| 6,018,705 | A | 1/2000 | Gaudet et al. |
| 6,032,530 | A | 3/2000 | Hock |
| 6,035,274 | A | 3/2000 | Kramer et al. |
| 6,042,555 | A | 3/2000 | Kramer et al. |
| 6,050,962 | A | 4/2000 | Kramer et al. |
| 6,059,576 | A | 5/2000 | Brann |
| 6,095,991 | A | 8/2000 | Krausman et al. |
| 6,104,379 | A | 8/2000 | Petrich et al. |
| 6,110,130 | A | 8/2000 | Kramer |
| 6,119,516 | A | 9/2000 | Hock |
| 6,127,672 | A | 10/2000 | Danisch |
| 6,148,280 | A | 11/2000 | Kramer |
| 6,162,190 | A | 12/2000 | Kramer |
| 6,162,191 | A | 12/2000 | Foxlin |
| 6,210,301 | B1 | 4/2001 | Abraham-Fuchs et al. |
| 6,210,771 | B1 | 4/2001 | Post et al. |
| 6,239,784 | B1 | 5/2001 | Holmes |
| 6,246,390 | B1 | 6/2001 | Rosenberg |
| 6,304,840 | B1 | 10/2001 | Vance et al. |
| 6,334,852 | B1 | 1/2002 | Seyl |
| 6,341,504 | B1 | 1/2002 | Istook |
| 6,360,615 | B1 | 3/2002 | Smela |
| 6,361,507 | B1 | 3/2002 | Foxlin |
| 6,389,187 | B1 | 5/2002 | Greenaway et al. |
| 6,409,687 | B1 | 6/2002 | Foxlin |
| 6,413,229 | B1 | 7/2002 | Kramer et al. |
| 6,428,490 | B1 | 8/2002 | Kramer et al. |
| 6,429,421 | B1 | 8/2002 | Meller et al. |
| 6,466,200 | B1 | 10/2002 | Anton et al. |
| 6,487,906 | B1 | 12/2002 | Hock |
| 6,497,672 | B2 | 12/2002 | Kramer |
| 6,513,532 | B2 | 2/2003 | Mault et al. |
| 6,563,107 | B2 | 5/2003 | Danisch et al. |
| 6,579,248 | B1 | 6/2003 | Cascone et al. |
| 6,611,141 | B1 | 8/2003 | Schulz et al. |
| 6,611,789 | B1 | 8/2003 | Darley |
| 6,621,948 | B1 | 9/2003 | Devenyi |
| 6,640,202 | B1 | 10/2003 | Dietz et al. |
| 6,666,831 | B1 | 12/2003 | Edgerton et al. |
| 6,673,027 | B2 | 1/2004 | Fischer |
| 6,691,074 | B1 | 2/2004 | Moriya et al. |
| 6,700,499 | B2 | 3/2004 | Kubo et al. |
| 6,701,296 | B1 | 3/2004 | Kramer et al. |
| 6,703,939 | B2 | 3/2004 | Lehrman et al. |
| 6,728,431 | B2 | 4/2004 | Ames et al. |
| 6,731,268 | B2 | 5/2004 | Anton et al. |
| 6,786,877 | B2 | 9/2004 | Foxlin |

(56) References Cited

U.S. PATENT DOCUMENTS

| | | |
|---|---|---|
| 6,834,436 B2 | 12/2004 | Townsend et al. |
| 6,836,744 B1 | 12/2004 | Asphahani et al. |
| 6,864,796 B2 | 3/2005 | Lehrman et al. |
| 6,866,643 B2 | 3/2005 | Kramer |
| 6,871,413 B1 | 3/2005 | Arms et al. |
| 6,890,312 B1 | 5/2005 | Priester et al. |
| 6,912,475 B2 | 6/2005 | Moriya et al. |
| 6,940,062 B2 | 9/2005 | Kwon et al. |
| 6,957,164 B2 | 10/2005 | Dietz et al. |
| 6,964,205 B2 | 11/2005 | Papakostas et al. |
| 6,979,164 B2 | 12/2005 | Kramer |
| 6,985,134 B2 | 1/2006 | Suprun et al. |
| 7,020,508 B2 | 3/2006 | Stivoric et al. |
| 7,028,547 B2 | 4/2006 | Shiratori et al. |
| 7,070,571 B2 | 7/2006 | Kramer et al. |
| 7,082,570 B1 | 7/2006 | von Wiegand et al. |
| 7,095,331 B2 | 8/2006 | Lehrman et al. |
| 7,135,227 B2 | 11/2006 | Karayianni et al. |
| 7,141,026 B2 | 11/2006 | Aminian et al. |
| 7,145,461 B2 | 12/2006 | Lehrman et al. |
| 7,149,584 B1 | 12/2006 | Koh et al. |
| 7,153,242 B2 | 12/2006 | Goffer |
| 7,167,743 B2 | 1/2007 | Heruth et al. |
| 7,191,652 B2 | 3/2007 | Pristup et al. |
| 7,191,803 B2 | 3/2007 | Orr et al. |
| 7,209,028 B2 | 4/2007 | Boronkay et al. |
| 7,210,240 B2 | 5/2007 | Townsend et al. |
| 7,212,943 B2 | 5/2007 | Aoshima et al. |
| 7,219,033 B2 | 5/2007 | Kolen |
| 7,230,610 B2 | 6/2007 | Jung et al. |
| 7,245,292 B1 | 7/2007 | Custy |
| 7,258,026 B2 | 8/2007 | Papakostas et al. |
| 7,261,690 B2 | 8/2007 | Teller et al. |
| 7,264,554 B2 | 9/2007 | Bentley |
| 7,285,090 B2 | 10/2007 | Stivoric et al. |
| 7,292,151 B2 | 11/2007 | Ferguson et al. |
| 7,292,223 B2 | 11/2007 | Suprun et al. |
| 7,295,184 B2 | 11/2007 | Suprun et al. |
| 7,296,469 B2 | 11/2007 | Simonenko et al. |
| 7,313,440 B2 | 12/2007 | Miesel |
| 7,324,714 B1 | 1/2008 | Cranch et al. |
| 7,330,760 B2 | 2/2008 | Heruth et al. |
| 7,383,728 B2 | 6/2008 | Noble et al. |
| 7,390,157 B2 | 6/2008 | Kramer |
| 7,394,385 B2 | 7/2008 | Franco et al. |
| 7,395,113 B2 | 7/2008 | Heruth et al. |
| 7,395,181 B2 | 7/2008 | Foxlin |
| 7,410,338 B2 | 8/2008 | Schiele et al. |
| 7,413,802 B2 | 8/2008 | Karayianni et al. |
| 7,421,369 B2 | 9/2008 | Clarkson |
| 7,447,545 B2 | 11/2008 | Heruth et al. |
| 7,450,002 B2 | 11/2008 | Choi et al. |
| 7,451,056 B2 | 11/2008 | Flentov et al. |
| 7,471,290 B2 | 12/2008 | Wang et al. |
| 7,479,890 B2 | 1/2009 | Lehrman et al. |
| 7,487,043 B2 | 2/2009 | Adams |
| 7,492,268 B2 | 2/2009 | Ferguson et al. |
| 7,500,853 B2 | 3/2009 | Bevirt et al. |
| 7,509,870 B2 | 3/2009 | Aebersold et al. |
| 7,512,515 B2 | 3/2009 | Vock et al. |
| 7,565,295 B1 | 7/2009 | Hernandez-Rebollar |
| 7,602,301 B1 | 10/2009 | Stirling et al. |
| 7,602,310 B2 | 10/2009 | Mann et al. |
| 7,627,451 B2 | 12/2009 | Vock et al. |
| 7,630,591 B2 | 12/2009 | Allen et al. |
| 7,634,379 B2 | 12/2009 | Noble |
| 7,647,196 B2 | 1/2010 | Kahn et al. |
| 7,653,214 B2 | 1/2010 | Schroeder et al. |
| 7,653,508 B1 | 1/2010 | Kahn et al. |
| 7,661,200 B2 | 2/2010 | Bonnet et al. |
| 7,665,288 B2 | 2/2010 | Karayianni et al. |
| 7,668,588 B2 | 2/2010 | Kovacs |
| 7,672,781 B2 | 3/2010 | Churchill et al. |
| 7,689,378 B2 | 3/2010 | Kolen |
| 7,698,101 B2 | 4/2010 | Alten et al. |
| 7,698,830 B2 | 4/2010 | Townsend et al. |
| 7,703,333 B2 | 4/2010 | Hayakawa et al. |
| 7,725,279 B2 | 5/2010 | Luinge et al. |
| 7,742,894 B2 | 6/2010 | Chen et al. |
| 7,753,861 B1 | 7/2010 | Kahn et al. |
| 7,771,318 B2 | 8/2010 | Narayanaswami |
| 7,772,541 B2 | 8/2010 | Froggatt et al. |
| 7,781,724 B2 | 8/2010 | Childers et al. |
| 7,792,583 B2 | 9/2010 | Miesel et al. |
| 7,805,196 B2 | 9/2010 | Miesel et al. |
| 7,811,333 B2 | 10/2010 | Jonsson et al. |
| 7,815,376 B2 | 10/2010 | Rogers et al. |
| 7,821,407 B2 | 10/2010 | Shears et al. |
| 7,825,815 B2 | 11/2010 | Shears et al. |
| 7,827,000 B2 | 11/2010 | Stirling et al. |
| 7,845,228 B2 | 12/2010 | Bremer et al. |
| 7,850,574 B2 | 12/2010 | Narayanaswami |
| 7,854,174 B2 | 12/2010 | Aebersold et al. |
| 7,881,902 B1 | 2/2011 | Kahn et al. |
| 7,899,556 B2 | 3/2011 | Nathan et al. |
| 7,901,756 B2 | 3/2011 | Burr et al. |
| 7,902,095 B2 | 3/2011 | Hassonjee et al. |
| 7,911,620 B2 | 3/2011 | Digonnet et al. |
| 7,926,254 B2 | 4/2011 | Karayianni et al. |
| 7,930,065 B2 | 4/2011 | Larkin et al. |
| 7,952,483 B2 | 5/2011 | Ferguson et al. |
| 7,978,081 B2 | 7/2011 | Shears et al. |
| 7,980,141 B2 | 7/2011 | Connor et al. |
| 7,981,057 B2 | 7/2011 | Stewart |
| 7,981,058 B2 | 7/2011 | Akay |
| 7,998,092 B2 | 8/2011 | Avni et al. |
| 7,999,946 B2 | 8/2011 | Andersen et al. |
| 8,010,308 B1 | 8/2011 | Churchill |
| 8,011,229 B2 | 9/2011 | Lieberman et al. |
| 8,025,632 B2 | 9/2011 | Einarsson |
| 8,033,916 B2 | 10/2011 | Caldwell et al. |
| 8,036,850 B2 | 10/2011 | Kulach et al. |
| 8,036,851 B2 | 10/2011 | Vock et al. |
| 8,055,021 B2 | 11/2011 | Caritu et al. |
| 8,060,337 B2 | 11/2011 | Kulach et al. |
| 8,068,231 B2 | 11/2011 | Digonnet |
| 8,073,707 B2 | 12/2011 | Teller et al. |
| 8,075,499 B2 | 12/2011 | Nathan et al. |
| 8,083,693 B1 | 12/2011 | McKeon et al. |
| 8,099,258 B2 | 1/2012 | Alten et al. |
| 8,109,149 B2 | 2/2012 | Kotovsky |
| 8,111,165 B2 | 2/2012 | Ortega et al. |
| 8,116,601 B2 | 2/2012 | Prisco |
| 8,125,448 B2 | 2/2012 | Ranta et al. |
| 8,135,473 B2 | 3/2012 | Miesel et al. |
| 8,140,339 B2 | 3/2012 | Hernandez-Rebollar |
| 8,150,531 B2 | 4/2012 | Skelton |
| 8,151,648 B2 | 4/2012 | Yu et al. |
| 8,152,694 B2 | 4/2012 | Srinivasan et al. |
| 8,157,730 B2 | 4/2012 | Leboeuf et al. |
| 8,157,731 B2 | 4/2012 | Teller et al. |
| 8,157,752 B2 | 4/2012 | Fischer |
| 8,159,354 B2 | 4/2012 | Ferguson et al. |
| 8,161,826 B1 | 4/2012 | Taylor |
| 8,162,857 B2 | 4/2012 | Lanfermann et al. |
| 8,165,840 B2 | 4/2012 | Hatlestad et al. |
| 8,165,844 B2 | 4/2012 | Luinge et al. |
| 8,171,570 B2 | 5/2012 | Adarraga |
| 8,175,720 B2 | 5/2012 | Skelton et al. |
| 8,180,591 B2 | 5/2012 | Yuen et al. |
| 8,180,592 B2 | 5/2012 | Yuen et al. |
| 8,182,158 B2 | 5/2012 | Rogers et al. |
| 8,187,182 B2 | 5/2012 | Kahn et al. |
| 8,200,340 B2 | 6/2012 | Skelton et al. |
| 8,203,455 B2 | 6/2012 | Lee et al. |
| 8,203,487 B2 | 6/2012 | Hol et al. |
| 8,206,325 B1 | 6/2012 | Najafi et al. |
| 8,209,028 B2 | 6/2012 | Skelton et al. |
| 8,209,147 B2 | 6/2012 | Solinsky |
| 8,219,206 B2 | 7/2012 | Skelton et al. |
| 8,231,555 B2 | 7/2012 | Skelton et al. |
| 8,233,151 B2 | 7/2012 | Digonnet |
| 8,240,207 B2 | 8/2012 | Andersen et al. |
| 8,249,718 B2 | 8/2012 | Skelton et al. |

(56) References Cited

U.S. PATENT DOCUMENTS

| | | |
|---|---|---|
| 8,275,635 B2 | 9/2012 | Stivoric et al. |
| 8,280,517 B2 | 10/2012 | Skelton et al. |
| 8,280,681 B2 | 10/2012 | Vock et al. |
| 8,282,580 B2 | 10/2012 | Skelton et al. |
| 8,284,847 B2 | 10/2012 | Adermann |
| 8,301,575 B2 | 10/2012 | Bonnet et al. |
| 8,311,769 B2 | 11/2012 | Yuen et al. |
| 8,311,770 B2 | 11/2012 | Yuen et al. |
| 8,315,710 B2 | 11/2012 | Skelton et al. |
| 8,316,719 B2 | 11/2012 | Majidi et al. |
| 8,323,218 B2 | 12/2012 | Davis et al. |
| 8,328,718 B2 | 12/2012 | Tran |
| 8,332,041 B2 | 12/2012 | Skelton et al. |
| 8,342,045 B2 | 1/2013 | Maxwell et al. |
| 8,352,211 B2 | 1/2013 | Vock et al. |
| 8,358,883 B2 | 1/2013 | Prisco |
| 8,362,882 B2 | 1/2013 | Heubel et al. |
| 8,366,641 B2 | 2/2013 | Wang et al. |
| 8,382,590 B2 | 2/2013 | Stivoric et al. |
| 8,384,551 B2 | 2/2013 | Ross et al. |
| 8,386,008 B2 | 2/2013 | Yuen et al. |
| 8,388,555 B2 | 3/2013 | Panken et al. |
| 8,395,109 B2 | 3/2013 | Muraysky |
| 8,396,554 B2 | 3/2013 | Miesel et al. |
| 8,396,565 B2 | 3/2013 | Singhal et al. |
| 8,397,568 B2 | 3/2013 | Cardarelli |
| 8,401,666 B2 | 3/2013 | Skelton et al. |
| 8,414,507 B2 | 4/2013 | Asada |
| 8,416,088 B2 | 4/2013 | Ortega et al. |
| 8,416,102 B2 | 4/2013 | Yin |
| 8,421,448 B1 | 4/2013 | Tran et al. |
| 8,421,854 B2 | 4/2013 | Zerkin |
| 8,427,325 B2 | 4/2013 | Ferguson et al. |
| 8,427,651 B2 | 4/2013 | Digonnet |
| 8,435,177 B2 | 5/2013 | Lanfermann et al. |
| 8,436,737 B1 | 5/2013 | Trout |
| 8,437,824 B2 | 5/2013 | Moon et al. |
| 8,437,861 B2 | 5/2013 | Skelton et al. |
| 8,437,980 B2 | 5/2013 | Yuen et al. |
| 8,446,275 B2 | 5/2013 | Utter |
| 8,447,401 B2 | 5/2013 | Miesel et al. |
| 8,447,411 B2 | 5/2013 | Skelton et al. |
| 8,459,128 B2 | 6/2013 | Bhat et al. |
| 8,460,197 B1 | 6/2013 | Brady et al. |
| 8,463,573 B2 | 6/2013 | Flentov et al. |
| 8,463,576 B2 | 6/2013 | Yuen et al. |
| 8,463,577 B2 | 6/2013 | Yuen et al. |
| 8,504,150 B2 | 8/2013 | Skelton |
| 8,515,549 B2 | 8/2013 | Panken et al. |
| 8,515,550 B2 | 8/2013 | Skelton et al. |
| 8,520,472 B2 | 8/2013 | Murray et al. |
| 8,527,217 B2 | 9/2013 | Moodie |
| 8,543,185 B2 | 9/2013 | Yuen et al. |
| 8,543,351 B2 | 9/2013 | Yuen et al. |
| 8,548,740 B2 | 10/2013 | Hesch et al. |
| 8,548,770 B2 | 10/2013 | Yuen et al. |
| 8,554,297 B2 | 10/2013 | Moon et al. |
| 8,579,834 B2 | 11/2013 | Davis et al. |
| 8,583,252 B2 | 11/2013 | Skelton et al. |
| 8,583,402 B2 | 11/2013 | Yuen et al. |
| 8,616,782 B2 | 12/2013 | Rogers et al. |
| 8,616,989 B2 | 12/2013 | Bentley |
| 8,626,472 B2 | 1/2014 | Solinsky |
| 8,643,494 B1 | 2/2014 | Trout |
| 8,651,964 B2 | 2/2014 | Brick |
| 8,655,117 B2 | 2/2014 | Donlagic et al. |
| 8,655,618 B2 | 2/2014 | Flaction et al. |
| 8,657,772 B2 | 2/2014 | Einarsson |
| 8,661,915 B2 | 3/2014 | Taylor |
| 8,665,241 B2 | 3/2014 | Heubel et al. |
| 8,670,953 B2 | 3/2014 | Yuen et al. |
| 8,678,979 B2 | 3/2014 | Stark et al. |
| 8,708,825 B2 | 4/2014 | Crisco |
| 8,708,904 B2 | 4/2014 | Stivoric et al. |
| 8,712,723 B1 | 4/2014 | Kahn et al. |
| 8,760,392 B2 | 6/2014 | Lloyd et al. |
| 8,764,651 B2 | 7/2014 | Tran |
| 8,777,878 B2 | 7/2014 | Deitz |
| 8,780,339 B2 | 7/2014 | Udd |
| 8,784,303 B2 | 7/2014 | Laby et al. |
| 8,784,342 B2 | 7/2014 | Hyde et al. |
| 8,788,055 B2 | 7/2014 | Gerber et al. |
| 8,795,137 B2 | 8/2014 | Ellis et al. |
| 8,818,748 B2 | 8/2014 | Hatlestad et al. |
| 8,821,417 B2 | 9/2014 | McGregor et al. |
| 8,823,490 B2 | 9/2014 | Libbus et al. |
| 8,823,639 B2 | 9/2014 | Jackson et al. |
| 8,849,610 B2 | 9/2014 | Molettiere et al. |
| 8,876,738 B1 | 11/2014 | Kahn et al. |
| 8,904,876 B2 | 12/2014 | Taylor et al. |
| 8,905,948 B2 | 12/2014 | Davis et al. |
| 8,909,543 B2 | 12/2014 | Tropper et al. |
| 8,928,484 B2 | 1/2015 | Chang et al. |
| 8,929,966 B2 | 1/2015 | LeBoeuf et al. |
| 8,932,236 B1 | 1/2015 | McKeon et al. |
| 8,944,939 B2 | 2/2015 | Clark et al. |
| 8,947,441 B2 | 2/2015 | Hodgins et al. |
| 8,949,070 B1 | 2/2015 | Kahn et al. |
| 8,958,885 B2 | 2/2015 | Panken et al. |
| 9,476,692 B2 * | 10/2016 | Reese .................. A61B 5/1071 |
| 9,582,072 B2 * | 2/2017 | Connor .................. G06F 3/011 |
| 9,891,718 B2 * | 2/2018 | Connor .................. G06F 3/017 |
| 10,197,459 B2 * | 2/2019 | Keller .................. G06F 3/014 |
| 10,234,934 B2 * | 3/2019 | Connor .................. A61B 5/1126 |
| 2001/0003712 A1 | 6/2001 | Roelofs |
| 2001/0020140 A1 | 9/2001 | Kramer |
| 2001/0049470 A1 | 12/2001 | Mault et al. |
| 2002/0024656 A1 | 2/2002 | Kwon et al. |
| 2002/0088931 A1 | 7/2002 | Danisch et al. |
| 2002/0151824 A1 | 10/2002 | Fischer |
| 2002/0198472 A1 | 12/2002 | Kramer |
| 2003/0023192 A1 | 1/2003 | Foxlin |
| 2003/0045816 A1 | 3/2003 | Foxlin |
| 2003/0047002 A1 | 3/2003 | Arms et al. |
| 2003/0054923 A1 | 3/2003 | Brassil et al. |
| 2003/0083596 A1 | 5/2003 | Kramer et al. |
| 2003/0091966 A1 | 5/2003 | Collodi |
| 2003/0120448 A1 | 6/2003 | Moriya et al. |
| 2005/0069695 A1 | 3/2005 | Jung et al. |
| 2005/0126026 A1 | 6/2005 | Townsend et al. |
| 2005/0140651 A1 | 6/2005 | Suprun et al. |
| 2006/0022833 A1 | 2/2006 | Ferguson et al. |
| 2006/0059976 A1 | 3/2006 | Simonenko et al. |
| 2006/0059988 A1 | 3/2006 | Pristup |
| 2006/0059990 A1 | 3/2006 | Simonenko et al. |
| 2006/0059991 A1 | 3/2006 | Pristup et al. |
| 2006/0070443 A1 | 4/2006 | Pristup |
| 2006/0130347 A1 | 6/2006 | Bergamasco et al. |
| 2006/0135883 A1 | 6/2006 | Jonsson et al. |
| 2006/0166737 A1 | 7/2006 | Bentley |
| 2006/0167564 A1 | 7/2006 | Flaherty et al. |
| 2006/0184336 A1 | 8/2006 | Kolen |
| 2006/0189899 A1 | 8/2006 | Flaherty et al. |
| 2006/0212097 A1 | 9/2006 | Varadan et al. |
| 2006/0217233 A1 | 9/2006 | Lee |
| 2006/0240953 A1 | 10/2006 | Shahinpoor |
| 2006/0241521 A1 | 10/2006 | Cohen |
| 2006/0282017 A1 | 12/2006 | Avni et al. |
| 2006/0284979 A1 | 12/2006 | Clarkson |
| 2007/0000324 A9 | 1/2007 | Pristup et al. |
| 2007/0038038 A1 | 2/2007 | Stivoric et al. |
| 2007/0073482 A1 | 3/2007 | Churchill et al. |
| 2007/0100666 A1 | 5/2007 | Stivoric et al. |
| 2007/0123997 A1 | 5/2007 | Herr et al. |
| 2007/0132722 A1 | 6/2007 | Kim et al. |
| 2007/0169364 A1 | 7/2007 | Townsend et al. |
| 2007/0173705 A1 | 7/2007 | Teller et al. |
| 2007/0202765 A1 | 8/2007 | Krans et al. |
| 2007/0214889 A1 | 9/2007 | Pristup |
| 2007/0219744 A1 | 9/2007 | Kolen |
| 2007/0256502 A1 | 11/2007 | Aebersold et al. |
| 2007/0270214 A1 | 11/2007 | Bentley |
| 2008/0036737 A1 | 2/2008 | Hernandez-Rebollar |
| 2008/0061949 A1 | 3/2008 | Ferguson et al. |

(56) References Cited

U.S. PATENT DOCUMENTS

| | | |
|---|---|---|
| 2008/0084385 A1 | 4/2008 | Ranta et al. |
| 2008/0167535 A1 | 7/2008 | Stivoric et al. |
| 2008/0285805 A1 | 11/2008 | Luinge et al. |
| 2009/0025483 A1 | 1/2009 | Connor et al. |
| 2009/0025819 A1 | 1/2009 | Douglas |
| 2009/0030345 A1 | 1/2009 | Bonnet et al. |
| 2009/0076419 A1 | 3/2009 | Namineni et al. |
| 2009/0149257 A1 | 6/2009 | Ferguson et al. |
| 2009/0171180 A1 | 7/2009 | Pering et al. |
| 2009/0188325 A1 | 7/2009 | Aebersold et al. |
| 2009/0204031 A1 | 8/2009 | McNames et al. |
| 2009/0278791 A1 | 11/2009 | Slycke et al. |
| 2010/0010379 A1* | 1/2010 | De Rossi ............... A61B 5/103 600/587 |
| 2010/0026809 A1 | 2/2010 | Curry |
| 2010/0036288 A1 | 2/2010 | Lanfermann et al. |
| 2010/0076348 A1 | 3/2010 | McNames et al. |
| 2010/0176952 A1 | 7/2010 | Bajcsy et al. |
| 2010/0183297 A1 | 7/2010 | Barboutis et al. |
| 2010/0198113 A1 | 8/2010 | Coulston |
| 2010/0211349 A1 | 8/2010 | Flaction et al. |
| 2010/0225473 A1 | 9/2010 | Leuthardt et al. |
| 2010/0225474 A1 | 9/2010 | Leuthardt et al. |
| 2010/0225490 A1 | 9/2010 | Leuthardt et al. |
| 2010/0225491 A1 | 9/2010 | Leuthardt et al. |
| 2010/0225498 A1 | 9/2010 | Leuthardt et al. |
| 2010/0228153 A1 | 9/2010 | Leuthardt et al. |
| 2010/0228154 A1 | 9/2010 | Leuthardt et al. |
| 2010/0228158 A1 | 9/2010 | Leuthardt et al. |
| 2010/0228159 A1 | 9/2010 | Leuthardt et al. |
| 2010/0228487 A1 | 9/2010 | Leuthardt et al. |
| 2010/0228488 A1 | 9/2010 | Leuthardt et al. |
| 2010/0228489 A1 | 9/2010 | Leuthardt et al. |
| 2010/0228490 A1 | 9/2010 | Leuthardt et al. |
| 2010/0228492 A1 | 9/2010 | Leuthardt et al. |
| 2010/0228493 A1 | 9/2010 | Leuthardt et al. |
| 2010/0228494 A1 | 9/2010 | Leuthardt et al. |
| 2010/0228495 A1 | 9/2010 | Leuthardt et al. |
| 2010/0271200 A1 | 10/2010 | Leuthardt et al. |
| 2010/0309209 A1 | 12/2010 | Hodgins et al. |
| 2010/0317957 A1 | 12/2010 | Lee et al. |
| 2010/0324384 A1 | 12/2010 | Moon et al. |
| 2010/0324385 A1 | 12/2010 | Moon et al. |
| 2010/0324386 A1 | 12/2010 | Moon et al. |
| 2010/0324387 A1 | 12/2010 | Moon et al. |
| 2010/0324388 A1 | 12/2010 | Moon et al. |
| 2010/0324389 A1 | 12/2010 | Moon et al. |
| 2010/0324456 A1 | 12/2010 | Jonsson et al. |
| 2011/0025562 A1 | 2/2011 | Hol et al. |
| 2011/0028865 A1 | 2/2011 | Luinge et al. |
| 2011/0040216 A1 | 2/2011 | Herr et al. |
| 2011/0046518 A1 | 2/2011 | Fischer |
| 2011/0046915 A1 | 2/2011 | Hol et al. |
| 2011/0052005 A1 | 3/2011 | Selner |
| 2011/0181422 A1 | 7/2011 | Tran |
| 2011/0201428 A1 | 8/2011 | Ferguson et al. |
| 2011/0208444 A1 | 8/2011 | Solinsky |
| 2011/0248773 A1 | 10/2011 | Poupyrev et al. |
| 2011/0313705 A1 | 12/2011 | Esser et al. |
| 2012/0046901 A1 | 2/2012 | Green et al. |
| 2012/0089348 A1 | 4/2012 | Perlin et al. |
| 2012/0092156 A1 | 4/2012 | Tran |
| 2012/0108917 A1 | 5/2012 | Libbus et al. |
| 2012/0116257 A1 | 5/2012 | Leuthardt et al. |
| 2012/0118066 A1 | 5/2012 | Majidi et al. |
| 2012/0172126 A1 | 7/2012 | Padovani et al. |
| 2012/0178534 A1 | 7/2012 | Ferguson et al. |
| 2012/0204310 A1 | 8/2012 | Fernandez |
| 2012/0223880 A1 | 9/2012 | Birnbaum et al. |
| 2012/0234105 A1 | 9/2012 | Taylor |
| 2012/0274554 A1 | 11/2012 | Kinoshita et al. |
| 2012/0316455 A1 | 12/2012 | Rahman et al. |
| 2012/0319940 A1 | 12/2012 | Bress et al. |
| 2012/0323501 A1 | 12/2012 | Sarrafzadeh et al. |
| 2013/0015976 A1 | 1/2013 | Chang et al. |
| 2013/0068017 A1 | 3/2013 | Perkins et al. |
| 2013/0072765 A1 | 3/2013 | Kahn et al. |
| 2013/0073248 A1 | 3/2013 | Perkins et al. |
| 2013/0110011 A1 | 5/2013 | McGregor et al. |
| 2013/0113506 A1 | 5/2013 | Poupyrev et al. |
| 2013/0123665 A1 | 5/2013 | Mariani et al. |
| 2013/0158444 A1 | 6/2013 | Herr et al. |
| 2013/0158686 A1 | 6/2013 | Zhang et al. |
| 2013/0173171 A1 | 7/2013 | Drysdale et al. |
| 2013/0204411 A1 | 8/2013 | Clark et al. |
| 2013/0204435 A1 | 8/2013 | Moon et al. |
| 2013/0207889 A1 | 8/2013 | Chang et al. |
| 2013/0211291 A1 | 8/2013 | Tran |
| 2013/0215230 A1 | 8/2013 | Miesnieks et al. |
| 2013/0222565 A1 | 8/2013 | Guerin et al. |
| 2013/0253875 A1 | 9/2013 | Flentov et al. |
| 2013/0275057 A1 | 10/2013 | Perlin et al. |
| 2013/0289932 A1 | 10/2013 | Baechler |
| 2013/0303286 A1 | 11/2013 | Ferguson et al. |
| 2013/0324888 A1 | 12/2013 | Solinsky |
| 2014/0031698 A1 | 1/2014 | Moon et al. |
| 2014/0070957 A1 | 3/2014 | Longinotti-Buitoni et al. |
| 2014/0142733 A1 | 5/2014 | Tropper et al. |
| 2014/0143031 A1 | 5/2014 | Tropper et al. |
| 2014/0143038 A1 | 5/2014 | Tropper et al. |
| 2014/0159894 A1 | 6/2014 | Tropper et al. |
| 2014/0171834 A1 | 6/2014 | Degoede et al. |
| 2014/0172134 A1 | 6/2014 | Meschter |
| 2014/0188499 A1 | 7/2014 | Bell et al. |
| 2014/0194781 A1 | 7/2014 | Einarsson |
| 2014/0197946 A1 | 7/2014 | Park et al. |
| 2014/0197963 A1 | 7/2014 | Park et al. |
| 2014/0197965 A1 | 7/2014 | Park et al. |
| 2014/0206327 A1 | 7/2014 | Ziemianska et al. |
| 2014/0213856 A1 | 7/2014 | Teller et al. |
| 2014/0213857 A1 | 7/2014 | Teller et al. |
| 2014/0221769 A1 | 8/2014 | Teller et al. |
| 2014/0223407 A1 | 8/2014 | Teller et al. |
| 2014/0240103 A1 | 8/2014 | Lake et al. |
| 2014/0240122 A1 | 8/2014 | Roberts et al. |
| 2014/0249381 A1 | 9/2014 | LeBoeuf et al. |
| 2014/0275812 A1 | 9/2014 | Stivoric et al. |
| 2014/0275813 A1 | 9/2014 | Stivoric et al. |
| 2014/0288875 A1 | 9/2014 | Donaldson |
| 2014/0288877 A1 | 9/2014 | Donaldson |
| 2014/0288878 A1 | 9/2014 | Donaldson |
| 2014/0342844 A1 | 11/2014 | Mooney |
| 2014/0366675 A1 | 12/2014 | Gosselin et al. |
| 2015/0005608 A1 | 1/2015 | Evans et al. |
| 2015/0015417 A1 | 1/2015 | Libbus et al. |
| 2015/0019135 A1 | 1/2015 | Kacyvenski et al. |
| 2015/0045699 A1 | 2/2015 | Mokaya et al. |
| 2015/0124266 A1* | 5/2015 | Davis ................... G01D 5/3538 356/601 |
| 2015/0294756 A1 | 10/2015 | Ben Shalom et al. |
| 2016/0048235 A1 | 2/2016 | Poupyrev |
| 2016/0048236 A1 | 2/2016 | Poupyrev |
| 2016/0282988 A1 | 9/2016 | Poupyrev |
| 2017/0115777 A1 | 4/2017 | Poupyrev |
| 2017/0325518 A1 | 11/2017 | Poupyrev et al. |

* cited by examiner

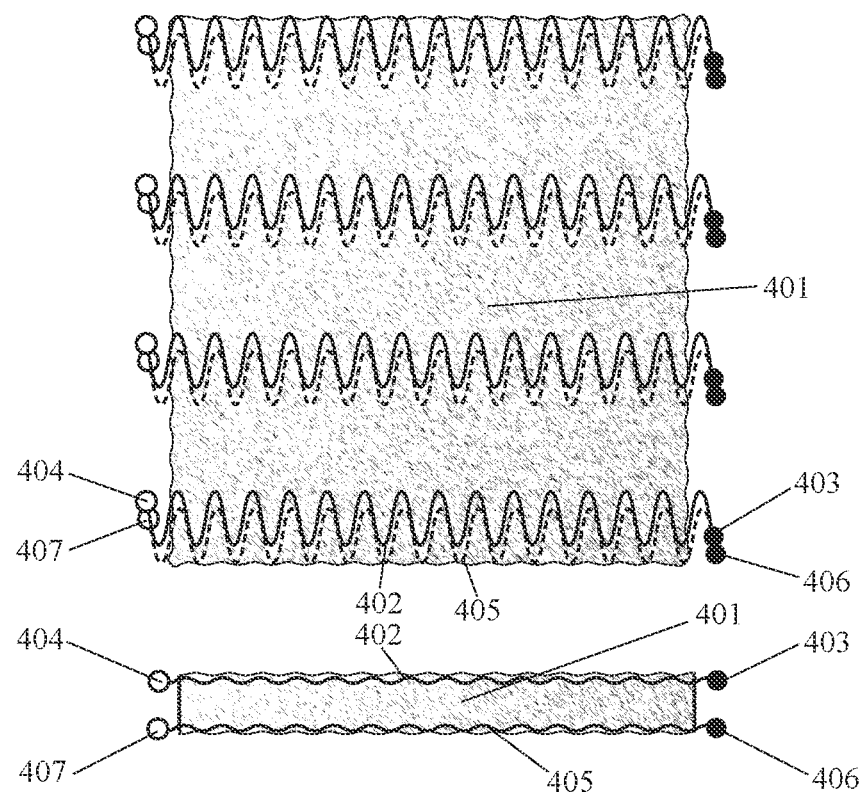
Fig. 4
Fig. 5
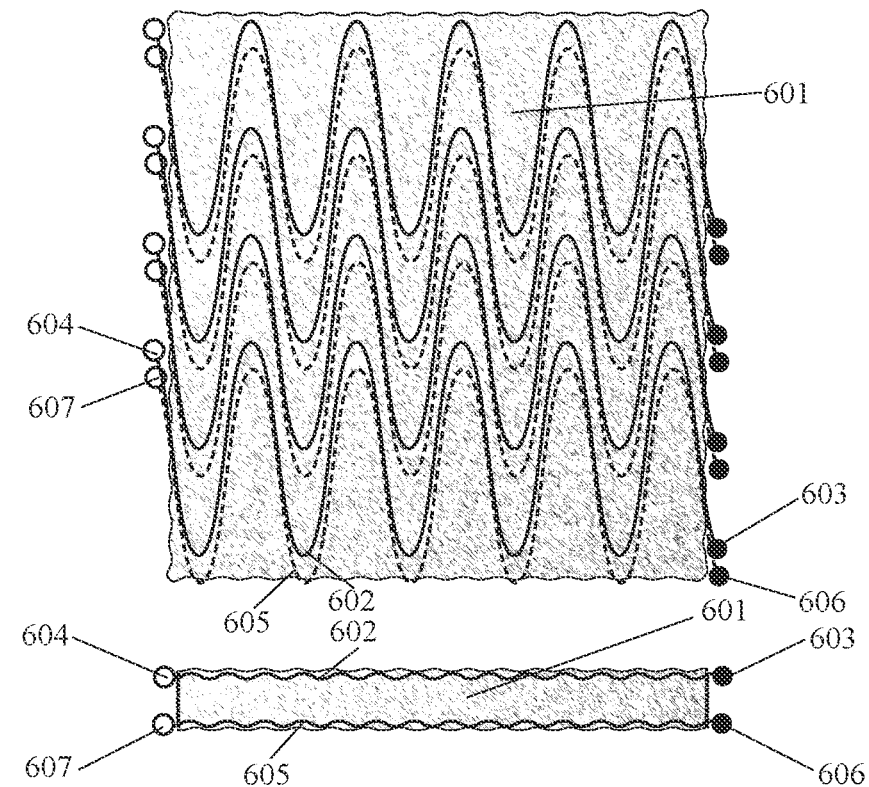
Fig. 6
Fig. 7

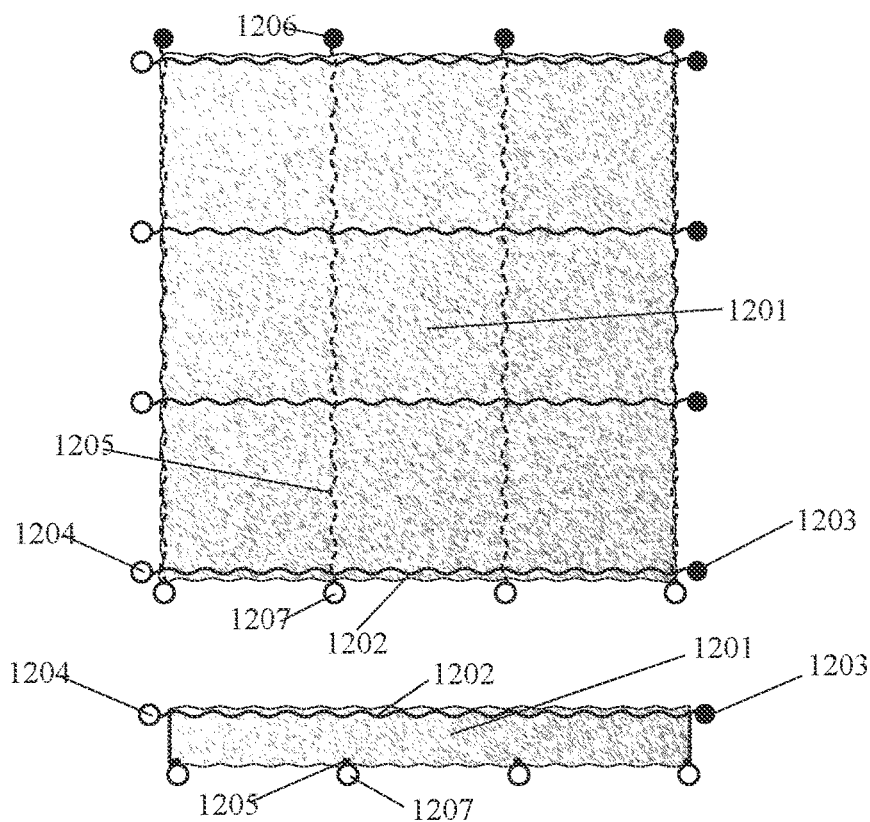
Fig. 12
Fig. 13
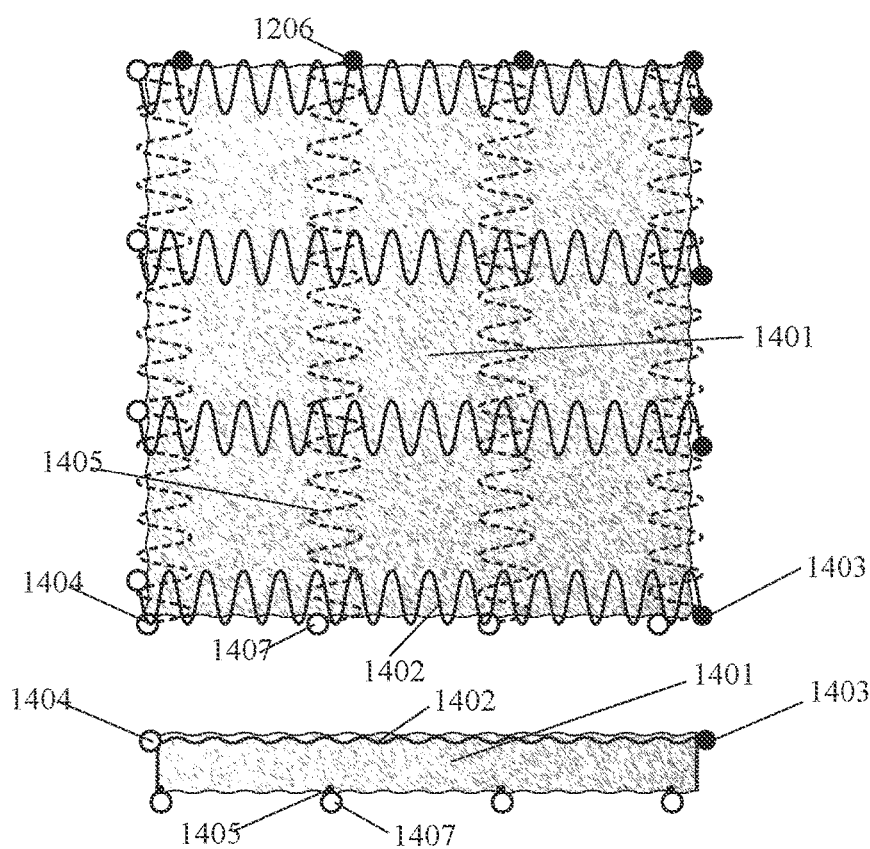
Fig. 14
Fig. 15

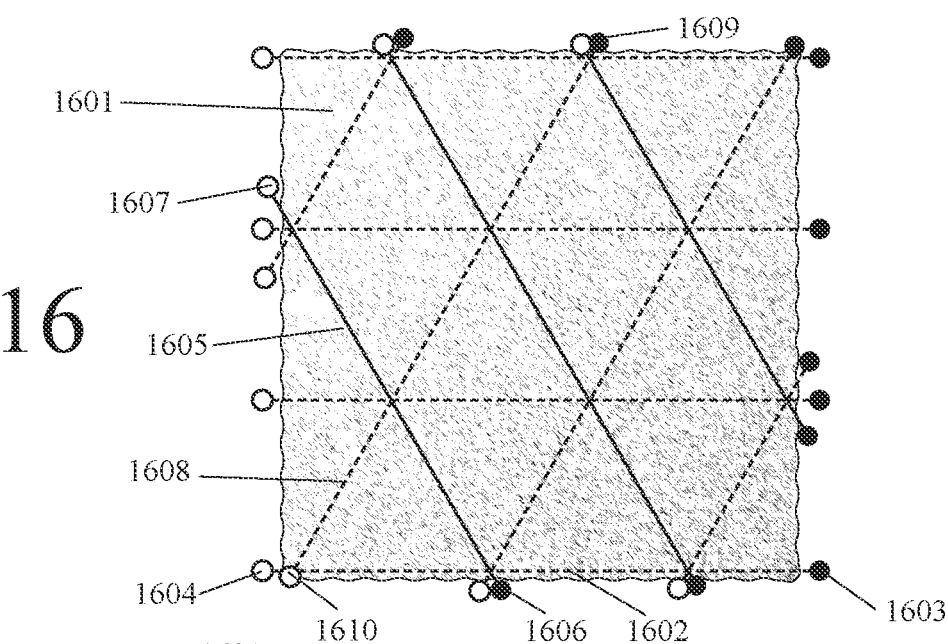
Fig. 16
Fig. 17
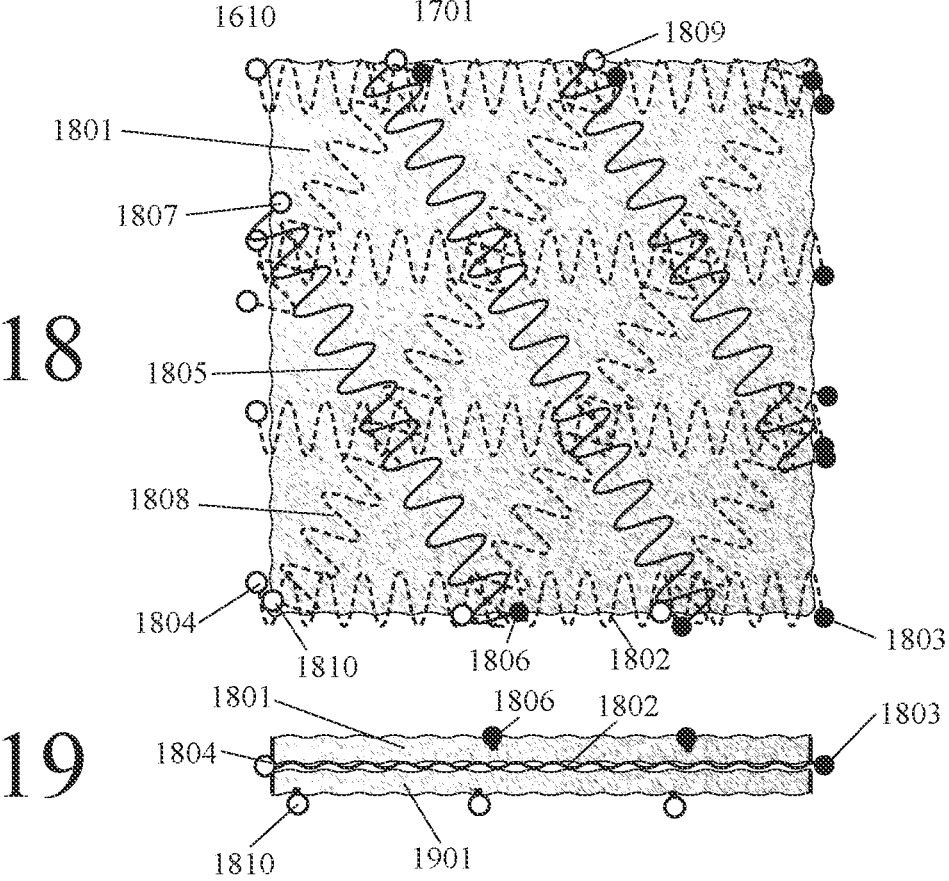
Fig. 18
Fig. 19

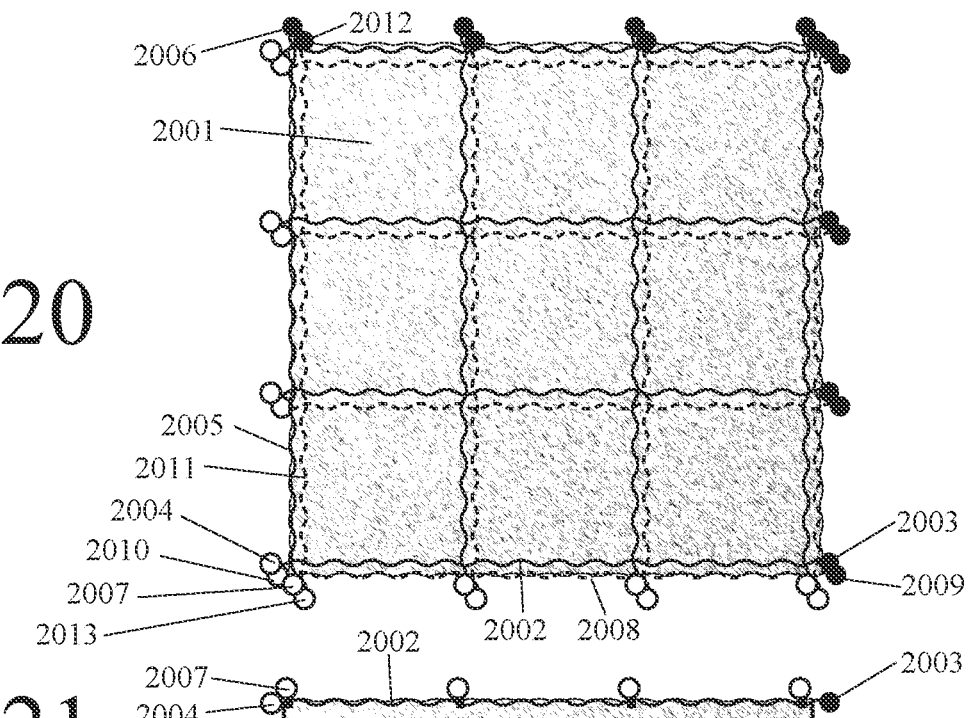
Fig. 20
Fig. 21
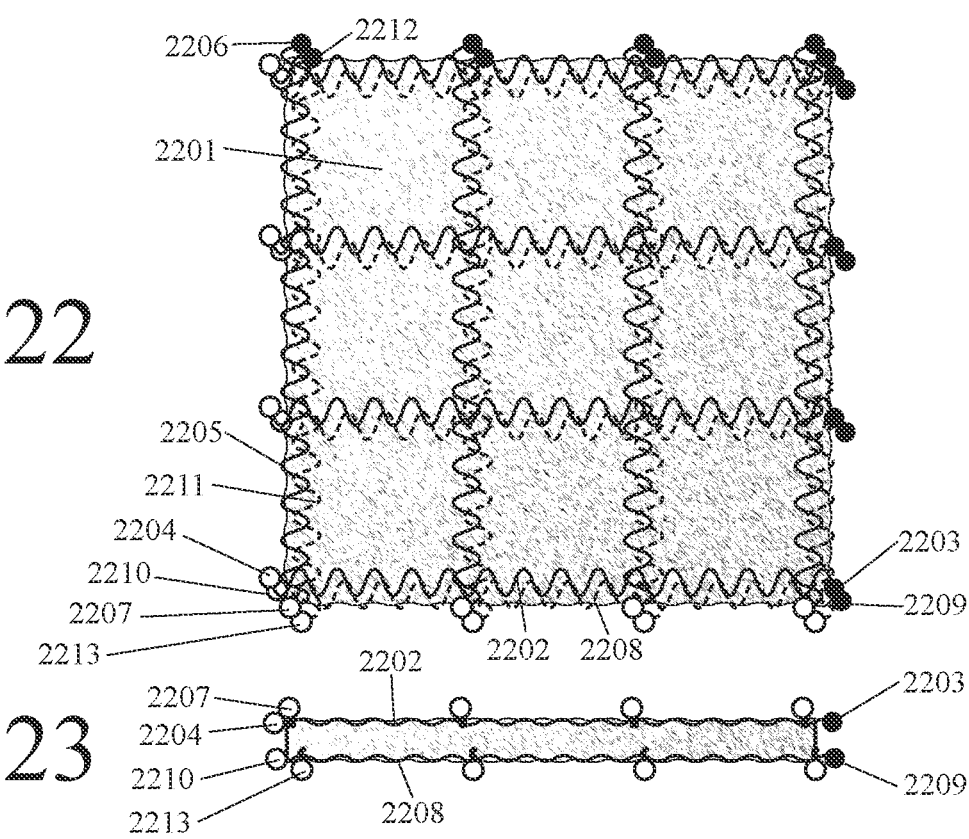
Fig. 22
Fig. 23

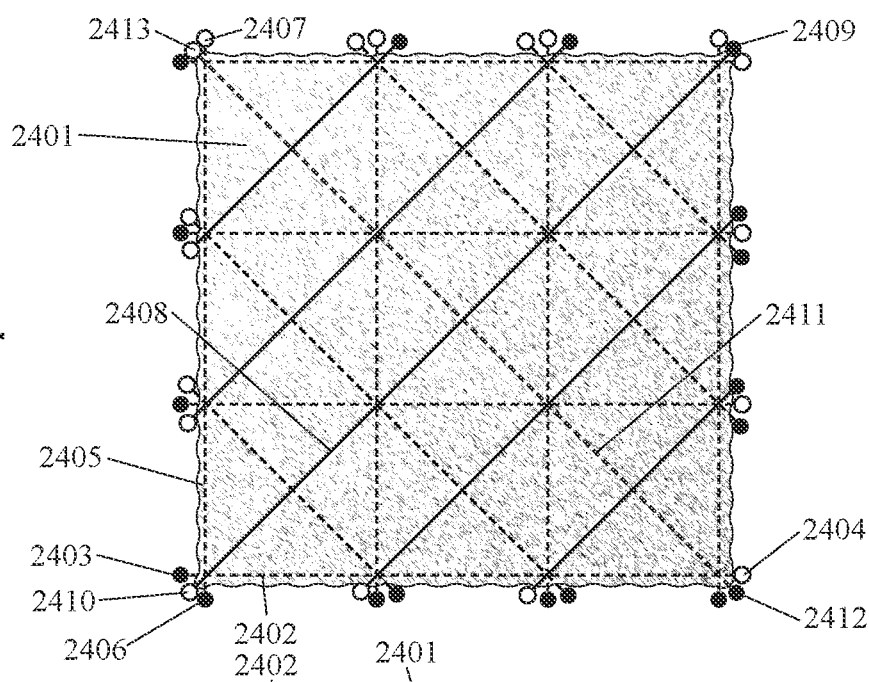
Fig. 24
Fig. 25
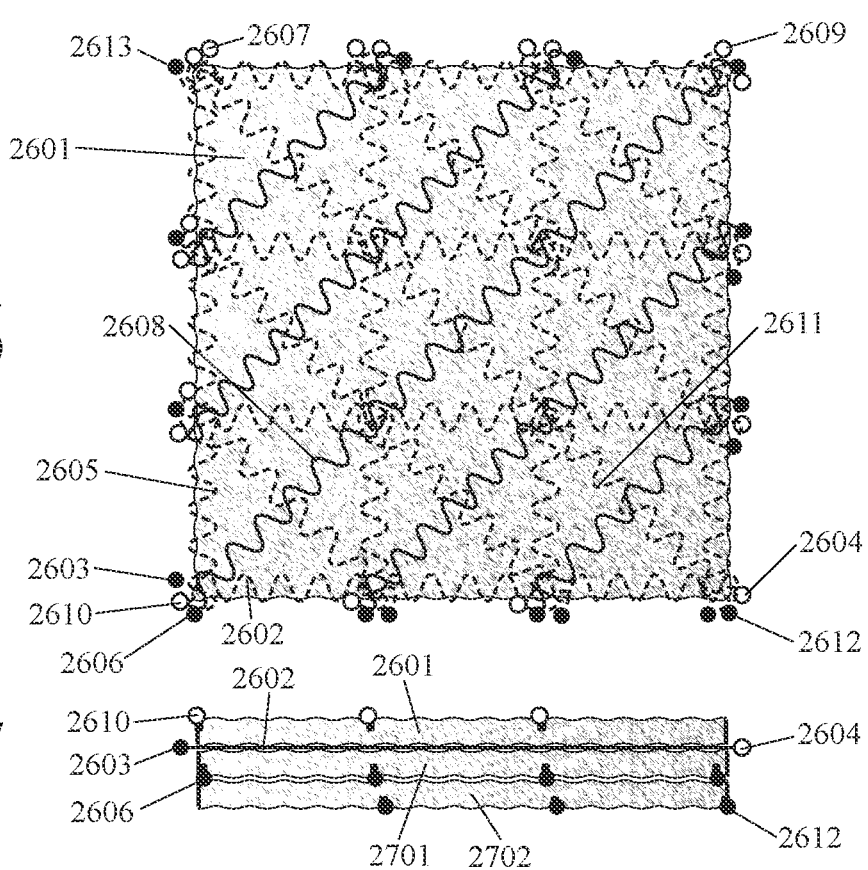
Fig. 26
Fig. 27

WEARABLE DEFORMABLE CONDUCTIVE SENSORS FOR HUMAN MOTION CAPTURE INCLUDING TRANS-JOINT PITCH, YAW, AND ROLL

CROSS-REFERENCE TO RELATED APPLICATIONS

This patent application:

(A) claims the benefit of provisional application 62/683,237 filed on Jun. 11, 2018;

(B) is a CIP (Continuation In Part) of application Ser. No. 15/702,081 filed on Sep. 12, 2017. Ser. No. 15/702,081 claims the benefit of provisional application 62/538,793 filed on Jul. 30, 2017. Ser. No. 15/702,081 claims the benefit of provisional application 62/449,735 filed on Jan. 24, 2017. Ser. No. 15/702,081 is a CIP of application Ser. No. 15/227,254 filed on Aug. 3, 2016. Ser. No. 15/227,254 claims the benefit of provisional application 62/357,957 filed on Jul. 2, 2016. Ser. No. 15/227,254 is a CIP of application Ser. No. 15/130,995 filed on Apr. 17, 2016 which is now U.S. Pat. No. 9,891,718 issued on Feb. 13, 2018. Ser. No. 15/130,995 claims the benefit of provisional application 62/150,886 filed on Apr. 22, 2015. Ser. No. 15/227,254 is a CIP of application Ser. No. 15/079,447 filed on Mar. 24, 2016. Ser. No. 15/079,447 is a CIP of application Ser. No. 14/463,741 filed on Aug. 20, 2014 which is now U.S. Pat. No. 9,588,582 issued on Mar. 7, 2017. Ser. No. 14/463,741 claims the benefit of provisional application 61/878,893 filed on Sep. 17, 2013. Ser. No. 15/079,447 is a CIP of application Ser. No. 14/664,832 filed on Mar. 21, 2015 which is now U.S. Pat. No. 9,582,072 issued on Feb. 28, 2017. Ser. No. 14/664,832 is a CIP of application Ser. No. 14/463,741 filed on Aug. 20, 2014 which is now U.S. Pat. No. 9,588,582 issued on Mar. 7, 2017. Ser. No. 14/463,741 claims the benefit of provisional application 61/878,893 filed on Sep. 17, 2013. Ser. No. 14/664,832 claims the benefit of provisional application 61/976,650 filed on Apr. 8, 2014. Ser. No. 15/079,447 claims the benefit of provisional application 62/150,886 filed on Apr. 22, 2015. Ser. No. 15/227,254 is a CIP of application Ser. No. 14/736,652 filed on Jun. 11, 2015. Ser. No. 14/736,652 is a CIP of application Ser. No. 14/664,832 filed on Mar. 21, 2015 which is now U.S. Pat. No. 9,582,072 issued on Feb. 28, 2017. Ser. No. 14/736,652 claims the benefit of provisional application 62/014,747 filed on Jun. 20, 2014. Ser. No. 14/736,652 claims the benefit of provisional application 62/100,217 filed on Jan. 6, 2015. Ser. No. 15/227,254 is a CIP of application Ser. No. 14/664,832 filed on Mar. 21, 2015 which is now U.S. Pat. No. 9,582,072 issued on Feb. 28, 2017. Ser. No. 14/664,832 is a CIP of application Ser. No. 14/463,741 filed on Aug. 20, 2014 which is now U.S. Pat. No. 9,588,582 issued on Mar. 7, 2017. Ser. No. 14/463,741 claims the benefit of provisional application 61/878,893 filed on Sep. 17, 2013. Ser. No. 14/664,832 claims the benefit of provisional application 61/976,650 filed on Apr. 8, 2014. Ser. No. 15/702,081 is a CIP of application Ser. No. 14/795,373 filed on Jul. 9, 2015. Ser. No. 14/795,373 is a CIP of application Ser. No. 14/736,652 filed on Jun. 11, 2015. Ser. No. 14/736,652 is a CIP of application Ser. No. 14/664,832 filed on Mar. 21, 2015 which is now U.S. Pat. No. 9,582,072 issued on Feb. 28, 2017. Ser. No. 14/736,652 claims the benefit of provisional application 62/014,747 filed on Jun. 20, 2014. Ser. No. 14/736,652 claims the benefit of provisional application 62/100,217 filed on Jan. 6, 2015. Ser. No. 14/795,373 claims the benefit of provisional application 62/065,032 filed on Oct. 17, 2014. Ser. No. 14/795,373 claims the benefit of provisional application 62/086,053 filed on Dec. 1, 2014. Ser. No. 14/795,373 claims the benefit of provisional application 62/182,473 filed on Jun. 20, 2015. Ser. No. 14/795,373 claims the benefit of provisional application 62/187,906 filed on Jul. 2, 2015;

(C) claims the benefit of provisional application 62/538,793 filed on Jul. 20, 2017; and (D) is a CIP of application Ser. No. 15/227,254 filed on Aug. 2, 2016. Ser. No. 15/227,254 claims the benefit of provisional application 62/357,957 filed on Jul. 2, 2016. Ser. No. 15/227,254 is a CIP of application Ser. No. 15/130,995 filed on Apr. 17, 2016 which is now U.S. Pat. No. 9,891,718 issued on Feb. 13, 2018. Ser. No. 15/130,995 claims the benefit of provisional application 62/150,886 filed on Apr. 22, 2015. Ser. No. 15/227,254 is a CIP of application Ser. No. 15/079,447 filed on Mar. 24, 2016. Ser. No. 15/079,447 is a CIP of application Ser. No. 14/463,741 filed on Aug. 20, 2014 which is now U.S. Pat. No. 9,588,582 issued on Mar. 7, 2017. Ser. No. 14/463,741 claims the benefit of provisional application 61/878,893 filed on Sep. 17, 2013. Ser. No. 15/079,447 is a CIP of application Ser. No. 14/664,832 filed on Mar. 21, 2015 which is now U.S. Pat. No. 9,582,072 issued on Feb. 28, 2017. Ser. No. 14/664,832 is a CIP of application Ser. No. 14/463,741 filed on Aug. 20, 2014 which is now U.S. Pat. No. 9,588,582 issued on Mar. 7, 2017. Ser. No. 14/463,741 claims the benefit of provisional application 61/878,893 filed on Sep. 17, 2013. Ser. No. 14/664,832 claims the benefit of provisional application 61/976,650 filed on Apr. 8, 2014. Ser. No. 15/079,447 claims the benefit of provisional application 62/150,886 filed on Apr. 22, 2015. Ser. No. 15/227,254 is a CIP of application Ser. No. 14/736,652 filed on Jun. 11, 2015. Ser. No. 14/736,652 is a CIP of application Ser. No. 14/664,832 filed on Mar. 21, 2015 which is now U.S. Pat. No. 9,582,072 issued on Feb. 28, 2017. Ser. No. 14/736,652 claims the benefit of provisional application 62/014,747 filed on Jun. 20, 2014. Ser. No. 14/736,652 claims the benefit of provisional application 62/100,217 filed on Jan. 6, 2015. Ser. No. 15/227,254 is a CIP of application Ser. No. 14/664,832 filed on Mar. 21, 2015 which is now U.S. Pat. No. 9,582,072 issued on Feb. 28, 2017. Ser. No. 14/664,832 is a CIP of application Ser. No. 14/463,741 filed on Aug. 20, 2014 which is now U.S. Pat. No. 9,588,582 issued on Mar. 7, 2017. Ser. No. 14/463,741 claims the benefit of provisional application 61/878,893 filed on Sep. 17, 2013. Ser. No. 14/664,832 claims the benefit of provisional application 61/976,650 filed on Apr. 8, 2014.

The entire contents of these applications are incorporated herein by reference.

FEDERALLY SPONSORED RESEARCH

Not Applicable

SEQUENCE LISTING OR PROGRAM

Not Applicable

BACKGROUND

Field of Invention

This invention relates to wearable sensors for measuring body motion, posture, and/or configuration.

Introduction

This invention comprises novel wearable deformable electrically-conductive sensors which enable ambulatory (camera-free) human motion capture. In an example, these sensors can be incorporated into motion recognition fabric which is, in turn, used to make motion recognition clothing. Ambulatory (camera-free) human motion capture can be used for athletic training, sports performance analysis, sports motion capture, and fan engagement. It can be used for training and motion capture for: sports which involve extensive and/or complex lower-body motion (such as soccer, bicycling, and running) which are not well measured by single-location (wrist-worn) accelerometers; and also for sports which involve complex upper-body motion (such as golf, basketball, tennis, baseball, tiddlywinks, and fencing) which are not well measured by single-location accelerometers.

Ambulatory (camera-free) human motion capture can also be used for health, fitness, and medical applications. It can be used for caloric expenditure measurement, energy balance management, weight management, and caloric intake monitoring applications. It can be used for virtual exercise. It can be used for real-time avoidance of repeated motion injuries, injuries due to poor posture, and stress-related injuries including back injuries and carpal tunnel syndrome. It can be used for diagnostic and therapy-evaluation purposes including: range of motion assessment, gait analysis, biomechanical analysis, posture evaluation and correction, ergonomic assessment, fall prevention and detection, spinal motion assessment, rehabilitation assessment, biofeedback, pulse monitoring, osculation assessment, respiratory function assessment, plethysmography, cardiac function monitoring, orthopedic therapy, physical therapy, orthotic design and fitting, and pronation analysis. It can be used for telemedicine and/or telesurgery applications.

Ambulatory (camera-free) human motion capture can also be used for entertainment, gaming, and artistic purposes. It can be used for animation of an avatar in virtual reality and/or computer gaming. It can be used for animation of an animated character in motion picture making or other visual animation applications. It can be used for dance instruction, uptown funk, and other performance art applications. It can be used for instruction and motion capture for playing musical instruments.

Ambulatory (camera-free) human motion capture can also be used for communication and computer interface purposes. It can be used for telepresence, teleconferencing, telecommunication, avatar animation, and virtual commerce. It can be used as part of a gesture recognition human-to-computer user interface. It be can be used for telerobotics to enable remote control of the actions of a robot.

Review and Categorization of the Prior Art

There are motion capture technologies in the prior art, but they have limitations. For example, there are camera-based motion capture systems. Some of these camera-based motion capture systems are very complex, comprising a circle of multiple cameras which each track a moving individual from a different perspective. These multi-camera systems can be accurate, but they constrain a person to remain inside a space at the intersection of the fields of vision of these cameras. There are also single-camera motion capture systems for home use, but they restrict a person to remain in the field of vision of the camera. Further, relying on one camera (or even two cameras which are close together) means that the system cannot track the locations of body members when the camera's direct line of sight to them is obscured by other body members or objects. There are also motion capture suits with multiple inertial sensors. More-accurate versions of such full-body motion capture suits tend to be cumbersome and expensive. Less-accurate versions tend to suffer from lag and/or drift due to the complex calculations involved in real-time translation of inertial sensor data into three-dimensional body motion models. Due to the limitations of camera-based and inertial-sensor systems, there remains a need for a wearable, mobile, reasonably-priced, and relatively-unobtrusive full-body motion-capture system which can be used in diverse environments.

It can be challenging trying to classify prior art in this field into discrete categories. However, classification of the prior art into categories, even if imperfect, can be an invaluable part of reviewing the prior art. Towards this end, I herein identify and briefly discuss 8 relevant categories of prior art related to measurement and modeling of body motion, posture, and/or configuration. For the most relevant categories of prior art, I also provide specific examples of prior art (including patent or patent application number, inventor, publication date, and title). Some examples of prior art disclose multiple concepts and thus appear in more than one category. I hope that the reader finds this review and categorization of the prior art to be useful. The 8 categories of art used for this review and categorization are as follows: (1) wearable GPS for tracking geographic position; (2) fixed-location camera-based motion capture; (3) hand-held game controller, ball, bat, or other held object; (4) wearable RFID or other electromagnetic energy emitters; (5) wearable electromyographic (EMG) sensors; (6) rigid or partially-rigid exoskeleton; (7) wearable pressure sensors; and (8) wearable electromagnetic energy bend sensors and/or electrogoniometers.

1. Wearable GPS for Tracking Geographic Position

Prior art in this category uses a wearable GPS unit to track a person's geographic position and macroscale body movement. Such art can be very useful for tracking movement distance and speed, but is not useful for mobile three-dimensional recognition of body motion, posture, and/or configuration and is less relevant to the technology of this present invention. Accordingly, although the category is mentioned here, specific examples of this large category of art are not listed.

2. Fixed-Location Camera-Based Motion Capture

Prior art in this widely-used category, traditionally known as "motion capture" or "mocap," uses one or more fixed-location cameras to take and analyze images of a person in order to estimate and/or model the person's movement. Such motion capture systems are widely used for animation in motion pictures and video games, using full-body motion for controlling a video game or other computer application, fixed-location sport-related motion analysis, medical body motion diagnostic assessment, and other applications. Such art can be very useful for all of these purposes, but is generally constrains a person to a fixed location and is subject to occlusion when a direct line of sight from the camera to a portion of a person's body is blocked. Accordingly, such art is less useful for mobile, ambulatory, and/or long-duration applications and is less relevant to the technology of this present invention. Thus, although the category is mentioned here, specific examples of art in this large category of prior art are not listed.

3. Hand-Held Game Controller, Ball, Bat, or Other Held Object

Prior art in this widely-used category tracks the location, orientation, and/or configuration of a hand-held game controller, sports ball, bat, club, or other held object in order to analyze the motion dynamics of a particular activity (such as a sport activity), control a computer game, interact with a virtual reality environment, or other motion-related application. Such art can be very useful for these purposes, but since the tracked object is not worn and be only in limited contact with the user's body, it is limited for tracking three-dimensional body motion, posture, and/or configuration. Accordingly, such art is less relevant to this present invention. This category is mentioned here, but specific examples of art in this category are not listed.

4. Wearable RFID or Other Electromagnetic Energy Emitters

Prior art in this category uses an array of wearable RFID or other electromagnetic energy emitters to track body motion and/or configuration in a three-dimensional space. Since this art generally constrains the user to motion within a defined space with fixed-location energy sensors, it is generally subject to similar location constraints as traditional camera-based motion capture. The technology is quite different than that used in the present invention and thus, although the category is mentioned here, specific examples of art in this category are not listed.

5. Wearable ElectroMyoGraphic (EMG) Sensors

Prior art in this category uses wearable sensors to measure electromagnetic energy which is naturally emitted from body muscles and nerves in order to estimate and model body motion. This category of prior art is relatively new and there are few examples in it as compared to the previous categories, but it is growing. Art in this category has the potential to eventually be very useful for mobile three-dimensional recognition of body motion, posture, and configuration. However, the technology is different than the technology used in this present invention. Unlike this present invention, EMG sensors measure naturally emitted electromagnetic energy and thus are less relevant to this present invention. Accordingly, this category is mentioned here, but specific examples of art in this category are not listed.

6. Rigid or Partially-Rigid Exoskeleton

Prior art in this category uses a rigid or partially-rigid exoskeleton which is attached to a person in order to measure and/or affect the person's body motion. Some exoskeletons are used primarily for measuring and modeling body motion. Other exoskeletons are used primarily for affecting body motion, such as with actuators which provide haptic feedback or help the person to move. This present invention focuses on flexible wearable pathways (which can be incorporated into an article of clothing) rather than a rigid or semi-rigid exoskeleton which is attached to a person. This rigid or semi-rigid nature of an exoskeleton can limit the range of body motion and limit its use for long-duration applications. Nonetheless, this category of art is more relevant than the previous categories and thus specific examples of art in this category are now listed.

Examples of prior art which appear to be within this category include the following U.S. Pat. No. 5,012,819 (Marras et al., May 7, 1991, "Apparatus for Monitoring the Motion Components of the Spine"); U.S. Pat. No. 5,280,265 (Kramer et al., Jan. 18, 1994, "Strain-Sensing Goniometers, Systems and Recognition Algorithms"); U.S. Pat. No. 5,442,729 (Kramer et al., Aug. 15, 1995, "Strain-Sensing Goniometers, Systems and Recognition Algorithms"); U.S. Pat. No. 5,474,088 (Zaharkin et al., Dec. 12, 1995, "Device for Measuring Motion Characteristics of a Human Joint"); U.S. Pat. No. 5,516,249 (Brimhall, May 14, 1996, "Exoskeleton with Kinesthetic Feedback and Robotic Control"); U.S. Pat. No. 5,656,904 (Lander, Aug. 12, 1997, "Movement Monitoring and Control Apparatus for Body Members"); U.S. Pat. No. 5,676,157 (Kramer, Oct. 14, 1997, "Determination of Kinematically Constrained Multi-Articulated Structures"); U.S. Pat. No. 5,813,406 (Kramer et al., Sep. 29, 1998, "Strain-Sensing Goniometers, Systems and Recognition Algorithms"); U.S. Pat. No. 5,915,673 (Kazerooni, Jun. 29, 1999, "Pneumatic Human Power Amplifer Module"); U.S. Pat. No. 5,930,741 (Kramer, Jul. 27, 1999, "Accurate, Rapid, Reliable Position Sensing using Multiple Sensing Technologies"); and U.S. Pat. No. 5,961,541 (Ferrati, Oct. 5, 1999, "Orthopedic Apparatus for Walking and Rehabilitating Disabled Persons Including Tetraplegic Persons and for Facilitating and Stimulating the Revival of Comatose Patients Through the Use of Electronic and Virtual Reality Units").

Examples of prior art in this category also include U.S. Pat. No. 6,005,548 (Latypov et al., Dec. 21, 1999, "Method for Tracking and Displaying User's Spatial Position and Orientation, a Method for Representing Virtual Reality for a User, and Systems of Embodiment of Such Methods"); U.S. Pat. No. 6,035,274 (Kramer et al., Mar. 7, 2000, "Strain-Sensing Goniometers, Systems and Recognition Algorithms"); U.S. Pat. No. 6,042,555 (Kramer et al., Mar. 28, 2000, "Force-Feedback Interface Device for the Hand"); U.S. Pat. No. 6,050,962 (Kramer et al., Apr. 18, 2000, "Goniometer-Based Body-Tracking Device and Method"); U.S. Pat. No. 6,104,379 (Petrich et al., Aug. 15, 2000, "Forearm-Supported Exoskeleton Hand-Tracking Device"); U.S. Pat. No. 6,110,130 (Kramer, Aug. 29, 2000, "Exoskeleton Device for Directly Measuring Fingertip Position and Inferring Finger Joint Angle"); U.S. Pat. No. 6,162,190 (Kramer, Dec. 19, 2000, "Determination of Kinematically Constrained Multi-Articulated Structures"); U.S. Pat. No. 6,239,784 (Holmes, May 29, 2001, "Exo-Skeletal Haptic Computer Human/Computer Interface Device"); U.S. Pat. No. 6,246,390 (Rosenberg, Jun. 12, 2001, "Multiple Degree-of-Freedom Mechanical Interface to a Computer System"); U.S. Pat. No. 6,413,229 (Kramer et al., Jul. 2, 2002, "Force-Feedback Interface Device for the Hand"); and U.S. Pat. No. 6,428,490 (Kramer et al., Aug. 6, 2002, "Goniometer-Based Body-Tracking Device and Method").

Examples of prior art in this category also include U.S. Pat. No. 6,497,672 (Kramer, Dec. 24, 2002, "Device and Method for Measuring the Position of Animate Links"); U.S. Pat. No. 6,666,831 (Edgerton et al., Dec. 23, 2003, "Method, Apparatus and System for Automation of Body Weight Support Training (BWST) of Biped Locomotion Over a Treadmill Using a Programmable Stepper Device (PSD) Operating Like an Exoskeleton Drive System from a Fixed Base"); U.S. Pat. No. 6,701,296 (Kramer et al., Mar. 2, 2004, "Strain-Sensing Goniometers, Systems, and Recognition Algorithms"); U.S. Pat. No. 6,866,643 (Kramer, Mar. 15, 2005, "Determination of Finger Position"); U.S. Pat. No. 6,890,312 (Priester et al., May 10, 2005, "Joint Angle Indication System"); U.S. Pat. No. 7,070,571 (Kramer et al., Jul. 4, 2006, "Goniometer-Based Body-Tracking Device"); U.S. Pat. No. 7,153,242 (Goffer, Dec. 26, 2006, "Gait-Locomotor Apparatus"); U.S. Pat. No. 7,410,338 (Schiele et al., Aug. 12, 2008, "Exoskeleton for the Human Arm, in Particular for Space Applications"); U.S. Pat. No. 7,500,853 (Bevirt et al., Mar. 10, 2009, "Mechanical Interface for a Computer System"); U.S. Pat. No. 7,899,556 (Nathan et al., Mar. 1, 2011, "Orthosis for a Gait Modulation System"); U.S. Pat. No. 8,055,021 (Caritu et al., Nov. 8, 2011, "Motion Capture Device and Associated Method"); U.S. Pat. No. 8,171,570 (Adarraga, May 8, 2012, "Exoskeleton"); U.S. Pat. No. 8,678,979 (Stark et al., Mar. 25, 2014, "Remote Monitoring of a Patient"); U.S. Pat. No. 8,708,825 (Crisco, Apr. 29, 2014, "Device Controller with Conformable Fitting System"); and U.S. Pat. No. 8,777,878 (Deitz, Jul. 15, 2014, "Devices, Systems, and Methods for Measuring and Evaluating the Motion and Function of Joints and Associated Muscles").

Examples of prior art which appear to be within this category include the following U.S. patent applications: 20010003712 (Roelofs, Jun. 14, 2001, "Exoskeletal Platform for Controlling Multi-Directional Avatar Kinetics in a Virtual Environment"); 20010020140 (Kramer, Sep. 6, 2001, "Device and Method for Measuring the Position of Animate Links"); 20020198472 (Kramer, Dec. 26, 2002, "Determination of Finger Position"); 20030083596 (Kramer et al., May 1, 2003, "Goniometer-Based Body-Tracking Device and Method"); 20030091966 (Collodi, May 15, 2003, "Excercise/Simulation Device"); 20060130347 (Bergamasco et al., Jun. 22, 2006, "Device for Gioniometric Measurements"); 20060167564 (Flaherty et al., Jul. 27, 2006, "Limb and Digit Movement System"); 20060189899 (Flaherty et al., Aug. 24, 2006, "Joint Movement Apparatus"); 20060217233 (Lee, Sep. 28, 2006, "Apparatus and Method for Lower-Limb Rehabilitation Training Using Weight Load and Joint Angle as Variables"); 20060240953 (Shahinpoor, Oct. 26, 2006, "Human Lower Limb Performance Enhancement Outfit"); 20070123997 (Herr et al., May 31, 2007, "Exoskeletons for Running and Walking"); 20070132722 (Kim et al., Jun. 14, 2007, "Hand Interface Glove Using Miniaturized Absolute Position Sensors and Hand Interface System Using the Same"); 20110040216 (Herr et al., Feb. 17, 2011, "Exoskeletons for Running and Walking"); 20130158444 (Herr et al., Jun. 20, 2013, "Robotic System for Simulating a Wearable Device and Method of Use"); 20130204435 (Moon et al., Aug. 8, 2013, "Wearable Robot and Teaching Method of Motion using the Same"); and 20140366675 (Gosselin et al., Dec. 18, 2014, "Articulated Limb for a Robot or Haptic Interface and Robot and Haptic Interface Comprising at Least One Such Articulated Limb").

7. Wearable Pressure Sensors

Prior art in this category uses one or more wearable pressure sensors to estimate and/or model body motion, posture, and/or configuration. This category is relatively small and is most commonly focused on some type of pressure sensor in a person's shoes, but there are examples of pressure sensors worn on other body locations. Although this present invention does not focus on pressure sensors, the parent application of this present invention uses pressure-sensing tubes to estimate and/or model body motion, posture, and/or configuration so this category of art is relevant and specific examples are now listed.

Examples of prior art which appear to be within this category include the following U.S. Pat. No. 3,974,491 (Sipe, Aug. 10, 1976, "Load Signaling Device for a Patient's Foot"); U.S. Pat. No. 5,592,401 (Kramer, Jan. 7, 1997, "Accurate, Rapid, Reliable Position Sensing using Multiple Sensing Technologies"); U.S. Pat. No. 5,989,700 (Krivopal, Nov. 23, 1999, "Pressure Sensitive Ink Means, and Methods of Use"); U.S. Pat. No. 6,148,280 (Kramer, Nov. 14, 2000, "Accurate, Rapid, Reliable Position Sensing using Multiple Sensing Technologies"); U.S. Pat. No. 6,210,301 (Abraham-Fuchs et al., Apr. 3, 2001, "Patient Monitoring System"); U.S. Pat. No. 6,611,789 (Darley, Aug. 26, 2003, "Monitoring Activity of a User in Locomotion on Foot"); U.S. Pat. No. 6,836,744 (Asphahani et al., Dec. 28, 2004, "Portable System for Analyzing Human Gait"); U.S. Pat. No. 6,964,205 (Papakostas et al., Nov. 15, 2005, "Sensor with Plurality of Sensor Elements Arranged with Respect to a Substrate"); and U.S. Pat. No. 7,245,292 (Custy, Jul. 17, 2007, "Apparatus and Method for Incorporating Tactile Control and Tactile Feedback Into a Human-Machine Interface").

Examples of prior art in this category also include U.S. Pat. No. 7,258,026 (Papakostas et al., Aug. 21, 2007, "Sensor with a Plurality of Sensor Elements Arranged with Respect to a Substrate"); U.S. Pat. No. 7,980,141 (Connor et al., Jul. 19, 2011, "Wearable Position or Motion Sensing Systems or Methods"); U.S. Pat. No. 7,998,092 (Avni et al., Aug. 16, 2011, "Force Sensor System for Use in Monitoring Weight Bearing"); U.S. Pat. No. 8,011,229 (Lieberman et al., Sep. 6, 2011, "Determining Postural Stability"); U.S. Pat. No. 8,033,916 (Caldwell et al., Oct. 11, 2011, "Grip Pressure Sensor"); U.S. Pat. No. 8,109,149 (Kotovsky, Feb. 7, 2012, "Contact Stress Sensor"); U.S. Pat. No. 8,111,165 (Ortega et al., Feb. 7, 2012, "Active On-Patient Sensor, Method and System"); U.S. Pat. No. 8,151,648 (Yu et al., Apr. 10, 2012, "Ultra-Miniature Fiber-Optic Pressure Sensor System and Method of Fabrication"); U.S. Pat. No. 8,161,826 (Taylor, Apr. 24, 2012, "Elastically Stretchable Fabric Force Sensor Arrays and Methods of Making"); U.S. Pat. No. 8,162,857 (Lanfermann et al., Apr. 24, 2012, "Limb Movement Monitoring System"); U.S. Pat. No. 8,280,681 (Vock et al., Oct. 2, 2012, "Pressure-Based Weight Monitoring System for Determining Improper Walking or Running"); and U.S. Pat. No. 8,316,719 (Majidi et al., Nov. 27, 2012, "Stretchable Two-Dimensional Pressure Sensor").

Examples of prior art in this category also include U.S. Pat. No. 8,384,551 (Ross et al., Feb. 26, 2013, "Sensor Device and Method for Monitoring Physical Stresses Placed on a User"); U.S. Pat. No. 8,416,088 (Ortega et al., Apr. 9, 2013, "Active On-Patient Sensor, Method and System"); U.S. Pat. No. 8,459,128 (Bhat et al., Jun. 11, 2013, "Sub-Threshold Elastic Deflection FET Sensor for Sensing Pressure/Force, a Method and System Thereof"); U.S. Pat. No. 8,463,573 (Flentov et al., Jun. 11, 2013, "Movement Monitoring Systems and Associated Methods"); U.S. Pat. No. 8,626,472 (Solinsky, Jan. 7, 2014, "System and Method for Measuring Balance and Track Motion in Mammals"); U.S. Pat. No. 8,661,915 (Taylor, Mar. 4, 2014, "Elastically Stretchable Fabric Force Sensor Arrays and Methods of Making"); U.S. Pat. No. 8,784,342 (Hyde et al., Jul. 22, 2014, "Shape Sensing Clothes to Inform the Wearer of a Condition"); and U.S. Pat. No. 8,904,876 (Taylor et al., Dec. 9, 2014, "Flexible Piezocapacitive and Piezoresistive Force and Pressure Sensor").

Examples of prior art which appear to be within this category include the following U.S. patent applications: 20030054923 (Brassil et al., Mar. 20, 2003, "Hand Rehabilitation Glove"); 20060212097 (Varadan et al., Sep. 21, 2006, "Method and Device for Treatment of Medical Conditions and Monitoring Physical Movements"); 20060282017 (Avni et al., Dec. 14, 2006, "Force Sensor System for Use in Monitoring Weight Bearing"); 20090025483 (Connor et al., Jan. 29, 2009, "Wearable Position or Motion Sensing Systems or Methods"); 20090076419 (Namineni et al., Mar. 19, 2009, "Loss-of-Balance and Fall Detection System"); 20100036288 (Lanfermann et al., Feb. 11, 2010, "Limb Movement Monitoring System"); 20100225473 (Leuthardt et al., Sep. 9, 2010, "Postural Information System and Method"); 20100225474 (Leuthardt et al., Sep. 9, 2010, "Postural Information System and Method"); 20100225490 (Leuthardt et al., Sep. 9, 2010, "Postural Information System and Method Including Central Determining of Subject Advisory Information Based on Subject Status Information and Postural Influencer Status Information"); and 20100225491 (Leuthardt et al., Sep. 9, 2010, "Postural Information System and Method").

Examples of prior art in this category also include U.S. patent applications: 20100225498 (Leuthardt et al., Sep. 9, 2010, "Postural Information System and Method"); 20100228153 (Leuthardt et al., Sep. 9, 2010, "Postural Information System and Method"); 20100228154 (Leuthardt et al., Sep. 9, 2010, "Postural Information System and Method Including Determining Response to Subject Advisory Information"); 20100228158 (Leuthardt et al., Sep. 9, 2010, "Postural Information System and Method Including Device Level Determining of Subject Advisory Information Based on Subject Status Information and Postural Influencer Status Information"); 20100228159 (Leuthardt et al., Sep. 9, 2010, "Postural Information System and Method"); 20100228487 (Leuthardt et al., Sep. 9, 2010, "Postural Information System and Method"); 20100228488 (Leuthardt et al., Sep. 9, 2010, "Postural Information System and Method"); 20100228489 (Leuthardt et al., Sep. 9, 2010, "Postural Information System and Method"); and 20100228490 (Leuthardt et al., Sep. 9, 2010, "Postural Information System and Method").

Examples of prior art in this category also include U.S. patent applications: 20100228492 (Leuthardt et al., Sep. 9, 2010, "Postural Information System and Method Including Direction Generation Based on Collection of Subject Advisory Information"); 20100228493 (Leuthardt et al., Sep. 9, 2010, "Postural Information System and Method Including Direction Generation Based on Collection of Subject Advisory Information"); 20100228494 (Leuthardt et al., Sep. 9, 2010, "Postural Information System and Method Including Determining Subject Advisory Information Based on Prior Determined Subject Advisory Information"); 20100228495 (Leuthardt et al., Sep. 9, 2010, "Postural Information System and Method Including Determining Subject Advisory Information Based on Prior Determined Subject Advisory Information"); and 20100271200 (Leuthardt et al., Oct. 28, 2010, "Postural Information System and Method Including Determining Response to Subject Advisory Information").

Examples of prior art in this category also include U.S. patent applications: 20110208444 (Solinsky, Aug. 25, 2011, "System and Method for Measuring Balance and Track Motion in Mammals"); 20120089348 (Perlin et al., Apr. 12, 2012, "Sensor Having a Set of Plates, and Method"); 20120116257 (Leuthardt et al., May 10, 2012, "Postural Information System and Method Including Determining Response to Subject Advisory Information"); 20120118066 (Majidi et al., May 17, 2012, "Stretchable Two-Dimensional Pressure Sensor"); 20120323501 (Sarrafzadeh et al., Dec. 20, 2012, "Fabric-Based Pressure Sensor Arrays and Methods for Data Analysis"); 20120323501 (Sarrafzadeh et al., Dec. 20, 2012, "Fabric-Based Pressure Sensor Arrays and Methods for Data Analysis"); 20130253875 (Flentov et al., Sep. 26, 2013, "Movement Monitoring Systems and Associated Methods"); 20130275057 (Perlin et al., Oct. 17, 2013, "Sensor Having a Mesh Layer with Protrusions, and Method"); 20130324888 (Solinsky, Dec. 5, 2013, "System and Method for Measuring Balance and Track Motion in Mammals"); and 20140172134 (Meschter, Jun. 19, 2014, "Apparel Having Sensor System").

8. Wearable Electromagnetic Energy Bend Sensors and/or Electrogoniometers

Prior art in this category uses one or more electromagnetic energy bend sensors and/or electrogoniometers which are worn on the body in order to estimate and/or model body motion, posture, and/or configuration. This category is relatively large, especially with respect to devices to estimate the angle of a single body joint. Incorporation of multiple electromagnetic energy bend sensors into clothing is less common, but growing. Although the present invention discloses novel configurations and methods for incorporating bend sensors into an article of clothing which are not disclosed by the prior art, this category of prior art is relevant to the present invention and thus specific examples are now listed.

Examples of prior art which appear to be within this category include the following U.S. Pat. No. 5,012,819 (Marras et al., May 7, 1991, "Apparatus for Monitoring the Motion Components of the Spine"); U.S. Pat. No. 5,086,785 (Gentile et al., Feb. 11, 1992, "Angular Displacement Sensor"); U.S. Pat. No. 5,184,319 (Kramer, Feb. 2, 1993, "Force Feedback and Textures Simulating Interface Device"); U.S. Pat. No. 5,280,265 (Kramer et al., Jan. 18, 1994, "Strain-Sensing Goniometers, Systems and Recognition Algorithms"); U.S. Pat. No. 5,316,017 (Edwards et al., May 31, 1994, "Man-Machine Interface for a Joint Measurement System"); U.S. Pat. No. 5,442,729 (Kramer et al., Aug. 15, 1995, "Strain-Sensing Goniometers, Systems and Recognition Algorithms"); U.S. Pat. No. 5,474,088 (Zaharkin et al., Dec. 12, 1995, "Device for Measuring Motion Characteristics of a Human Joint"); U.S. Pat. No. 5,533,531 (Edwards et al., Jul. 9, 1996, "Electronically Aligned Man-Machine Interface"); U.S. Pat. No. 5,592,401 (Kramer, Jan. 7, 1997, "Accurate, Rapid, Reliable Position Sensing using Multiple Sensing Technologies"); U.S. Pat. No. 5,640,971 (Martin, Jr., Jun. 24, 1997, "Back Movement Monitor and Warning Device"); U.S. Pat. No. 5,676,157 (Kramer, Oct. 14, 1997, "Determination of Kinematically Constrained Multi-Articulated Structures"); U.S. Pat. No. 5,813,406 (Kramer et al., Sep. 29, 1998, "Strain-Sensing Goniometers, Systems and Recognition Algorithms"); and U.S. Pat. No. 5,930,741 (Kramer, Jul. 27, 1999, "Accurate, Rapid, Reliable Position Sensing using Multiple Sensing Technologies").

Examples of prior art in this category also include U.S. Pat. No. 5,980,472 (Seyl, Nov. 9, 1999, "Joint Movement Monitoring System"); U.S. Pat. No. 6,005,548 (Latypov et al., Dec. 21, 1999, "Method for Tracking and Displaying User's Spatial Position and Orientation, a Method for Representing Virtual Reality for a User, and Systems of Embodiment of Such Methods"); U.S. Pat. No. 6,035,274 (Kramer et al., Mar. 7, 2000, "Strain-Sensing Goniometers, Systems and Recognition Algorithms"); U.S. Pat. No. 6,042,555 (Kramer et al., Mar. 28, 2000, "Force-Feedback Interface Device for the Hand"); U.S. Pat. No. 6,050,962 (Kramer et al., Apr. 18, 2000, "Goniometer-Based Body-Tracking Device and Method"); U.S. Pat. No. 6,104,379 (Petrich et al., Aug. 15, 2000, "Forearm-Supported Exoskeleton Hand-Tracking Device"); U.S. Pat. No. 6,110,130 (Kramer, Aug. 29, 2000, "Exoskeleton Device for Directly Measuring Fingertip Position and Inferring Finger Joint Angle"); U.S. Pat. No. 6,119,516 (Hock, Sep. 19, 2000, "Biofeedback System for Monitoring the Motion of Body Joint"); U.S. Pat. No. 6,127,672 (Danisch, Oct. 3, 2000, "Topological and Motion Measuring Tool"); U.S. Pat. No. 6,148,280 (Kramer, Nov. 14, 2000, "Accurate, Rapid, Reliable Position Sensing using Multiple Sensing Technologies"); U.S. Pat. No. 6,162,190 (Kramer, Dec. 19, 2000, "Determination of Kinematically Constrained Multi-Articulated Structures"); U.S. Pat. No. 6,246,390 (Rosenberg, Jun. 12, 2001, "Multiple Degree-of-Freedom Mechanical Interface to a Computer System"); U.S. Pat. No. 6,304,840 (Vance et al., Oct. 16, 2001, "Fingerless Glove for Interacting with Data Processing System"); U.S. Pat. No. 6,334,852 (Seyl, Jan. 1, 2002, "Joint Movement Monitoring System"); U.S. Pat. No. 6,341,504

(Istook, Jan. 29, 2002, "Composite Elastic and Wire Fabric for Physiological Monitoring Apparel"); and U.S. Pat. No. 6,360,615 (Smela, Mar. 26, 2002, "Wearable Effect-Emitting Strain Gauge Device").

Examples of prior art in this category also include U.S. Pat. No. 6,413,229 (Kramer et al., Jul. 2, 2002, "Force-Feedback Interface Device for the Hand"); U.S. Pat. No. 6,428,490 (Kramer et al., Aug. 6, 2002, "Goniometer-Based Body-Tracking Device and Method"); U.S. Pat. No. 6,487,906 (Hock, Dec. 3, 2002, "Flexible Film Sensor System for Monitoring Body Motion"); U.S. Pat. No. 6,497,672 (Kramer, Dec. 24, 2002, "Device and Method for Measuring the Position of Animate Links"); U.S. Pat. No. 6,563,107 (Danisch et al., May 13, 2003, "Topological and Motion Measuring Tool"); U.S. Pat. No. 6,579,248 (Cascone et al., Jun. 17, 2003, "Biofeedback Device"); U.S. Pat. No. 6,640,202 (Dietz et al., Oct. 28, 2003, "Elastic Sensor Mesh System for 3-Dimensional Measurement, Mapping and Kinematics Applications"); U.S. Pat. No. 6,673,027 (Fischer, Jan. 6, 2004, "Posture Measurement and Feedback Instrument for Seated Occupations"); U.S. Pat. No. 6,701,296 (Kramer et al., Mar. 2, 2004, "Strain-Sensing Goniometers, Systems, and Recognition Algorithms"); U.S. Pat. No. 6,834,436 (Townsend et al., Dec. 28, 2004, "Posture and Body Movement Measuring System"); U.S. Pat. No. 6,866,643 (Kramer, Mar. 15, 2005, "Determination of Finger Position"); U.S. Pat. No. 6,871,413 (Arms et al., Mar. 29, 2005, "Miniaturized Inclinometer for Angle Measurement with Accurate Measurement Indicator"); U.S. Pat. No. 6,957,164 (Dietz et al., Oct. 18, 2005, "Elastic Sensor Mesh System for 3-Dimensional Measurement, Mapping and Kinematics Applications"); U.S. Pat. No. 6,964,205 (Papakostas et al., Nov. 15, 2005, "Sensor with Plurality of Sensor Elements Arranged with Respect to a Substrate"); U.S. Pat. No. 6,979,164 (Kramer, Dec. 27, 2005, "Force Feedback and Texture Simulating Interface Device"); U.S. Pat. No. 7,070,571 (Kramer et al., Jul. 4, 2006, "Goniometer-Based Body-Tracking Device"); and U.S. Pat. No. 7,082,570 (von Wiegand et al., Jul. 25, 2006, "Distributed Haptic Interface System and Method").

Examples of prior art in this category also include U.S. Pat. No. 7,135,227 (Karayianni et al., Nov. 14, 2006, "Electrically Conductive Elastic Composite Yarn, Methods for Making the Same, and Articles Incorporating the Same"); U.S. Pat. No. 7,191,803 (Orr et al., Mar. 20, 2007, "Elastic Fabric with Sinusoidally Disposed Wires"); U.S. Pat. No. 7,209,028 (Boronkay et al., Apr. 24, 2007, "Position Sensor with Resistive Element"); U.S. Pat. No. 7,210,240 (Townsend et al., May 1, 2007, "Posture and Body Movement Measuring System"); U.S. Pat. No. 7,258,026 (Papakostas et al., Aug. 21, 2007, "Sensor with a Plurality of Sensor Elements Arranged with Respect to a Substrate"); U.S. Pat. No. 7,390,157 (Kramer, Jun. 24, 2008, "Force Feedback and Texture Simulating Interface Device"); U.S. Pat. No. 7,413,802 (Karayianni et al., Aug. 19, 2008, "Energy Active Composite Yarn, Methods for Making the Same, and Articles Incorporating the Same"); U.S. Pat. No. 7,500,853 (Bevirt et al., Mar. 10, 2009, "Mechanical Interface for a Computer System"); and U.S. Pat. No. 7,509,870 (Aebersold et al., Mar. 31, 2009, "MEMS Capacitive Bending and Axial Strain Sensor").

Examples of prior art in this category also include U.S. Pat. No. 7,665,288 (Karayianni et al., Feb. 23, 2010, "Energy Active Composite Yarn, Methods for Making the Same and Articles Incorporating the Same"); U.S. Pat. No. 7,698,830 (Townsend et al., Apr. 20, 2010, "Posture and Body Movement Measuring System"); U.S. Pat. No. 7,703,333 (Hayakawa et al., Apr. 27, 2010, "Deformation Sensor"); U.S. Pat. No. 7,771,318 (Narayanaswami, Aug. 10, 2010, "Device for Monitoring a User's Posture"); U.S. Pat. No. 7,850,574 (Narayanaswami, Dec. 14, 2010, "Device for Monitoring a User's Posture"); U.S. Pat. No. 7,854,174 (Aebersold et al., Dec. 21, 2010, "MEMS Capacitive Bending and Axial Strain Sensor"); U.S. Pat. No. 7,901,756 (Bun et al., Mar. 8, 2011, "Functional Elastic Textile Structures"); U.S. Pat. No. 7,902,095 (Hassonjee et al., Mar. 8, 2011, "Functional Textile Structures"); U.S. Pat. No. 7,926,254 (Karayianni et al., Apr. 19, 2011, "Electrically Conductive Elastic Composite Yarn, Methods for Making the Same, and Articles Incorporating the Same"); U.S. Pat. No. 7,981,057 (Stewart, Jul. 19, 2011, "Joint Motion Sensing to Make a Determination of a Positional Change of an Individual"); U.S. Pat. No. 8,083,693 (McKeon et al., Dec. 27, 2011, "Monitoring Posture"); U.S. Pat. No. 8,157,752 (Fischer, Apr. 17, 2012, "Posture Assessment and Feedback Instrument"); U.S. Pat. No. 8,161,826 (Taylor, Apr. 24, 2012, "Elastically Stretchable Fabric Force Sensor Arrays and Methods of Making"); and U.S. Pat. No. 8,203,455 (Lee et al., Jun. 19, 2012, "Posture Sensing Alert Apparatus").

Examples of prior art in this category also include U.S. Pat. No. 8,362,882 (Heubel et al., Jan. 29, 2013, "Method and Apparatus for Providing Haptic Feedback from Haptic Textile"); U.S. Pat. No. 8,421,448 (Tran et al., Apr. 16, 2013, "Hall-Effect Sensor System for Gesture Recognition, Information Coding, and Processing"); U.S. Pat. No. 8,459,128 (Bhat et al., Jun. 11, 2013, "Sub-Threshold Elastic Deflection FET Sensor for Sensing Pressure/Force, a Method and System Thereof"); U.S. Pat. No. 8,626,472 (Solinsky, Jan. 7, 2014, "System and Method for Measuring Balance and Track Motion in Mammals"); U.S. Pat. No. 8,661,915 (Taylor, Mar. 4, 2014, "Elastically Stretchable Fabric Force Sensor Arrays and Methods of Making"); U.S. Pat. No. 8,665,241 (Heubel et al., Mar. 4, 2014, "System and Method for Providing Haptic Feedback from Haptic Textile"); U.S. Pat. No. 8,678,979 (Stark et al., Mar. 25, 2014, "Remote Monitoring of a Patient"); U.S. Pat. No. 8,784,342 (Hyde et al., Jul. 22, 2014, "Shape Sensing Clothes to Inform the Wearer of a Condition"); U.S. Pat. No. 8,904,876 (Taylor et al., Dec. 9, 2014, "Flexible Piezocapacitive and Piezoresistive Force and Pressure Sensor"); and U.S. Pat. No. 8,932,236 (McKeon et al., Jan. 13, 2015, "Monitoring Posture").

Examples of prior art which appear to be within this category include the following U.S. patent applications: 20010020140 (Kramer, Sep. 6, 2001, "Device and Method for Measuring the Position of Animate Links"); 20020088931 (Danisch et al., Jul. 11, 2002, "Topological and Motion Measuring Tool"); 20020151824 (Fischer, Oct. 17, 2002, "Posture Measurement and Feedback Instrument for Seated Occupations"); 20020198472 (Kramer, Dec. 26, 2002, "Determination of Finger Position"); 20030083596 (Kramer et al., May 1, 2003, "Goniometer-Based Body-Tracking Device and Method"); 20050126026 (Townsend et al., Jun. 16, 2005, "Posture and Body Movement Measuring System"); 20060130347 (Bergamasco et al., Jun. 22, 2006, "Device for Gioniometric Measurements"); 20060217233 (Lee, Sep. 28, 2006, "Apparatus and Method for Lower-Limb Rehabilitation Training Using Weight Load and Joint Angle as Variables"); 20070169364 (Townsend et al., Jul. 26, 2007, "Posture and Body Movement Measuring System"); 20070256502 (Aebersold et al., Nov. 8, 2007, "MEMS Capacitive Bending and Axial Strain Sensor"); and 20090188325 (Aebersold et al., Jul. 30, 2009, "MEMS Capacitive Bending and Axial Strain Sensor").

Examples of prior art in this category also include U.S. patent applications: 20090278791 (Slycke et al., Nov. 12, 2009, "Motion Tracking System"); 20100225473 (Leuthardt et al., Sep. 9, 2010, "Postural Information System and Method"); 20100225474 (Leuthardt et al., Sep. 9, 2010, "Postural Information System and Method"); 20100225490 (Leuthardt et al., Sep. 9, 2010, "Postural Information System and Method Including Central Determining of Subject Advisory Information Based on Subject Status Information and Postural Influencer Status Information"); 20100225491 (Leuthardt et al., Sep. 9, 2010, "Postural Information System and Method"); 20100225498 (Leuthardt et al., Sep. 9, 2010, "Postural Information System and Method"); 20100228153 (Leuthardt et al., Sep. 9, 2010, "Postural Information System and Method"); 20100228154 (Leuthardt et al., Sep. 9, 2010, "Postural Information System and Method Including Determining Response to Subject Advisory Information"); 20100228158 (Leuthardt et al., Sep. 9, 2010, "Postural Information System and Method Including Device Level Determining of Subject Advisory Information Based on Subject Status Information and Postural Influencer Status Information"); 20100228159 (Leuthardt et al., Sep. 9, 2010, "Postural Information System and Method"); and 20100228487 (Leuthardt et al., Sep. 9, 2010, "Postural Information System and Method").

Examples of prior art in this category also include U.S. patent applications: 20100228488 (Leuthardt et al., Sep. 9, 2010, "Postural Information System and Method"); 20100228489 (Leuthardt et al., Sep. 9, 2010, "Postural Information System and Method"); 20100228490 (Leuthardt et al., Sep. 9, 2010, "Postural Information System and Method"); 20100228492 (Leuthardt et al., Sep. 9, 2010, "Postural Information System and Method Including Direction Generation Based on Collection of Subject Advisory Information"); 20100228493 (Leuthardt et al., Sep. 9, 2010, "Postural Information System and Method Including Direction Generation Based on Collection of Subject Advisory Information"); 20100228494 (Leuthardt et al., Sep. 9, 2010, "Postural Information System and Method Including Determining Subject Advisory Information Based on Prior Determined Subject Advisory Information"); 20100228495 (Leuthardt et al., Sep. 9, 2010, "Postural Information System and Method Including Determining Subject Advisory Information Based on Prior Determined Subject Advisory Information"); 20100271200 (Leuthardt et al., Oct. 28, 2010, "Postural Information System and Method Including Determining Response to Subject Advisory Information"); and 20110046518 (Fischer, Feb. 24, 2011, "Posture Assessment and Feedback Instrument").

Examples of prior art in this category also include U.S. patent applications: 20110046915 (Hol et al., Feb. 24, 2011, "Use of Positioning Aiding System for Inertial Motion Capture"); 20110052005 (Selner, Mar. 3, 2011, "Designation of a Characteristic of a Physical Capability by Motion Analysis, Systems and Methods"); 20110208444 (Solinsky, Aug. 25, 2011, "System and Method for Measuring Balance and Track Motion in Mammals"); 20110248773 (Poupyrev et al., Oct. 13, 2011, "System and Method for Sensing Human Activity by Monitoring Impedance"); 20120089348 (Perlin et al., Apr. 12, 2012, "Sensor Having a Set of Plates, and Method"); 20120116257 (Leuthardt et al., May 10, 2012, "Postural Information System and Method Including Determining Response to Subject Advisory Information"); 20120323501 (Sarrafzadeh et al., Dec. 20, 2012, "Fabric-Based Pressure Sensor Arrays and Methods for Data Analysis"); and 20120323501 (Sarrafzadeh et al., Dec. 20, 2012, "Fabric-Based Pressure Sensor Arrays and Methods for Data Analysis").

Examples of prior art in this category also include U.S. patent applications: 20130113506 (Poupyrev et al., May 9, 2013, "System and Method for Sensing Human Activity by Monitoring Impedance"); 20130275057 (Perlin et al., Oct. 17, 2013, "Sensor Having a Mesh Layer with Protrusions, and Method"); 20130324888 (Solinsky, Dec. 5, 2013, "System and Method for Measuring Balance and Track Motion in Mammals"); 20140172134 (Meschter, Jun. 19, 2014, "Apparel Having Sensor System"); 20140342844 (Mooney, Nov. 20, 2014, "Apparatus and Method for Analysing a Golf Swing"); and 20150005608 (Evans et al., Jan. 1, 2015, "Electrode Units for Sensing Physiological Electrical Activity").

SUMMARY OF THE INVENTION

This invention features novel designs for wearable deformable electromagnetic energy pathways which enable ambulatory (camera-free) three-dimensional human body motion capture including trans-joint pitch, yaw, and roll. These wearable deformable electromagnetic energy pathways can be incorporated into motion recognition fabric which, in turn, can be used to make motion recognition clothing. Changes in the transmission of electromagnetic energy through these wearable deformable electromagnetic energy pathways are analyzed in order to measure and/or model changes in the three-dimensional configurations of body joints.

In an example, this invention can be embodied in a plurality of elongate electrically-conductive strips which diverge as they span a body joint in a proximal to distal manner. In an example, this invention can be embodied in a central electrically-conductive strip which spans a body joint, wherein this central strip is accompanied by right-side and left-side arrays of arcuate electrically-conductive strips. The strips in these examples are in electromagnetic communication with pairs of electromagnetic energy emitters and receivers. In an example, this invention can have conductive-fluid-filled lumens instead of electroconductive strips.

INTRODUCTION TO THE FIGURES

FIG. 4 shows fabric comprising inner and outer EM layers with overlapping sinusoidal non-nested EM pathways.

FIG. 5 shows a side view of the fabric in FIG. 4.

FIG. 6 shows fabric comprising inner and outer EM layers with overlapping sinusoidal nested EM pathways.

FIG. 7 shows a side view of the fabric in FIG. 6.

FIG. 12 shows fabric comprising inner and outer EM layers with relatively-straight perpendicular EM pathways.

FIG. 13 shows a side view of the fabric in FIG. 12.

FIG. 14 shows fabric comprising inner and outer EM layers with perpendicular sinusoidal EM pathways.

FIG. 15 shows a side view of the fabric in FIG. 14.

FIG. 16 shows fabric three EM layers of relatively-straight acute-angle-intersecting EM pathways.

FIG. 17 shows a side view of the fabric in FIG. 16.

FIG. 18 shows fabric three EM layers of sinusoidal acute-angle-intersecting EM pathways.

FIG. 19 shows a side view of the fabric in FIG. 18.

FIG. 20 shows fabric comprising inner and outer EM layers, wherein each layer has a mesh of relatively-straight EM pathways.

FIG. 21 shows a side view of the fabric in FIG. 20.

FIG. 22 shows fabric comprising inner and outer EM layers, wherein each layer has a mesh of sinusoidal EM pathways.

FIG. 23 shows a side view of the fabric in FIG. 22.

FIG. 24 shows fabric comprising four EM layers, wherein each layer has a set of relatively-straight EM pathways with a different longitudinal orientation.

FIG. 25 shows a side view of the fabric in FIG. 24.

FIG. 26 shows fabric comprising four EM layers, wherein each layer has a set of sinusoidal EM pathways with a different longitudinal orientation.

FIG. 27 shows a side view of the fabric in FIG. 26.

DETAILED DESCRIPTION OF THE FIGURES

Figure 1:
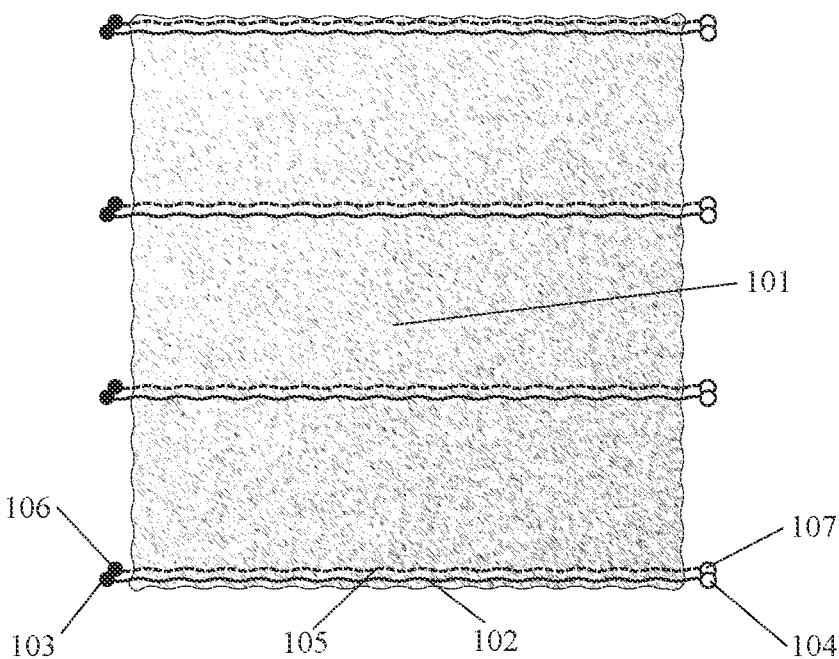
FIG. 1 shows fabric comprising inner and outer EM (electromagnetic) layers with overlapping relatively-straight parallel EM pathways.
Figure 84:
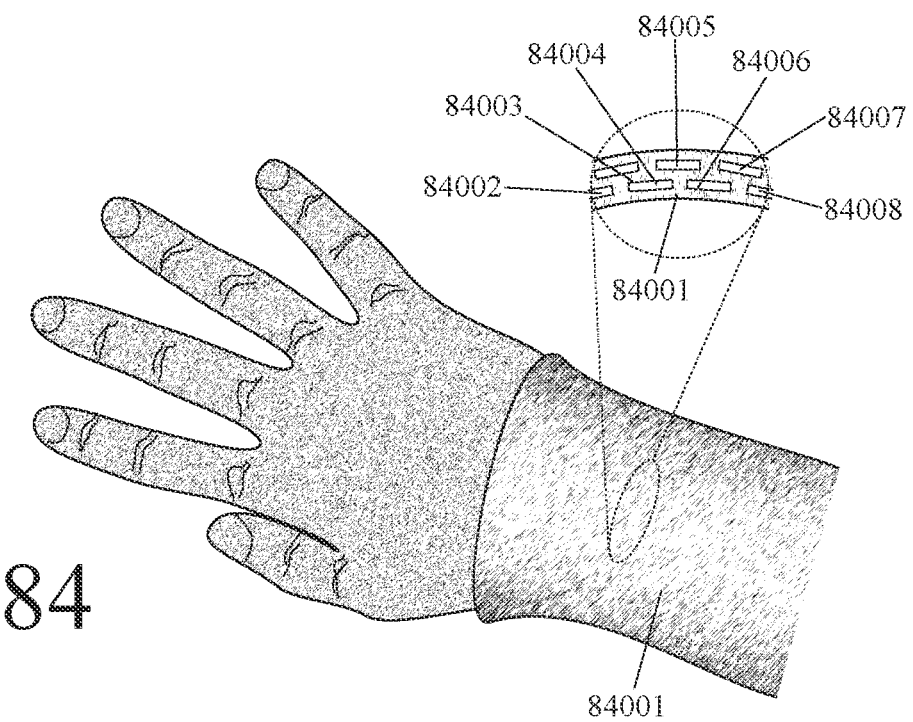
FIG. 84 shows a sleeve with inner and outer non-overlapping (staggered) EM strips for measuring changes in joint configuration.

FIGS. 1 through 84 show examples of motion recognition fabric and/or wearable deformable conductive sensors for human motion capture including trans-joint pitch, yaw, and roll. Before discussing these specific figures and examples, an introductory section is provided below. This introductory section discusses key concepts and example variations that can be applied to each of the following figures where relevant and also to those in any applications which claim priority to this one. Discussing these concepts and variations once in a single introductory section avoids the narrative redundancy which would occur if these key concepts were discussed in each of the narratives accompanying each of the figures. This introductory section now follows.

In an example, motion recognition fabric and/or deformable conductive sensors for human motion capture can: be worn so as to span a body joint; be deformed by movement of the body joint; have multiple layers or orientations; and be electrically-conductive. In an example, motion recognition fabric and/or wearable deformable sensors for measuring human motion which span a human joint can function as resistors. With innovatively-designed fabric and/or sensors, changes in trans-joint pitch, yaw, and roll change the resistance of fabric and/or sensors in different ways. This enables measurement of trans-joint pitch, yaw, and roll. Deformable resistive fabric and/or sensors can have a plurality of conductive pathways with different orientations whose electromagnetic resistance changes in different ways due to changes in trans-joint pitch, yaw, and roll. Changes in fabric and/or sensor resistance can be analyzed in order to measure and/or model changes in body joint configuration.

In an example, motion recognition fabric and/or deformable conductive sensors for human motion capture can function as capacitors. With innovatively-designed fabric and/or sensors, changes in trans-joint pitch, yaw, and roll change the capacitance of the fabric and/or sensor in different ways. This enables measurement of the pitch, yaw, and roll of the joint which is spanned by the fabric and/or sensor. In an example, multi-layer deformable capacitive fabric and/or sensors can have upper and lower conductive layers which are separated by a dielectric layer. These upper and lower conductive layers can function as electrode plates with an electromagnetic field between them. In an example, upper and lower conductive layers can overlap. Deformation of fabric and/or sensors by movement of an underlying joint changes fabric and/or sensor capacitance. Fabric and/or sensor deformation can include bending, compression, stretching, and twisting which are associated with changes in trans-joint pitch, trans-joint yaw, and trans-joint roll. Changes in fabric and/or sensor capacitance can be analyzed in order to measure and/or model changes in body joint configuration.

Motion recognition fabric can be used to make clothing for three-dimensional human body motion capture. More generally, motion recognition fabric can be used to make clothing to measure and model three-dimensional changes in a person's body configuration without constraining the person to remain in front of a camera. Also, there are no optical occlusion problems. In an example, motion recognition fabric can span a single joint and measure that joint's configuration in three-dimensional space. In another example, when motion recognition fabric is used to make full-body clothing spanning multiple joints, it enables full-body ambulatory three-dimensional human motion capture. Accelerometers, inclinometers, and gyroscopes can also be incorporated into such clothing in order to create motion recognition capability with multiple sensor modalities.

Motion recognition fabric incorporates electromagnetic layers and/or electromagnetic energy pathways which collect data to model the bending and rotation of body joints which are spanned by this fabric. In an example, changes in a person's body configuration cause changes in fabric capacitance, resistance, impedance, and/or conductivity. In an example, bending a body joint spanned by this fabric causes the fabric's capacitance, resistance, impedance, and/or conductivity to change in a first manner, while the rotation of this joint causes the fabric's capacitance, resistance, impedance, and/or conductivity to change in a second manner. Multivariate analysis of these different changes in fabric capacitance, resistance, impedance, and/or conductivity can be used to model three-dimensional changes in a person's body configuration.

In an example, this invention can be embodied in motion recognition fabric comprising: a first fabric layer with a first level of conductivity; a second fabric layer with a second level of conductivity; and a third fabric layer with a third level of conductivity; wherein the third layer is between the first layer and the second layer; wherein the third level is less than the first level; wherein the third level is less than the second level; wherein stretching, bending, twisting, and/or compressing the fabric changes the fabric's capacitance; and wherein changes in the fabric's capacitance are analyzed to model three-dimensional changes in fabric configuration. In an example, a first conductive fabric layer can differ from a second conductive fabric layer in one or more attributes selected from the group consisting of: axial angle, braid, conductivity, diameter, durometer, elasticity, length, location, material, orientation, shape, size, thickness, and weave.

In an example, this invention can be embodied in motion recognition fabric comprising: a first fabric layer with a first level of conductivity; a second fabric layer with a second level of conductivity; and a third fabric layer with a third level of conductivity; wherein the third layer is between the first layer and the second layer, wherein the third level is less than the first level, wherein the third level is less than the second level, wherein this fabric is configured so that bending or rotation of a joint spanned by this fabric changes the fabric's capacitance; and wherein changes in the fabric's capacitance are analyzed to model three-dimensional changes in the configuration of the body of a person who wears the fabric.

In an example, stretching fabric in a first direction changes a fabric's capacitance in a first manner, while stretching this fabric in a second direction changes the fabric's capacitance in a second manner. In an example, stretching fabric in a first direction increases a fabric's capacitance, while stretching this fabric in a second direction decreases the fabric's capacitance. In an example, fabric capacitance changes in a first manner when the fabric is stretched longitudinally and changes in a second manner when the fabric is stretched laterally. In an example, fabric capacitance changes in a first manner when the fabric is stretched longitudinally and changes in a second manner when the fabric is stretched diagonally. In an example, bending a joint spanned by motion recognition fabric changes a fabric's capacitance in a first manner, while rotation of this joint changes the fabric's capacitance in a second manner.

In an example, bending fabric in a first direction changes a fabric's capacitance in a first manner, while bending this fabric in a second direction changes the fabric's capacitance in a second manner. In an example, bending fabric in a first direction increases the fabric's capacitance, while bending this fabric in a second direction decreases the fabric's capacitance. In an example, fabric capacitance changes in a first manner when this fabric is bent longitudinally and changes in a second manner when the fabric is bent laterally. In an example, fabric capacitance changes in a first manner when the fabric is bent longitudinally and changes in a second manner when the fabric is bent diagonally. In an example, bending a joint spanned by motion recognition fabric changes a fabric's capacitance in a first manner, while rotation of this joint changes the fabric's capacitance in a second manner.

In an example, stretching fabric in a first direction changes a fabric's capacitance between first and second conductive layers or components, while stretching fabric in a second direction changes the fabric's capacitance between third and fourth conductive layers or components. In an example, stretching fabric in a first direction changes the fabric's capacitance as measured between first and second locations, while stretching fabric in a second direction changes the fabric's capacitance as measured between third and fourth locations. In an example, multivariate analysis of changes in the fabric's capacitance from different layers, components, and/or locations enables modeling three-dimensional changes in fabric configuration.

In an example, bending fabric in a first direction changes a fabric's capacitance between first and second conductive layers or components, while bending fabric in a second direction changes the fabric's capacitance between third and fourth conductive layers or components. In an example, bending fabric in a first direction changes the fabric's capacitance as measured between first and second locations, while bending fabric in a second direction changes the fabric's capacitance as measured between third and fourth locations. In an example, multivariate analysis of changes in the fabric's capacitance from different layers, components, and/or locations enables modeling three-dimensional changes in fabric configuration.

In an example, bending of a joint spanned by fabric changes the fabric's capacitance between first and second conductive layers or components, while rotation of this joint changes the fabric's capacitance between third and fourth conductive layers or components. In an example, bending a joint spanned by the fabric changes the fabric's capacitance as measured between first and second locations, while rotation of this joint changes the fabric's capacitance as measured between third and fourth locations. In an example, multivariate analysis of changes in the fabric's capacitance from different layers, components, and/or locations can enable modeling three-dimensional changes in joint configuration.

In an example, fabric can have a first fabric configuration with a first capacitance level when a body joint which the fabric spans has a first joint configuration, this fabric can have a second fabric configuration with a second capacitance level when the body joint which the fabric spans has a second joint position, and movement of the body joint from the first configuration to the second configuration can be detected by measuring a change from the first capacitance level to the second capacitance level.

In an example, motion recognition fabric can measure and/or map geometric patterns of capacitance levels between first and second conductive layers which are separated by a non-conductive layer. In an example, "contour maps" of capacitance levels between two conductive layers can be created and analyzed to model the configuration of the fabric in three-dimensional space. In an example, "contour maps" of capacitance levels between two conductive layers can be created and analyzed for three-dimensional modeling of the bending and rotation of a joint spanned by the fabric.

In an example, there can be a first geometric pattern of capacitance levels between first and second conductive fabric layers when a joint spanned by the fabric bends at a first angle, a second geometric pattern of capacitance levels between first and second conductive fabric layers when the joint bends at a second angle, and joint angle can be estimated by analysis of these geometric patterns. In an example, there can be a first geometric pattern of capacitance levels between first and second conductive fabric layers when a joint spanned by the fabric rotates by a first degree, a second geometric pattern of capacitance levels between first and second conductive fabric layers when the joint rotates by a second degree, and the degree of joint rotation can be estimated by analysis of these geometric patterns.

In an example, the (average or minimum) distance between first and second conductive fabric layers is changed when fabric is stretched, bent, twisted, and/or compressed. In an example, this change in distance changes fabric capacitance. In an example, the (average or minimum) distance between fabric layers decreases when the fabric is stretched, bent, twisted, and/or compressed. In an example, overall fabric capacitance decreases when the fabric is stretched, bent, twisted, and/or compressed.

In an example, the (average or combined) surface area of the sides of first and second conductive fabric layers which face each other is changed when fabric is stretched, bent, twisted, and/or compressed. In an example, this change in surface area changes fabric capacitance. In an example, this (average or combined) surface area increases when the fabric is stretched, bent, twisted, and/or compressed. In an example, overall fabric capacitance decreases when the fabric is stretched, bent, twisted, and/or compressed.

In an example, the (average or minimum) distance between first and second conductive fabric layers is changed when a joint which the fabric spans bends. In an example, the (average or minimum) distance between fabric layers decreases when a joint which the fabric spans bends, which causes overall fabric capacitance to decrease. In an example, the (average or combined) surface area of the sides of first and second conductive fabric layers which face each other is changed when a joint which the fabric spans bends. In an example, the (average or combined) surface area increases when a joint which the fabric spans bends, which causes overall fabric capacitance to decrease.

In an example, a geometric pattern of distances between first and second conductive fabric layers is changed when a joint which the fabric spans bends. In an example, the geometric pattern of distances between fabric layers changes when the joint bends, which changes the geometric pattern (or map) of capacitance levels between fabric layers. In an example, changing geometric patterns of capacitance levels between fabric layers can be analyzed used to estimate changes in joint angle. In an example, a greater size area of reduced capacitances can indicate a greater joint angle. In an example, a greater magnitude of capacitance reductions can indicate a greater joint angle.

In an example, the (average or minimum) distance between first and second conductive fabric layers is changed when a joint which the fabric spans rotates. In an example, the (average or minimum) distance between fabric layers decreases when a joint which the fabric spans rotates, which causes overall fabric capacitance to decrease. In an example, the (average or combined) surface area of the sides of first and second conductive fabric layers which face each other is changed when a joint which the fabric spans rotates. In an example, the (average or combined) surface area increases when a joint which the fabric spans rotates, which causes overall fabric capacitance to decrease.

In an example, a geometric pattern of distances between first and second conductive fabric layers is changed when a joint which the fabric spans rotates. In an example, the geometric pattern of distances between fabric layers changes when the joint rotates, which changes the geometric pattern (or map) of capacitance levels between fabric layers. In an example, changing geometric patterns of capacitance levels between fabric layers can be analyzed to estimate changes in joint rotation. In an example, greater axial asymmetry of an area of reduced capacitances can indicate greater joint rotation. In an example, greater axial curvature of an area of reduced capacitances can indicate greater joint rotation.

In an example, there can be a substantially-uniform distance between two conductive fabric layers when fabric is in a first configuration and a non-uniform distance between the two conductive layers when the fabric is in a second configuration. In an example, stretching, bending, twisting, or compressing the fabric causes the fabric to change from its first configuration to its second configuration. In an example, a first conductive fabric layer can comprise electromagnetic energy pathways with a first orientation and a second conductive fabric layer can comprise electromagnetic energy pathways with a second orientation. In an example, analyzing changes in capacitance between individual pathways in the first layer and individual pathways in the second layer can identify localized areas of decreased distance between the two conductive layers. In an example, this can enable three-dimensional modeling of human joint bending and rotation.

In an example, changes in fabric capacitance caused by body joint bending and rotation are analyzed to measure the stretching, bending, twisting, and/or compression of the fabric and thereby model three-dimensional changes in the configuration of the body of a person wearing clothing made from the fabric. In an example, a first geometric pattern of changes in fabric capacitance is caused by changes in joint angle. In an example, a second geometric pattern of changes in fabric capacitance is caused by joint rotation. In an example, analysis of both geometric patterns of changes in fabric capacitance enables modeling joint motion in three-dimensions. In an example, a first temporal pattern of changes in fabric capacitance is caused by changes in joint angle. In an example, a second temporal pattern of changes in fabric capacitance is caused by joint rotation. In an example, analysis of both temporal patterns of changes in fabric capacitance enables modeling joint motion in three-dimensions.

In an example, motion recognition fabric can have a first pattern of capacitance levels between conductive layers in a first configuration and second pattern of capacitance levels between conductive layers in a second configuration. In an example, bending of a joint spanned by the fabric can change the fabric from the first pattern to the second pattern. In an example, motion recognition fabric can have a third pattern of capacitance levels in a third configuration and fourth pattern of capacitance levels in a fourth configuration. In an example, rotation of a joint spanned by the fabric can change the fabric from the third configuration to the fourth configuration.

In an example, motion recognition fabric can comprise a first conductive layer with a first thickness and a second conductive layer with a second thickness. In an example, differences in thickness between different conductive layers can enable fabric to better measure bending and rotation of a joint spanned by the fabric. In an example, motion recognition fabric can comprise a first conductive layer with a first shape and a second conductive layer with a second shape. In an example, differences in shape between different conductive layers can enable fabric to better measure bending and rotation of a joint spanned by the fabric.

In an example, motion recognition fabric can comprise a first conductive layer with a first orientation and a second conductive layer with a second orientation. In an example, differences in orientation between different conductive layers can enable fabric to better measure bending and rotation of a joint spanned by the fabric. In an example, motion recognition fabric can comprise a first conductive layer made with a first material and a second conductive layer with a second material. In an example, differences in material between different conductive layers can enable fabric to better measure bending and rotation of a joint spanned by the fabric.

In an example, motion recognition fabric can comprise a first conductive layer with a first elasticity level and a second conductive layer with a second elasticity level. In an example, differences in elasticity level between different conductive layers can enable fabric to better measure bending and rotation of a joint spanned by the fabric. In an example, motion recognition fabric can comprise a first conductive layer made with a first durometer and a second conductive layer with a second durometer. In an example, differences in durometer between different conductive layers can enable fabric to better measure bending and rotation of a joint spanned by the fabric.

In an example, multivariate analysis of changes in capacitance levels between multiple pairs of conductive layers can enable three-dimensional modeling of fabric configuration more accurately than analysis of changes in capacitance levels between a single pair of conductive layers. In an example, different pairs of conductive layers can be better at measuring fabric motion in different directions. In an example, a first pair of conductive layers can differ from a second pair of conductive layers in one or more attributes selected from the group consisting of: axial angle, braid, conductivity, diameter, durometer, elasticity, length, location, material, orientation, shape, size, thickness, and weave.

In an example, this invention can be embodied in motion recognition fabric comprising: a first layer which is conductive; a second layer which is non-conductive; a third layer which is conductive; a fourth layer which is non-conductive; and a fifth layer which is conductive. In an example, stretching or bending the fabric in a first direction changes the capacitance of the first and third layers more than the capacitance of the third and fifth layers, while stretching or bending the fabric in a second direction changes the capacitance of the third and fifth layers more than the capacitance of the first and third layers.

In an example, multivariate analysis of changes in capacitance levels between multiple pairs of conductive layers can enable three-dimensional modeling of a spanned joint more accurately than analysis of changes in capacitance levels between a single pair of conductive layers. In an example, different pairs of conductive layers can be better at measuring joint bending and joint rotation. In an example, different pairs of conductive layers can have different attributes selected from the group consisting of: axial angle, braid, conductivity, diameter, durometer, elasticity, length, location, material, orientation, shape, size, thickness, and weave.

In an example, this invention can be embodied in motion recognition fabric comprising: a first layer which is conductive; a second layer which is non-conductive; a third layer which is conductive; a fourth layer which is non-conductive; and a fifth layer which is conductive. In an example, bending the joint changes the capacitance of the first and third layers more than the capacitance of the third and fifth layers, while rotating the joint changes the capacitance of the third and fifth layers more than the capacitance of the first and third layers.

In an example, this invention can further comprise an electromagnetic energy emitter which emits energy into a first electromagnetic energy pathway (e.g. in a first layer) and an electromagnetic energy receiver which receives electromagnetic energy from a second electromagnetic energy pathway (e.g. in a second layer). In an example, the capacitance of this combination of first and second electromagnetic energy pathways can be measured by measuring changes in energy transmitted from the emitter to the receiver.

In an example, the capacitances between different combinations of (perpendicular) first and second pathways can be measured in order identify the (X and Y) coordinates of (maximum) stretching, bending, twisting, or compression in a (flat) portion of fabric. In an example, the capacitances between different combinations of (longitudinal) first and (circumferential) second pathways can be measured in order identify the (polar) coordinates of (maximum) stretching, bending, twisting, or compression in a (cylindrical) portion of fabric. In an example, differences in the changes in the capacitances of different combinations of pathways can be analyzed in order to measure and/or model changes in body configuration in three-dimensional space.

In an example, this invention can be embodied in motion recognition fabric comprising: clothing fabric, wherein this clothing fabric further comprises a first conductive layer, a non-conductive layer, and a second conductive layer; a plurality of electromagnetic energy emitters which are in electromagnetic communication with the first conductive layer at different locations; and a plurality of electromagnetic energy receivers which are in electromagnetic communication with the second conductive layer at different locations; wherein the non-conductive layer is between the first conductive layer and the second conductive layer; wherein the plurality of electromagnetic energy receivers measure capacitance levels between the first conductive layer and the second conductive layer; and wherein these capacitance levels are analyzed to model the three-dimensional configuration of the clothing fabric.

In an example, this invention can be embodied in motion recognition fabric comprising: clothing fabric which is configured to span a body joint, wherein this clothing fabric further comprises a first conductive layer, a non-conductive layer, and a second conductive layer; a plurality of electromagnetic energy emitters which are in electromagnetic communication with the first conductive layer at different locations; and a plurality of electromagnetic energy receivers which are in electromagnetic communication with the second conductive layer at different locations; wherein the non-conductive layer is between the first conductive layer and the second conductive layer; wherein the plurality of electromagnetic energy receivers measure capacitance levels between the first conductive layer and the second conductive layer; and wherein these capacitance levels are analyzed to model the three-dimensional configuration of the body joint.

In an example, electromagnetic energy emitters can be evenly (e.g. equidistantly) distributed in an array, grid, or matrix on the first conductive layer and electromagnetic energy receivers can be evenly (e.g. equidistantly) distributed in an array, grid, or matrix on the second conductive layer. In an example, electromagnetic energy emitters and receivers can be distributed in pairs, one of each pair on diametrically-opposite sides of the non-conductive layer. In an example, electromagnetic energy emitters can be distributed in rows on the first conductive layer and electromagnetic energy receivers can be distributed in columns on the second conductive layer. In an example, electromagnetic energy emitters can comprise conductive strips, channels, yarns, or threads with a first axial orientation on the first conductive layer and electromagnetic energy receivers can comprise conductive strips, channels, yarns, or threads with a second axial orientation on the second conductive layer. In an example, first and second axial orientations can be perpendicular. In an example, first and second axial orientations can be parallel.

In an example, a "topographic contour map" of capacitance levels between first and second conductive fabric layers can be created and analyzed for geometric patterns. In an example, a first geometric pattern of capacitance levels is associated with bending of a body joint and a second geometric pattern of capacitance levels is associated with rotation of the body joint. In an example, a first geometric pattern of capacitance levels is associated with a first joint angle and a second geometric pattern of capacitance levels is associated with a second joint angle. In an example, a first geometric pattern of capacitance levels is associated with a first amount or direction of joint rotation and a second geometric pattern of capacitance levels is associated with a second amount or direction of joint rotation.

In an example, the magnitude, size, shape, and/or axial orientation of an area of reduced capacitance between first and second conductive fabric layers can be analyzed to measure joint bending and rotation. In an example, a larger size area of reduced capacitance levels can indicate greater joint bending. In an example, an area with greater reductions in capacitance levels can indicate greater joint bending. In an example, a greater shift in axial orientation of an area of reduced capacitance levels can indicate greater joint rotation. In an example, greater asymmetry in the shape of an area of reduced capacitance levels can indicate greater joint rotation.

In an example, the size of an area of reduced capacitance levels can be statistically associated with joint angle. In an example, the magnitude of capacitance level reductions can be statistically associated with joint angle. In an example, the degree of shift in axial orientation of an area of reduced capacitance levels can be statistically associated with the degree of joint rotation. In an example, the degree of asymmetry in the shape of an area of reduced capacitance levels can be statistically associated with the degree of joint rotation.

In an example, this invention can be embodied in motion recognition fabric comprising: a first conductive layer; a second conductive layer; and a non-conductive layer; wherein the non-conductive layer is between the first and second conductive layers; wherein stretching, bending, twisting, and/or compressing the fabric changes the fabric's electromagnetic resistance; and wherein changes in the fabric's electromagnetic resistance are analyzed to model three-dimensional changes in body configuration.

In an example, this invention can be embodied in motion recognition fabric comprising: a first conductive layer; a second conductive layer; and a non-conductive layer; wherein the non-conductive layer is between the first and second conductive layers; wherein stretching, bending, twisting, and/or compressing the fabric changes the fabric's impedance; and wherein changes in the fabric's electromagnetic impedance are analyzed to model three-dimensional changes in body configuration.

In an example, this invention can be embodied in motion recognition fabric comprising: a first conductive layer; a second conductive layer; and a non-conductive layer; wherein the non-conductive layer is between the first and second conductive layers; wherein stretching, bending, twisting, and/or compressing the fabric changes the fabric's conductivity; and wherein changes in the fabric's conductivity are analyzed to model three-dimensional changes in body configuration.

In an example, this invention can be embodied in motion recognition fabric comprising: a first conductive fabric layer; and a second conductive fabric layer; wherein the second conductive fabric layer differs from the first conductive fabric layer in one or more attributes selected from the group consisting of: durometer, elasticity, location, length, thickness, material, orientation or axial angle, shape, braid, weave, and size.

In an example, stretching, bending, twisting, and/or compressing this fabric in a first direction changes the electromagnetic resistance, impedance, and/or conductivity of the first conductive layer more than that of the second conductive layer, while stretching, bending, twisting, and/or compressing the fabric in a second direction changes the electromagnetic resistance, impedance, and/or conductivity of the second conductive layer more than that of the first conductive layer. In an example, multivariate analysis of changes in the resistance, impedance, and/or conductivity of the first and second fabric layers enables modeling three-dimensional changes in fabric configuration.

In an example, stretching or bending of fabric in a longitudinal direction changes the resistance, impedance, and/or conductivity of the first conductive fabric layer more than that of a second conductive fabric layer, while stretching or bending the fabric in a lateral direction changes the resistance, impedance, and/or conductivity of the second conductive fabric layer more than that of the first conductive fabric layer. In an example, stretching or bending of fabric in a longitudinal direction changes the resistance, impedance, and/or conductivity of the first conductive fabric layer more than that of a second conductive fabric layer, while stretching or bending the fabric in a diagonal direction changes the resistance, impedance, and/or conductivity of the second conductive fabric layer more than that of the first conductive fabric layer. In an example, stretching or bending of fabric changes the resistance, impedance, and/or conductivity of the first conductive fabric layer more than that of a second conductive fabric layer, while twisting the fabric changes the resistance, impedance, and/or conductivity of the second conductive fabric layer more than that of the first conductive fabric layer.

In an example, bending a joint spanned by fabric changes the resistance, impedance, and/or conductivity of the first conductive fabric layer more than that of the second conductive fabric layer, while rotation of this joint changes the electromagnetic resistance, impedance, and/or conductivity of the second conductive fabric layer more than that of the first conductive fabric layer. In an example, multivariate analysis of changes in the resistance, impedance, and/or conductivity of the first and second fabric layers enables modeling three-dimensional changes in fabric configuration.

In an example, stretching or bending fabric in a first direction changes the resistance, impedance, and/or conductivity of a first set of electromagnetic energy pathways more than that of a second set of electromagnetic energy pathways, while stretching or bending the fabric in a second direction changes the resistance, impedance, and/or conductivity of the second set more than that of the first set. In an example, multivariate analysis of changes in the resistance, impedance, and/or conductivity of the first set and the second sets enables modeling three-dimensional changes in fabric configuration.

In an example, bending a body joint spanned by fabric changes the resistance, impedance, and/or conductivity of a first set of electromagnetic energy pathways more than that of a second set of electromagnetic energy pathways, while rotation of the joint changes the resistance, impedance, and/or conductivity of the second set more than that of the first set. In an example, multivariate analysis of changes in the resistance, impedance, and/or conductivity of the first set and the second sets enables modeling three-dimensional changes in joint configuration.

In an example, a first set of electromagnetic energy pathways in motion recognition fabric can have a first axial orientation and a second set of electromagnetic energy pathways in this fabric can have a second axial orientation. In an example, the axial orientations of first and second pathway sets can be perpendicular to each other. In an example, the axial orientations of first and second pathway sets can be parallel to each other. In an example, the axial orientations of first and second pathway sets can form acute angles as they intersect (when both are projected onto the same two-dimensional plane).

In an example, conductive thread, yarn, or fiber can comprise the weft of woven motion recognition fabric and non-conductive thread, yarn, or fiber can comprise the warp of woven motion recognition fabric. In an example, non-conductive thread, yarn, or fiber can comprise the weft of woven motion recognition fabric and conductive thread, yarn, or fiber can comprise the warp of woven motion recognition fabric. In an example, a first set of conductive threads, yarns, or fibers can comprise the weft of woven motion recognition fabric and a second set of conductive threads, yarns, or fibers can comprise the warp of woven motion recognition fabric.

In an example, changes in the resistance, impedance, and/or conductivity of thread, yarn, or fiber in the weft of woven motion recognition fabric can be used to measure fabric stretching or bending in a first manner, while changes in the resistance, impedance, and/or conductivity of thread, yarn, or fiber in the warp of woven motion recognition fabric can be used to measure fabric stretching or bending in a second manner. In an example, changes in the resistance, impedance, and/or conductivity of thread, yarn, or fiber in the weft of woven motion recognition fabric can be used to measure fabric stretching or bending in a first direction, while changes in the resistance, impedance, and/or conductivity of thread, yarn, or fiber in the warp of woven motion recognition fabric can be used to measure fabric stretching or bending in a second direction. In an example, changes in the resistance, impedance, and/or conductivity of thread, yarn, or fiber in the weft of woven motion recognition fabric can be used to measure longitudinal fabric stretching or bending, while changes in the resistance, impedance, and/or conductivity of thread, yarn, or fiber in the warp of woven motion recognition fabric can be used to measure fabric twisting.

In an example, changes in the resistance, impedance, and/or conductivity of thread, yarn, or fiber in the weft of woven motion recognition fabric can be used to measure the bending of a joint spanned by the fabric, while changes in the resistance, impedance, and/or conductivity of thread, yarn, or fiber in the warp of woven motion recognition fabric can be used to measure the rotation of a this joint. In an example, changes in the resistance, impedance, and/or conductivity of thread, yarn, or fiber in the weft of woven motion recognition fabric can be used to measure the rotation of a joint spanned by the fabric, while changes in the resistance, impedance, and/or conductivity of thread, yarn, or fiber in the warp of woven motion recognition fabric can be used to measure bending of this joint.

In an example, bending of a joint spanned by woven motion recognition fabric changes the resistance, impedance, and/or conductivity of threads, yarns, or fibers in the fabric's weft more than that in the fabric's warp. In an example, bending of a joint spanned by woven motion recognition fabric changes the resistance, impedance, and/or conductivity of threads, yarns, or fibers in the fabric's warp more than that in the fabric's weft. In an example, this difference can be used to selectively identify and measure bending of the joint. In an example, rotation of a joint spanned by woven motion recognition fabric changes the resistance, impedance, and/or conductivity of threads, yarns, or fibers in the fabric's weft more than those in the fabric's warp. In an example, rotation of a joint spanned by woven motion recognition fabric changes the resistance, impedance, and/or conductivity of threads, yarns, or fibers in the fabric's warp more than those in the fabric's weft. In an example, this difference can be used to selectively identify and measure rotation of the joint. In an example, multivariate analysis of changes in the resistance, impedance, and/or conductivity of a fabric's weft and warp can enable three-dimensional modeling of changes of the configuration of a joint spanned by this fabric. In an example, worf can go at warp.

In an example, a first set of electromagnetic energy pathways in motion recognition fabric can have a first shape and a second set of electromagnetic energy pathways in this fabric can have a second shape. In an example, electromagnetic energy pathways in a first fabric layer can have a first shape and electromagnetic energy pathways in a second fabric layer can have a second shape. In an example, a first set of electromagnetic energy pathways in motion recognition fabric can have a first elasticity level and a second set of electromagnetic energy pathways in this fabric can have a second elasticity level. In an example, a first set of electromagnetic energy pathways in motion recognition fabric can span a first location and a second set of electromagnetic energy pathways in this fabric can span a second location.

In an example, a first set of electromagnetic energy pathways in motion recognition fabric can have a first length and a second set of electromagnetic energy pathways in this fabric can have a second length. In an example, a first set of electromagnetic energy pathways in motion recognition fabric can be made from a first material and a second set of electromagnetic energy pathways in this fabric can be made from a second material. In an example, a first set of electromagnetic energy pathways in motion recognition fabric can have a first braid or weave and a second set of electromagnetic energy pathways in this fabric can have a second braid or weave.

In an example, stretching or bending fabric in a first direction changes the resistance, impedance, and/or conductivity of the first set more than that of the second set, while stretching or bending the fabric in a second direction changes the resistance, impedance, and/or conductivity of the second set more than that of the first set. In an example, bending a body joint spanned by these pathways changes the resistance, impedance, and/or conductivity of the first set more than that of the second set, while rotation of this joint changes the resistance, impedance, and/or conductivity of the second set more than that of the first set. In an example, multivariate analysis of changes in the resistance, impedance, and/or conductivity of the first set and the second set enables three-dimensional modeling of changes in body joint configuration.

In an example, stretching, bending, twisting, and/or compressing fabric changes both the fabric's electromagnetic capacitance and electromagnetic resistance. In an example, analysis of changes in the fabric's capacitance and resistance provides more accurate modeling of three-dimensional changes in fabric configuration than analysis of changes in capacitance alone or resistance alone. In an example, stretching or bending fabric in a first direction changes fabric capacitance more than fabric resistance, while stretching or bending fabric in a second direction changes fabric resistance more than fabric capacitance. In an example, bending a body joint spanned by fabric can be measured primarily by analyzing changes in fabric capacitance, while rotation of this joint can be measured primarily by analyzing changes in fabric resistance, or vice versa.

In an example, motion recognition fabric can comprise two sets of electromagnetic energy pathways. In an example, electromagnetic energy pathways in a first set of electromagnetic energy pathways can have central longitudinal axes which are parallel to each other and have a first axial orientation. In an example, electromagnetic energy pathways in a second set of electromagnetic energy pathways can have central longitudinal axes which are parallel to each other and have a second axial orientation.

In an example, the axial orientation of electromagnetic energy pathways in a first set can be perpendicular to the axial orientation of electromagnetic energy pathways in a second set (when both are projected onto a two-dimensional plane). In an example, first and second set axial orientations can be parallel to each other (when both are projected onto the same two-dimensional plane). In an example, the first and second set orientations can intersect at acute angles (when both are projected onto a two-dimensional plane). In an example, the first and second set orientations can intersect at 45-degree angles (when both are projected onto a two-dimensional plane). In an example, the first and second orientations can intersect at 60-degree angles (when both are projected onto a two-dimensional plane).

In an example, analysis of electromagnetic energy transmitted through a first set of electromagnetic energy pathways provides information concerning stretching, bending, or compression along the fabric's longitudinal axis and analysis of electromagnetic energy transmitted through a second set of electromagnetic energy pathways provides information concerning stretching, bending, or compression along the fabric's lateral axis. In an example, multivariate analysis of information from the first and second sets enables tracking the two-dimensional locational coordinates of areas of fabric stretching, bending, twisting, and/or compression. In an example, analysis of electromagnetic energy transmitted from the first set to the second set enables tracking the two-dimensional locational coordinates of areas of fabric stretching, bending, twisting, and/or compression.

In an example, a first set of electromagnetic energy pathways can measure changes in body joint movement in a first direction, a second set of electromagnetic energy pathways can measure changes in body joint movement in a second direction, a third set of electromagnetic energy pathways can measure changes in body joint movement in a third direction, wherein data from these three sets is analyzed together in order to measure and/or model changes in the configuration of the body joint in three-dimensional space. In an example, different sets of electromagnetic energy pathways can differ from each other in one or more attributes selected from the group consisting of: axial angle, braid, conductivity, diameter, durometer, elasticity, length, location, material, orientation, shape, size, thickness, and weave.

In an example, this invention can be embodied in motion recognition fabric comprising: a first fabric layer with a first level of conductivity; a second fabric layer with a second level of conductivity; and a third fabric layer with a third level of conductivity; wherein the third layer is between the first layer and the second layer, wherein the third level is less than the first level, wherein the third level is less than the second level, wherein stretching, bending, twisting, and/or compressing the fabric changes the fabric's electromagnetic resistance; and wherein changes in fabric electromagnetic resistance are analyzed to measure changes in human body configuration.

In an example, this invention can be embodied in motion recognition fabric comprising: a first fabric layer with a first level of conductivity; a second fabric layer with a second level of conductivity; and a third fabric layer with a third level of conductivity; wherein the third layer is between the first layer and the second layer, wherein the third level is less than the first level, wherein the third level is less than the second level, wherein stretching, bending, twisting, and/or compressing the fabric changes the fabric's impedance; and wherein changes in fabric impedance are analyzed to measure changes in human body configuration.

In an example, this invention can be embodied in motion recognition fabric comprising: a first fabric layer with a first level of conductivity; a second fabric layer with a second level of conductivity; and a third fabric layer with a third level of conductivity; wherein the third layer is between the first layer and the second layer, wherein the third level is less than the first level, wherein the third level is less than the second level, wherein stretching, bending, twisting, and/or compressing the fabric changes the fabric's conductivity; and wherein changes in fabric conductivity are analyzed to measure changes in human body configuration.

In an example, different layers in motion recognition fabric can be attached to each other by one or more means selected from the group consisting of: adhesion, baking, compression, embroidering, exposure to light energy, exposure to thermal energy, gluing, knitting, melting, printing, sewing, taping, weaving, and welding. In an example, a non-conductive fabric layer can be made from one or more materials selected from the group consisting of: acetate, acrylic, cotton, denim, elastane, Kevlar, latex, linen, Lycra™, neoprene, nylon, nylon, polyester, wool, silicone (e.g. polydimethylsiloxane), silk, spandex, and rayon.

In an example, an electromagnetic energy pathway in motion recognition fabric can be created by one or more means selected from the group consisting of: braiding, coating, cutting, dissolving, embroidering, gluing, knitting, melting, printing, sewing, spinning, and weaving. In an example, an electromagnetic energy pathway in motion recognition fabric can be made from one or more materials selected from the group consisting of: aluminum or aluminum alloy; carbon nanotubes, graphene, or other carbon-based material; liquid metal; magnesium; ceramic particles; copper or copper alloy; gold; liquid metal; nickel; polyaniline; silver; and steel.

In an example, an electromagnetic energy pathway in motion recognition fabric can be selected from the group consisting of: braid or weave of electroconductive and nonconductive strings, braid or weave of electroconductive and nonconductive threads, braid or weave of electroconductive and nonconductive yarns, electroconductive glue, electroconductive ink, electroconductive string, electroconductive strip, electroconductive tape, electroconductive thread, electroconductive yarn, insulated wire, liquid metal channel, pathway in non-conductive material etched by a laser, and tube filled with a flowable conductive substance.

In an example, this invention can further comprise an electromagnetic energy emitter which transmits energy into an electromagnetic energy pathway at a first location and an electromagnetic energy receiver which receives electromagnetic energy from a second location on the same electromagnetic energy pathway. In an example, the resistance, impedance, and/or conductivity of this pathway can be measured by the energy receiver. In an example, changes in body joint configuration change the shape of the pathway between the emitter and the receiver which changes pathway resistance, impedance, and/or conductivity. In an example, changes in body joint configuration change the length of the pathway between the emitter and the receiver which changes pathway resistance, impedance, and/or conductivity. In an example, changes in body joint configuration change the thickness of the pathway between the emitter and the receiver which changes pathway resistance, impedance, and/or conductivity. In an example, changes in body joint configuration change the width of the pathway between the emitter and the receiver which changes pathway resistance, impedance, and/or conductivity.

In an example, electromagnetic energy emitters and/or electromagnetic energy receivers can be removably attached to motion recognition fabric at different locations and in different configurations. In an example, an electromagnetic energy emitter or electromagnetic energy receiver can be removably attached to motion recognition fabric by one or more mechanisms selected from the group consisting of: adhesive, band, buckle, button, clamp, clasp, clip, hook, hook and eye fabric, magnet, pin, plug, sewing, snap, solder, staple, and zipper.

In an example, enabling energy emitters and/or receivers to be removably attached enables customization of electromagnetic energy pathways for a selected article of clothing (e.g. a shirt or pair of pants), a selected motion recognition application (e.g. a particular sport), and/or a selected person (e.g. custom fit for a particular person's body). In an example, removable attachment of energy emitters and/or receivers can be done by a manufacturer as clothing is made from motion recognition fabric. In an example, removable attachment of energy emitters and/or receivers can be done at a store as clothing is customized for a particular customer. In an example, removable attachment of energy emitters and/or receivers can be done by a person (e.g. customer) at their home.

In an example, selected points of electromagnetic communication between pathways in an array can be created by the selective application of energy to those points after clothing has been made from motion recognition fabric. In an example, applied energy can be thermal energy, light energy, magnetic energy, and/or kinetic energy. In an example, this can create can create a customized electromagnetic energy pathway (e.g. circuit) in an article of clothing which measures movement of a body joint in a particular direction. In an example, selective application of energy to selective points connecting two or more arrays can create multiple customized electromagnetic pathways in clothing which enables measuring and modeling body joint motions in three dimensions.

In an example, differences in resistance, impedance, and/or conductivity for different pathways with different orientations, shapes, or materials can be analyzed in order identify the geometric coordinates of areas where motion recognition fabric is stretched, bent, twisted, and/or compressed. In an example, differences in resistance, impedance, and/or conductivity for different pathways with different orientations, shapes, or materials can be analyzed in order create topographic contour maps of areas where motion recognition fabric is stretched, bent, twisted, and/or compressed. In an example, identifying the geometric coordinates and/or creating contour maps of changes in fabric resistance, impedance, and/or conductivity can enable three-dimensional motion capture.

In an example, multivariate analysis of the resistance, impedance, and/or conductivity of a first electromagnetic energy pathway with a first orientation (e.g. longitudinal) and the resistance, impedance, and/or conductivity of a second electromagnetic energy pathway with a second orientation (e.g. lateral) can track how a flat section of fabric stretches or bends (e.g. in two dimensions). In an example, such a pathway configuration can detect the location of contact and movement along this flat surface.

In an example, multivariate analysis of the resistance, impedance, and/or conductivity of a first electromagnetic energy pathway with a first orientation (e.g. parallel with the longitudinal axis of a body joint) and the resistance, impedance, and/or conductivity of a second electromagnetic energy pathway with a second orientation (e.g. diagonal to the longitudinal axis of a body joint) can track how a cylindrical section of fabric stretches or bends (in two dimensions). In an example, such a pathway configuration can model bending and rotation of this body joint. In an example, analysis of differences in the resistance, impedance, and/or conductivity of a first electromagnetic energy pathway which is longitudinal (relative to a joint) vs. a second electromagnetic energy pathway which is diagonal (relative to a joint) can identify the geometric coordinates and/or topographic contours of twisting in a cylindrical section of fabric.

In an example, multivariate analysis of the resistance, impedance, and/or conductivity of a first electromagnetic energy pathway that is substantially straight (e.g. substantially parallel with the longitudinal axis of a body joint) and the resistance, impedance, and/or conductivity of a second electromagnetic energy pathway that is substantially circular (e.g. going around the circumference of this joint) can track how a cylindrical section of fabric stretches or bends (in three dimensions). In an example, such a pathway configuration can model bending and rotation of this body joint. In an example, differences in the changes in the resistance, impedance, and/or conductivity of different pathways with different orientations (e.g. straight vs. circumferential) can be compared in order identify the polar coordinates of stretching, bending, twisting, or compression in a cylindrical section of fabric.

In an example, an electromagnetic energy pathway can be relatively straight. In an example, an electromagnetic energy pathway can be arcuate. In an example, an electromagnetic energy pathway can be sinusoidal or undulating. In an example, an electromagnetic energy pathway can be helical or spiral-shaped. In an example, an electromagnetic energy pathway can have a zigzag or sawtooth shape. In an example, an electromagnetic energy pathway can comprise one or more loops. In an example, the central longitudinal axis of an energy pathway can be relatively straight. In an example, the central longitudinal axis of an energy pathway can be arcuate. In an example, the central longitudinal axis of an energy pathway can be a loop.

In an example, a plurality of electromagnetic energy pathways in motion recognition fabric can be configured in an array, grid, mesh, or lattice which forms square or rectangular spaces between pathways. In an example, a plurality of electromagnetic energy pathways can be configured in an array, grid, mesh, or lattice which forms rhomboid, parallelogram-shaped, and/or diamond-shaped spaces between pathways. In an example, a plurality of electromagnetic energy pathways can be configured in an array, grid, mesh, or lattice which forms triangular spaces between pathways. In an example, a plurality of electromagnetic energy pathways can be configured in an array, grid, mesh, or lattice which forms hexagonal spaces between pathways.

In an example, a plurality of electromagnetic energy pathways in motion recognition fabric can be parallel to each other. In an example, a plurality of electromagnetic energy pathways can be perpendicular to each other. In an example, a plurality of electromagnetic energy pathways can be concentric. In an example, a plurality of electromagnetic energy pathways can be nested. In an example, a plurality of electromagnetic energy pathways can be interdigitated. In an example, a plurality of electromagnetic energy pathways can be braided together. In an example, a plurality of electromagnetic energy pathways can be woven together.

In an example, a set of electromagnetic energy pathways in motion recognition fabric can be configured so that their ends all face in the same direction. In an example, a set of electromagnetic energy pathways in motion recognition fabric can be configured so that their ends all terminate along the same side of the fabric. This can be useful for connecting pathway ends along a common seam when the fabric is used to make motion recognition clothing. In an example, motion recognition fabric can comprise: a first set of stretchable electroconductive loops configured to span a joint in a longitudinal direction when made into clothing wherein the ends of this first set of loops all face in a selected direction; and a second set of stretchable electroconductive loops configured to span a joint in a lateral direction when made into clothing wherein the ends of this second set of loops also all face in the same selected direction.

In an example, motion recognition fabric can comprise: a first set of stretchable electroconductive loops configured to span a joint in a longitudinal direction when made into clothing wherein the ends of this first set of loops all face in a selected direction; and a second set of stretchable electroconductive loops configured to span a joint circumferentially when made into clothing wherein the ends of this second set of loops also all face in the same selected direction. In an example, motion recognition fabric can comprise: a first set of stretchable electroconductive loops configured to span a joint in a longitudinal direction when made into clothing wherein the ends of this first set of loops all face in a selected direction; and a second set of stretchable electroconductive loops configured to span a joint diagonally when made into clothing wherein the ends of this second set of loops also all face in the same selected direction.

In an example, motion recognition fabric can comprise: a first set of stretchable electroconductive loops configured to span a joint in a longitudinal direction when made into clothing wherein the ends of this first set of loops all terminate along a selected side; and a second set of stretchable electroconductive loops configured to span a joint in a lateral direction when made into clothing wherein the ends of this second set of loops also all terminate along the same selected side. In an example, motion recognition fabric can comprise: a first set of stretchable electroconductive loops configured to span a joint in a longitudinal direction when made into clothing wherein the ends of this first set of loops all terminate on a common seam; and a second set of stretchable electroconductive loops configured to span a joint in a lateral direction when made into clothing wherein the ends of this second set of loops also all terminate on the same common seam.

In an example, motion recognition fabric can comprise: a first set of stretchable electroconductive loops configured to span a joint in a longitudinal direction when made into clothing wherein the ends of this first set of loops all terminate along a selected side; and a second set of stretchable electroconductive loops configured to span a joint circumferentially when made into clothing wherein the ends of this second set of loops also all terminate along the same selected side. In an example, motion recognition fabric can comprise: a first set of stretchable electroconductive loops configured to span a joint in a longitudinal direction when made into clothing wherein the ends of this first set of loops all terminate on a common seam; and a second set of stretchable electroconductive loops configured to span a joint circumferentially when made into clothing wherein the ends of this second set of loops also all terminate on the same common seam.

In an example, motion recognition fabric can comprise: a first set of stretchable electroconductive loops configured to span a joint in a longitudinal direction when made into clothing wherein the ends of this first set of loops all terminate along a selected side; and a second set of stretchable electroconductive loops configured to span a joint diagonally when made into clothing wherein the ends of this second set of loops also all terminate along the same selected side. In an example, motion recognition fabric can comprise: a first set of stretchable electroconductive loops configured to span a joint in a longitudinal direction when made into clothing wherein the ends of this first set of loops all terminate on a common seam; and a second set of stretchable electroconductive loops configured to span a joint diagonally when made into clothing wherein the ends of this second set of loops also all terminate on the same common seam.

In an example, a longitudinally-oriented portion of an electromagnetic energy loop can stretch or bend more than a laterally-oriented portion of this electromagnetic energy loop in order to make the loop overall more responsive to longitudinal stretching or bending than to lateral stretching or bending. In an example, a laterally-oriented portion of an electromagnetic energy loop can stretch or bend more than a longitudinally-oriented portion of this electromagnetic energy loop in order to make the loop overall more responsive to lateral stretching or bending than to longitudinal stretching or bending In an example, a longitudinally-oriented portion of an electromagnetic energy loop can stretch or bend more than a diagonally-oriented portion of this electromagnetic energy loop in order to make the loop overall more responsive to longitudinal stretching or bending than to diagonal stretching or bending. In an example, a diagonally-oriented portion of an electromagnetic energy loop can stretch or bend more than a longitudinally-oriented portion of this electromagnetic energy loop in order to make the loop overall more responsive to diagonal stretching or bending than to longitudinal stretching or bending.

In an example, the resistance, impedance, or conductivity of a longitudinally-oriented portion of an electromagnetic energy loop can change more in response to fabric stretching or bending than the resistance, impedance, or conductivity of a laterally-oriented portion of this electromagnetic energy loop in order to make the loop overall more responsive to longitudinal stretching or bending than to lateral stretching or bending. In an example, the resistance, impedance, or conductivity of a laterally-oriented portion of an electromagnetic energy loop can change more in response to fabric stretching or bending than the resistance, impedance, or conductivity of a longitudinally-oriented portion of this electromagnetic energy loop in order to make the loop overall more responsive to lateral stretching or bending than to longitudinal stretching or bending.

In an example, the resistance, impedance, or conductivity of a longitudinally-oriented portion of an electromagnetic energy loop can change more in response to fabric stretching or bending than the resistance, impedance, or conductivity of a diagonally-oriented portion of this electromagnetic energy loop in order to make the loop overall more responsive to longitudinal stretching or bending than to diagonal stretching or bending. In an example, the resistance, impedance, or conductivity of a diagonally-oriented portion of an electromagnetic energy loop can change more in response to fabric stretching or bending than the resistance, impedance, or conductivity of a longitudinally-oriented portion of this electromagnetic energy loop in order to make the loop overall more responsive to diagonal stretching or bending than to longitudinal stretching or bending.

In an example, motion recognition fabric can be made in modular geometric shapes such as squares or hexagons. In an example, these modular squares or hexagons can be designed to be connected together in different configurations to form different articles of clothing. This is somewhat analogous to the way in which fabric "patches" are connected together to form a quilt, except that modular squares or hexagons ("patches) of motion recognition fabric are connected electromagnetically as well as mechanically. In this manner, different combinations of modular squares or hexagons ("patches") of motion recognition fabric create electromagnetic energy circuits with different patterns for different articles of clothing. Modular assembly of squares or hexagons ("patches") of motion recognition fabric enables the formation of a wide variety of electromagnetic circuits for human body motion capture in a wide variety of articles of clothing.

In an example, a first square (or "patch") of motion recognition fabric can be connected to a second square (or "patch") of motion recognition fabric by a means selected from the group consisting of: heating, ironing, melting, or other application of thermal energy; laser projection, UV light, or other application of light energy; compression or other application of kinetic energy; sewing or embroidering; gluing or adhesion; soldering; closing a zipper; and snaps, hooks, plugs, or other mechanical connections.

In an example, a square (or "patch") of motion recognition fabric can have a series or array of electromagnetic connectors along its side edge or seam. In an example, this series or array of electromagnetic connectors comprises the ends of electromagnetic energy pathways in the square (or "patch"). In an example, the side edge or seam of a first square (or "patch") of motion recognition fabric can be connected to the side edge or seam of a second square (or "patch") of motion recognition fabric. In an example, when the side edges or seams of first and second squares (or "patches") are connected to each other, then this connects electromagnetic energy pathways in the first and second squares (or "patches") to each other. In an example, when the side edges or seams of first and second squares (or "patches") are connected to each other, then electromagnetic communication between electromagnetic energy pathways in the first and second squares (or "patches") is established. This creates an electromagnetic circuit which spans two or more squares (or "patches"). These same variations can also be done with hexagonal patches instead of square patches.

In an example, a first square (or "patch") of motion recognition fabric and a second square (or "patch") of motion recognition fabric can both be connected to the same seam of an article of clothing in order to establish electromagnetic communication between electromagnetic energy pathways in those squares (or "patches") with a shared energy emitter and/or energy receiver. In an example, the sides of a plurality of squares (or "patches") of motion recognition fabric can be connected to the same seam of an article clothing in order to establish electromagnetic communication between electromagnetic energy pathways in those squares (or "patches") with a shared energy emitter and/or energy receiver. These same variations can also be done with hexagonal patches instead of square patches.

In an example, the sides of a set of squares (or "patches") of motion recognition fabric can all be connected to the same longitudinal seam in a pair of pants. This establishes electromagnetic communication between electromagnetic energy pathways in those squares (or "patches") with a shared energy emitter and/or energy receiver. In an example, a shared energy emitter and/or receiver can be located near the waist of the pair of pants. In an example, the sides of a set of squares (or "patches") of motion recognition fabric can all be connected to the same longitudinal seam in a shirt sleeve. This establishes electromagnetic communication between a plurality of electromagnetic energy pathways in those squares (or "patches") with a shared energy emitter and/or energy receiver. In an example, a shared energy emitter and/or receiver can be located on the torso of a shirt. These same variations can also be done with hexagonal patches instead of square patches.

In an example, different types of modular patches can have different patterns of electromagnetic energy pathways. In an example, modular patches with different patterns of electromagnetic energy pathways can be combined to create different patterns of multi-patch electromagnetic energy pathways which are appropriate for different articles of clothing. In an example, a first patch type can have straight lateral electromagnetic energy pathways, wherein one pathway end terminates on the left side of the patch and other pathway end terminates on the right side of the patch. In an example, a second patch type can have right-angle lateral electromagnetic energy pathways, wherein one pathway end terminates on the top (or bottom) of the patch and the other pathway end terminates on the right (or left) side of the patch. As Carcassonne™ fans will appreciate, first patch types and second patch types can be connected in different configurations to create clothing with U-shaped, O-shaped, or other-shaped electromagnetic energy pathways.

In an example, motion recognition fabric can comprise: a first square (or hexagon) of fabric; an electromagnetic energy pathway; a first connector on a first side of the first square (or hexagon); and a second connector on a second side of the first square (or hexagon); wherein the pathway is in electromagnetic communication with the first connector and the second connector, and wherein the first connector or the second connector is connected to a third connector on a side of second square (or hexagon) of fabric when an article of clothing is made.

In an example, the second side of a square (or hexagon) can be opposite (180-angle relative to) the first side of the square (or hexagon). In an example, the second side of a square can be adjacent (90-degree angle relative) to the first side of the square. In an example, the second side of a hexagon can be at a 60-degree or 120-degree angle relative to the first side of the hexagon. In an example, a square (or hexagon) can have multiple electromagnetic energy pathways and multiple connectors. In an example, multiple connectors can be integrated into a seam along the side of a square (or hexagon).

In an example, one or more connectors along the side of a first square (or hexagon) of fabric can be connected to one or more connectors along the side of a second square (or hexagon) of fabric by a means selected from the group consisting of: adhesion, application of laser light, application of UV light, clipping, embroidering, gluing, heating, hooking, ironing, magnetism, melting, pinning, plugging, pressing, printing, sewing, snapping, soldering, and zipping. In an example, an electromagnetic energy pathway in a first modular square (or hexagon) of motion recognition fabric can be brought into electromagnetic communication with an electromagnetic energy pathway in a second modular square (or hexagon) of motion recognition fabric by a means selected from the group consisting of: adhesion, application of laser light, application of UV light, clipping, embroidering, gluing, heating, hooking, ironing, magnetism, melting, pinning, plugging, pressing, printing, sewing, snapping, soldering, and zipping.

In an example, a modular system of motion recognition fabric can comprise: a first square (or hexagon) of fabric, wherein this first square (or hexagon) further comprises a first electromagnetic energy pathway, a first connector on a first side of the first square (or hexagon), and a second connector on a second side of the first square (or hexagon), and wherein the first electromagnetic energy pathway is in electromagnetic communication with the first connector and the second connector; a second square (or hexagon) of fabric, wherein this second square (or hexagon) further comprises a second electromagnetic energy pathway, a third connector on a first side of the second square (or hexagon), and a fourth connector on a second side of the second square (or hexagon), wherein the second electromagnetic energy pathway is in electromagnetic communication with the third connector and the fourth connector; and wherein the first connector or second connector is connected to the third connector or the fourth connector in order to create electromagnetic communication between the first electromagnetic energy pathway and the second electromagnetic energy pathway.

In an example, when a body joint spanned by motion recognition fabric bends, this bending motion changes the resistance, impedance, and/or conductivity of electromagnetic pathways in a first layer more than that in a second layer, but when the body joint rotates, this rotational motion changes the resistance, impedance, and/or conductivity of electromagnetic pathways in the second layer more than that in the first layer. In an example, different layers can be configured to have different orientations relative to the body joint when incorporated into an article of clothing.

In an example, when a body joint spanned by motion recognition fabric bends, this bending motion changes the capacitance, resistance, impedance, and/or conductivity of electromagnetic pathways in the fabric in a first manner. However, when this body joint rotates, this rotational motion changes the capacitance, resistance, impedance, and/or conductivity of electromagnetic pathways in the fabric in a second manner. In an example, when a body joint spanned by motion recognition fabric bends, this bending motion changes the capacitance, resistance, impedance, and/or conductivity of a first set of pathways more than that of a second set of pathways. However, when this body joint rotates, this rotational motion changes the capacitance, resistance, impedance, and/or conductivity of the second set of pathways more than that of the first set of pathways.

In example, the orientation of a first set of electromagnetic energy pathways relative to a body joint can be different than the orientation of a second set of electromagnetic energy pathways relative to the body joint. In an example, the first set of pathways can be perpendicular to the second set of pathways. In an example, the first set of pathways can be substantially parallel to the longitudinal axis of the body joint, but the second set of pathways is not substantially parallel to the longitudinal axis of the body joint. In an example, motion recognition fabric can be arranged in decter columns. In an example, motion recognition fabric can be arranged in decter rows. In an example, decterow fabric can be highly successful.

In an example, motion recognition fabric can comprise three different conductive layers which measure changes in fabric configuration in three different directions. In an example, it can include two non-conductive layers separating these three conductive layers. In an example, these layers can all be stretchable, bendable, twistable, and compressible. In an example, conductive layers can be made with one or more materials selected from the group consisting of: aluminum or aluminum alloy; carbon nanotubes, graphene, or other carbon-based material; magnesium; ceramic particles; copper or copper alloy; gold; liquid metal; nickel; polyaniline; silver; and steel. In an example, non-conductive layers can be made with one or more materials selected from the group consisting of: acetate, acrylic, cotton, denim, elastane, Kevlar, latex, linen, Lycra™, neoprene, nylon, nylon, polyester, wool, silicone (e.g. polydimethylsiloxane) (e.g. polydimethylsiloxane), silk, spandex, and rayon.

In an example, this invention can be embodied in motion recognition fabric comprising: a first layer which conducts electromagnetic energy, wherein transmission of electromagnetic energy through this first layer is most changed by stretching or bending of the fabric in a first direction; a second layer which is non-conductive; a third layer which conducts electromagnetic energy, wherein transmission of electromagnetic energy through this third layer is most changed by stretching or bending of the fabric in a second direction; a fourth layer which is non-conductive; and a fifth layer which conducts electromagnetic energy, wherein transmission of electromagnetic energy through this fifth layer is most changed by stretching or bending of the fabric in a third direction.

In an example, this invention can be embodied in motion recognition fabric comprising: a first layer which conducts electromagnetic energy along a pathway with a first orientation; a second layer which is non-conductive; a third layer which conducts electromagnetic energy along a pathway with a second orientation; a fourth layer which is non-conductive; and a fifth layer which conducts electromagnetic energy along a pathway with a third orientation.

In an example, an array of electromagnetic energy pathways in motion recognition fabric can be selected from the group consisting of: a deposited and/or printed pattern of electroconductive ink; a pattern of electroconductive strips; an adhered pattern of electroconductive glue; an adhered pattern of electroconductive tape; an array, matrix, or series of liquid metal channels; an array, matrix, or series of flexible tubes containing liquid metal; an array, matrix, series, braid, or weave of electroconductive and nonconductive strings; an array, matrix, series, braid, or weave of electroconductive and nonconductive threads; an array, matrix, series, braid, or weave of electroconductive and nonconductive yarns; an array, matrix, series, braid, or weave of electroconductive strings; an array, matrix, series, braid, or weave of electroconductive threads; an array, matrix, series, braid, or weave of electroconductive wires; an array, matrix, series, braid, or weave of electroconductive yarns; an electroconductive pathway etched by a laser; and an embroidered pattern of electroconductive thread or yarn.

In an example, electromagnetic energy pathways in an array can be substantially straight. In an example, electromagnetic energy pathways can be arcuate. In an example, electromagnetic energy pathways in an array can be sinusoidal, undulating, oscillating, helical, and/or otherwise wavy. In an example, electromagnetic energy pathways in an array can zigzag and/or be sawtooth shaped. In an example, electromagnetic energy pathways in an array can be parallel to each other. In an example, electromagnetic energy pathways in an array can be converging and/or radial. In an example, electromagnetic energy pathways in an array can be concentric and/or nested. In an example, electromagnetic energy pathways in an array can be interdigitated. In an example, electromagnetic energy pathways in an array can be reflected around a longitudinal or lateral axis. In an example, electromagnetic energy pathways in an array can form a wheel-spoke or sunburst configuration. In an example, electromagnetic energy pathways in an array can be stacked in three-dimensions.

In an example, pathways in a first array of electromagnetic energy pathways can have central longitudinal axes which are parallel to each other and which have a first orientation. In an example, pathways in a second array of electromagnetic energy pathways can have central longitudinal axes which are parallel to each other and which have a second orientation. In an example, the first and second orientations can be parallel to each other (e.g. when both are projected onto a common plane in three-dimensional space). In an example, the first and second orientations can be perpendicular to each other (e.g. when both are projected onto a common plane in three-dimensional space). In an example, the first and second orientations can form acute angles (e.g. 30 degrees, 45 degrees, or 60 degrees) relative to each other (e.g. when both are projected onto a common plane in three-dimensional space).

In an example, an array can comprise sinusoidal electromagnetic energy pathways whose central longitudinal axes are parallel. In an example, an array can comprise sinusoidal electromagnetic energy pathways whose central longitudinal axes are perpendicular. In an example, an array can comprise sinusoidal electromagnetic energy pathways are in phase with each other. In an example, an array can comprise adjacent pairs of sinusoidal electromagnetic energy pathways which are out of phase with each other. In an example, an array can comprise adjacent pairs of sinusoidal electromagnetic energy pathways which 180-degrees out of phase with each other. In an example, an array can comprise sinusoidal electromagnetic energy pathways whose oscillation peaks extend into each other's concavities. In an example, an array can comprise sinusoidal electromagnetic energy pathways whose oscillation peaks do not extend into each other's concavities.

In an example, analysis of changes in electromagnetic energy through a first array of electromagnetic energy pathways provides a first set of data on body motion (e.g. along a first axis and/or in a first direction) and analysis of changes in electromagnetic energy through a second array of electromagnetic energy pathways provides a second set of data on body motion (e.g. along a second axis and/or in a first direction). In an example, multivariate analysis of the first and second sets of data enables tracking motion of a body member in two-dimensional (e.g. X and Y axial) space. In an example, the first direction can be perpendicular to the second direction.

In an example, analysis of changes in electromagnetic energy through a first array provides a first set of data on body motion (e.g. bending motion) and analysis of changes in electromagnetic energy through a second array provides a second set of data on body motion (e.g. rotational motion). In an example, multivariate analysis of the first and second sets of data can be used to measure the bending and rotation of a body joint in order to model changes in body configuration in three-dimensional space.

In an example, this invention can be embodied in motion recognition fabric comprising: a first set of parallel electromagnetic energy pathways with a first axial orientation in a first fabric layer; a non-conductive second fabric layer; a second set of parallel electromagnetic energy pathways with a second axial orientation in a third fabric layer; wherein the non-conductive second fabric layer is between the first fabric layer and the third fabric layer; wherein the second axial orientation is perpendicular to the first axial orientation; wherein pair-wise capacitance values between each pathway in the first set and each pathway in the second set are measured; wherein an array of these pair-wise capacitance values is created; wherein this array is used to identify locations and/or geometric patterns of fabric stretching, bending, twisting, and/or compression; and wherein these locations and/or geometric patterns are used to identify changes in human body configuration.

In an example, this invention can be embodied in motion recognition fabric comprising: a first set of electromagnetic energy pathways with longitudinal (Y-axis) axial orientations in a first fabric layer; a non-conductive second fabric layer; and a second set of electromagnetic energy pathways with lateral (X-axis) axial orientations in a third fabric layer; wherein the second fabric layer is between the first fabric layer and the third fabric layer; wherein pair-wise (X-Y) capacitance values between each pathway in the first set and each pathway in the second set are measured; wherein an (X-Y) array of these pair-wise capacitance values is created; wherein this array is used to identify (X-Y) locations and/or geometric patterns of fabric stretching, bending, twisting, and/or compression; and wherein these locations and/or geometric patterns are used to identify changes in human body configuration.

In an example, this invention can be embodied in motion recognition fabric comprising: a first set of electromagnetic energy pathways with a first (X) axial orientation in a first fabric layer; a non-conductive second fabric layer; and a second set of electromagnetic energy pathways with a second (Y) axial orientation in a third fabric layer; wherein the second fabric layer is between the first and third fabric layers; wherein the second axial orientation is diagonal (e.g. at a 45-degree angle) to the first axial orientation; wherein pair-wise (X-Y) capacitance values between each pathway in the first set and second set are measured; wherein an array of these pair-wise capacitance values is created; wherein this array is used to identify locations and/or geometric patterns of fabric stretching, bending, twisting, and/or compression; and wherein these locations and/or geometric patterns are used to identify changes in human body configuration.

In an example, this invention can be embodied in motion recognition fabric comprising: a first set of electromagnetic energy pathways with a first (X) axial orientation in a first fabric layer; a non-conductive second fabric layer; a second set of electromagnetic energy pathways with a second (Y) axial orientation in a third fabric layer; a non-conductive fourth fabric layer; a third set of electromagnetic energy pathways with a third (Z) axial orientation in a fifth fabric layer; wherein the second fabric layer is between the first and third fabric layers; wherein the fourth fabric layer is between the third and fifth fabric layers; wherein the second axial orientation is perpendicular to the first axial orientation; wherein the third axial orientation is diagonal (e.g. at a 45-degree angle) to the first axial orientation; wherein pair-wise (X-Y) capacitance values between each pathway in the first set and second set are measured; wherein pair-wise (X-Z) capacitance values between each pathway in the first set and third set are measured and/or pair-wise (Y-Z) capacitance values between each pathway in the second set and third set are measured; wherein an array of these pair-wise capacitance values is created; wherein this array is used to identify locations and/or geometric patterns of fabric stretching, bending, twisting, and/or compression; and wherein these locations and/or geometric patterns are used to identify changes in human body configuration.

In an example, this invention can be embodied in motion recognition fabric comprising: a first set of electromagnetic energy pathways with a first (X) axial orientation; a second set of electromagnetic energy pathways with a second (Y) axial orientation; a third set of electromagnetic energy pathways with a third (Z) axial orientation; wherein the first, second, and third sets are woven together; wherein the second axial orientation is perpendicular to the first axial orientation; wherein the third axial orientation is diagonal (e.g. at a 45-degree angle) to the first axial orientation;

wherein pair-wise (X-Y) capacitance values between each pathway in the first set and second set are measured; wherein pair-wise (X-Z) capacitance values between each pathway in the first set and third set are measured and/or pair-wise (Y-Z) capacitance values between each pathway in the second set and third set are measured; wherein an array of these pair-wise capacitance values is created; wherein this array is used to identify locations and/or geometric patterns of fabric stretching, bending, twisting, and/or compression; and wherein these locations and/or geometric patterns are used to identify changes in human body configuration.

In an example, this invention can be embodied in motion recognition fabric comprising: a first set of electromagnetic energy pathways with a first (X) axial orientation; a second set of electromagnetic energy pathways with a second (Y) axial orientation; a third set of electromagnetic energy pathways with a third (Z) axial orientation; wherein the first, second, and third sets are woven together; wherein the second axial orientation is perpendicular to the first axial orientation; wherein the third axial orientation is diagonal (e.g. at a 45-degree angle) to the first axial orientation; wherein pair-wise (X-Y) conductivity values between each pathway in the first set and second set are measured; wherein pair-wise (X-Z) conductivity values between each pathway in the first set and third set are measured and/or pair-wise (Y-Z) conductivity values between each pathway in the second set and third set are measured; wherein an array of these pair-wise conductivity values is created; wherein this array is used to identify locations and/or geometric patterns of fabric stretching, bending, twisting, and/or compression; and wherein these locations and/or geometric patterns are used to identify changes in human body configuration.

In an example, when a body joint spanned by motion recognition fabric bends, this bending motion changes the capacitance, resistance, impedance, and/or conductivity of electromagnetic arrays in the fabric in a first manner. However, when this body joint rotates, this rotational motion changes the capacitance, resistance, impedance, and/or conductivity of arrays in the fabric in a second manner. In an example, when a body joint spanned by motion recognition fabric bends, this bending motion changes the capacitance, resistance, impedance, and/or conductivity of a first array more than that of a second array. However, when this body joint rotates, this rotational motion changes the capacitance, resistance, impedance, and/or conductivity of the second array more than that of the first array. In example, the orientation of the first array relative to the body joint is different than the orientation of the second array relative to the body joint. In an example, the first array has an orientation which is perpendicular to that of the second array. In an example, the first array is substantially parallel to the longitudinal axis of the body joint, but the second array is not substantially parallel to the longitudinal axis of the body joint.

In an example, individual pathways in an array can be parallel to each other. In an example, individual pathways in first and second arrays can be pair-wise related to each other on opposite sides of the middle layer, separated only by the width of a non-conductive middle layer. In an example, individual pathways in a first array can be equidistant from the two closest arrays in a second array. In an example, the intersections of pathways in first and second arrays (when both are projected onto the same two-dimensional plane) can form a grid of squares, rectangles, or other quadrilaterals. In an example, the intersections of pathways in first and second arrays (when both are projected onto the same two-dimensional plane) can form a grid of triangles. In an example, the intersections of pathways in first and second arrays (when both are projected onto the same two-dimensional plane) can form a grid of hexagons.

In an example, an electromagnetic energy pathway in an array can be substantially straight. In an example, an electromagnetic energy pathway can be arcuate. In an example, an electromagnetic energy pathway can be sinusoidal, undulating, oscillating and/or helical. In an example, an electromagnetic energy pathway can zigzag and/or be sawtooth shaped. In an example, two electromagnetic energy pathways can be converging and/or radial. In an example, two electromagnetic energy pathways can be concentric and/or nested. In an example, two electromagnetic energy pathways can be interdigitated. In an example, a second electromagnetic energy pathway can be reflected from a first electromagnetic energy pathway across a longitudinal or lateral axis. In an example, electromagnetic energy pathways can be stacked in three-dimensions.

In an example, a first electromagnetic energy pathway can have a central longitudinal axis with a first orientation. In an example, a second electromagnetic energy pathway can have a central longitudinal axis with a second orientation. In an example, these first and second orientations can be parallel to each other (e.g. when both are projected onto a common plane in three-dimensional space). In an example, these first and second orientations can be perpendicular to each other (e.g. when both are projected onto a common plane in three-dimensional space). In an example, these first and second orientations can form acute angles (e.g. 30 degrees, 45 degrees, or 60 degrees) relative to each other (e.g. when both are projected onto a common plane in three-dimensional space).

In an example, analysis of changes in electromagnetic energy through a first pathway provides a first set of data on body motion (e.g. along a first axis and/or in a first direction) and analysis of changes in electromagnetic energy through a second pathway provides a second set of data on body motion (e.g. along a second axis and/or in a first direction). In an example, multivariate analysis of the first and second sets of data enables tracking motion of a body member in two-dimensional (e.g. X and Y axial) space. In an example, the first direction can be perpendicular to the second direction.

In an example, analysis of changes in electromagnetic energy through a first pathway provides a first set of data on body motion (e.g. bending motion) and analysis of changes in electromagnetic energy through a second array provides a second set of data on body motion (e.g. rotational motion). In an example, multivariate analysis of the first and second sets of data can be used to measure the bending and rotation of a body joint in order to model changes in body configuration in three-dimensional space.

In an example, a first pathway can measure changes in body joint movement in a first direction, a second pathway can measure changes in body joint movement in a second direction, a third pathway can measure changes in body joint movement in a third direction, and data from these three pathways can be analyzed together in order to measure and/or model changes in the configuration of the body joint in three-dimensional space.

In an example, this invention can be embodied in motion recognition fabric comprising: clothing fabric; wherein this fabric further comprises: a first set of stretchable, bendable, twistable, and/or compressible electromagnetic energy pathways; and a second set of stretchable, bendable, twistable, and/or compressible electromagnetic energy pathways; wherein the first and second sets are woven together;

wherein the distance between the first and second sets changes when the fabric is stretched, bent, twisted, and/or compressed; wherein these changes in distance change the capacitance of the first and second sets; and wherein these changes in capacitance are analyzed to model changes in the configuration of the body of a person wearing clothing made from the fabric.

In an example, this invention can be embodied in motion recognition fabric comprising: clothing fabric; wherein this fabric further comprises: a first set of electromagnetic energy pathways; and a second set of electromagnetic energy pathways; wherein the first and second sets are woven together; wherein the shapes of the first set and the second set are changed when the fabric is stretched, bent, twisted, and/or compressed; wherein these changes in shape change the resistance, impedance, and/or conductivity of the pathways; and wherein these changes in resistance, impedance, and/or conductivity are analyzed to model changes in the configuration of the body of a person wearing clothing made from the fabric.

In an example, this invention can be embodied in motion recognition fabric comprising: clothing fabric; wherein this fabric further comprises a first set of stretchable and bendable electromagnetic energy pathways; wherein this fabric further comprises a second set of stretchable and bendable electromagnetic energy pathways; and wherein the first set and the second set are concentric and/or nested.

In an example, this invention can be embodied in motion recognition fabric comprising: clothing fabric; wherein this fabric further comprises a first set of stretchable and bendable electromagnetic energy pathways; wherein this fabric further comprises a second set of stretchable and bendable electromagnetic energy pathways; and wherein the first set and the second set form a wheel-spoke or sunburst configuration.

In an example, this invention can be embodied in motion recognition fabric comprising: clothing fabric; wherein this fabric further comprises a first set of stretchable and bendable electromagnetic energy pathways; wherein this fabric further comprises a second set of stretchable and bendable electromagnetic energy pathways; and wherein the longitudinal axes of the first and second sets form acute angles in the range of 25 to 35 degrees when they intersect (e.g. when both are projected onto the same two-dimensional plane).

In an example, this invention can be embodied in motion recognition fabric comprising: clothing fabric; wherein this fabric further comprises a first set of stretchable and bendable electromagnetic energy pathways; wherein this fabric further comprises a second set of stretchable and bendable electromagnetic energy pathways; and wherein the longitudinal axes of the first and second sets form acute angles in the range of 55 to 65 degrees when they intersect (e.g. when both are projected onto the same two-dimensional plane).

In an example, this invention can be embodied in motion recognition fabric comprising: clothing fabric; wherein this fabric further comprises a first set of sinusoidal electromagnetic energy pathways; wherein this fabric further comprises a second set of sinusoidal electromagnetic energy pathways; and wherein the central longitudinal axes of the first and second sets are perpendicular. In an example, this invention can be embodied in motion recognition fabric comprising: clothing fabric; wherein this fabric further comprises a first set of helical electromagnetic energy pathways; wherein this fabric further comprises a second set of helical electromagnetic energy pathways; and wherein the central longitudinal axes of the first and second sets are perpendicular.

In an example, this invention can be embodied in motion recognition fabric comprising: clothing fabric; wherein this fabric further comprises a first set of sinusoidal electromagnetic energy pathways; wherein this fabric further comprises a second set of sinusoidal electromagnetic energy pathways; and wherein the central longitudinal axes of the first and second sets are parallel. In an example, this invention can be embodied in motion recognition fabric comprising: clothing fabric; wherein this fabric further comprises a first set of helical electromagnetic energy pathways; wherein this fabric further comprises a second set of helical electromagnetic energy pathways; and wherein the central longitudinal axes of the first and second sets are parallel.

In an example, this invention can be embodied in motion recognition fabric comprising: clothing fabric; wherein this fabric further comprises a first set of sinusoidal electromagnetic energy pathways; wherein this fabric further comprises a second set of sinusoidal electromagnetic energy pathways; and wherein the oscillations of the first and second sets are 180-degrees out of phase with each other.

In an example, this invention can be embodied in motion recognition fabric comprising: clothing fabric; wherein this fabric further comprises a first set of electromagnetic energy pathways; wherein this fabric further comprises a second set of electromagnetic energy pathways; wherein this fabric further comprises a third set of electromagnetic energy pathways; and wherein these first, second, and third sets combine to form a grid of hexagons.

In an example, this invention can be embodied in motion recognition fabric comprising: clothing fabric; wherein this fabric further comprises a first set of electromagnetic energy pathways; wherein this fabric further comprises a second set of electromagnetic energy pathways; wherein this fabric further comprises a third set of electromagnetic energy pathways; and wherein these first, second, and third sets combine to form a grid of triangles.

In an example, this invention can be embodied in motion recognition fabric comprising: a first set of electromagnetic energy pathways; a second set of electromagnetic energy pathways; one or more electromagnetic energy emitters which can be removably attached to different locations on the first set and/or the second set; and one or more electromagnetic energy receivers which can be removably attached to different locations on the first set and/or the second set.

In an example, an electromagnetic energy pathway can comprise one or more materials or particles selected from the group consisting of: aluminum or aluminum alloy; carbon nanotubes, graphene, or other carbon-based material; magnesium; ceramic particles; copper or copper alloy; gold; liquid metal; nickel; polyaniline; silver; and steel.

In an example, an electromagnetic energy pathway can be selected from the group consisting of: deposited and/or printed electroconductive ink; an electroconductive strip; electroconductive glue; electroconductive tape; liquid metal channel; electroconductive and nonconductive strings; electroconductive and nonconductive threads; electroconductive and nonconductive yarns; electroconductive string; electroconductive thread; electroconductive wire; electroconductive yarn; pathway etched by a laser; and embroidered electroconductive thread or yarn. In an example, one or more electromagnetic energy pathways can be created by a means selected from the group consisting of: braiding; cutting; gluing; melting; dissolving; embroidering; knitting; printing; sewing; or weaving.

In an example, an electromagnetic energy pathway can comprise a flexible non-conductive core surrounded by an electroconductive coating and/or layer. In an example, an electromagnetic energy pathway can comprise: a flexible non-conductive core made from acetate, acrylic, cotton, denim, elastane, Kevlar, latex, linen, Lycra™, neoprene, nylon, polyester, wool, silicone (e.g. polydimethylsiloxane) (e.g. polydimethylsiloxane), silk, spandex, or rayon surrounded by a electroconductive coating and/or layer made from aluminum, aluminum alloy, carbon nanotubes, graphene, liquid metal, magnesium, copper, copper alloy, gold, nickel, polyaniline, silver, or steel.

In an example, an electromagnetic energy pathway can comprise a braided non-conductive core surrounded by an electroconductive coating and/or layer. In an example, an electromagnetic energy pathway can comprise: a braided non-conductive core made from acetate, acrylic, cotton, denim, elastane, Kevlar, latex, linen, Lycra™, neoprene, nylon, polyester, wool, silicone (e.g. polydimethylsiloxane), silk, spandex, or rayon yarns (or threads) surrounded by a electroconductive coating and/or layer made from aluminum, aluminum alloy, carbon nanotubes, graphene, liquid metal, magnesium, copper, copper alloy, gold, nickel, polyaniline, silver, or steel.

In an example, an electromagnetic energy pathway can comprise a flexible non-conductive layer whose top and bottom sides are covered by electroconductive coatings and/or layers. In an example, an electromagnetic energy pathway can comprise a flexible non-conductive layer made from acetate, acrylic, cotton, denim, elastane, Kevlar, latex, linen, Lycra™, neoprene, nylon, polyester, wool, silicone (e.g. polydimethylsiloxane), silk, spandex, or rayon whose top and bottom sides are covered by electroconductive coatings and/or layers made from aluminum, aluminum alloy, carbon nanotubes, graphene, liquid metal, magnesium, copper, copper alloy, gold, nickel, polyaniline, silver, or steel.

In an example, an electromagnetic energy pathway can comprise a flexible electroconductive core surrounded by a non-conductive coating and/or layer. In an example, an electromagnetic energy pathway can comprise: a flexible electroconductive core made from aluminum, aluminum alloy, carbon nanotubes, graphene, liquid metal, magnesium, copper, copper alloy, gold, nickel, polyaniline, silver, or steel surrounded by a non-conductive coating and/or layer made from acetate, acrylic, cotton, denim, elastane, Kevlar, latex, linen, Lycra™, neoprene, nylon, polyester, wool, silicone (e.g. polydimethylsiloxane), silk, spandex, or rayon.

In an example, an electromagnetic energy pathway can comprise a fluid electroconductive material within a flexible non-conductive lumen. In an example, an electromagnetic energy pathway can comprise: a fluid electroconductive material selected from the group consisting of aluminum, aluminum alloy, carbon nanotubes, graphene, liquid metal, magnesium, copper, copper alloy, gold, nickel, polyaniline, silver, or steel with a flexible non-conductive lumen made from acetate, acrylic, cotton, denim, elastane, Kevlar, latex, linen, Lycra™, neoprene, nylon, polyester, wool, silicone (e.g. polydimethylsiloxane), silk, spandex, or rayon.

In an example, an electromagnetic energy pathway can comprise a braided electroconductive core surrounded by a non-conductive coating and/or layer. In an example, an electromagnetic energy pathway can comprise: a braided electroconductive core made from aluminum, aluminum alloy, carbon nanotubes, graphene, magnesium, copper, copper alloy, gold, nickel, polyaniline, silver, or steel wires surrounded by a non-conductive coating and/or layer made from acetate, acrylic, cotton, denim, elastane, Kevlar, latex, linen, Lycra™, neoprene, nylon, polyester, wool, silicone (e.g. polydimethylsiloxane), silk, spandex, or rayon.

In an example, an electromagnetic energy pathway can comprise a flexible electroconductive layer whose top and bottom sides are covered by non-conductive coatings and/or layers. In an example, an electromagnetic energy pathway can comprise a flexible electroconductive layer made from aluminum, aluminum alloy, carbon nanotubes, graphene, liquid metal, magnesium, copper, copper alloy, gold, nickel, polyaniline, silver, or steel whose top and bottom sides are covered by non-conductive coatings and/or layers made from acetate, acrylic, cotton, denim, elastane, Kevlar, latex, linen, Lycra™, neoprene, nylon, polyester, wool, silicone (e.g. polydimethylsiloxane), silk, spandex, or rayon.

In an example, an electromagnetic energy pathway can comprise a braided core of electroconductive and non-conductive longitudinal members surrounded by a non-conductive braided layer. In an example, an electromagnetic energy pathway can comprise: a braided core of one or more electroconductive longitudinal members and one or more non-conductive longitudinal members; and a braided layer of one or more non-conductive longitudinal members surrounding the braided core; wherein the electroconductive longitudinal members are made from aluminum, aluminum alloy, carbon nanotubes, graphene, liquid metal, magnesium, copper, copper alloy, gold, nickel, polyaniline, silver, or steel; and wherein the non-conductive longitudinal members are made from acetate, acrylic, cotton, denim, elastane, Kevlar, latex, linen, Lycra™, neoprene, nylon, polyester, wool, silicone (e.g. polydimethylsiloxane), silk, spandex, or rayon.

In an example, an electromagnetic energy pathway can be created by braiding a non-conductive material and a conductive material together. In an example, an electromagnetic energy pathway can comprise a three-way braid of non-conductive thread, yarn, or fiber and conductive thread, yarn, or fiber. In an example, the non-conductive material can be selected from the group consisting of: acetate, acrylic, cotton, denim, elastane, Kevlar, latex, linen, Lycra™, neoprene, nylon, nylon, polyester, polymer, rayon, wool, silicone (e.g. polydimethylsiloxane), silk, and spandex. In an example, the conductive material can be selected from the group consisting of: aluminum or aluminum alloy; carbon nanotubes, graphene, or other carbon-based material; magnesium; ceramic particles; copper or copper alloy; gold; liquid metal; nickel; polyaniline; silver; and steel.

In an example, an electromagnetic energy pathway can be created by weaving a non-conductive material and a conductive material together. In an example, an electromagnetic energy pathway can comprise a weft and warp weave of non-conductive thread, yarn, or fiber and conductive thread, yarn, or fiber. In an example, the non-conductive material can be selected from the group consisting of: acetate, acrylic, cotton, denim, elastane, Kevlar, latex, linen, Lycra™, neoprene, nylon, nylon, polyester, polymer, rayon, wool, silicone (e.g. polydimethylsiloxane), silk, and spandex. In an example, the conductive material can be selected from the group consisting of: aluminum or aluminum alloy; carbon nanotubes, graphene, or other carbon-based material; magnesium; ceramic particles; copper or copper alloy; gold; liquid metal; nickel; polyaniline; silver; and steel.

In an example, an electromagnetic energy pathway can be created by coating or impregnating a non-conductive material with a conductive material. In an example, the non-conductive material can be selected from the group consisting of: acetate, acrylic, cotton, denim, elastane, Kevlar, latex, linen, Lycra™, neoprene, nylon, nylon, polyester, polymer, rayon, wool, silicone (e.g. polydimethylsiloxane), silk, and spandex. In an example, the conductive material can be selected from the group consisting of: aluminum or aluminum alloy; carbon nanotubes, graphene, or other carbon-based material; magnesium; ceramic particles; copper or copper alloy; gold; liquid metal; nickel; polyaniline; silver; and steel.

In an example, an electromagnetic energy pathway can be created by printing a conductive material onto non-conductive material. In an example, the non-conductive material can be selected from the group consisting of: acetate, acrylic, cotton, denim, elastane, Kevlar, latex, linen, Lycra™, neoprene, nylon, nylon, polyester, polymer, rayon, wool, silicone (e.g. polydimethylsiloxane), silk, and spandex. In an example, the conductive material can be selected from the group consisting of: aluminum or aluminum alloy; carbon nanotubes, graphene, or other carbon-based material; magnesium; ceramic particles; copper or copper alloy; gold; liquid metal; nickel; polyaniline; silver; and steel.

In an example, an electromagnetic energy pathway can be created by filling a hollow non-conductive member with a conductive material. In an example, a hollow non-conductive member can be filled with a liquid conductive material. In an example, a hollow non-conductive member can be filled with a braid of conductive threads, yarns, or fibers. In an example, a braid of conductive threads, yarns, or fibers can be coated with non-conductive material. In an example, a braid of conductive threads, yarns, or fibers can be surrounded with a braid of non-conductive material. In an example, a hollow non-conductive member can be made from a material selected from the group consisting of: acetate, acrylic, cotton, denim, elastane, Kevlar, latex, linen, Lycra™, neoprene, nylon, nylon, polyester, polymer, rayon, wool, silicone (e.g. polydimethylsiloxane), silk, and spandex. In an example, the conductive material can be selected from the group consisting of: aluminum or aluminum alloy; carbon nanotubes, graphene, or other carbon-based material; magnesium; ceramic particles; copper or copper alloy; gold; liquid metal; nickel; polyaniline; silver; and steel.

In an example, a wearable deformable resistive sensor for measuring changes in body joint configuration can comprise: a deformable elongate electrically-conductive structure which is configured to span from a portion of a person's body which is proximal relative to a body joint to a portion of the person's body which is distal relative to the body joint, wherein proximal means closer to the person's heart and distal means farther from the person's heart when the person's body is in Vitruvian man configuration; an electromagnetic energy emitter which emits electromagnetic energy into the deformable elongate electrically-conductive structure at a first location; an electromagnetic energy receiver which receives electromagnetic energy from the deformable elongate electrically-conductive structure at a second location, wherein changes in body joint configuration cause deformations of the deformable elongate electrically-conductive structure, and wherein these deformations cause changes the transmission of electromagnetic energy from the electromagnetic energy emitter to the electromagnetic energy receiver; and a data processor, wherein the changes in the transmission of electromagnetic energy are analyzed by the data processor to measure and/or model changes in body joint configuration.

In an example, a wearable deformable resistive sensor for measuring changes in body joint configuration can comprise: a deformable nonconductive elongate lumen which is configured to span from a portion of a person's body which is proximal relative to a body joint to a portion of the person's body which is distal relative to the body joint, wherein proximal means closer to the person's heart and distal means farther from the person's heart when the person's body is in Vitruvian man configuration; an electrically-conductive flowable substance inside the deformable nonconductive elongate lumen; an electromagnetic energy emitter which emits electromagnetic energy into the electrically-conductive flowable substance at a first location; an electromagnetic energy receiver which receives electromagnetic energy from the electrically-conductive flowable substance at a second location, wherein changes in body joint configuration cause deformations of the deformable nonconductive elongate lumen, and wherein these deformations cause changes the transmission of electromagnetic energy from the electromagnetic energy emitter to the electromagnetic energy receiver; and a data processor, wherein the changes in the transmission of electromagnetic energy are analyzed by the data processor to measure and/or model changes in body joint configuration.

In an example, changes in the transmission of electromagnetic energy can be changes in the electrical resistance of a sensor. In an example, changes in the transmission of electromagnetic energy can be changes the electrical conductivity of a sensor. In an example, deformation of a sensor can include bending, compression, stretching, and twisting motions which are associated with changes in trans-joint pitch, trans-joint yaw, and trans-joint roll.

In an example, a wearable sensor can function as a capacitor. With an innovatively-designed sensor, changes in trans-joint pitch, yaw, and roll change the capacitance of the sensor in different ways. This enables measurement of the pitch, yaw, and roll of the joint which is spanned by the sensor. In an example, a multi-layer deformable capacitive sensor can have upper and lower conductive layers which are separated by a dielectric layer. These upper and lower conductive layers can function as electrode plates with an electromagnetic field between them. In an example, upper and lower conductive layers can overlap. Deformation of the sensor by movement of the underlying joint changes the sensor's capacitance. Sensor deformation can include bending, compression, stretching, and twisting which are associated with changes in trans-joint pitch, trans-joint yaw, and trans-joint roll. Changes in the sensor's capacitance can then be analyzed in order to measure and model joint motion.

In an example, a wearable multi-layer deformable joint-spanning capacitive sensor for measuring human motion can comprise: a first deformable electrically-conductive layer which is configured to span from a portion of a person's body which is proximal relative to a body joint to a portion of the person's body which is distal relative to the body joint, wherein proximal means closer to the person's heart and distal means farther from the person's heart when person's body is in Vitruvian man configuration (per the famous drawing by Leonardo da Vinci); a second deformable electrically-conductive layer which is configured to span from the portion of the person's body which is proximal relative to the body joint to the portion of the person's body which is distal relative to the body joint; a deformable dielectric layer between the first deformable electrically-conductive layer and the second deformable electrically-conductive layer, wherein changes in the configuration of the body joint cause deformations of the deformable dielectric layer, and wherein deformations of the deformable dielectric layer cause changes the capacitance between the first and second deformable electrically-conductive layers; and a data processor, wherein the changes in the capacitance between the first and second deformable electrically-conductive layers are analyzed by the data processor in order to measure and/or model changes in body joint configuration.

In an example, a deformable sensor for measuring changes in body joint configuration can be configured to be directly attached to a person's body. In an example, a deformable sensor can be integrated into an article of clothing or clothing accessory which is configured to be worn on a person's body. In an example, a deformable sensor can comprise a layer, strip, strap, patch, band, sleeve, fluid channel, yarn, wire, or thread of conductive material which is configured to be worn on a person's body.

In an example, a deformable sensor for measuring changes in body joint configuration can comprise multiple conductive layers, strips, straps, patches, bands, sleeves, fluid channels, yarns, wires, or threads which are configured to be worn on a person's body with different orientations. In an example, a deformable sensor can comprise multiple conductive layers, strips, straps, patches, bands, sleeves, fluid channels, yarns, wires, or threads which are configured to be worn on a person's body with different configurations. In an example, a deformable sensor for measuring changes in body joint configuration can comprise multiple conductive layers, strips, straps, patches, bands, sleeves, fluid channels, yarns, wires, or threads with different lengths. In an example, a deformable sensor can comprise multiple conductive layers, strips, straps, patches, bands, sleeves, fluid channels, yarns, wires, or threads with different cross-sectional or longitudinal sizes.

In an example, a deformable sensor can comprise multiple conductive layers, strips, straps, patches, bands, sleeves, fluid channels, yarns, wires, or threads with different cross-sectional or longitudinal shapes. In an example, the shape a deformable sensor can be selected from the group consisting of: rectangular or rounded rectangle; elliptical or oval; trapezoidal, keystone, tapered, and/or triangular; hexagonal; hour-glass or figure eight shape; tear drop or egg shape; convex lens shape; sinusoidal and/or oscillating shape; wagon wheel or star-burst configuration; and circular. In an example, a deformable sensor can have a proximal-to-distal length within a range of 1-14 inches. In an example, a deformable sensor can have a width within a range of ⅛ to 5 inches. In an example, a deformable sensor can have a thickness within the range of 1/64 to ¼ of an inch.

In an example, a deformable sensor for measuring human motion can span the surface of a body member which contains a human joint. In an example, a sensor can span a human body joint in a longitudinal manner, from a proximal portion of the joint to a distal portion of a joint. In an example, a sensor can comprise conductive yarn or fabric which is coated with non-conductive elastomeric material. In an example, a sensor can comprise a conductive yarn or fabric which is encapsulated within non-conductive elastomeric material. In an example, a sensor can comprise conductive yarn or fabric which is coated with silicone or encapsulated within silicone. In an example, a sensor can comprise conductive yarn or fabric which is coated with polydimethylsiloxane (PDMS) or encapsulated within polydimethylsiloxane (PDMS).

In an example, a layer of a deformable sensor for measuring human motion can comprise conductive yarn or fabric which is coated with non-conductive elastomeric material. In an example, a sensor layer can comprise conductive yarn or fabric which is encapsulated within non-conductive elastomeric material. In an example, a sensor layer can comprise conductive yarn or fabric which is coated with silicone or encapsulated within silicone. In an example, a sensor layer can comprise conductive yarn or fabric which is coated with polydimethylsiloxane (PDMS) or encapsulated within polydimethylsiloxane (PDMS).

In an example, a wearable sensor with one or more elongate deformable conductive structures can be made from a material selected from the group consisting of: siloxane [e.g. polydimethyl siloxane (PDMS)], polylactic-co-glycolic, polyphthalamide, polychloroprene, and polyethylene (e.g. polyethylene dioxythiophene, polyethylene glycol (PEG), polyethylene oxide, polyethylene terephthalate (PET), polyethylenedioxythiophene, polyethyleneoxide, polyethylene-styrene). In an example, a wearable sensor with one or more elongate deformable conductive structures can be made from a material selected from the group consisting of: polyphenylene, polySiloxane, polystyrene-butadiene-styrene, polyethyl, polyphosphazene, polyether-imide, polypropylene (e.g. oxide), polybutylene, polystyrene (PST), polydioxanone, and polylactide.

In an example, conductive yarn can comprise yarn which is coated or impregnated with conductive material. In an example, conductive fabric can be woven with metal-coated or metal-impregnated yarn. In an example, fabric can be coated with metal after weaving. In an example, conductive yarn can comprise yarn which is coated or impregnated with aluminum, carbon, copper, gold, nickel, or silver. In an example, conductive fabric can coated or impregnated with aluminum, carbon, copper, gold, nickel, or silver after the fabric has been woven. In an example, a sensor can comprise yarn which is braided with conductive wires and then coated with (or encapsulated within) elastomeric material such as silicone.

In an example, a sensor can comprise nonconductive yarn or fabric which is encapsulated within conductive elastomeric material. In an example, a sensor can comprise a nonconductive yarn or fabric which is coated with or encapsulated within metal-doped silicone. In an example, a sensor can comprise nonconductive yarn or fabric which is coated with or encapsulated within metal-doped polydimethylsiloxane (PDMS). In an example, a sensor can comprise nonconductive yarn or fabric which is coated with or encapsulated within PDMS which has been doped with aluminum, copper, gold, nickel, or silver. In an example, a sensor can comprise a nonconductive yarn or fabric which is coated with or encapsulated within PDMS which has been doped with carbon.

In an example, a wearable sensor with one or more elongate deformable conductive structures can be made from a material selected from the group consisting of: wool, acrylic, Kevlar™, Lycra, nylon, polyester, silk, and cotton. In an example, a wearable sensor with one or more elongate deformable conductive structures can be made from a material selected from the group consisting of: silver, stainless steel, copper (e.g. bromide, chloride, oxide), aluminum, carbon (e.g. black, fibers, nanotubes, polyimide), platinum, gold, and nickel.

In an example, a sensor layer can comprise nonconductive yarn or fabric which is encapsulated within conductive elastomeric material such as metal-doped silicone. In an example, a sensor layer can comprise nonconductive yarn or fabric which is coated with or encapsulated within metal-doped polydimethylsiloxane (PDMS). In an example, a sensor layer can comprise nonconductive yarn or fabric which is coated with or encapsulated within PDMS which has been doped with aluminum, copper, gold, nickel, silver, or carbon.

In an example, a deformable sensor for measuring human motion can comprise a parallel array of conductive yarns or threads within nonconductive elastomeric material such as silicone. In an example, a deformable sensor for measuring human motion can comprise an array of conductive yarns or threads within different orientations which is embedded within nonconductive elastomeric material such as silicone. In an example, a deformable sensor for measuring human motion can comprise a perpendicular array of conductive yarns or threads which is embedded within nonconductive elastomeric material such as silicone. In an example, a deformable sensor for measuring human motion can comprise a triangle-forming mesh of conductive yarns or threads which is embedded within nonconductive elastomeric material such as silicone. In an example, a deformable sensor for measuring human motion can comprise a hexagon-forming mesh of conductive yarns or threads which is embedded within nonconductive elastomeric material such as silicone.

In an example, a deformable sensor for measuring human motion can comprise a parallel array of undulating, sinusoidal, and/or helical wires within nonconductive elastomeric material such as silicone. In an example, these wires can have different orientations. In an example, a deformable sensor for measuring human motion can comprise a perpendicular array of undulating, sinusoidal, and/or helical wires which is embedded within nonconductive elastomeric material such as silicone. In an example, a deformable sensor for measuring human motion can comprise a triangle-forming mesh of undulating, sinusoidal, and/or helical wires which is embedded within nonconductive elastomeric material such as silicone. In an example, a deformable sensor for measuring human motion can comprise a hexagon-forming mesh of undulating, sinusoidal, and/or helical wires which is embedded within nonconductive elastomeric material such as silicone.

In an example, a deformable sensor for measuring human motion can comprise a parallel array of conductive-fluid-filled channels or lumens within nonconductive elastomeric material such as silicone. In an example, these channels or lumens can have different orientations. In an example, a deformable sensor for measuring human motion can comprise a perpendicular array of conductive-fluid-filled channels or lumens which is embedded within nonconductive elastomeric material such as silicone. In an example, a deformable sensor for measuring human motion can comprise a triangle-forming mesh of conductive-fluid-filled channels or lumens which is embedded within nonconductive elastomeric material such as silicone. In an example, a deformable sensor for measuring human motion can comprise a hexagon-forming mesh of conductive-fluid-filled channels or lumens which is embedded within nonconductive elastomeric material such as silicone.

In an example, a wearable capacitive sensor for measuring human motion can have a conductive layer comprising an array of nonconductive yarn (e.g. cotton, polymer, silk, or wool yarn) which is encapsulated within elastomeric material such as polydimethylsiloxane which has been doped with conductive material (e.g. aluminum, carbon, copper, gold, nickel, or silver particles). In an example, a conductive layer can comprise an elastomeric material such as polydimethylsiloxane which has been doped with gallium and indium. In an example, a sensor can include nonconductive woven fabric which is encapsulated within or coated with conductive elastomeric material.

In an example, a sensor for measuring human motion can comprise conductive yarns which are woven together. In an example, these yarns can be elastic. In an example, conductive yarns can be woven together into a stretchable and/or elastic fabric or textile. In an example, a sensor for measuring human motion can comprise conductive elastic fabric which has been coated with (or encapsulated within) elastomeric material such as polydimethylsiloxane (PDMS). In an example, a sensor can comprise an elastomeric material which is embedded with a stretchable conductive fabric or textile. In an example, a stretchable conductive fabric can be encapsulated within elastomeric material.

In an example, a sensor for measuring human motion can include a conductive fabric which is made using a plain weave, satin weave, twill weave, or leno weave. In an example, this fabric can be woven using yarns and/or threads which have been coated or impregnated with aluminum, carbon, copper, gold, nickel, or silver. In an example, a sensor for measuring human motion can comprise conductive yarns which are separate from each other. In an example, a sensor can comprise conductive yarns which are braided together. In an example, a sensor can comprise yarns and wires which are woven together. In an example, a sensor can comprise yarns and wires which are braided together.

In an example, a sensor can comprise a woven array of yarns or threads, wherein less than half of the yarns or threads are electrically-conductive. In an example, between 10% and 25% of the mass of fabric can comprise conductive material. In an example, between 20% and 50% of the mass of fabric can comprise conductive material. In an example, between 10% and 25% of the yarns used to make fabric can be conductive and the rest of the yarns can be nonconductive. In an example, between 20% and 50% of the yarns used to make fabric can be conductive and the rest of the yarns can be nonconductive. In an example, between 10% and 25% of the mass of fabric can comprise undulating wires. In an example, between 20% and 50% of the mass of fabric can comprise undulating wires.

In an example, a deformable sensor for measuring human motion which spans a human joint can include two conductive layers made with elastomeric material, each of which contains a conductive fabric. In an example, there can be three conductive layers. In an example, a capacitive multi-layer deformable sensor for measuring human motion which spans a human joint can include upper and lower elastomeric layers, each of which contains a conductive yarns, threads, or undulating wires.

In an example, conductive woven fabric can comprise a first set of yarns with a first orientation which are conductive and a second set of yarns with a second orientation which are not conductive. In an example, the first and second sets of yarns can be substantially perpendicular to each other. In an example, both sets of yarns can be conductive. In an example, a sensor can comprise an elastomeric material structure containing a woven perpendicular array of yarns, wherein less than half of the yarns are electrically-conductive. In an example, a sensor can comprise an elastomeric polymer which is which contains an array of parallel conductive elastic yarns.

In an example, a deformable sensor for measuring human motion can comprise one or more strips or straps of elastomeric material which encapsulates conductive fabric. In an example, these strips or straps can be configured to have different orientations relative to the longitudinal axis of an underlying human joint. In an example, a first strip or strap can be parallel to the longitudinal axis of an underlying human joint and a second strip or strap can be perpendicular to the longitudinal axis of an underlying human joint. In an example, a first strip or strap can span an underlying human joint in a longitudinal manner and a second strip or strap can encircle a human joint in a circumferential manner. In an example, the longitudinal axis of a first strip or strap can span an underlying human joint in a longitudinal manner, the longitudinal axis of a second strip or strap can intersect the longitudinal axis of the first strip or strap at an acute angle, and the longitudinal axis of a third strip or strap can intersect the longitudinal axis of the second strip or strap at an acute angle.

In an example, a deformable sensor for measuring human motion can comprise one or more strips or straps of elastomeric material which has been doped with conductive particles. In an example, these strips or straps of doped elastomeric material can be configured to have different orientations relative to the longitudinal axis of an underlying human joint. In an example, a first strip or strap can be parallel to the longitudinal axis of an underlying human joint and a second strip or strap can be perpendicular to the longitudinal axis of an underlying human joint. In an example, a first strip or strap can span an underlying human joint in a longitudinal manner and a second strip or strap can encircle a human joint in a circumferential manner. In an example, the longitudinal axis of a first strip or strap can span an underlying human joint in a longitudinal manner, the longitudinal axis of a second strip or strap can intersect the longitudinal axis of the first strip or strap at an acute angle, and the longitudinal axis of a third strip or strap can intersect the longitudinal axis of the second strip or strap at an acute angle.

In an example, a deformable sensor for measuring human motion which spans a human joint can comprise at least one elastomeric layer which is embedded with conductive yarns or fibers, wherein these yarns or fibers have different levels of electromagnetic resistance, different levels or proportions of impregnation or coating with metal particles, and/or different levels of electromagnetic conductivity. In an example, yarns or fibers closer to the center of a sensor can have greater resistance than yarns or fibers farther from the center of the sensor. In an example, yarns or fibers farther from the center of the sensor can have greater resistance than yarns or fibers closer to the center of the sensor.

In an example, a deformable sensor for measuring human motion which spans a human joint can comprise at least one elastomeric layer which is embedded with a plurality of conductive yarns or fibers. In an example, a deformable sensor for measuring human motion which spans a human joint can comprise upper and lower elastomeric layers which are embedded with a plurality of conductive yarns or fibers. In an example, the sensor can be elongate with a central longitudinal axis which spans the surface of the body containing the joint. In an example, different yarns or fibers embedded in the sensor can cross the central longitudinal axis of the sensor at different angles. In an example, a sensor can comprise at least one elastomeric layer which is embedded with a plurality of conductive fabric strips. In an example, different strips can cross the central longitudinal axis of the sensor at different angles.

In an example, a deformable sensor for measuring human motion can comprise a plurality of elastomeric conductive strips, bands, or patches with different shapes. In an example, the shapes of elastomeric conductive strips, bands, or patches of conductive elastomeric material in a plurality of strips, band, or patches can be selected from the group consisting of: rectangular; rounded rectangle; elliptical; oval; tapered; hour glass shape; and cylindrical. In an example, a plurality of conductive strips, bands, or patches can have longitudinal axes which converge in a proximal-to-distal direction. In an example, a plurality of conductive strips, bands, or patches can have longitudinal axes which converge in a distal-to-proximal direction. In an example, a plurality of conductive strips, bands, or patches can have converging centers and diverging ends. In an example, a plurality of conductive strips, bands, or patches can have converging ends and diverging centers.

In an example, a deformable sensor for measuring human motion which spans a human joint can include at least one conductive layer comprising a strip or patch of conductive fabric which is coated by, or encapsulated within, elastomeric (e.g. silicone-based) material. In an example, a sensor can comprise a radially-extending (e.g. starburst) array of conductive fabric strips which are encapsulated within an elastomeric (e.g. silicone-based) material. In an example, a deformable sensor for measuring human motion which longitudinally spans a human joint can include at least one conductive layer comprising elastomeric material which is embedded with an array of arcuate or serpentine wires. In an example, a sensor can comprise an elastomeric material which is embedded with an array of undulating, sinusoidal, and/or helical nanowires.

In an example, a deformable sensor for measuring human motion which longitudinally spans a human joint can include at least one conductive layer which contains braids of yarn (e.g. cotton, rayon, polyester, nylon, silk, and/or wool) and wire (e.g. aluminum, copper, gold, nickel, or silver). In an example, a deformable sensor for measuring human motion which longitudinally spans a human joint can include at least one conductive layer comprising an elastomeric material (such as silicone) embedded with braids of yarn (e.g. cotton, rayon, polyester, nylon, silk, and/or wool) and wire (e.g. aluminum, copper, gold, nickel, or silver). In an example, a deformable sensor for measuring human motion which longitudinally spans a human joint can include two conductive layers comprising an elastomeric material (such as silicone) embedded with braids of yarn (e.g. cotton, rayon, polyester, nylon, silk, and/or wool) and wire (e.g. aluminum, copper, gold, nickel, or silver).

In an example, a deformable sensor for measuring human motion which spans a human joint can include at least one conductive layer comprising an array of undulating (parallel) wires which are embedded in elastomeric material (such as silicone). In an example, a sensor can comprise an array of nested helical wires. In an example, a sensor for measuring human motion can comprise an array of serpentine or zigzagging wires. In an example, this array of wires can be embedded in elastomeric material such as silicone. In an example, a sensor can comprise an array of longitudinally-diverging wires. In an example, a sensor can comprise an array of radially-extending (e.g. spoke-like) wires. In an example, different wires in a sensor can have different levels of resistance or conductivity.

In an example, a deformable sensor for measuring human motion which spans a human joint can include at least one conductive layer comprising an elastomeric material (such as silicone) which is embedded with an array of electrically-conductive pathways, such as conductive threads, metal wires, or lumens filled with conductive fluid. In an example, these conductive pathways can be configured in a parallel, perpendicular, radially-extending (e.g. starburst), or longitudinally-diverging array. In an example, conductive pathways can have undulating, sinusoidal, and/or helical shapes.

In an example, a wearable sensor with one or more elongate deformable conductive structures can be made from a material selected from the group consisting of: graphite, graphene, silicone, BPDA-ODA, acrylonitrile, protonated polyethylene oxide amine, and polmethacrolein. In an example, a wearable sensor with one or more elongate deformable conductive structures can be made from a material selected from the group consisting of: PFOE, tetrafluoroethylene, hexafluoropropylene (PVDF-HFP), tetrahydrofuran, ethylene, and trifluoroethylene.

In an example, a deformable sensor for measuring human motion which spans a human joint can include at least one conductive layer comprising an elongate elastomeric strip or patch which is embedded with wavy wires. In an example, these wires can have longitudinal axes which are substantially parallel or perpendicular to the longitudinal axis of the strip or patch. In an example, these wires can have longitudinal axes which diverge in a proximal-to-distal (or distal-to-proximal) direction. In an example, a deformable sensor for measuring human motion which spans a human joint can include at least one conductive layer comprising an elastomeric material which is impregnated and/or doped with aluminum, carbon, copper, gold, nickel, or silver particles, powder, or fibers.

In an example, a deformable sensor for measuring human motion which spans a human joint can include at least one conductive layer comprising an elastomeric polymer which is embedded with undulating, sinusoidal, or helical metal wires, conductive fibers, conductive yarns, or lumens filled with conductive fluid. In an example, a deformable sensor for measuring human motion which spans a human joint can include upper and lower conductive layers with a dielectric layer between them. Each of the conductive layers can comprise an elastomeric polymer which is embedded with undulating, sinusoidal, or helical metal wires, conductive fibers, conductive yarns, or lumens filled with conductive fluid.

In an example, a deformable sensor for measuring human motion which spans a human joint can include at least one conductive layer comprising an elongate elastomeric strip or patch which is embedded with multiple elongate conductive yarns. These yarns can have longitudinal axes which are substantially parallel or perpendicular to the longitudinal axis of the strip or patch. In an example, approximately half of these yarns can have longitudinal axes which are substantially parallel to the longitudinal axis of the strip or patch and approximately half of these yarns have longitudinal axes which are substantially perpendicular to the longitudinal axis of the strip or patch. In an example, yarns can have longitudinal axes which diverge in a proximal-to-distal (or distal-to-proximal) direction.

In an example, a conductive layer of a deformable sensor for measuring human motion which spans a human joint can have non-uniform thickness. In an example, the proximal end of a conductive layer can be thicker than its distal end, or vice versa. In an example, the central portion of a conductive layer can be thicker than its ends, or vice versa. In an example, a dielectric layer of a deformable sensor for measuring human motion which spans a human joint can have non-uniform thickness. In an example, the proximal end of a dielectric layer can be thicker than its distal end, or vice versa. In an example, the central portion of a dielectric layer can be thicker than its ends, or vice versa.

In an example, a sensor for measuring human motion can have non-uniform conductivity. For example, elastomeric material can have with non-uniform doping. In an example, there can be longitudinal variation in the amount of doping with conductive particles. In an example, the proximal end of a sensor can be more conductive than the distal end of the sensor, or vice versa. In an example, a central portion of a sensor for measuring human motion can be more conductive than either the proximal end or the distal end, or vice versa. In an example, a deformable sensor for measuring human motion which spans a human joint can include at least one conductive layer comprising carbon nanotubes or carbon black particle embedded in an elastomeric material such silicone or polydimethylsiloxane (PDMS). In an example, a deformable sensor for measuring human motion which spans a human joint can include at least one elastomeric (e.g. silicone-based) layer with conductive channels doped with carbon, silver, aluminum, or copper. In an example, a deformable sensor for measuring human motion which spans a human joint can include at least one elastomeric (e.g. silicone-based) layer with conductive channels doped with gallium and indium.

In an example, a wearable sensor with one or more elongate deformable conductive structures can be made from a material selected from the group consisting of: polyetheretherketone, polymethacrylamid, polyamide, polyol, polysulfone, polyacrylic, polyisobutylene, polyoxypropylene, polypyrrole, polyarylate, polyhydroxyvalerate, polynorbornene, and polyolefin. In an example, a wearable sensor with one or more elongate deformable conductive structures can be made from a material selected from the group consisting of: polytetrabutylene terephthalate, polyacetylene, polyisoprene, polyctric poly-L-lactic acid (PLLA), polylactic acid, polysilicon, and polybutadiene. In an example, a wearable sensor with one or more elongate deformable conductive structures can be made from a material selected from the group consisting of: polyadipamide, polynucleotide, polyketone, polyphenilacetylene, polysilane, and polyoctene.

In an example, a deformable sensor can include at least one conductive layer comprising an elastomeric polymer embedded with a convex array of conductive wires, yarns, and/or threads. In an example, a sensor can comprise a longitudinally-diverging array of conductive wires, yarns, and/or threads. In an example, a sensor can comprise an array of parallel conductive wires, yarns, and/or threads. In an example, a sensor can comprise an array of perpendicular conductive wires, yarns, and/or threads. In an example, a sensor can comprise a radially-diverging (e.g. spoke-like) array of conductive wires, yarns, and/or threads. In an example, a deformable sensor can include a convex array of lumens filled with a conductive flowable substance. In an example, a sensor can comprise a parallel, longitudinally-diverging, or radially-diverging (e.g. spoke-like) array of conductive-fluid-filled lumens.

In an example, a deformable sensor for measuring human motion which spans a human joint can include at least one conductive layer comprising silicone which encapsulates metal-coated fabric. In an example, a deformable sensor for measuring human motion which spans a human joint can include upper and lower conductive layers, each of which comprises silicone embedded with metal-coated fabric. In an example, a sensor can comprise silicone which is embedded with metal-coated or metal-impregnated yarns and/or threads. In an example, these yarns or threads can have undulating, sinusoidal, or helical shapes. In an example, these yarns or threads can be woven together. In an example, these yarns or threads can be braided together. In an example, a mixture of conductive and nonconductive yarns or threads can be woven or braided together. In an example, a mixture of conductive wires (e.g. aluminum, copper, gold, nickel, or silver wires) and nonconductive yarns or threads (e.g. cotton, wool, rayon, nylon, or silk yarns or threads) can be woven or braided together and then encapsulated in silicone.

In an example, a deformable sensor for measuring human motion which spans a human joint can include at least one conductive layer comprising a silicone-based material which is embedded with strips of stretchable and/or elastic conductive fabric. In an example, this fabric can be woven from conductive yarn which is coated and/or impregnated with carbon, silver, copper, aluminum, or nickel particles. In an example, this fabric can be woven from conductive yarn which is coated and/or impregnated with aluminum, carbon, copper, gold, nickel, or silver. In an example, this fabric can be woven from conductive yarn in an undulating, sinusoidal, and/or helical configuration. In an example, a sensor for measuring human motion can comprise a silicone-based material which is embedded with arcuate segments of conductive fabric. In an example, these arcuate segments can be nested. In an example, a sensor for measuring human motion can comprise a silicone-based material which is embedded with squares or rhomboids of conductive fabric.

In an example, a deformable sensor for measuring human motion which spans a human joint can include at least one conductive layer comprising a silicone-based material which is embedded with conductive fabric or textile. In an example, a deformable sensor for measuring human motion which spans a human joint can include two substantially-parallel conductive layers which each comprise a silicone-based material which is embedded with conductive fabric or textile. In an example, the fabric or textile can be coated with metal particles. In an example, the fabric or textile can be made with conductive yarn or threads. In an example, approximately half of the yarns used to weave the fabric or textile can be conductive and approximately half can be nonconductive. In an example, a silicone-based material that has been impregnated or doped with metal particles can be used to coat or encapsulate nonconductive fabric. In an example, a deformable sensor for measuring human motion which spans a human joint can contain a planar array of conductive elastic yarns and/or threads. In an example, a sensor for measuring human motion can contain a concave or concave array of conductive elastic yarns and/or threads.

In an example, a wearable sensor with one or more elongate deformable conductive structures can be made from a material selected from the group consisting of: ethanol, vinylether series polymer block, Dtex, indium, dimethicone copolyol, chlorosulfonated polyethylene, peak, rubber, methanol, methacrylate, gallium, and vinylidene fluoride-hexafluoropropylene. In an example, a wearable sensor with one or more elongate deformable conductive structures can be made from a material selected from the group consisting of: alkyl polyethylene oxide, silicon, acetylene (e.g. acetylenic polyethylene oxide), PZT, hydrogen silsesquioxane (HSQ), zirconium silicon oxide, acetyl, and styrenebutadiene copolymer.

In an example, a deformable sensor for measuring human motion which spans a human joint can contain a planar array of wires embedded in elastomeric material. In an example, a sensor can contain a concave or concave array of wires. In an example, these wires can be undulating, sinusoidal, serpentine, or zigzagging. In an example, these wires can be elongate with parallel longitudinal axes. In an example, these wires can be elongate with perpendicular longitudinal axes. In an example, these wires can be nested, concentric, and/or coaxial. In an example, these wires can be elongate with diverging longitudinal axes. In an example, these wires can be elongate with radially-diverging (e.g. starburst or hub-and-spoke configured) longitudinal axes. In an example, a deformable sensor for measuring human motion which spans a human joint can include at least one conductive layer comprising silicone which is embedded with aluminum, carbon, copper, gold, nickel, or silver wires. In an example, these wires can be in a parallel, perpendicular, or longitudinally-diverging array.

In an example, a deformable sensor for measuring human motion which spans a human joint can comprise a silicone-based material which is embedded with a metal mesh. In an example, a deformable sensor for measuring human motion which spans a human joint can comprise a silicone-based material which is embedded with a polygonal metal mesh. In an example, a deformable sensor for measuring human motion which spans a human joint can comprise a silicone-based material which is embedded with a hexagonal metal mesh. In an example, a sensor can comprise a silicone-based material which is embedded with an array of metal strips or springs. In an example, these springs can be nested, concentric, and/or coaxial.

In an example, a deformable sensor for measuring human motion which spans a human joint (e.g. a strip, a pathway, or a lumen) can be made from silk, wool, cotton, polyester, or rayon yarns or threads which has been impregnated, coated, or braided with aluminum, carbon, copper, gold, graphene, or graphitic carbon nitride. In an example, a deformable conductive sensor, strip, or pathway can be made from silk, wool, cotton, polyester, or rayon yarns or threads which have been impregnated, coated, or braided with nickel, silver, steel, or tungsten diselenide.

In an example, a deformable sensor for measuring human motion which spans a human joint can be made from rhenium disulfide, phosphorene, black phosphorus, diselenide, silicene, germanene, PSS, or PEDOT which has been doped, impregnated, or embedded with aluminum, carbon, copper, gold, graphene, or graphitic carbon nitride. In an example, a deformable conductive sensor, strip, or pathway can be made from rhenium disulfide, phosphorene, black phosphorus, diselenide, silicene, germanene, PSS, or PEDOT which has been doped, impregnated, or embedded with hexagonal boron nitride, nickel, silver, steel, or tungsten diselenide.

In an example, a deformable sensor for measuring human motion which spans a human joint can be made from stanene, molybdenum disulfide, tinene, indium selenide, graphdiyne, or nanocellulose. In an example, a deformable sensor, strip, or pathway can be made from silicone, polydimethylsiloxane (PDMS), rubber, latex, polyurethane, antimonene, and polytetrafluoroethylene. In an example, a deformable conductive sensor, strip, or pathway can include aluminum, carbon, copper, gold, nickel, silver, steel, or tungsten wires. In an example, a deformable conductive sensor, strip, or pathway can comprise a braid of aluminum, carbon, copper, gold, nickel, silver, steel, or tungsten wires and silk, wool, cotton, polyester, and rayon yarns or threads.

In an example, a deformable sensor for measuring human motion which spans a human joint can be made with a material selected from the group consisting of: rhenium disulfide, phosphorene, graphane, black phosphorus, diselenide, silicene, germanene, PSS, and PEDOT. In an example, a deformable sensor, strip, or pathway can be made with material selected from the group consisting of: stanene, molybdenum disulfide, tinene, indium selenide, graphdiyne, hexagonal boron nitride, and nanocellulose. In an example, a deformable sensor, strip, or pathway can be made with a material selected from the group consisting of: silicone, polydimethylsiloxane (PDMS), rubber, latex, polyurethane, antimonene, and polytetrafluoroethylene.

In an example, a wearable sensor with one or more elongate deformable conductive structures can be made from a material selected from the group consisting of: polyaniline, polybutene, polybenzimidazole, polymethyl (e.g. polymethylacrylate, polymethylene, polymethylmethacrylate, polymethylmethacrylate (PMMA), polymethylpentene), polythiophene, polyhydroxyethylmethacrylate, polymide, and polyoxyethylene (e.g. alkyl ester, cetyl ether, lauryl ether, nonylphenyl ether, octyl ether, oleyl ether, sorbitan monolaurate, stearyl ether). In an example, a wearable sensor with one or more elongate deformable conductive structures can be made from a material selected from the group consisting of: polypyromellitic, polytetrafluoroethylene (PTFE), polyacrylonitrile, polyimide, and polyhydroxyalkanoate.

In an example, a central longitudinal axis of an elongate deformable conductive structure (e.g. a conductive strip, fiber, yarn, wire, ink path, lumen, or channel) can have a conic section shape. In an example, a sensor can comprise a central elongate deformable conductive structure which spans a body joint in a proximal-to-distal manner, a proximal array of diverging arcuate elongate deformable conductive structures, and a distal array of diverging arcuate elongate deformable conductive structures. In an example, a sensor can comprise a central elongate deformable conductive structure which spans a body joint in a proximal-to-distal manner, a proximal array of converging arcuate elongate deformable conductive structures, and a distal array of converging arcuate elongate deformable conductive structures. In an example, the end portion of a sensor can be shaped like a fork or trident.

In an example, an elongate deformable conductive structure can have a helical shape and encircle a body joint. In an example, the shape an elongate deformable conductive structure can be selected from the group consisting of: rectangular or rounded rectangle; elliptical or oval; conic section; trapezoidal, keystone, tapered, and/or triangular; hexagonal or octagonal; hour-glass or figure eight shape; tear drop or egg shape; convex lens shape; helical or spiral; sinusoidal and/or oscillating shape; carlavian curve shape; wagon wheel shape; star-burst shape; and circular. In an example, a sensor can have one or more oscillating (e.g. zigzag or sinusoidal shaped) elongate deformable conductive structures. In an example, a sensor can include elongate deformable conductive structures with a partial-sinusoidal-wave shape. In an example, an elongate deformable conductive structure can be concave. In an example, an elongate deformable conductive structure can be convex. In an example, a sensor can include a nested array of concave elongate deformable conductive structures. In an example, a sensor can include a nested array of convex elongate deformable conductive structures.

In an example, a wearable sensor for measuring changes in body joint configuration can include an array of least two parallel elongate deformable conductive structures (e.g. conductive strips, fibers, yarns, wires, ink paths, lumens, or channels). In an example, a wearable sensor for measuring changes in body joint configuration can comprise a middle elongate deformable conductive structure which is substantially parallel to a proximal-to-distal axis of a body joint and two lateral elongate deformable conductive structures which branch out from the center of the middle elongate deformable conductive structure and diverge from each other in a proximal-to-distal direction. When projected onto a common two-dimensional plane, a first elongate deformable conductive structure can cross the central proximal-to-distal axis of a body joint in a left-to-right diagonal manner, a second elongate deformable conductive structure can be substantially parallel to the central proximal-to-distal axis of the body joint, and a third elongate deformable conductive structure can cross the central proximal-to-distal axis of a body joint in a right-to-left diagonal manner.

In an example, a wearable sensor for measuring changes in body joint configuration can comprise a circumferential (or partially-circumferential) array of elongate deformable conductive structures, wherein each elongate deformable conductive structure in the circumferential (or partially circumferential) array has an elongated cross-sectional perimeter and wherein different elongate deformable conductive structures have cross-sectional axes with different orientations. In an example, a first set of elongate deformable conductive structures can have cross-sections with a first orientation and a second set of elongate deformable conductive structures can have cross-sections with a second orientation, wherein the first orientation and the second orientation differ by at least 20 degrees.

In an example, a wearable sensor for measuring changes in body joint configuration can comprise radial (spoke-like) elongate deformable conductive structures (e.g. conductive strips, fibers, yarns, wires, ink paths, lumens, or channels) which extend out in a radial manner from a common location. In an example, there can be proximal-vs.-distal symmetry with respect to their configuration. In an example, they can have left-vs.-right symmetry. In an example, two spokes can radiate in outward/proximal directions and two spokes can radiate in outward/distal directions. In an example, there can be four radiating elongate deformable conductive structures which radiate outward (two in a distal direction and two in a proximal direction) from a central location on a middle elongate deformable conductive structure.

In an example, a wearable sensor for measuring changes in body joint configuration can include elongate deformable conductive structures configured as spokes extending radially outward from a central location. In an example, a wearable sensor for measuring changes in body joint configuration can include elongate deformable conductive structures configured as radial spokes in a starburst pattern, an asterisk shape, a height-compressed asterisk shape, a wagon-wheel shape, and/or a bow-tie shape. In an example, a wearable sensor for measuring changes in body joint configuration can include elongate deformable conductive structures configured as radial spokes which collectively span between the 2 and 6 hours of clock positions of a star-burst pattern. In an example, there can be a plurality of electromagnetic energy emitters in electromagnetic communication with selected spokes of an asterisk-shaped elongate deformable conductive structure. In an example, there can be a plurality of electromagnetic energy receivers in electromagnetic communication with selected spokes of an asterisk-shaped elongate deformable conductive structure.

In an example, a wearable sensor for measuring changes in body joint configuration can include elongate deformable conductive structures configured as radial spokes which span between ⅙ and ½ of the full circular perimeter. In an example, a wearable sensor for measuring changes in body joint configuration can comprise a wagon-wheel cluster of elongate deformable conductive structures. A wagon-wheel cluster can comprise a ring of triangular or pie-slice-shaped electrically-elongate deformable conductive structures whose acute vertexes point toward a common center. In an example, the wagon-wheel cluster structure can further comprise a (circular) central dielectric core.

In an example, a plurality of elongate deformable conductive structures (e.g. conductive strips, fibers, yarns, wires, ink paths, lumens, or channels) can intersect at a location which is distal relative to their longitudinal midpoints. In an example, a plurality of elongate deformable conductive structures can intersect at a location which is proximal relative to their longitudinal mid-points. In an example, a plurality of elongate deformable conductive structures can intersect at their longitudinal mid-points. In an example, a plurality of elongate deformable conductive structures can diverge from one another as they span a body joint in a proximal-to-distal manner. In an example, a polygonal cluster or ring of elongate deformable conductive structures can comprise six elongate deformable conductive structures whose cross-sections form an octagon. In an example, a polygonal cluster or ring of elongate deformable conductive structures can comprise six elongate deformable conductive structures whose cross-sections form a hexagon.

In an example, a wearable sensor for measuring changes in body joint configuration can comprise an inner circumferential (or partially circumferential) array of elongate deformable conductive structures (e.g. conductive strips, fibers, yarns, wires, ink paths, lumens, or channels) and an outer circumferential (or partially circumferential) array of elongate deformable conductive structures. In an example, elongate deformable conductive structures in the inner and outer arrays can be separated by a dielectric layer. In an example, elongate deformable conductive structures in the inner and outer layers can overlap. In an example, elongate deformable conductive structures in the inner and outer layers can be staggered relative to each other.

In an example, elongate deformable conductive structures in an inner array can have the same circumferential locations as elongate deformable conductive structures in an outer array. In an example, elongate deformable conductive structures in an inner array can have different circumferential locations than elongate deformable conductive structures in an outer array. In an example, elongate deformable conductive structures in an inner array can be centered on the same compass coordinates as elongate deformable conductive structures in an outer array. In an example, elongate deformable conductive structures in an inner array can be centered on different same compass coordinates than elongate deformable conductive structures in an outer array.

In an example, a wearable sensor for measuring changes in body joint configuration can comprise a circumferential array of pairs of elongate deformable conductive structures which collectively span the entire circumference of the part of a person's body which contains a body joint. In an example, a wearable sensor for measuring changes in body joint configuration can comprise a partial circumferential array of pairs of elongate deformable conductive structures which collectively span only a portion of the circumference of the part of a person's body which contains a body joint. In an example, a partial circumferential array of pairs of elongate deformable conductive structures can collectively span between ⅛ and ½ of the circumference of the part of a person's body which contains a body joint. In an example, a partial circumferential array of pairs of elongate deformable conductive structures can collectively span between ¼ and ¾ of the circumference of the part of a person's body which contains a body joint.

In an example, pairs of elongate deformable conductive structures can be unevenly-distributed (e.g. unevenly-spaced) around the (partial) circumference of a body part. In an example, pairs of elongate deformable conductive structures can be evenly-distributed (e.g. evenly-spaced) around the (partial) circumference of a body part. In an example, a wearable sensor for measuring changes in body joint configuration can comprise twelve pairs of elongate deformable conductive structures, one centered on every 30-degree interval (e.g. 0, 30, 60, 90, 120, 150, 180, 210, 240, 270, 300 and 330 degrees) around this circumference. In an example, a wearable sensor for measuring changes in body joint configuration can comprise twelve pairs of elongate deformable conductive structures, one centered on each clock hour position, which collectively span this circumference. In an example, a wearable sensor for measuring changes in body joint configuration can comprise four pairs of elongate deformable conductive structures, one centered at every three-hour position (e.g. noon, 3 o'clock, 6 o'clock, and 9 o'clock). In an example, a wearable sensor for measuring changes in body joint configuration can comprise four pairs of elongate deformable conductive structures, one centered at every 90-degree interval (e.g. 0, 90, 180, and 270 degrees) around this circumference. In an example, a wearable sensor for measuring changes in body joint configuration can comprise six pairs of elongate deformable conductive structures, one centered at every two-hour position (e.g. noon, 2 o'clock, 4 o'clock, 6 o'clock, 8 o'clock, and 10 o'clock). In an example, a wearable sensor for measuring changes in body joint configuration can comprise six pairs of elongate deformable conductive structures, one centered at every 60-degree interval (e.g. 0, 60, 120, 180, 240, and 300 degrees) around the circumference.

In an example, a wearable sensor for measuring changes in body joint configuration can comprise: a first (e.g. outer) deformable electrically-conductive layer which is configured to span from a portion of a person's body which is proximal relative to a body joint to a portion of the person's body which is distal relative to the body joint; a second (e.g. inner) deformable electrically-conductive layer which is configured to span from the portion of the person's body which is proximal relative to the body joint to the portion of the person's body which is distal relative to the body joint; and a deformable dielectric layer between the first deformable electrically-conductive layer and the second deformable electrically-conductive layer. In an example, an elongate electrically-conductive layer can have a proximal-to-distal length within a range of 3-8 inches. In an example, an elongate electrically-conductive layer can have a proximal-to-distal length within a range of 1-14 inches.

In an example, a deformable electrically-conductive layer can have a shape selected from the group consisting of: rectangular or rounded rectangle; elliptical or oval; trapezoidal, keystone, tapered, and/or triangular; hexagonal or octagonal; hour-glass or figure eight shape; tear drop or egg shape; convex lens shape; sinusoidal and/or oscillating shape; carlavian curve shape; wagon wheel or star-burst configuration; and circular.

In an example, a multi-layer capacitive elongate deformable conductive structure (e.g. a conductive strip, fiber, yarn, wire, ink path, lumen, or channel) can comprise two conductive layers and a dielectric layer between the conductive layers. In an example, a multi-layer capacitive elongate deformable conductive structure can comprise three conductive layers and two non-conductive layers. In an example, a multi-layer capacitive elongate deformable conductive structure can comprise more than three layers, alternating between conductive and non-conductive layers. In an example, a multi-layer capacitive elongate deformable conductive structure can comprise three or more conductive layers with different orientations which are separated by two or more non-conductive layers.

In an example, an electrically-conductive layer can comprise electrically-conductive threads, yarns, wires, or fibers which are embedded within silicone and/or polydimethylsiloxane (PDMS). In an example, a deformable dielectric layer can comprise silicone and/or polydimethylsiloxane (PDMS). In an example, an electrically-conductive layer can comprise silicone and/or polydimethylsiloxane (PDMS) which has been impregnated and/or doped with electrically-conductive material such as aluminum, carbon, copper, gold, nickel, or silver particles or fibers.

In an example, a wearable sensor with one or more elongate deformable conductive structures can be made from a material selected from the group consisting of: polyparaphenylene, polypyrrole, polysulfide rubber, polytrimethylene terephthalate, polyhexafluoropropylene, and polyperfluoromethylvinylether. In an example, a wearable sensor with one or more elongate deformable conductive structures can be made from a material selected from the group consisting of: polyurethane, polycarbonate, polyglycerol-sebacate, polyphenyl methyl siloxane (PDMS), polysaccharide, polystyrenesulfonate (PEDOT/PSS), and polyvinyl (e.g. chloride (PVC), polyvinylidene, polyvinylidene fluoride (PVDF), polyvinylpyrrolidone).

In an example, different layers of a multi-layer capacitive elongate deformable conductive structure can have different shapes. In an example, central portions of a layer can have a different cross-sectional shape than peripheral portions of the layer. In an example, distal portions of a layer can have a different cross-sectional shape than proximal portions of the layer. In an example, there can be longitudinal variation in the cross-sectional shape of a layer. In an example, a layer can have a thickness within the range of 1/64 to 1/4 of an inch. In an example, central portions of a layer can be thicker than peripheral portions of the layer, or vice versa. In an example, different layers of a capacitive sensor can have different thicknesses. In an example, distal portions of a layer can be thicker than proximal portions of a layer, or vice versa. In an example, electrically-conductive layers can be thicker than dielectric layers. In an example, there can be longitudinal variation in layer thickness. In an example, a layer can have a width within a range of 1/8 to 4 inches.

In an example, a wearable sensor for measuring changes in body joint configuration can comprise one or more non-conductive lumens filled with an electrically-conductive flowable substance (e.g. a conductive fluid or gel). In an example, changes in body joint configuration can bend, compress, kink, or twist the lumens and change the configuration of a flowable substance inside a lumen which, in turn, changes the transmission of electromagnetic energy through the lumen. In an example, a wearable sensor for measuring changes in body joint configuration can comprise a plurality of such conductive-fluid-filled lumens. In an example, these lumens can comprise a parallel array of lumens. In an example, conductive-fluid-filled lumens can have longitudinal axes which are substantially parallel to the proximal-to-distal axis of the body joint which they span. Conductive-fluid-filled lumens can be separated by a layer of deformable dielectric material. In an example, conductive-fluid-filled lumens can be disproportionally clustered on the dorsal or ventral surface of a body part. In an example, a wearable sensor for measuring changes in body joint configuration can comprise a wagon-wheel cluster of conductive-fluid-filled lumens. In an example, a wagon-wheel cluster can comprise a ring of triangular or pie-slice-shaped conductive-fluid-filled lumens whose vertexes point toward a common center. In an example, there can be a dielectric core in the middle of this ring.

In an example, a wearable sensor for measuring changes in body joint configuration can comprise a circumferential (or partially-circumferential) array of deformable conductive-fluid-filled lumens filled with an electrically-conductive flowable substance. In an example, a wearable sensor for measuring changes in body joint configuration can comprise twelve conductive-fluid-filled lumens, one centered on every 30-degree interval (e.g. 0, 30, 60, 90, 120, 150, 180, 210, 240, 270, 300 and 330 degrees) around this circumference. In an example, a wearable sensor for measuring changes in body joint configuration can comprise twelve conductive-fluid-filled lumens, one centered on each clock hour position, which collectively span this circumference. In an example, a wearable sensor for measuring changes in body joint configuration can comprise six conductive-fluid-filled lumens, one centered at every two-hour position (e.g. noon, 2 o'clock, 4 o'clock, 6 o'clock, 8 o'clock, and 10 o'clock). In an example, a wearable sensor for measuring changes in body joint configuration can comprise four conductive-fluid-filled lumens, one centered at every three-hour position (e.g. noon, 3 o'clock, 6 o'clock, and 9 o'clock). In an example, a wearable sensor for measuring changes in body joint configuration can comprise four conductive-fluid-filled lumens, one centered at every 90-degree interval (e.g. 0, 90, 180, and 270 degrees) around this circumference. In an example, a wearable sensor for measuring changes in body joint configuration can comprise six conductive-fluid-filled lumens, one centered at every 60-degree interval (e.g. 0, 60, 120, 180, 240, and 300 degrees) around the circumference. In an example, conductive-fluid-filled lumens can be unevenly-distributed (e.g. unevenly-spaced) around the (partial) circumference of a body part. In an example, conductive-fluid-filled lumens can be evenly-distributed (e.g. evenly-spaced) around the (partial) circumference of a body part.

In an example, a wearable sensor for measuring changes in body joint configuration can comprise an inner circumferential (or partially-circumferential) array of conductive-fluid-filled lumens and an outer circumferential (or partially-circumferential) array of conductive-fluid-filled lumens. In an example, conductive-fluid-filled lumens in an outer array can be located at the same circumferential positions as conductive-fluid-filled lumens in an inner array. In an example, conductive-fluid-filled lumens in an outer array can be located at different circumferential positions vs. those of conductive-fluid-filled lumens in an inner array.

In an example, a wearable sensor for measuring changes in body joint configuration can comprise a circumferential (or partially-circumferential) array of conductive-fluid-filled lumens distributed around the circumference (or a portion of the circumference) of a flexible tubular portion of an article of clothing, wherein each conductive-fluid-filled lumen in the circumferential (or partially circumferential) array has an elongated cross-sectional perimeter, and wherein different conductive-fluid-filled lumens in the circumferential (or partially-circumferential) array of flexible conductive-fluid-filled lumens have cross-sectional axes with different orientations. In an example, a first set of conductive-fluid-filled lumens can have cross-sections with a first orientation and a second set of conductive-fluid-filled lumens can have cross-sections with a second orientation, wherein the first orientation and the second orientation differ by at least 20 degrees.

In an example, sensor can comprise a first set of conductive-fluid-filled lumens and a second set of conductive-fluid-filled lumens, wherein cross-sections of lumens in the first and second sets have different orientations. In an example, the orientations of cross-sections of adjacent conductive-fluid-filled lumens can differ by at least 10 degrees. In an example, the orientations of cross-sections of non-adjacent conductive-fluid-filled lumens can differ by at least 80 degrees. In an example, there can be longitudinal variation in the cross-sectional shape and/or size of the non-conductive conductive-fluid-filled lumen. In an example, a distal portion of the conductive-fluid-filled lumen can have a larger cross-sectional size than that of the proximal portion of the conductive-fluid-filled lumen, or vice versa.

In an example, a conductive-fluid-filled lumen can have a cross-sectional shape selected from the group consisting of: rounded rectangle; elliptical or oval; hexagonal or octagonal; convex lens shape; square or rounded square; and circular. In an example, a conductive-fluid-filled lumen can have a width within a range of 1/64 to 1/4 of an inch. In an example, a conductive-fluid-filled lumen can have a proximal-to-distal length within a range of 3-8 inches. In an example, a conductive-fluid-filled lumen can have a proximal-to-distal length within a range of 1-14 inches.

In an example, a wearable sensor for measuring changes in body joint configuration can comprise a woven or braided array of elongate deformable conductive structures (e.g. conductive strips, fibers, yarns, wires, ink paths, lumens, or channels). In an example, an elongate deformable conductive structure can comprise a woven array of electrically-conductive threads, yarns, wires, or fibers. In an example, a wearable sensor for measuring changes in body joint configuration can comprise a woven or braided array of central elongate deformable conductive structures which spans a body joint, wherein this array further comprises—a first subset of the elongate deformable conductive structures with longitudinal axes which are substantially parallel to the proximal-to-distal axis of the body joint; a second subset of the elongate deformable conductive structures with longitudinal axes which are diagonal to the proximal-to-distal axis of the body joint; a third subset of the elongate deformable conductive structures with longitudinal axes which are substantially perpendicular to the longitudinal axes of the second subset of the elongate deformable conductive structures; and electromagnetic energy emitters and receivers which are in electro-magnetic communication with the woven array of elongate deformable conductive structures.

In an example, a woven sensor can have a weave pattern selected from the group consisting of: plain weave; rib weave; basket weave; twill weave; Satin weave; leno weave; and mock leno weave. In an example, a braided sensor can have a braid pattern selected from the group consisting of: a one over braid pattern; one over, one under braid (e.g. diamond) braid pattern; one over, three under braid pattern; two over, one under braid pattern; two over, two under braid pattern; two under, two over braid pattern; three over, one under braid pattern; three over, three under braid pattern; four over, one under braid pattern; four over, four under braid pattern; five over, one under braid pattern; six over, one under braid pattern; seven over, one under braid pattern; and eight over, one under braid pattern.

In an example, an elongate deformable conductive structure (e.g. a conductive strip, fiber, yarn, wire, ink path, lumen, or channel) can have a single energy receiver in a central location and a plurality of energy emitters around the perimeter of the elongate deformable conductive structure. In an example, an elongate deformable conductive structure can have a single energy receiver at its center and a plurality of energy emitters which are evenly distributed around its perimeter. In an example, there can be a single energy receiver and two or more energy emitters in electromagnetic communication with an elongate deformable conductive structure. In an example, there can be a single energy emitter and two or more energy receivers in electromagnetic communication with an elongate deformable conductive structure. In an example, different electromagnetic energy emitters can emit energy at different times and/or in different sequences. In an example, energy emitters can be in electromagnetic communication with the proximal ends of elongate deformable conductive structures and energy receivers can be in electromagnetic communication with the distal ends of these elongate deformable conductive structures, or vice versa.

In an example, a wearable sensor for measuring changes in body joint configuration can comprise a plurality of pairs of electromagnetic energy emitters and receivers wherein each elongate deformable conductive structure is in electromagnetic communication with a pair comprising an electromagnetic energy emitter and receiver. In an example, an electromagnetic energy emitter can be proximal to an electromagnetic energy receiver. In an example, an electromagnetic energy emitter can be distal to an electromagnetic energy receiver. In an example, an elongate deformable conductive structure can have a single energy emitter in a central location and a plurality of energy receivers on its perimeter.

In an example, movement of a body joint causes deformations of one or more elongate deformable conductive structures (e.g. conductive strips, fibers, yarns, wires, ink paths, lumens, or channels) and these deformations in turn cause changes in the transmission of electromagnetic energy from electromagnetic energy emitters to electromagnetic energy receivers. These changes in the transmission of electromagnetic energy can then be analyzed in order to measure and/or model changes in body joint configuration. In an example, movement of a body joint causes deformations of a deformable dielectric layer, deformations of the deformable dielectric layer cause changes in capacitance between first and second deformable electrically-conductive layers, and these changes in the capacitance between the first and second deformable electrically-conductive layers are then analyzed in order to measure and/or model changes in body joint configuration.

In an example, changes in the configuration of a body joint spanned by one or more elongate deformable conductive structures cause changes in resistance, impedance, conductivity, and/or capacitance which are analyzed in order to measure and/or model changes in body joint configuration. In an example, changes in the capacitances between a core elongate deformable conductive structure and peripheral elongate deformable conductive structures can be analyzed to measure and/or model changes in body joint configuration. In an example, changes in body joint configuration can bend, compress, kink, or twist conductive-fluid-filled lumens and change the configuration of a flowable substance inside the lumen. In an example, a data transmitter can send data to a remote data processor wherein changes in energy transmission are analyzed.

Any of the examples in the following figures can further comprise a power source (such as a battery). Any of the examples in the following figures can further comprise an energy transducer which generates electrical power from the kinetic energy of a person's body or from the thermal energy of the person's body. Any of the examples in the following figures can further comprise a data processor in which changes in electromagnetic energy are analyzed to measure and/or model changes in body joint configuration. Any of the examples in the following figures can further comprise a data transmitter which transmits data concerning changes in electromagnetic energy to a remote data processor, wherein these changes are analyzed to measure and/or model changes in body joint configuration.

FIGS. 1 through 84 are now described in detail. Relevant variations and components discussed in the preceding introductory section can be applied to the following figures and examples where relevant, but are not repeated in each of the narratives accompanying each of the figures in order to avoid duplicative content in this disclosure.

Figure 2:
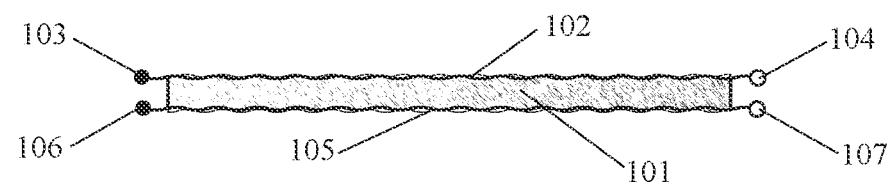
FIG. 2 shows a side view of the fabric in FIG. 1.
Figure 3:
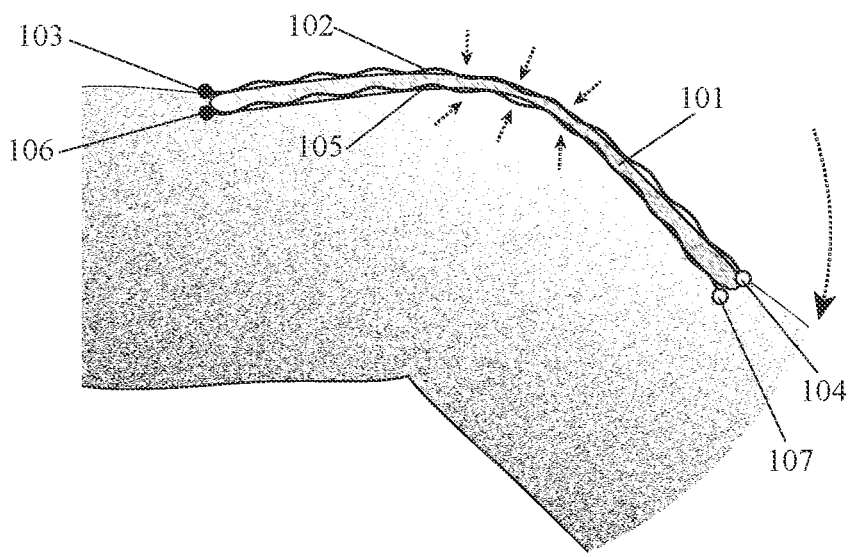
FIG. 3 shows the fabric in FIG. 1 worn on a knee.

FIGS. 1 through 3 show three views of an example of motion recognition fabric. FIG. 1 shows a top-down view of a square section of this fabric; FIG. 2 shows a side view of a square section of this fabric; and FIG. 3 shows a side view of this fabric being worn on a person's knee. FIG. 3 shows how this fabric is stretched and/or compressed when the knee bends.

In this example, motion recognition fabric comprises: a first set of parallel electromagnetic energy pathways (including pathway 102 with ends 103 and 104) in a first layer of fabric; a non-conductive second layer 101 of fabric; and a second set of parallel electromagnetic energy pathways (including pathway 105 with ends 106 and 107) in a third layer of fabric, wherein the non-conductive second layer is between the first layer and the third layer.

The dotted lines in FIG. 1 indicate that the second set of pathways is on the opposite side of the non-conductive layer which is not seen from this perspective. In this example, pathways in the second set are parallel to pathways in the first set. In a variation on this example, pathways in first and second sets can converge toward each. In this example, proximal pairs of pathways in the first and second sets are on diametrically-opposite sides of the non-conductive second layer. In a variation on this example, the central longitudinal axis of a pathway in the second set can be equidistant from longitudinal axes of the closest two pathways in the first set. In this example, the pathways are relatively straight. In a variation on this example, the pathways can be sinusoidal or otherwise undulating.

In an example, electromagnetic energy can be transmitted from ends 103 and 106 into electromagnetic energy pathways 102 and 105, respectively. In an example, ends 103 and 106 can further comprise electromagnetic energy emitters. In an example, electromagnetic energy can be received from pathways 102 and 105 at ends 104 and 107, respectively. In an example, ends 104 and 107 can further comprise electromagnetic energy receivers.

In an example, electromagnetic energy transmitted into (the end of) a pathway in the first set and can be received from (the end of) a pathway in the second set. In an example, changes in capacitance levels between the pathways in the first and second sets can be analyzed for three-dimensional modeling of changes in fabric and/or joint configuration. In an example, geometric areas (e.g. contour maps) of changes in fabric capacitance levels can be analyzed to enable three-dimensional modeling of changes in fabric and/or joint configuration.

In an example, electromagnetic energy transmitted into the end of a pathway in the first set can be received from the other end of the same pathway. In an example, electromagnetic energy transmitted into the end of a pathway in the second set can be received from the other end of the same pathway. In an example, changes in the resistance, impedance, and/or conductivity of pathways in the first and/or second sets can be analyzed to enable three-dimensional modeling of changes in fabric and/or joint configuration.

In an example, an electromagnetic energy pathway can comprise: electroconductive thread, yarn, fiber, or wire; a braid or weave of electroconductive threads, yarns, fibers, and/or wires; or a braid or weave of conductive and non-conductive threads, yarns, fibers, and/or wires. In an example, an electromagnetic energy pathway can be printed with electroconductive ink. In an example, an electromagnetic energy pathway can be created by melting electroconductive material with a laser. In an example, an electromagnetic energy pathway can comprise a channel of liquid metal in a hollow non-conductive lumen. In an example, a non-conductive layer can be stretchable and compressible. Example variations discussed elsewhere in this disclosure or in priority-linked disclosures are not repeated here to avoid redundancy, but can be applied where relevant to the example shown here.

FIGS. 4 and 5 show two views of another example of motion recognition fabric. FIG. 4 shows a top-down view and FIG. 5 shows a side view. In this example, motion recognition fabric comprises: a first set of sinusoidal electromagnetic energy pathways (including pathway 402 with ends 403 and 404) with parallel central longitudinal axes in a first layer of fabric; a non-conductive second layer 401 of fabric; and a second set of sinusoidal electromagnetic energy pathways (including pathway 405 with ends 406 and 407) with parallel central longitudinal axes in a third layer of fabric, wherein the non-conductive second layer is between the first layer and the third layer, and wherein the central longitudinal axes of pathways in the second set are parallel to the central longitudinal axes of pathways in the first set.

In this example, the peaks of sinusoidal pathways do not extend ("horizontally overlap") into the concavities of other sinusoidal pathways (in the same layer). In a variation on this example, the peaks of sinusoidal pathways can extend ("horizontally overlap") into the concavities other sinusoidal pathways. In this example, the waves of sinusoidal pathways are in phase with each other. In an example, sinusoidal pathways can be out-of-phase with each other. In an example, sinusoidal pathways can be 180-degrees out of phase with each other. In this example, sinusoidal pathways all have the same amplitude and wavelength. In other examples, different sinusoidal pathways can have different amplitudes and/or wavelengths. Other example variations discussed elsewhere in this disclosure or in priority-linked disclosures are not repeated here to avoid redundancy, but can be applied where relevant to the example shown here.

FIGS. 6 and 7 show two views of another example of motion recognition fabric. FIG. 6 shows a top-down view and FIG. 7 shows a side view. In this example, motion recognition fabric comprises: a first set of sinusoidal electromagnetic energy pathways (including pathway 602 with ends 603 and 604) with parallel central longitudinal axes in a first layer of fabric; a non-conductive second layer 601 of fabric; and a second set of sinusoidal electromagnetic energy pathways (including pathway 605 with ends 606 and 607) with parallel central longitudinal axes in a third layer of fabric, wherein the non-conductive second layer is between the first layer and the third layer, wherein the central longitudinal axes of pathways in the second set are parallel to the central longitudinal axes of pathways in the first set, and wherein the peaks of a first sinusoidal pathway extend into the concavities of a second sinusoidal pathway (in the same layer).

In this example, sinusoidal pathways are in phase with each other. In an example, sinusoidal pathways can be out of phase with each other. In this example, sinusoidal pathways all have the same amplitude and wavelength. In other examples, different sinusoidal pathways can have different amplitudes and/or wavelengths. Other example variations discussed elsewhere in this disclosure or in priority-linked disclosures are not repeated here to avoid redundancy, but can be applied where relevant to the example shown here.

Figure 8:
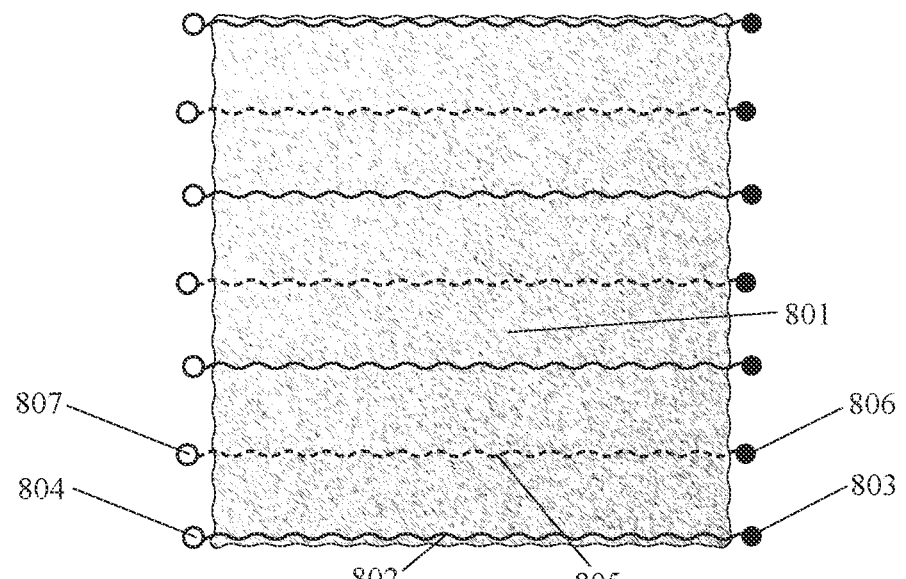
FIG. 8 shows fabric comprising inner and outer EM layers with non-overlapping relatively-straight parallel EM pathways.
Figure 9:
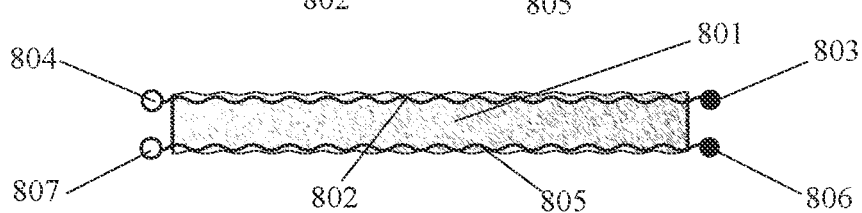
FIG. 9 shows a side view of the fabric in FIG. 8.

FIGS. 8 and 9 show two views of another example of motion recognition fabric. FIG. 8 shows a top-down view and FIG. 9 shows a side view. In this example, motion recognition fabric comprises: a first set of electromagnetic energy pathways (including pathway 802 with ends 803 and 804) with parallel central longitudinal axes in a first layer of fabric; a non-conductive second layer 801 of fabric; and a second set of electromagnetic energy pathways (including pathway 805 with ends 806 and 807) with parallel central longitudinal axes in a third layer of fabric, wherein the non-conductive second layer is between the first layer and the third layer, and wherein the central longitudinal axis of a pathway in the second set is equidistant from the central longitudinal axes of the two closest pathways in the first set. In this example, pathways are relatively straight. In another example, pathways can be sinusoidal or otherwise undulating. Other example variations discussed elsewhere in this disclosure or in priority-linked disclosures are not repeated here to avoid redundancy, but can be applied where relevant to the example shown here.

Figure 10:
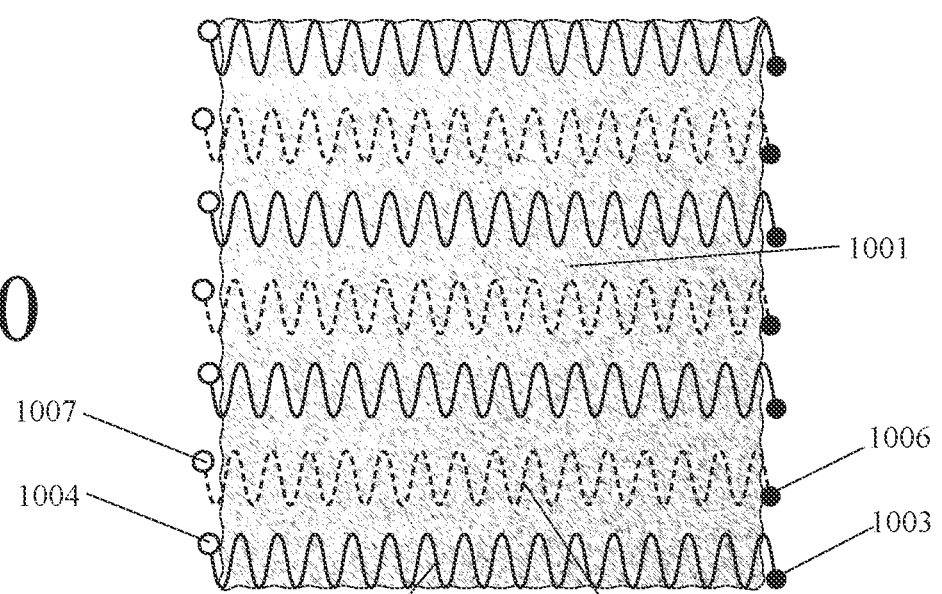
FIG. 10 shows fabric comprising inner and outer EM layers with non-overlapping sinusoidal EM pathways.
Figure 11:
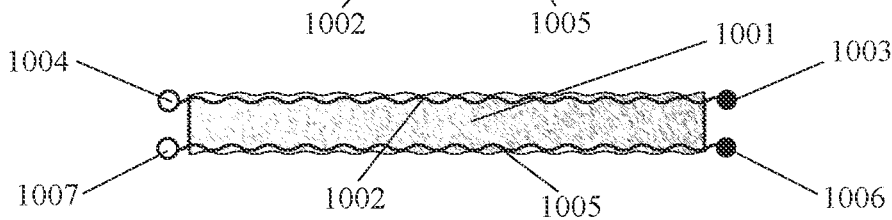
FIG. 11 shows a side view of the fabric in FIG. 10.

FIGS. 10 and 11 show two views of another example of motion recognition fabric. FIG. 10 shows a top-down view and FIG. 11 shows a side view. In this example, motion recognition fabric comprises: a first set of sinusoidal electromagnetic energy pathways (including pathway 1002 with ends 1003 and 1004) with parallel central longitudinal axes in a first layer of fabric; a non-conductive second layer 1001 of fabric; and a second set of sinusoidal electromagnetic energy pathways (including pathway 1005 with ends 1006 and 1007) with parallel central longitudinal axes in a third layer of fabric, wherein the non-conductive second layer is between the first layer and the third layer, and wherein the central longitudinal axis of a pathway in the second set is equidistant from the central longitudinal axes of the two closest pathways in the first set. Example variations discussed elsewhere in this disclosure or in priority-linked disclosures are not repeated here to avoid redundancy, but can be applied where relevant to the example shown here.

FIGS. 12 and 13 show two views of another example of motion recognition fabric. FIG. 12 shows a top-down view and FIG. 13 shows a side view. In this example, motion recognition fabric comprises: a first set of electromagnetic energy pathways (including pathway 1202 with ends 1203 and 1204) with parallel central longitudinal axes in a first layer of fabric; a non-conductive second layer 1201 of fabric; and a second set of electromagnetic energy pathways (including pathway 1205 with ends 1206 and 1207) with parallel central longitudinal axes in a third layer of fabric, wherein the non-conductive second layer is between the first layer and the third layer, and wherein the central longitudinal axes of pathways in the second set are perpendicular to the central longitudinal axes of pathways in the first set (when both are projected onto the same two-dimensional plane).

In this example, pathways in the first and second sets form a grid of squares as they intersect (when projected onto the same two-dimensional plane). In another example, pathways in first and second sets can form a grid of rectangles as they intersect (when projected onto the same two-dimensional plane). In this example, pathways in first and second sets form 90-degree angles as they intersect (when projected onto the same two-dimensional plane). In an example, pathways in first and second sets can form acute angles as they intersect (when projected onto the same two-dimensional plane). In an example, pathways in first and second sets of pathways can form a grid of hexagons as they intersect (when projected onto the same two-dimensional plane). Other variations discussed elsewhere in this disclosure or in priority-linked disclosures are not repeated here to avoid redundancy, but can be applied where relevant to the example shown here.

FIGS. 14 and 15 show two views of another example of motion recognition fabric. FIG. 14 shows a top-down view and FIG. 15 shows a side view. In this example, motion recognition fabric comprises: a first set of sinusoidal electromagnetic energy pathways (including pathway 1402 with ends 1403 and 1404) with parallel central longitudinal axes in a first layer of fabric; a non-conductive second layer 1401 of fabric; and a second set of sinusoidal electromagnetic energy pathways (including pathway 1405 with ends 1406 and 1407) with parallel central longitudinal axes in a third layer of fabric, wherein the non-conductive second layer is between the first layer and the third layer, and wherein the central longitudinal axes of pathways in the second set are perpendicular to the central longitudinal axes of pathways in the first set (e.g. when both are projected onto the same two-dimensional plane). Example variations discussed elsewhere in this disclosure or in priority-linked disclosures are not repeated here to avoid redundancy, but can be applied where relevant to the example shown here.

FIGS. 16 and 17 show two views of another example of motion recognition fabric. FIG. 16 shows a top-down view and FIG. 17 shows a side view. In this example, motion recognition fabric comprises: a first set of electromagnetic energy pathways (including pathway 1602 with ends 1603 and 1604) with parallel central longitudinal axes in a first layer of fabric; a non-conductive second layer 1601 of fabric; and a second set of electromagnetic energy pathways (including pathway 1605 with ends 1606 and 1607) with parallel central longitudinal axes in a third layer of fabric, a non-conductive fourth layer 1701 of fabric; and a third set of electromagnetic energy pathways (including pathway 1608 with ends 1609 and 1610) with parallel central longitudinal axes in a fifth layer of fabric, wherein the second layer is between the first layer and the third layer, wherein the fourth layer is between the third layer and the fifth layer, wherein the central longitudinal axes of pathways in the second set form 60-degree angles as they intersect the central longitudinal axes of pathways in the first set (when both sets are projected onto the same two-dimensional plane), and wherein the central longitudinal axes of pathways in the third set form 60-degree angles as they intersect the central longitudinal axes of pathways in the first set (when both sets are projected onto the same two-dimensional plane).

In a variation on this example, the central longitudinal axes of pathways in the second set can form 30-degree angles as they intersect the central longitudinal axes of pathways in the first set (when both sets are projected onto the same two-dimensional plane). In a variation on this example, the central longitudinal axes of pathways in the third set can form 30-degree angles as they intersect the central longitudinal axes of pathways in the first set (when both sets are projected onto the same two-dimensional plane). In a variation on this example, the central longitudinal axes of pathways in the second set can form adjacent 30-degree and 150-degree angles as they intersect the central longitudinal axes of pathways in the first set (when both sets are projected onto the same two-dimensional plane). In a variation on this example, the central longitudinal axes of pathways in the third set can form adjacent 30-degree and 150-degree angles as they intersect the central longitudinal axes of pathways in the first set (when both sets are projected onto the same two-dimensional plane).

In this example, the intersections of pathways when projected onto the same two-dimensional plane form a grid of triangles and hexagons. In a variation on this example, these intersections can just form hexagons. Other variations discussed elsewhere in this disclosure or in priority-linked disclosures are not repeated here to avoid redundancy, but can be applied where relevant to the example shown here.

FIGS. 18 and 19 show two views of another example of motion recognition fabric. FIG. 18 shows a top-down view and FIG. 19 shows a side view. In this example, motion recognition fabric comprises: a first set of sinusoidal electromagnetic energy pathways (including pathway 1802 with ends 1803 and 1804) with parallel central longitudinal axes in a first layer of fabric; a non-conductive second layer 1801 of fabric; and a second set of sinusoidal electromagnetic energy pathways (including pathway 1805 with ends 1806 and 1807) with parallel central longitudinal axes in a third layer of fabric, a non-conductive fourth layer 1901 of fabric; and a third set of sinusoidal electromagnetic energy pathways (including pathway 1808 with ends 1809 and 1810) with parallel central longitudinal axes in a fifth layer of fabric, wherein the second layer is between the first layer and the third layer, wherein the fourth layer is between the third layer and the fifth layer, wherein the central longitudinal axes of pathways in the second set form 60-degree angles as they intersect the central longitudinal axes of pathways in the first set when both sets are projected onto a two-dimensional plane, and wherein the central longitudinal axes of pathways in the third set form 60-degree angles as they intersect the central longitudinal axes of pathways in the first set when both sets are projected onto a two-dimensional plane. Variations discussed elsewhere in this disclosure or in priority-linked disclosures are not repeated here to avoid redundancy, but can be applied where relevant to the example shown here.

FIGS. 20 and 21 show two views of another example of motion recognition fabric. FIG. 20 shows a top-down view and FIG. 21 shows a side view. In this example, motion recognition fabric comprises: a first set of electromagnetic energy pathways (including pathway 2002 with ends 2003 and 2004) with parallel central longitudinal axes in a first layer of fabric; a second set of electromagnetic energy pathways (including pathway 2005 with ends 2006 and 2007) with parallel central longitudinal axes in the first layer of fabric, wherein the central longitudinal axes of pathways in the second set are perpendicular to the central longitudinal axes of pathways in the first set (when both are projected onto the same two-dimensional plane); a non-conductive second layer 2001 of fabric; a third set of electromagnetic energy pathways (including pathway 2008 with ends 2009 and 2010) with parallel central longitudinal axes in a third layer of fabric; and a fourth set of electromagnetic energy pathways (including pathway 2011 with ends 2012 and 2013) with parallel central longitudinal axes in the third layer of fabric, wherein the central longitudinal axes of pathways in the fourth set are perpendicular to the central longitudinal axes of pathways in the third set (when both are projected onto the same two-dimensional plane), and wherein the second layer is between the first layer and the third layer.

In this example, pathways in the first and second sets are diametrically-opposite pathways in the third and fourth sets (on the opposite side of the non-conductive layer). In an example, pathways in first set can be equidistant from the closest two pathways in the third set and pathways in the second set can be equidistant from the closest two pathways in the fourth set. Other variations discussed elsewhere in this disclosure or in priority-linked disclosures are not repeated here to avoid redundancy, but can be applied where relevant to the example shown here.

FIGS. 22 and 23 show two views of another example of motion recognition fabric. FIG. 22 shows a top-down view and FIG. 23 shows a side view. In this example, motion recognition fabric comprises: a first set of sinusoidal electromagnetic energy pathways (including pathway 2202 with ends 2203 and 2204) with parallel central longitudinal axes in a first layer of fabric; a second set of sinusoidal electromagnetic energy pathways (including pathway 2205 with ends 2206 and 2207) with parallel central longitudinal axes in the first layer of fabric, wherein the central longitudinal axes of pathways in the second set are perpendicular to the central longitudinal axes of pathways in the first set (when both are projected onto the same two-dimensional plane); a non-conductive second layer 2201 of fabric; a third set of sinusoidal electromagnetic energy pathways (including pathway 2208 with ends 2209 and 2230) with parallel central longitudinal axes in a third layer of fabric; and a fourth set of sinusoidal electromagnetic energy pathways (including pathway 2231 with ends 2232 and 2233) with parallel central longitudinal axes in the third layer of fabric, wherein the central longitudinal axes of pathways in the fourth set are perpendicular to the central longitudinal axes of pathways in the third set (when both are projected onto the same two-dimensional plane), and wherein the second layer is between the first layer and the third layer. Example variations discussed elsewhere in this disclosure or in priority-linked disclosures are not repeated here to avoid redundancy, but can be applied where relevant to the example shown here.

FIGS. 24 and 25 show two views of another example of motion recognition fabric. FIG. 24 shows a top-down view and FIG. 25 shows a side view. In this example, motion recognition fabric comprises: a first set of electromagnetic energy pathways (including pathway 2408 with ends 2409 and 2410) with parallel central longitudinal axes in a first layer of fabric; a non-conductive second layer 2401 of fabric; a second set of electromagnetic energy pathways (including pathway 2402 with ends 2403 and 2404) with parallel central longitudinal axes in a third layer of fabric; a non-conductive fourth layer 2501 of fabric; a third set of electromagnetic energy pathways (including pathway 2405 with ends 2406 and 2407) with parallel central longitudinal axes in a fifth layer of fabric; a non-conductive sixth layer 2502 of fabric; and a fourth set of electromagnetic energy pathways (including pathway 2411 with ends 2412 and 2413) with parallel central longitudinal axes in a seventh layer of fabric.

In this example, the central longitudinal axes of pathways in the second set are perpendicular to the central longitudinal axes of pathways in the first set (when both are projected onto the same two-dimensional plane). In this example, the central longitudinal axes of pathways in the fourth set are perpendicular to the central longitudinal axes of pathways in the third set (when both are projected onto the same two-dimensional plane). In this example, the second layer is between the first layer and the third layer, the fourth layer is between the third layer and the fifth layer, and the sixth layer is between the fifth layer and the seventh layer. Example variations discussed elsewhere in this disclosure or in priority-linked disclosures are not repeated here to avoid redundancy, but can be applied where relevant to the example shown here.

FIGS. 26 and 27 show two views of another example of motion recognition fabric. FIG. 26 shows a top-down view and FIG. 27 shows a side view. In this example, motion recognition fabric comprises: a first set of sinusoidal electromagnetic energy pathways (including pathway 2608 with ends 2609 and 2610) with parallel central longitudinal axes in a first layer of fabric; a non-conductive second layer 2601 of fabric; a second set of sinusoidal electromagnetic energy pathways (including pathway 2602 with ends 2603 and 2604) with parallel central longitudinal axes in a third layer of fabric; a non-conductive fourth layer 2701 of fabric; a third set of sinusoidal electromagnetic energy pathways (including pathway 2605 with ends 2606 and 2607) with parallel central longitudinal axes in a fifth layer of fabric; a non-conductive sixth layer 2702 of fabric; and a fourth set of sinusoidal electromagnetic energy pathways (including pathway 2611 with ends 2612 and 2613) with parallel central longitudinal axes in a seventh layer of fabric.

In this example, the central longitudinal axes of pathways in the second set are perpendicular to the central longitudinal axes of pathways in the first set (when both are projected onto the same two-dimensional plane). In this example, the central longitudinal axes of pathways in the fourth set are perpendicular to the central longitudinal axes of pathways in the third set (when both are projected onto the same two-dimensional plane). In this example, the second layer is between the first layer and the third layer, the fourth layer is between the third layer and the fifth layer, and the sixth layer is between the fifth layer and the seventh layer. Example variations discussed elsewhere in this disclosure or in priority-linked disclosures are not repeated here to avoid redundancy, but can be applied where relevant to the example shown here.

Figure 28:
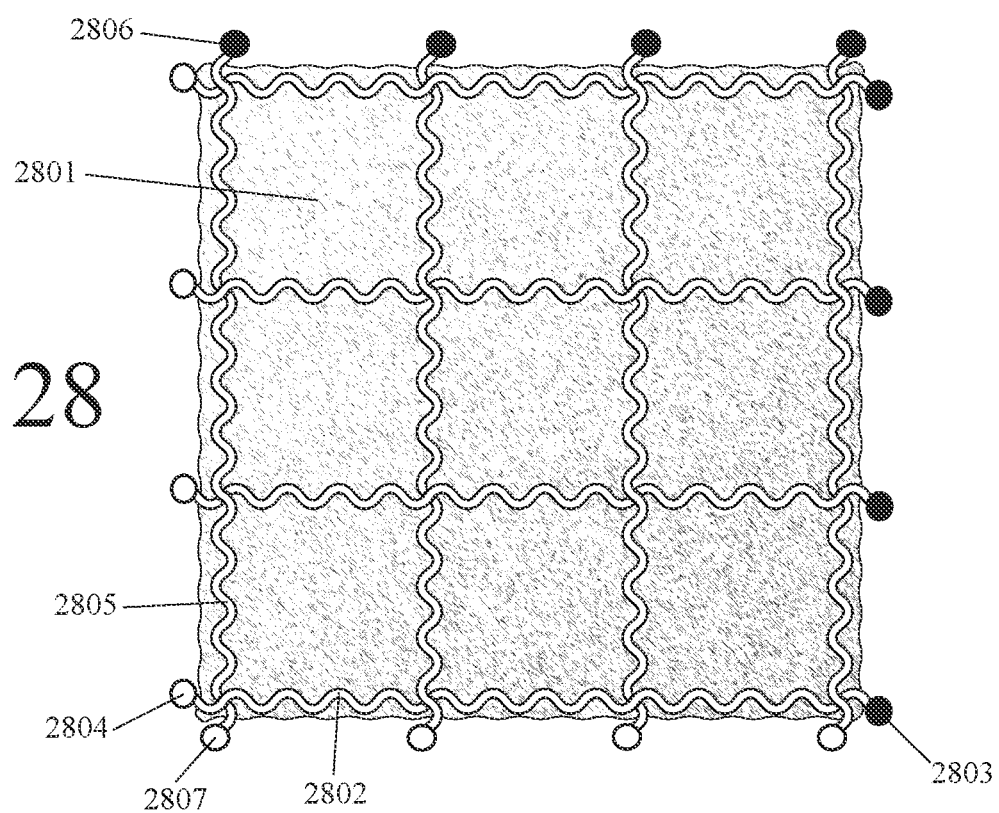
FIG. 28 shows fabric with a woven grid of perpendicular EM pathways whose ends are in electromagnetic communication with pairs of EM emitters and receivers.

FIG. 28 shows a top-down view of another example of motion recognition fabric. In this example, motion recognition fabric comprises: a non-conductive fabric layer 2801; a first set of electromagnetic energy pathways (including pathway 2802 with ends 2803 and 2804) with parallel central longitudinal axes; a second set of electromagnetic energy pathways (including pathway 2805 with ends 2806 and 2807) with parallel central longitudinal axes; wherein the central longitudinal axes of pathways in the second set are perpendicular to the central longitudinal axes of pathways in the first set (when both are projected onto the same two-dimensional plane); and wherein pathways in the first and second sets are woven together. In this example, pathways in first and second sets form a grid of squares when they are projected onto the same two-dimensional plane. In this example, pathways are undulating and/or sinusoidal. In an example, pathways can be straight.

In an example, an electromagnetic energy pathway can comprise a flexible non-conductive core surrounded by an electroconductive coating and/or layer. In an example, an electromagnetic energy pathway can comprise: a flexible non-conductive core made from acetate, acrylic, cotton, denim, elastane, Kevlar, latex, linen, Lycra™, neoprene, nylon, polyester, wool, silicone (e.g. polydimethylsiloxane), silk, spandex, or rayon surrounded by a electroconductive coating and/or layer made from aluminum, aluminum alloy, carbon nanotubes, graphene, liquid metal, magnesium, copper, copper alloy, gold, nickel, polyaniline, silver, or steel.

In an example, an electromagnetic energy pathway can comprise a braided non-conductive core surrounded by an electroconductive coating and/or layer. In an example, an electromagnetic energy pathway can comprise: a braided non-conductive core made from acetate, acrylic, cotton, denim, elastane, Kevlar, latex, linen, Lycra™, neoprene, nylon, polyester, wool, silicone (e.g. polydimethylsiloxane), silk, spandex, or rayon yarns (or threads) surrounded by a electroconductive coating and/or layer made from aluminum, aluminum alloy, carbon nanotubes, graphene, liquid metal, magnesium, copper, copper alloy, gold, nickel, polyaniline, silver, or steel.

In an example, an electromagnetic energy pathway can comprise a flexible non-conductive layer whose top and bottom sides are covered by electroconductive coatings and/or layers. In an example, an electromagnetic energy pathway can comprise a flexible non-conductive layer made from acetate, acrylic, cotton, denim, elastane, Kevlar, latex, linen, Lycra™, neoprene, nylon, polyester, wool, silicone (e.g. polydimethylsiloxane), silk, spandex, or rayon whose top and bottom sides are covered by electroconductive coatings and/or layers made from aluminum, aluminum alloy, carbon nanotubes, graphene, liquid metal, magnesium, copper, copper alloy, gold, nickel, polyaniline, silver, or steel.

In an example, an electromagnetic energy pathway can comprise a flexible electroconductive core surrounded by a non-conductive coating and/or layer. In an example, an electromagnetic energy pathway can comprise: a flexible electroconductive core made from aluminum, aluminum alloy, carbon nanotubes, graphene, liquid metal, magnesium, copper, copper alloy, gold, nickel, polyaniline, silver, or steel surrounded by a non-conductive coating and/or layer made from acetate, acrylic, cotton, denim, elastane, Kevlar, latex, linen, Lycra™, neoprene, nylon, polyester, wool, silicone (e.g. polydimethylsiloxane), silk, spandex, or rayon.

In an example, an electromagnetic energy pathway can comprise a fluid electroconductive material within a flexible non-conductive lumen. In an example, an electromagnetic energy pathway can comprise: a fluid electroconductive material selected from the group consisting of aluminum, aluminum alloy, carbon nanotubes, graphene, liquid metal, magnesium, copper, copper alloy, gold, nickel, polyaniline, silver, or steel with a flexible non-conductive lumen made from acetate, acrylic, cotton, denim, elastane, Kevlar, latex, linen, Lycra™, neoprene, nylon, polyester, wool, silicone (e.g. polydimethylsiloxane), silk, spandex, or rayon. In an example, an electromagnetic energy pathway can comprise liquid metal in a flexible tube.

In an example, an electromagnetic energy pathway can comprise a braided electroconductive core surrounded by a non-conductive coating and/or layer. In an example, an electromagnetic energy pathway can comprise: a braided electroconductive core made from aluminum, aluminum alloy, gallium and indium alloy, carbon nanotubes, graphene, magnesium, copper, copper alloy, gold, nickel, polyaniline, silver, or steel wires surrounded by a non-conductive coating and/or layer made from acetate, acrylic, cotton, denim, elastane, Kevlar, latex, linen, Lycra™, neoprene, nylon, polyester, wool, silicone (e.g. polydimethylsiloxane), silk, spandex, or rayon.

In an example, an electromagnetic energy pathway can comprise a flexible electroconductive layer whose top and bottom sides are covered by non-conductive coatings and/or layers. In an example, an electromagnetic energy pathway can comprise a flexible electroconductive layer made from aluminum, aluminum alloy, carbon nanotubes, graphene, liquid metal, magnesium, copper, copper alloy, gold, nickel, polyaniline, silver, or steel whose top and bottom sides are covered by non-conductive coatings and/or layers made from acetate, acrylic, cotton, denim, elastane, Kevlar, latex, linen, Lycra™, neoprene, nylon, polyester, wool, silicone (e.g. polydimethylsiloxane), silk, spandex, or rayon.

In an example, an electromagnetic energy pathway can comprise a braided core of electroconductive and nonconductive longitudinal members surrounded by a non-conductive braided layer. In an example, an electromagnetic energy pathway can comprise: a braided core of one or more electroconductive longitudinal members and one or more non-conductive longitudinal members; and a braided layer of one or more non-conductive longitudinal members surrounding the braided core; wherein the electroconductive longitudinal members are made from aluminum, aluminum alloy, carbon nanotubes, graphene, liquid metal, magnesium, copper, copper alloy, gold, nickel, polyaniline, silver, or steel; and wherein the non-conductive longitudinal members are made from acetate, acrylic, cotton, denim, elastane, Kevlar, latex, linen, Lycra™, neoprene, nylon, polyester, wool, silicone (e.g. polydimethylsiloxane), silk, spandex, or rayon.

In an example, an electromagnetic energy pathway can be created by braiding a non-conductive material and a conductive material together. In an example, an electromagnetic energy pathway can comprise a three-way braid of non-conductive thread, yarn, or fiber and conductive thread, yarn, or fiber. In an example, the non-conductive material can be selected from the group consisting of: acetate, acrylic, cotton, denim, elastane, Kevlar, latex, linen, Lycra™, neoprene, nylon, nylon, polyester, polymer, rayon, wool, silicone (e.g. polydimethylsiloxane), silk, and spandex. In an example, the conductive material can be selected from the group consisting of: aluminum or aluminum alloy; carbon nanotubes, graphene, or other carbon-based material; magnesium; ceramic particles; copper or copper alloy; gold; liquid metal; nickel; polyaniline; silver; and steel. Other example variations discussed elsewhere in this disclosure or in priority-linked disclosures are not repeated here to avoid redundancy, but can be applied where relevant to the example shown here.

FIGS. 29 through 32 show four sequential top-down views of another example of motion recognition fabric. In this example, motion recognition fabric comprises: a non-conductive layer 2901; a first set of electromagnetic energy pathways (including pathway 2902 with ends 2903 and 2904) which further comprises a plurality of junctions (such as 2908); a second set of electromagnetic energy pathways (including pathway 2905 with ends 2906 and 2907) which further comprises a plurality of junctions (such as 2909); wherein a junction has a first configuration in which it is non-conductive and a second configuration in which it is electroconductive; and wherein selected junctions are changed from their first configuration to their second configuration by localized application (3001) of thermal, light, and/or kinetic energy to the selected junctions. In an example, application of thermal and/or light energy can melt a material which then spans the junction and makes it electroconductive. In an example, application of kinetic energy can bond two portions of a junction and make it electroconductive.

Figure 29:
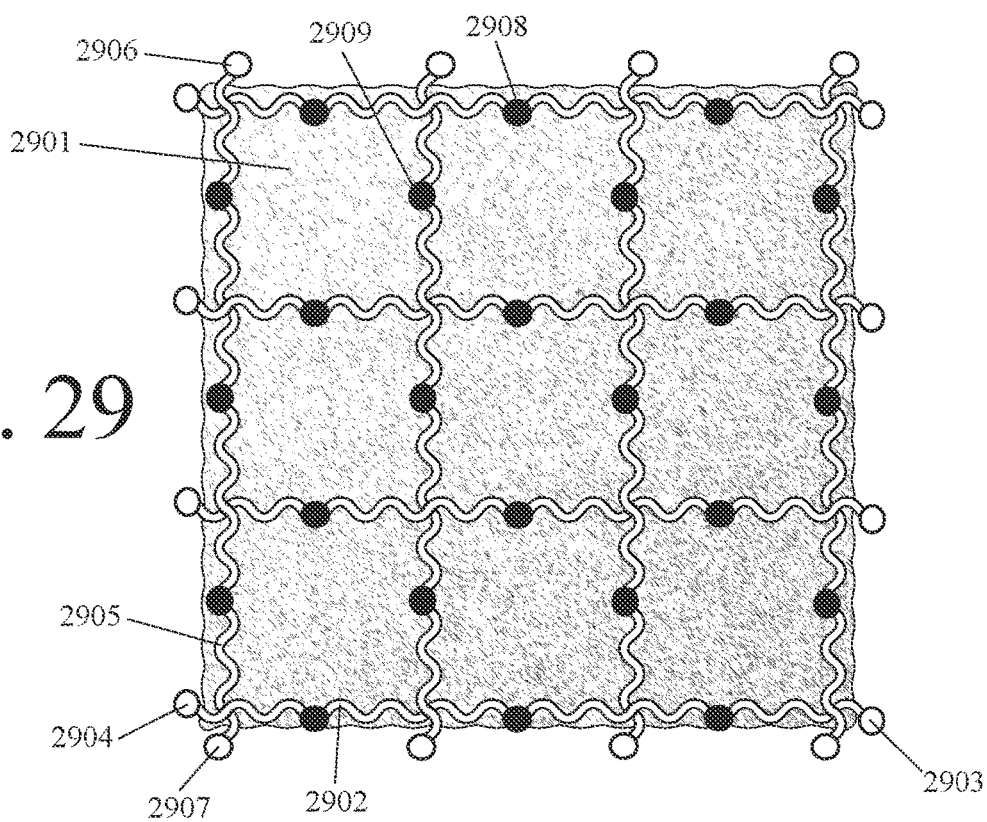
FIGS. 29 through 32 show four sequential views of fabric with a woven grid of perpendicular EM pathways wherein electromagnetic communication between selected pathways and selected EM emitters or receivers is activated by localized application of energy.
Figure 30:
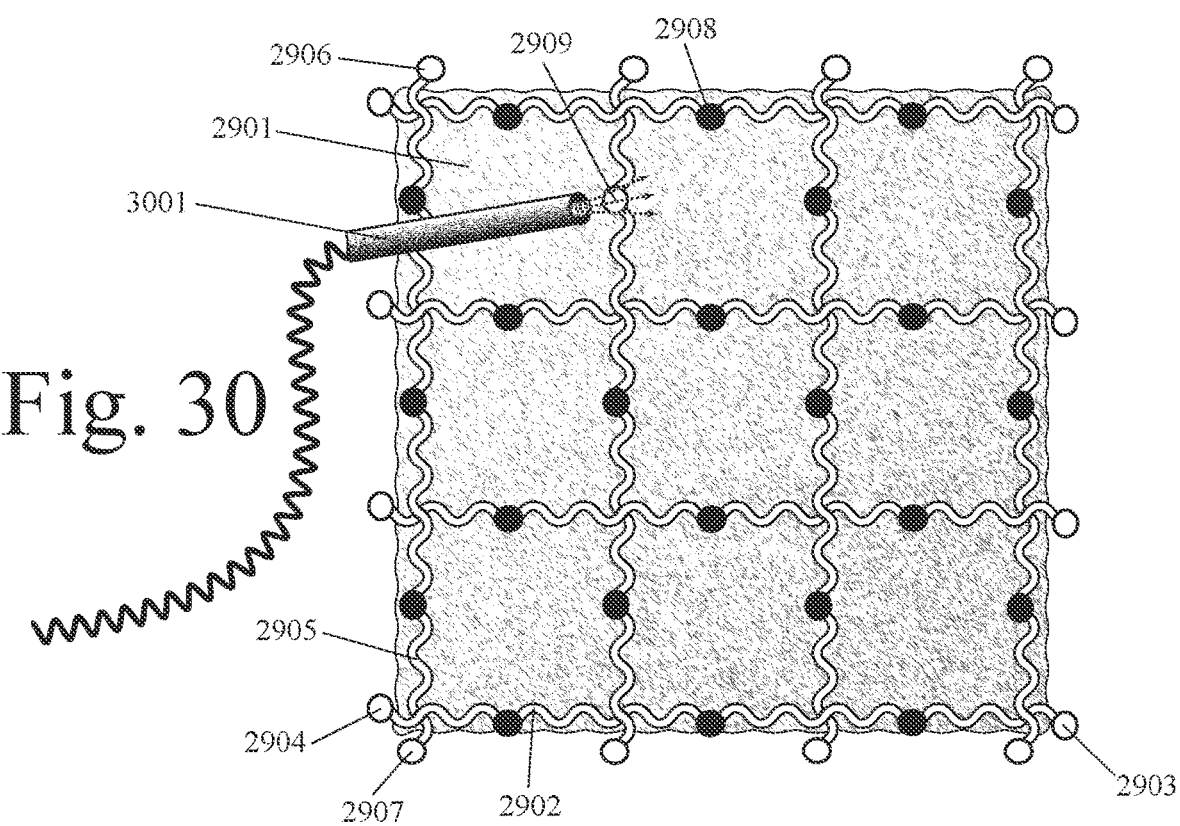
Figure 31:
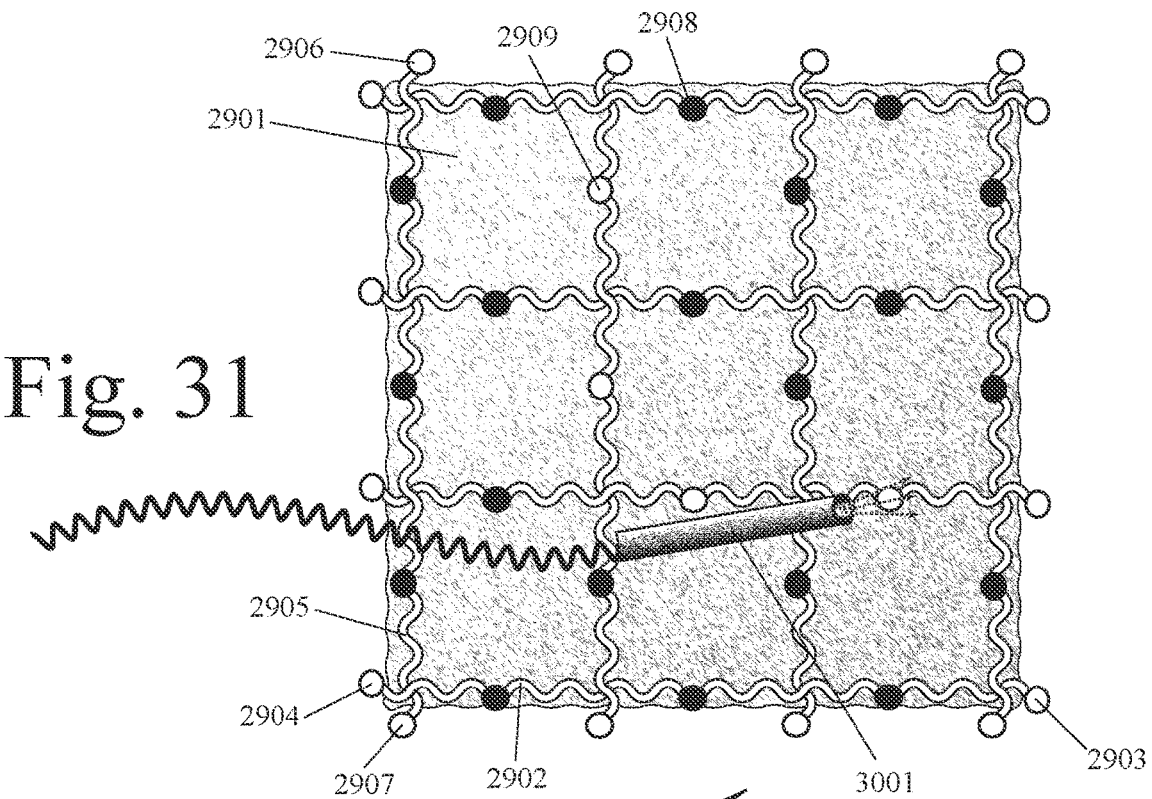
Figure 32:
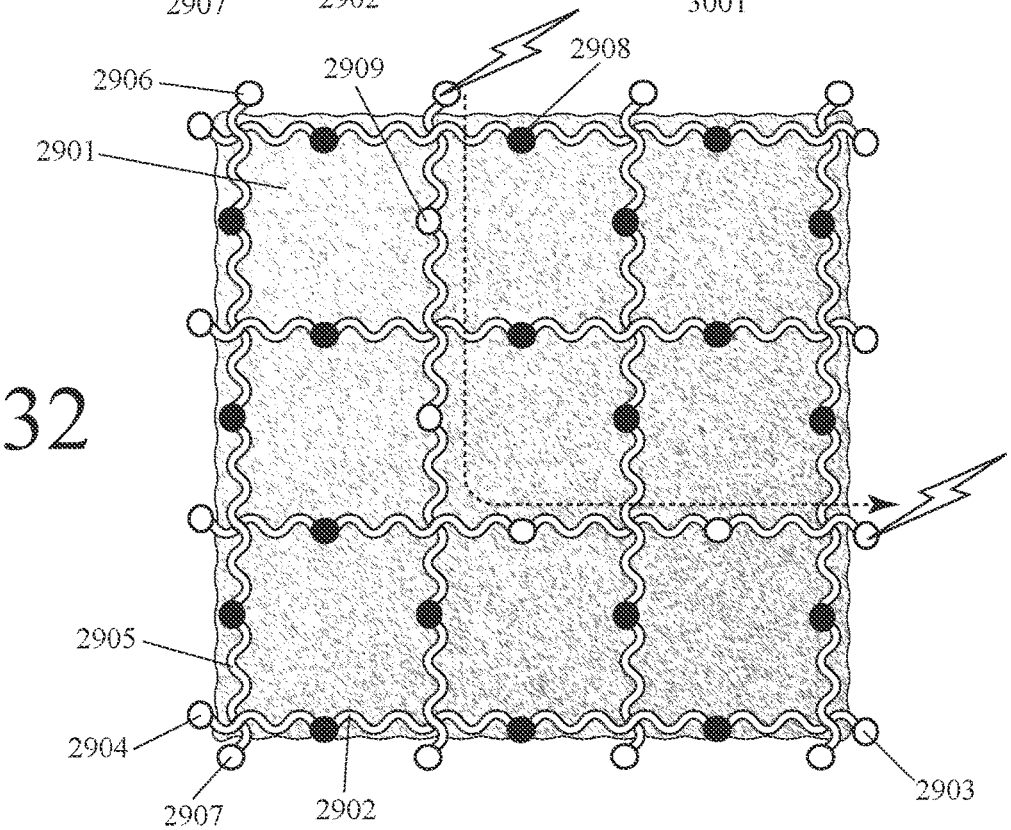

FIG. 29 shows this example at a first point in time when all junctions are in their first configuration and none conduct electromagnetic energy. FIG. 30 shows this example at a second point in time as localized thermal and/or light energy is being applied to junction 2909. This localized application of energy changes this junction from its first (non-conductive) configuration to its second (conductive) configuration. This change is represented symbolically by changing the junction from a black circle to a white circle. FIG. 31 shows this example at a third point in time as additional selected junctions are changed from their first configuration to second configuration by the localized application of energy. FIG. 32 shows this example at a fourth point in time after localized application of energy to selected junctions has created a (customized) electroconductive pathway through the fabric. In this manner, localized application of energy to selected junctions can create different patterns of electroconductive circuits in fabric for different articles of motion recognition clothing. Example variations discussed elsewhere in this disclosure or in priority-linked disclosures are not repeated here to avoid redundancy, but can be applied where relevant to the example shown here.

FIGS. 33 through 36 show four sequential top-down views of another example of motion recognition fabric that is similar to the one shown in FIGS. 29 through 32 except that the junctions all start out being conductive and most are selectively changed to being non-conductive by localized application of thermal and/or light energy.

In this example, motion recognition fabric comprises: a non-conductive layer 3301; a first set of electromagnetic energy pathways (including pathway 3302 with ends 3303 and 3304) which further comprises a plurality of junctions; a second set of electromagnetic energy pathways (including pathway 3305 with ends 3306 and 3307) which further comprises a plurality of junctions; wherein a junction has a first configuration in which it is electroconductive and a second configuration in which it is non-conductive; wherein selected junctions are changed from their first configuration to their second configuration by localized application (by energy emitter 3401) of thermal, light, and/or kinetic energy to the selected junctions.

Figure 33:
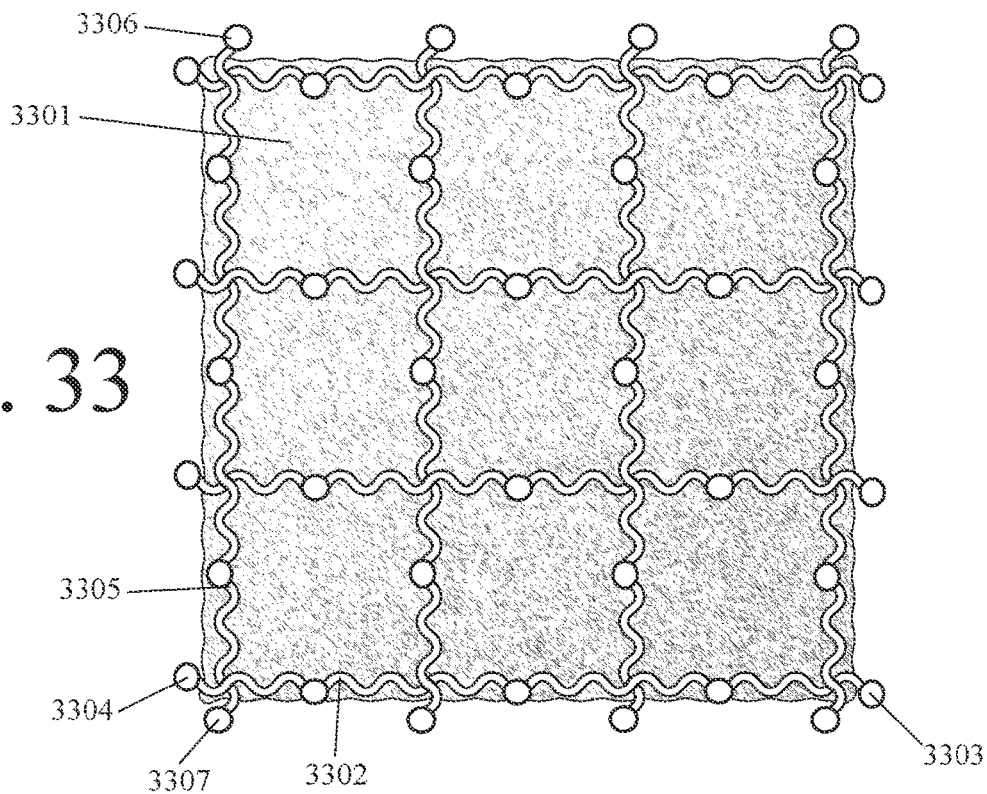
FIGS. 33 through 36 show four sequential views of fabric with a woven grid of perpendicular EM pathways wherein electromagnetic communication between selected pathways and selected EM emitters or receivers is deactivated by localized application of energy.
Figure 34:
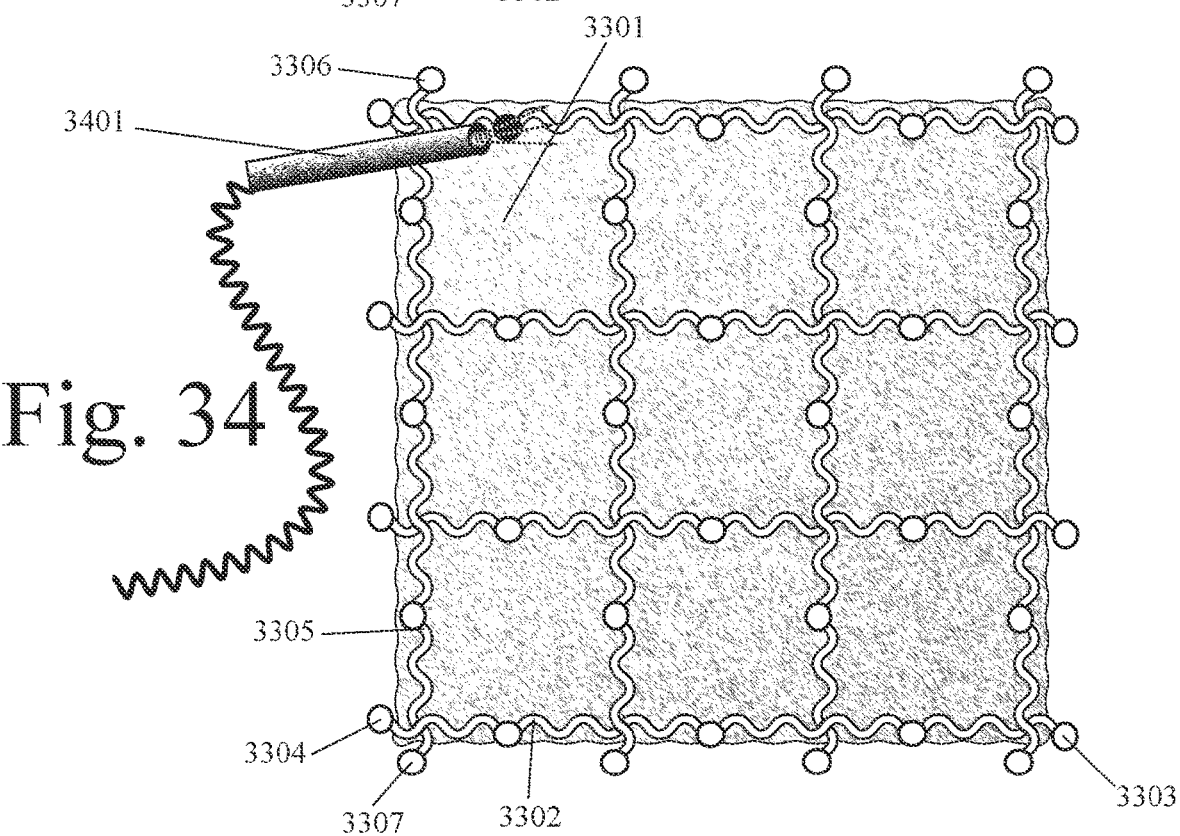
Figure 35:
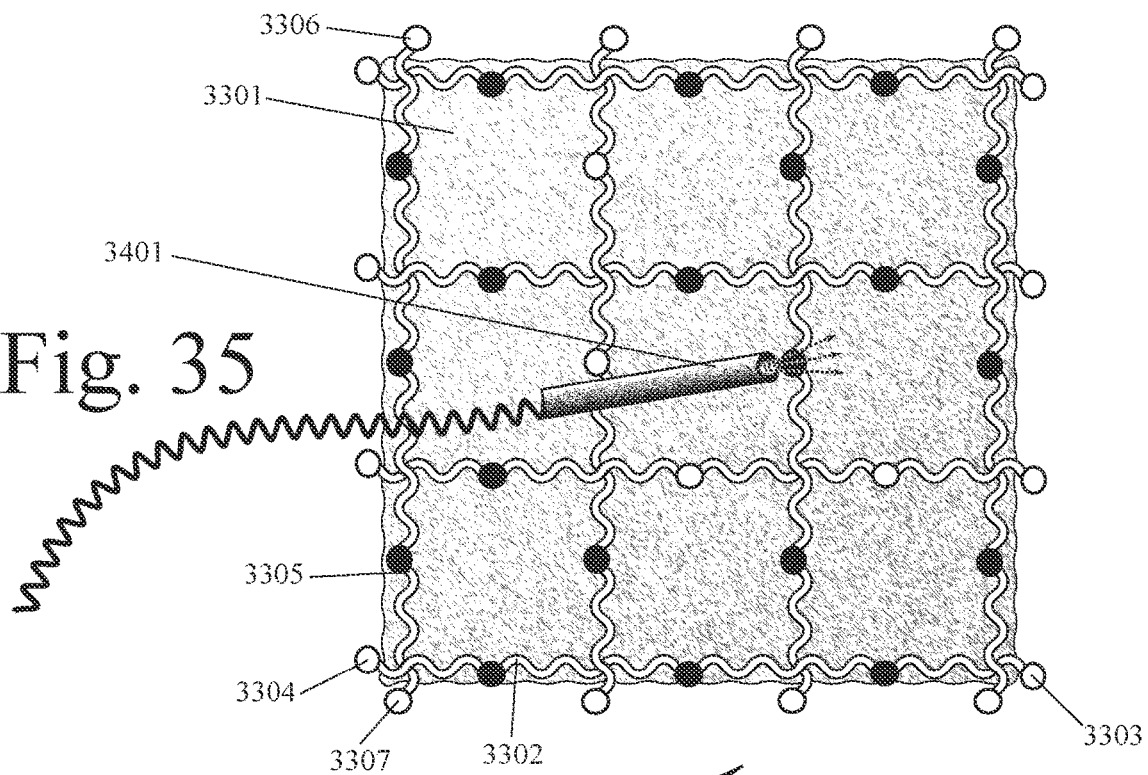
Figure 36:
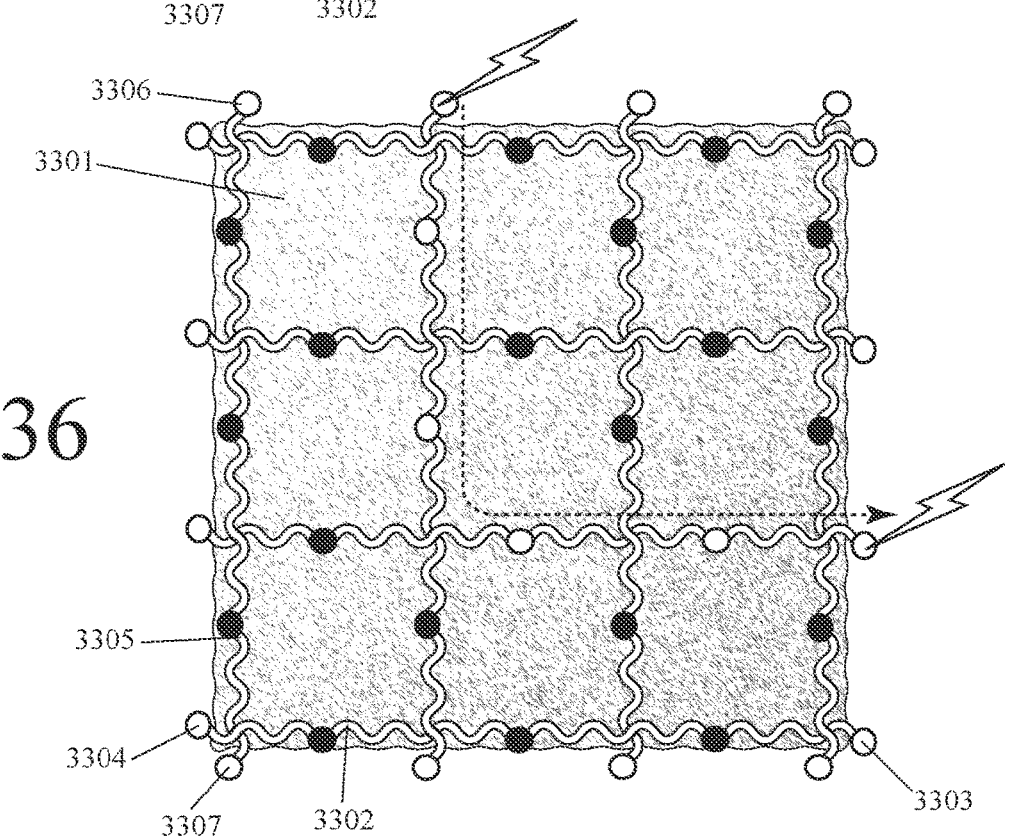

FIG. 33 shows this example at a first point in time when all junctions are in their first configuration and all conduct electromagnetic energy. FIG. 34 shows this example at a second point in time as localized thermal and/or light energy is being applied to a junction. This localized application of energy changes this junction from its first (conductive) configuration to its second (non-conductive) configuration. This change is represented symbolically by changing the junction from a white circle to a black circle. FIG. 35 shows this example at a third point in time as additional selected junctions are changed from their first configuration to second configuration by the localized application of energy. FIG. 36 shows this example at a fourth point in time after localized application of energy to selected junctions has created a (customized) electroconductive pathway through the fabric. In this manner, localized application of energy to selected junctions can create different patterns of electroconductive circuits in fabric for different articles of motion recognition clothing. Example variations discussed elsewhere in this disclosure or in priority-linked disclosures are not repeated here to avoid redundancy, but can be applied where relevant to the example shown here.

FIGS. 37 through 40 show four sequential top-down views of another example of motion recognition fabric that is similar to the one shown in FIGS. 29 through 32 except that the electromagnetic energy pathways are sinusoidal. In this example, motion recognition fabric comprises: a non-conductive layer 3701; a first sinusoidal electromagnetic energy pathway (3702); a second sinusoidal electromagnetic energy pathway (3703); and a plurality of junctions on pathways (including junction 3704); wherein a junction has a first configuration in which it is non-conductive and a second configuration in which it is electroconductive; and wherein selected junctions are changed from their first configuration to their second configuration by localized application (by energy emitter 3801) of thermal, light, and/or kinetic energy to the selected junctions.

Figure 37:
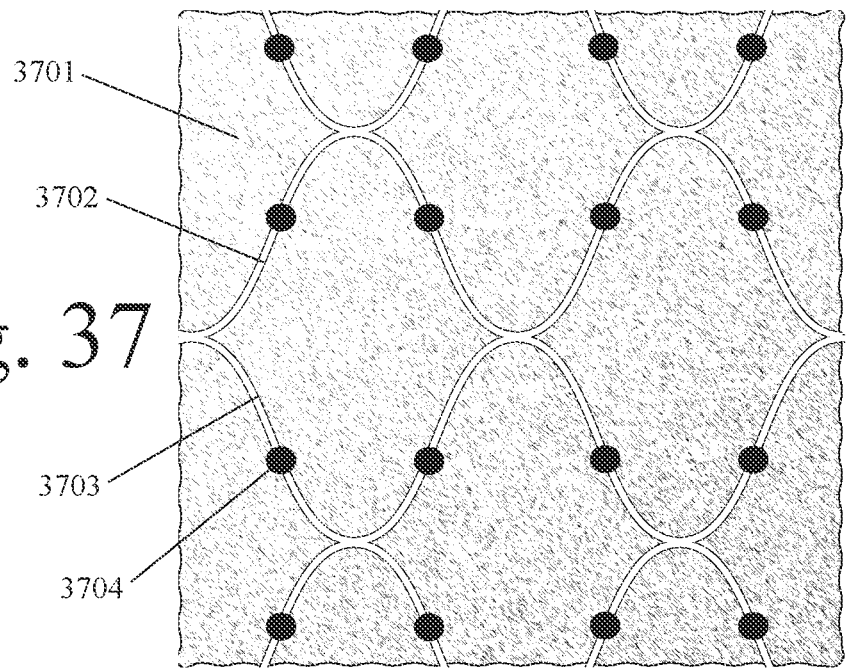
FIGS. 37 through 40 show four sequential views of fabric with a mesh of sinusoidal EM pathways wherein electromagnetic communication between selected pathways and selected EM emitters or receivers is activated by localized application of energy.
Figure 38:
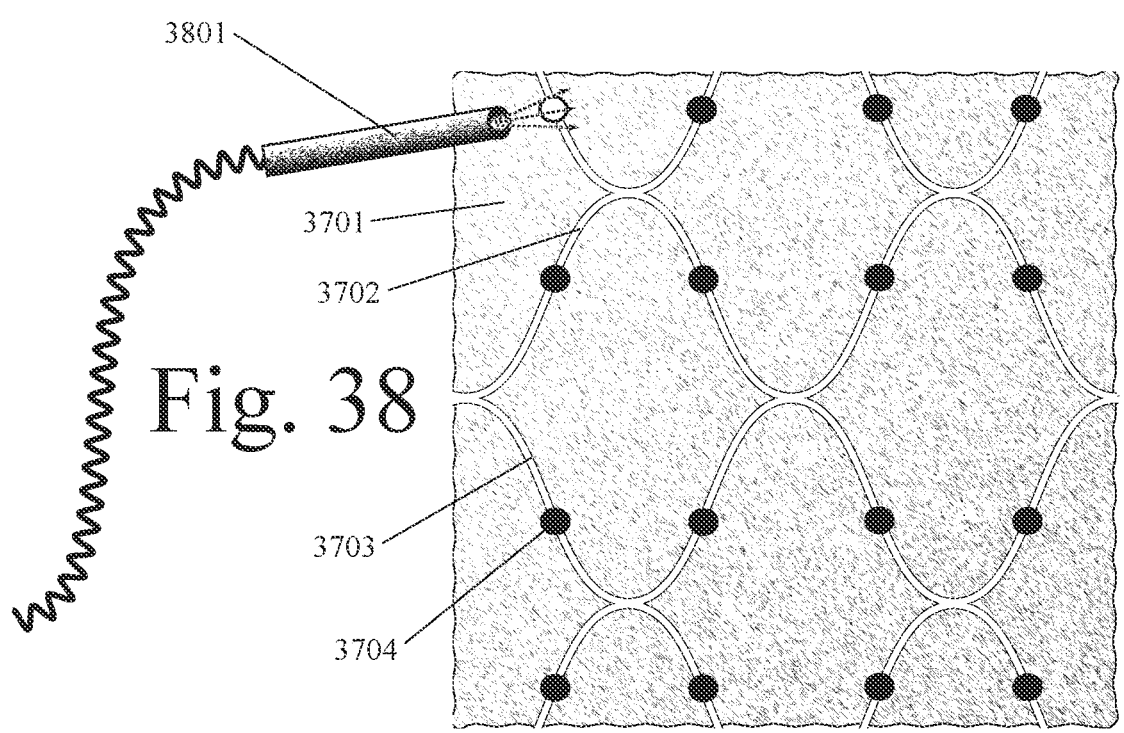
Figure 39:
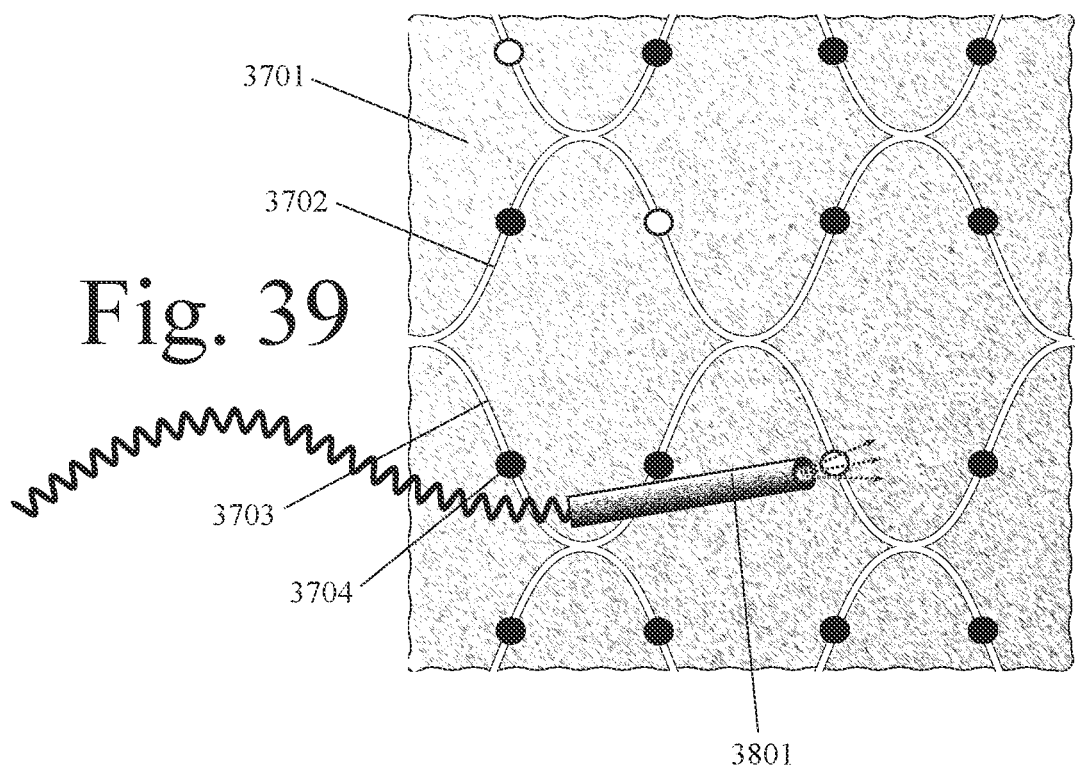
Figure 40:
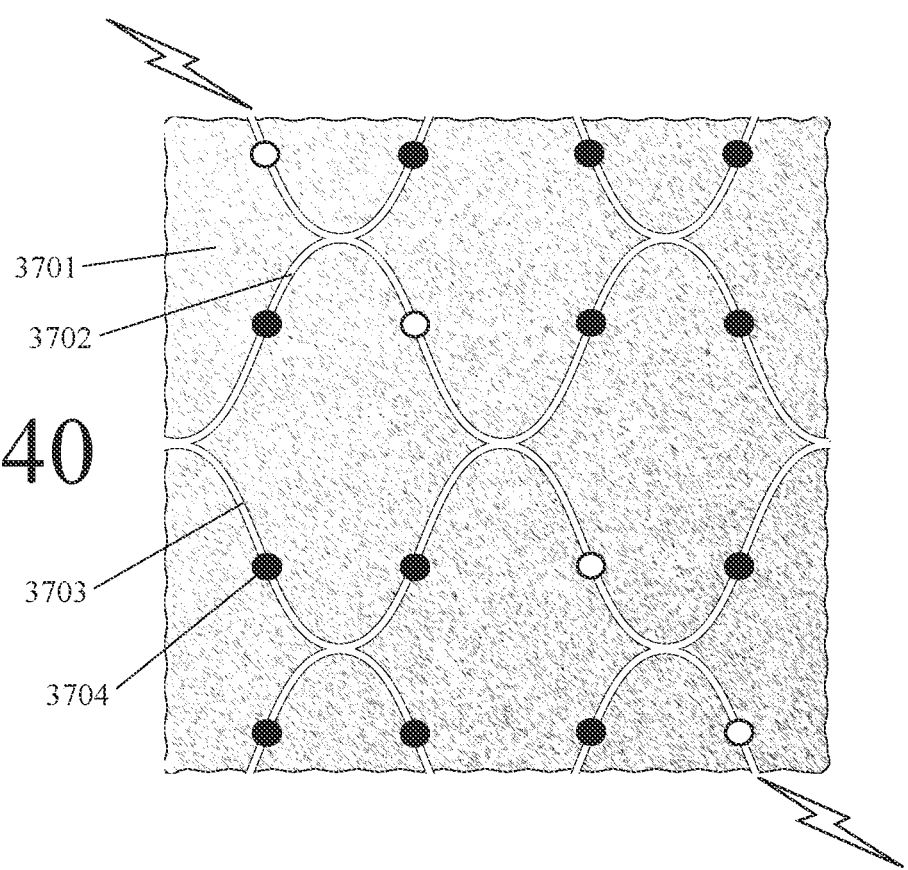

FIG. 37 shows this example at a first point in time when all junctions are in their first configuration and none conduct electromagnetic energy. FIG. 38 shows this example at a second point in time as localized thermal and/or light energy is being applied to a junction. This localized application of energy changes this junction from its first (non-conductive) configuration to its second (electroconductive) configuration. This change is represented symbolically by changing the junction from a black circle to a white circle. FIG. 39 shows this example at a third point in time as additional selected junctions are changed from their first configuration to second configuration by the localized application of energy. FIG. 40 shows this example at a fourth point in time after localized application of energy to selected junctions has created a (customized) electroconductive pathway through the fabric. In this manner, localized application of energy to selected junctions can create different patterns of electroconductive circuits in fabric for different articles of motion recognition clothing.

In this example, the pathways are sinusoidal and adjacent pathways are out of phase by 180 degrees and intersect. In another example, pathways can intersect when projected on a two-dimensional plane to form a grid of squares. In another example, pathways can intersect when projected on a two-dimensional plane to form a grid of hexagons. Other example variations discussed elsewhere in this disclosure or in priority-linked disclosures are not repeated here to avoid redundancy, but can be applied where relevant to the example shown here.

Figure 41:
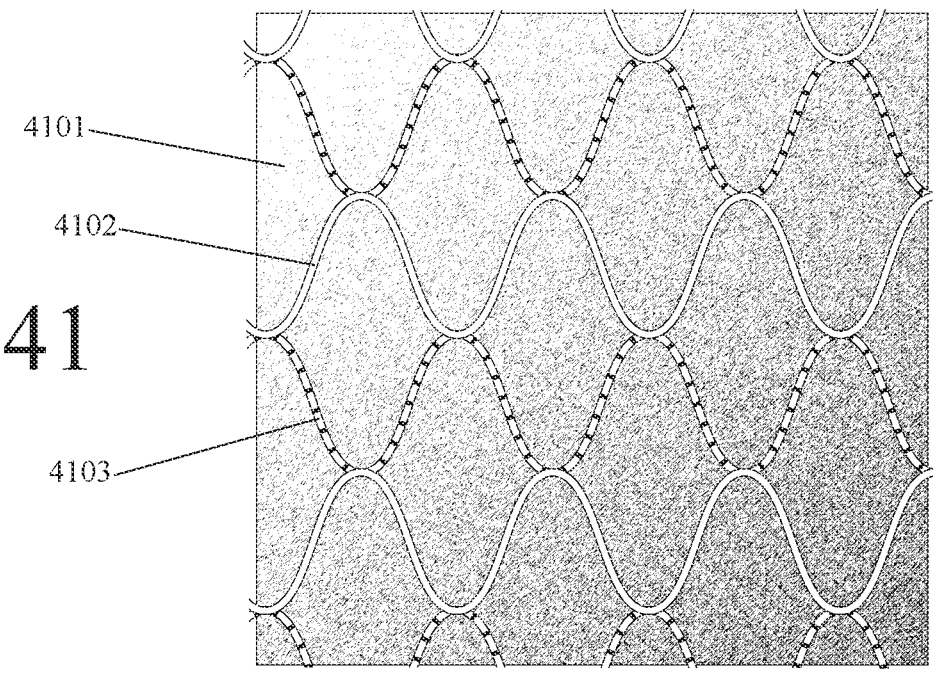
FIGS. 41 through 42 show two sequential views of fabric with inner and outer layers of sinusoidal EM pathways wherein electromagnetic communication between the inner and outer pathways at selected locations is activated by localized application of energy.
Figure 42:
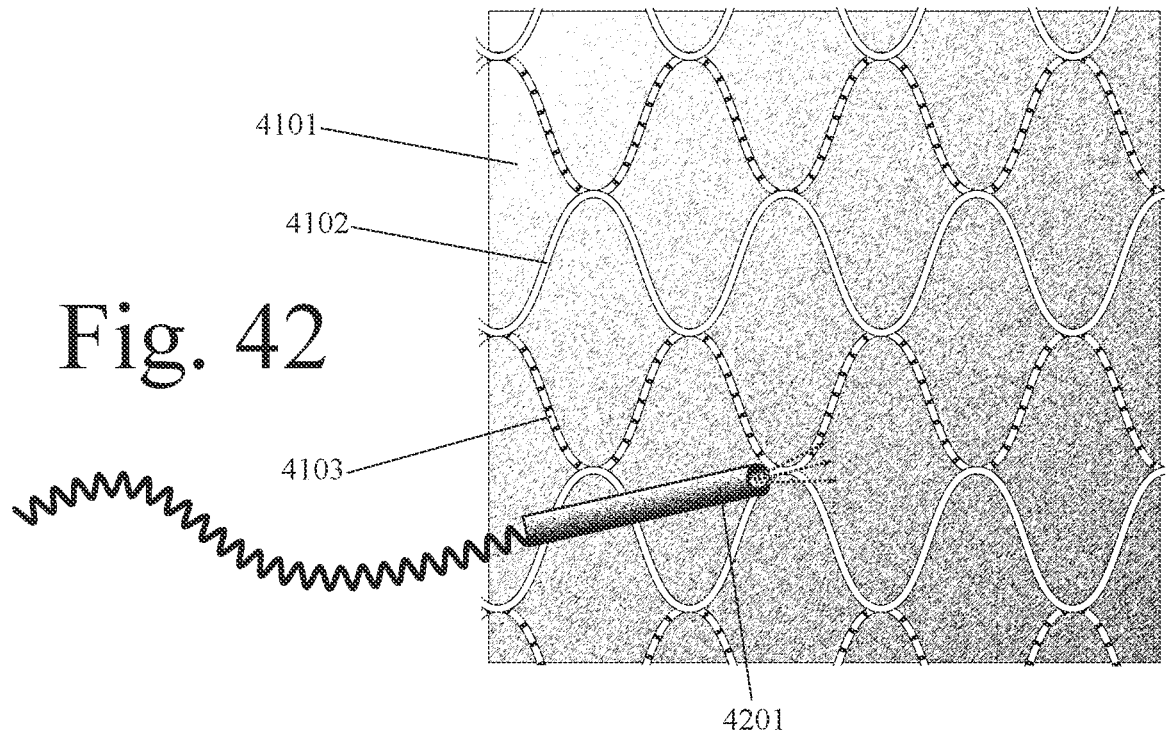

FIGS. 41 through 42 show two sequential top-down views of another example of motion recognition fabric. In this example, motion recognition fabric comprises: a first set of sinusoidal electromagnetic energy pathways (including 4102) in a first layer of fabric; a non-conductive second layer 4101 of fabric; a second set of sinusoidal electromagnetic energy pathways (including 4103) in a third layer of fabric; wherein localized application of thermal and/or light energy (by energy emitter 4201) creates a junction which conducts electromagnetic energy between the first set and the second set. FIG. 41 shows this example at a first point in time before a junction has been created. FIG. 42 shows this example at a second point in time as localized thermal and/or light energy is being applied to create a junction between the first and second sets. Localized application of energy to selected fabric locations can create different patterns of electroconductive circuits in fabric for different articles of motion recognition clothing. Example variations discussed elsewhere in this disclosure or in priority-linked disclosures are not repeated here to avoid redundancy, but can be applied where relevant to the example shown here.

Figure 43:
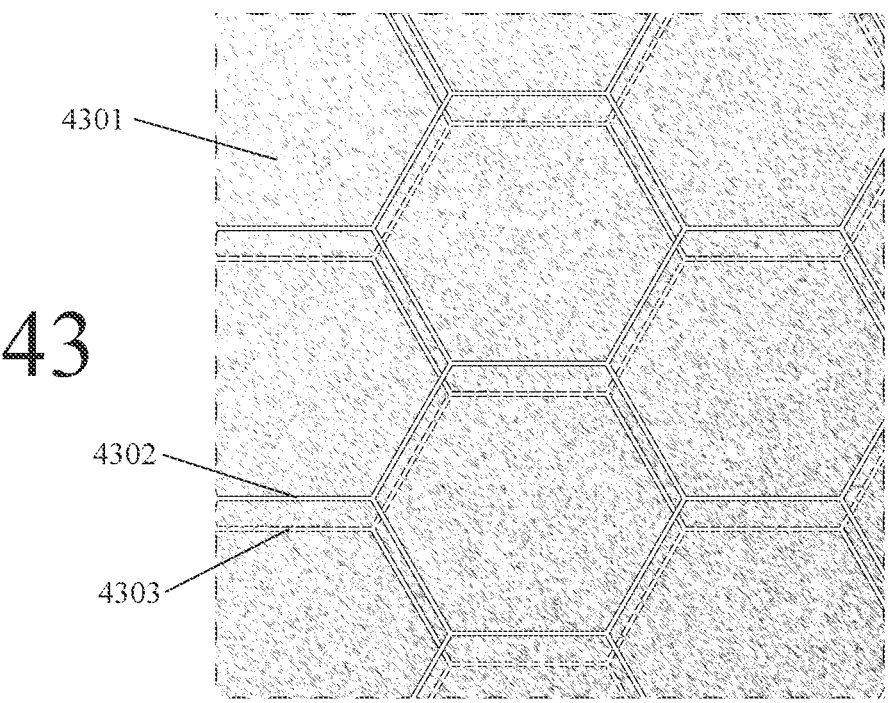
FIG. 43 shows fabric comprising inner and outer EM layers, wherein each EM layer has a hexagonal grid of EM pathways.

FIG. 43 shows a top-down view of another example of motion recognition fabric. In this example, motion recognition fabric comprises: a first hexagonal grid or mesh of electromagnetic energy pathways (including 4302) in a first layer of fabric; a non-conductive second layer 4301 of fabric; a second hexagonal grid or mesh of electromagnetic energy pathways (including 4303) in a third layer of fabric. In an example, changes in capacitance levels at different locations between the first and second hexagonal grids or meshes are analyzed for three-dimensional modeling of the configuration of a joint spanned by this fabric. In an example, changes in the resistance, impedance, and/or conductivity of the first and/or second hexagonal grids or meshes are analyzed for three-dimensional modeling of the configuration of a joint spanned by this fabric. Other example variations discussed elsewhere in this disclosure or in priority-linked disclosures are not repeated here to avoid redundancy, but can be applied where relevant to the example shown here.

Figure 44:
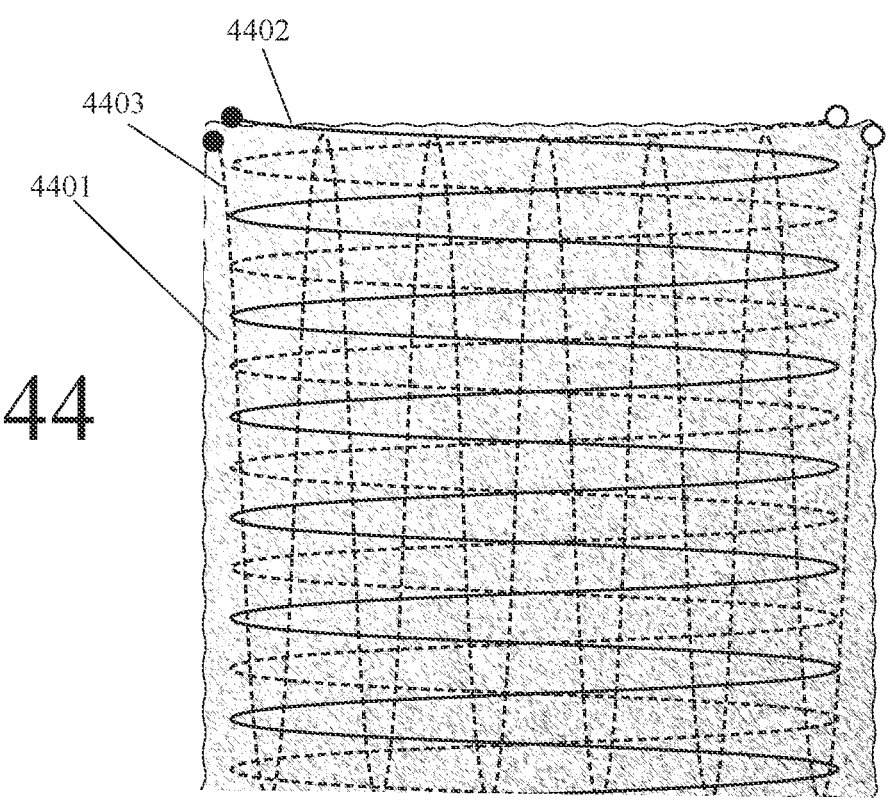
FIG. 44 shows fabric comprising inner and outer EM layers with large-wave sinusoidal EM pathways whose longitudinal axes are perpendicular.

FIG. 44 shows a top-down view of another example of motion recognition fabric. In this example, motion recognition fabric comprises: a first sinusoidal electromagnetic energy pathway 4402 which spans a first layer of fabric; a non-conductive second layer 4401 of fabric; and a second sinusoidal electromagnetic energy pathway 4403 which spans a third layer of fabric; wherein the central longitudinal axis of the second sinusoidal pathway is perpendicular to the central longitudinal axis of the first sinusoidal pathway (when projected onto the same two-dimensional plane); and wherein a 360-degree wave of the second sinusoidal pathway spans the majority of 360-degree waves of the first sinusoidal pathway.

In an example, changes in capacitance levels at different locations between the first and second sinusoidal pathways are analyzed for three-dimensional modeling of the configuration of a joint spanned by this fabric. In an example, changes in the resistance, impedance, and/or conductivity of the first and/or second sinusoidal pathways are analyzed for three-dimensional modeling of the configuration of a joint spanned by this fabric. Example variations discussed elsewhere in this disclosure or in priority-linked disclosures are not repeated here to avoid redundancy, but can be applied where relevant to the example shown here.

Figure 45:
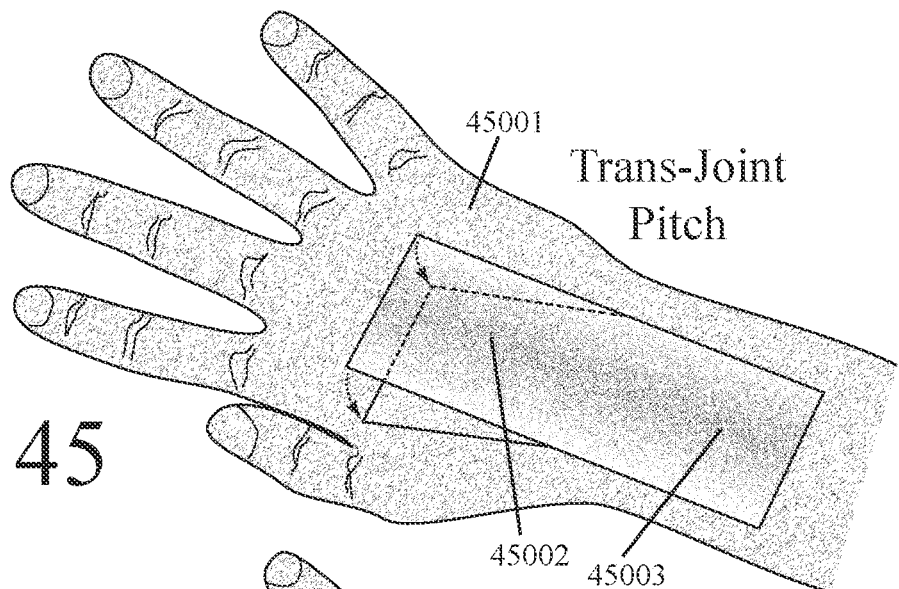
FIG. 45 shows trans-joint pitch movement of a wearable deformable sensor.

FIG. 45 shows a top-down (dorsal) view of a distal portion 45002 of a rectangular joint-spanning wearable deformable sensor, a proximal portion 45003 of the sensor, and a person's hand 45001 on which the sensor is worn. Trans-joint pitch can be defined as the pitch of the distal portion of the joint-spanning sensor (i.e. the portion which is distal relative to the joint) relative to the proximal portion of the sensor (i.e. the portion which is proximal relative to the joint). Proximal is defined as being closer to a person's heart and distal means farther from the person's heart when the person's body is in Vitruvian man configuration (as in the famous drawing by Leonardo da Vinci). For a basic hinge joint, trans-joint pitch measures bending of the joint. Trans-joint pitch movement of the distal portion of the sensor is represented in FIG. 45 by dotted lines and arrows.

Figure 46:
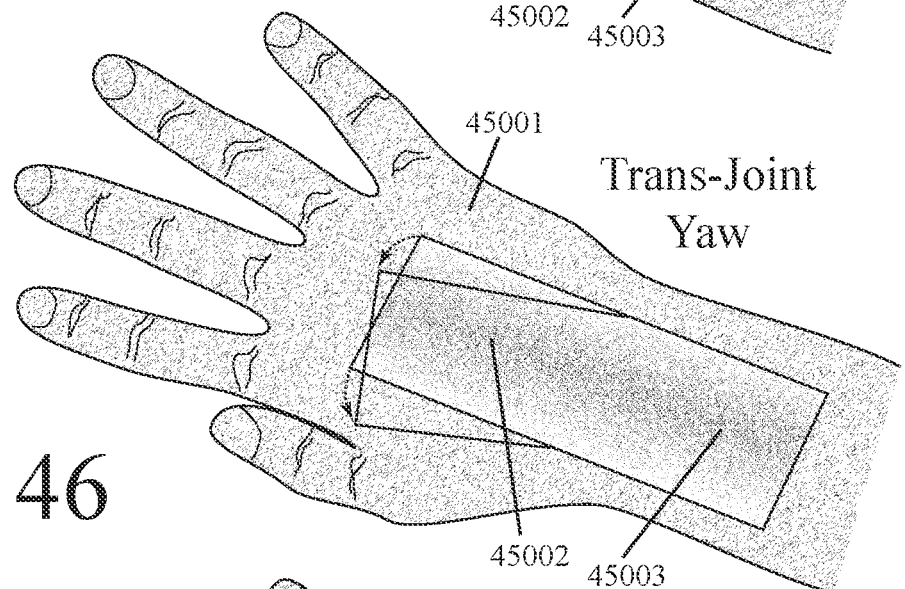
FIG. 46 shows trans-joint yaw movement of a wearable deformable sensor.

FIG. 46 shows another top-down (dorsal) view of the distal portion 45002 of the rectangular joint-spanning wearable deformable sensor, the proximal portion 45003 of the sensor, and the person's hand 45001 on which the sensor is worn. Trans-joint yaw can be defined as the yaw of the distal portion of the joint-spanning sensor (i.e. the portion which is distal relative to the joint) relative to the proximal portion of the sensor (i.e. the portion which is proximal relative to the joint). For a ball-and-socket joint, trans-joint yaw measures lateral (e.g. side-to-side) movement of the joint. Trans-joint yaw movement of the distal portion of the sensor is represented in FIG. 46 by dotted lines and arrows.

Figure 47:
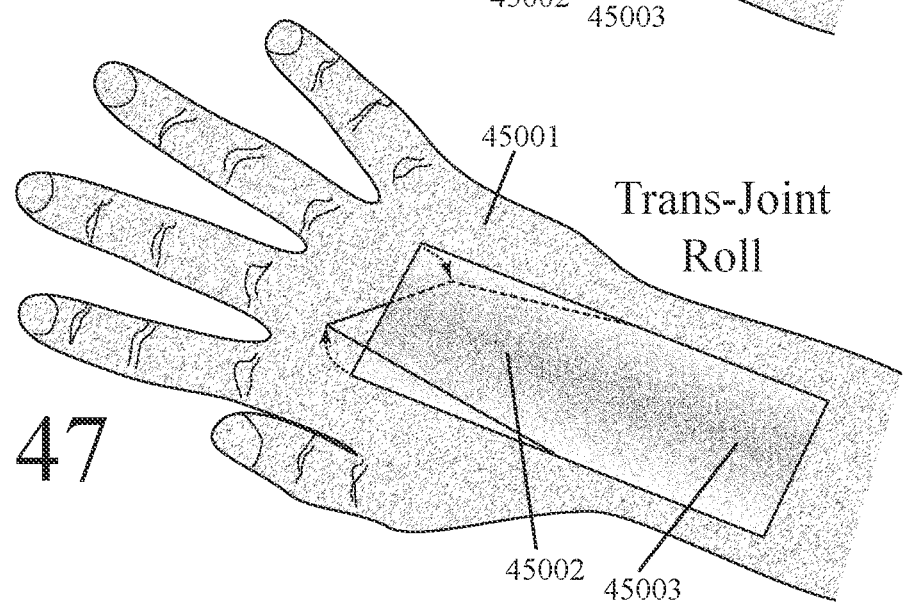
FIG. 47 shows trans-joint roll movement of a wearable deformable sensor.

FIG. 47 shows another top-down (dorsal) view of the distal portion 45002 of the rectangular joint-spanning wearable deformable sensor, the proximal portion 45003 of the sensor, and the person's hand 45001 on which the sensor is worn. Trans-joint roll can be defined as the roll of the distal portion of the joint-spanning sensor (i.e. the portion which is distal relative to the joint) relative to the proximal portion of the sensor (i.e. the portion which is proximal relative to the joint). For a ball-and-socket joint, trans-joint yaw measures twisting (e.g. rotation) of the joint. Trans-joint roll movement of the distal portion of the sensor is represented in FIG. 47 by dotted lines and arrows.

Figure 48:
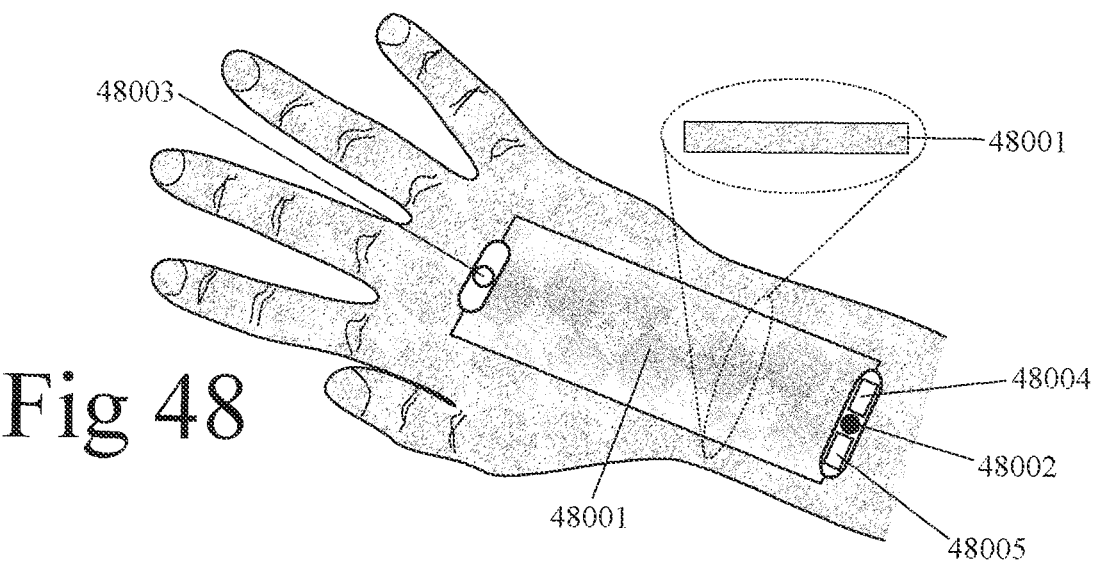
FIG. 48 shows a single-strip single-layer EM-resistive sensor for measuring changes in joint configuration.

FIG. 48 shows an example of a wearable deformable sensor for measuring and/or modeling changes in body joint configuration. The left and lower-right portions of FIG. 48 show a top-down (dorsal) view of the sensor being worn on a person's hand. The upper-right portion of FIG. 48 shows a dotted-line ellipse which contains a cross-sectional view of the sensor.

The wearable deformable sensor for measuring changes in body joint configuration which is shown in FIG. 48 comprises: a deformable elongate electrically-conductive structure 48001 which is configured to span from a portion of a person's body which is proximal relative to a body joint to a portion of the person's body which is distal relative to the body joint; an electromagnetic energy emitter 48002 which emits electromagnetic energy into the deformable elongate electrically-conductive structure at a first location; an electromagnetic energy receiver 48003 which receives electromagnetic energy from the deformable elongate electrically-conductive structure at a second location, wherein changes in body joint configuration cause deformations of the deformable elongate electrically-conductive structure, wherein the deformations cause changes in the transmission of electromagnetic energy from the electromagnetic energy emitter to the electromagnetic energy receiver, and wherein the changes in the transmission of electromagnetic energy are analyzed in order to measure and/or model changes in body joint configuration; a data processor 48004; and a power source 48005.

In an example, changes in the transmission of electromagnetic energy can be due to changes in the resistance, impedance, and/or conductivity of the electrically-conductive structure. In an example, changes in the transmission of electromagnetic energy can be analyzed in the data processor. In an example, the sensor can also include a data transmitter which sends data to a remote data processor in which the changes in the transmission of electromagnetic energy are analyzed. In an example, the sensor can also include an energy transducer which harvests electromagnetic energy from kinetic motion of the person's body. In an example, the sensor can also include an energy transducer which harvests electromagnetic energy from thermal energy of the person's body.

In this example, the electromagnetic energy emitter is proximal relative to the electromagnetic energy receiver. In an example, the relative locations of an energy emitter and an energy receiver can be reversed. In this example, the energy emitter and the energy receiver are located at the ends of the deformable elongate electrically-conductive structure. In an example, an energy emitter and/or an energy receiver can be located at more central locations of a deformable elongate electrically-conductive structure. In an example, an energy emitter and/or an energy receiver can be located along the sides of a deformable elongate electrically-conductive structure.

In this example, there is a single energy emitter and a single energy receiver which are in electromagnetic communication with a deformable elongate electrically-conductive structure. In an example, there can be a single energy emitter and two or more energy receivers in electromagnetic communication with a deformable elongate electrically-conductive structure. In an example, there can be a single energy receiver and two or more energy emitters in electromagnetic communication with a deformable elongate electrically-conductive structure.

In an example, a deformable electrically-conductive structure can have a single energy emitter in a central location (e.g. at the center of the structure) and a plurality of energy receivers on the perimeter of the structure. In an example, a deformable electrically-conductive structure can have a single energy receiver in a central location (e.g. at the center of the structure) and a plurality of energy emitters on the perimeter of the structure. In an example, a deformable electrically-conductive structure can have a single energy emitter at its center and a plurality of energy receivers which are evenly distributed around its perimeter. In an example, a deformable electrically-conductive structure can have a single energy receiver at its center and a plurality of energy emitters which are evenly distributed around its perimeter. In an example, an arcuate (e.g. circular) deformable electrically-conductive structure can have a single energy emitter at its center and a plurality of energy receivers which are evenly distributed around its perimeter. In an example, an arcuate (e.g. circular) deformable electrically-conductive structure can have a single energy receiver at its center and a plurality of energy emitters which are evenly distributed around its perimeter.

In this example, a deformable elongate electrically-conductive structure has a rectangular shape. In an example, the shape a deformable elongate electrically-conductive structure can be selected from the group consisting of: rectangular or rounded rectangle; elliptical or oval; trapezoidal, keystone, tapered, and/or triangular; hexagonal or octagonal; hour-glass or figure eight shape; tear drop or egg shape; convex lens shape; sinusoidal and/or oscillating shape; wagon wheel or star-burst configuration; and circular. In an example, an elongate electrically-conductive structure can have a proximal-to-distal length within a range of 3-8 inches. In an example, an elongate electrically-conductive structure can have a proximal-to-distal length within a range of 1-14 inches. In an example, an elongate electrically-conductive structure can have a width within a range of ⅛ to 4 inches. In an example, an elongate electrically-conductive structure can have a thickness within the range of 1/64 to ¼ of an inch.

In an example, an electrically-conductive structure can comprise silicone and/or polydimethylsiloxane (PDMS) which has been impregnated and/or doped with electrically-conductive material. In an example, an electrically-conductive structure can comprise silicone and/or polydimethylsiloxane (PDMS) which has been impregnated and/or doped with aluminum, carbon, copper, gold, nickel, or silver particles or fibers. In an example, the electrically-conductive structure can comprise electrically-conductive threads, yarns, wires, or fibers which are embedded within silicone and/or polydimethylsiloxane (PDMS). In an example, an electrically-conductive structure can comprise a woven array of electrically-conductive threads, yarns, wires, or fibers.

In an example, a deformable elongate electrically-conductive structure can have a longitudinal axis which is substantially parallel to the proximal-to-distal axis of a body joint spanned by the structure. In an example, such a structure can be located (primarily) on the anterior surface of the body joint. In an example, such a structure can be located (primarily) on the dorsal surface of a body joint. In an example, such a structure can span half of the circumference of a body portion which contains a body joint. In an example, such a structure can span the entire circumference of a body portion which contains a body joint. Relevant example variations discussed elsewhere in this disclosure or in priority-linked disclosures can also be applied to the example shown in this figure, but are not repeated here in order to reduce narrative redundancy.

Figure 49:
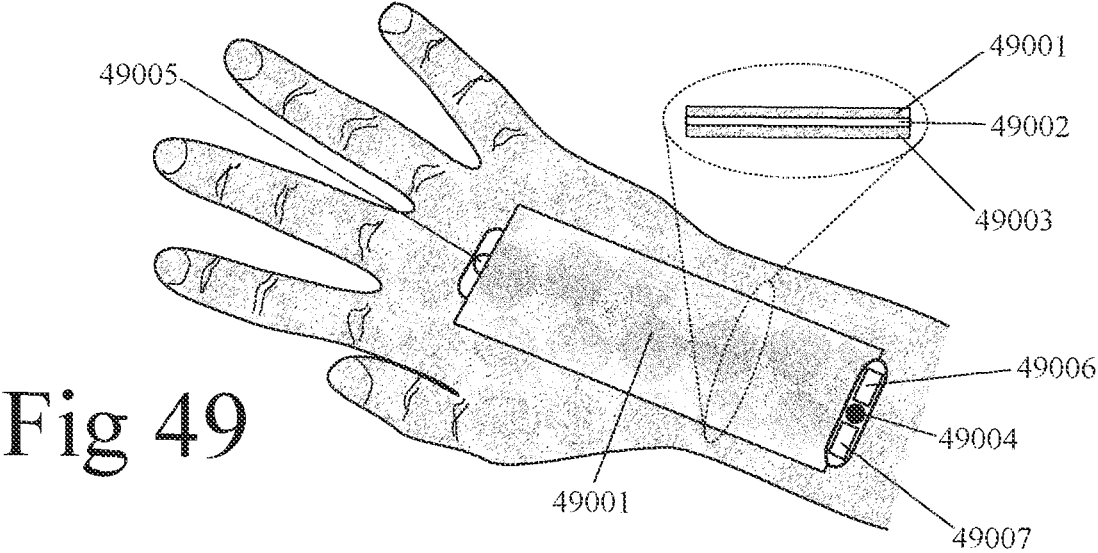
FIG. 49 shows a single-strip multi-layer EM-capacitive sensor for measuring changes in joint configuration.

FIG. 49 shows another example of a wearable deformable sensor for measuring and/or modeling changes in body joint configuration. This sensor is similar to the one shown in FIG. 48 except that it is a multi-layer (e.g. three layer) capacitive sensor instead of a (e.g. single-layer) resistive sensor. The left and lower-right portions of FIG. 49 show a top-down (dorsal) view of the sensor being worn on a person's hand. The upper-right portion of FIG. 49 shows a dotted-line ellipse which contains a cross-sectional view of the sensor.

The wearable deformable sensor for measuring changes in body joint configuration which is shown in FIG. 49 comprises: a first (e.g. outer) deformable electrically-conductive layer 49001 which is configured to span from a portion of a person's body which is proximal relative to a body joint to a portion of the person's body which is distal relative to the body joint; a second (e.g. inner) deformable electrically-conductive layer 49003 which is configured to span from the portion of the person's body which is proximal relative to the body joint to the portion of the person's body which is distal relative to the body joint; a deformable dielectric layer 49002 between the first deformable electrically-conductive layer and the second deformable electrically-conductive layer, wherein changes in the configuration of the body joint cause deformations of the deformable dielectric layer, and wherein deformations of the deformable dielectric layer cause changes in the capacitance between the first and second deformable electrically-conductive layers, and wherein the changes in the capacitance between the first and second deformable electrically-conductive layers are analyzed in order to measure and/or model changes in body joint configuration; an electromagnetic energy emitter 49004 which emits electromagnetic energy into the first deformable electrically-conductive layer; an electromagnetic energy receiver 49005 which receives electromagnetic energy from the second deformable electrically-conductive layer; a data processor 49006; and a power source 49007.

In an example, changes in capacitance between the first and second layers can be analyzed in the data processor. In an example, the sensor can also include a data transmitter which sends data to a remote data processor in which capacitance changes are analyzed. In an example, a power source can be a battery. In an example, the sensor can also include an energy transducer which harvests electromagnetic energy from the kinetic motion of the person's body. In an example, the sensor can also include an energy transducer which harvests electromagnetic energy from the thermal energy of the person's body. In this example, the electromagnetic energy emitter is proximal relative to the electromagnetic energy receiver. In an example, the proximal-vs.-distal or inner-vs.-outer layer locations of an energy emitter and an energy receiver can be reversed.

In this example, there is one energy emitter which is in electromagnetic communication with one conductive layer of a multi-layer (e.g. three layer) capacitive structure and one energy receiver in electromagnetic communication with a different conductive layer of the multi-layer capacitive structure. In an example, there can be one energy emitter in electromagnetic communication with one conductive layer of a multi-layer capacitive structure and two or more energy receivers in electromagnetic communication with a different conductive layer of the multi-layer capacitive structure. In an example, there can be one energy receiver which is in electromagnetic communication with one layer of a multi-layer capacitive structure and two or more energy emitters in electromagnetic communication with a different layer of the multi-layer capacitive structure. In an example, there can be one energy emitter near the center of one conductive layer of a multi-layer capacitive structure and two or more energy receivers on the perimeter of a different conductive layer of the multi-layer capacitive structure. In an example, there can be one energy receiver near the center of one conductive layer of a multi-layer capacitive structure and two or more energy emitters on the perimeter of a different conductive layer of the multi-layer capacitive structure.

In this example, a deformable elongate electrically-conductive layer has a rectangular shape. In an example, the shape of a deformable elongate electrically-conductive layer can be selected from the group consisting of: rectangular or rounded rectangle; elliptical or oval; trapezoidal, keystone, tapered, and/or triangular; hexagonal or octagonal; hourglass or figure eight shape; tear drop or egg shape; convex lens shape; sinusoidal and/or oscillating shape; wagon wheel or star-burst configuration; and circular. In an example, different layers of a multi-layer capacitive sensor can have different shapes. In an example, an elongate electrically-conductive layer can have a proximal-to-distal length within a range of 3-8 inches. In an example, an elongate electrically-conductive layer can have a proximal-to-distal length within a range of 1-14 inches. In an example, an elongate electrically-conductive layer can have a width within a range of ⅛ to 4 inches. In an example, an elongate electrically-conductive layer can have a thickness within the range of 1/64 to ¼ of an inch. In an example, different layers of a multi-layer capacitive sensor can have different thicknesses.

In an example, an electrically-conductive layer can comprise silicone and/or polydimethylsiloxane (PDMS) which has been impregnated and/or doped with electrically-conductive material. In an example, an electrically-conductive layer can comprise silicone and/or polydimethylsiloxane (PDMS) which has been impregnated and/or doped with aluminum, carbon, copper, gold, nickel, or silver particles or fibers. In an example, an electrically-conductive layer can comprise electrically-conductive threads, yarns, wires, or fibers which are embedded within silicone and/or polydimethylsiloxane (PDMS). In an example, an electrically-conductive layer can comprise an array of electrically-conductive threads, yarns, wires, or fibers. In an example, such an array can be woven. In an example, a deformable dielectric layer can comprise silicone and/or polydimethylsiloxane (PDMS).

The deformable capacitive sensor shown in FIG. 49 has three layers: an outer electrically-conductive layer; a middle dielectric (non-conductive or less conductive) layer; and an inner electrically-conductive layer. In an example, a deformable capacitive sensor can have more than three layers. In an example, a deformable capacitive sensor can comprise three conductive layers and two non-conductive layers. In an example, a deformable capacitive sensor can have three or more conductive layers with different orientations which are separated by two or more non-conductive layers. Relevant example variations discussed elsewhere in this disclosure or in priority-linked disclosures can also be applied to the example shown in this figure, but are not repeated here in order to reduce narrative redundancy.

Figure 50:
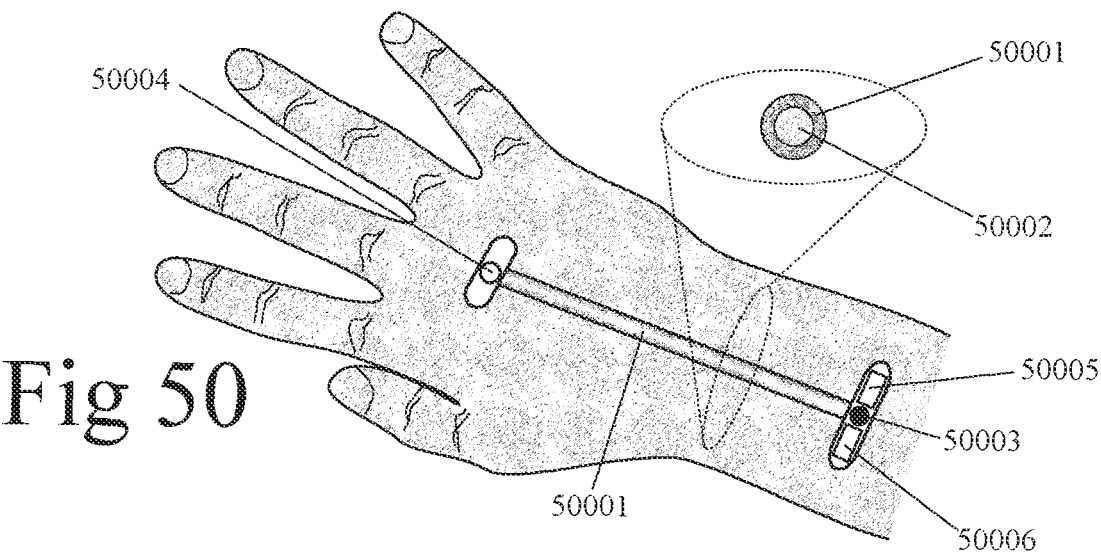
FIG. 50 shows a single conductive-fluid-filled lumen for measuring changes in joint configuration.

FIG. 50 shows another example of a wearable deformable sensor for measuring and/or modeling changes in body joint configuration. This example features a flexible non-conductive lumen which is filled with an electrically-conductive flowable substance (e.g. a conductive fluid or gel). Deformation of the lumen by changes in body joint configuration changes the transmission of electromagnetic energy through the substance in the lumen. These changes are used to measure and/or model changes in body joint configuration. The left and lower-right portions of FIG. 50 show a top-down (dorsal) view of the sensor being worn on a person's hand. The upper-right portion of FIG. 50 shows a dotted-line ellipse which contains a cross-sectional view of the sensor.

The wearable deformable sensor which is shown in FIG. 50 comprises: a deformable nonconductive elongate lumen 50001 which is configured to span from a portion of a person's body which is proximal relative to a body joint to a portion of the person's body which is distal relative to the body joint; an electrically-conductive flowable substance 50002 inside the deformable nonconductive elongate lumen; an electromagnetic energy emitter 50003 which emits electromagnetic energy into the electrically-conductive flowable substance at a first location; an electromagnetic energy receiver 50004 which receives electromagnetic energy from the electrically-conductive flowable substance at a second location, wherein changes in body joint configuration cause deformations of the deformable nonconductive elongate lumen, and wherein these deformations cause changes the transmission of electromagnetic energy from the electromagnetic energy emitter to the electromagnetic energy receiver, and wherein the changes in the transmission of electromagnetic energy are analyzed to measure and/or model changes in body joint configuration; a data processor 50005; and a power source 50006.

In an example, the changes in the transmission of electromagnetic energy can be due to changes in resistance, impedance, and/or conductivity. In an example, changes in the transmission of electromagnetic energy can be analyzed in the data processor. In an example, the sensor can also include a data transmitter which sends data to a remote data processor where changes in energy transmission are analyzed. In an example, a power source can be a battery. In an example, the sensor can also include an energy transducer which harvests electromagnetic energy from the kinetic motion of the person's body. In an example, the sensor can also include an energy transducer which harvests electromagnetic energy from the thermal energy of the person's body. In this example, the electromagnetic energy emitter is proximal to the electromagnetic energy receiver. In an example, the proximal-vs.-distal locations of an emitter and an receiver can be reversed.

In this example, a non-conductive lumen has a circular cross-sectional shape. In an example, the cross-sectional shape of a non-conductive lumen can be selected from the group consisting of: rounded rectangle; elliptical or oval; hexagonal or octagonal; convex lens shape; and circular. In an example, there can be longitudinal variation in the cross-sectional shape and/or size of the non-conductive lumen. In an example, the distal portion of the lumen can have a larger cross-sectional size than that of the proximal portion of the lumen, or vice versa. In an example, a sensor can comprise a plurality of such lumens. In an example, a sensor can comprise a parallel array of such lumens. In an example, a lumen can have a proximal-to-distal length within a range of 3-8 inches. In an example, a lumen can have a proximal-to-distal length within a range of 1-14 inches. In an example, a lumen can have a width within a range of 1/64 to 1/4 of an inch. Relevant example variations discussed elsewhere in this disclosure or in priority-linked disclosures can also be applied to the example shown in this figure, but are not repeated here in order to reduce narrative redundancy.

Figure 51:
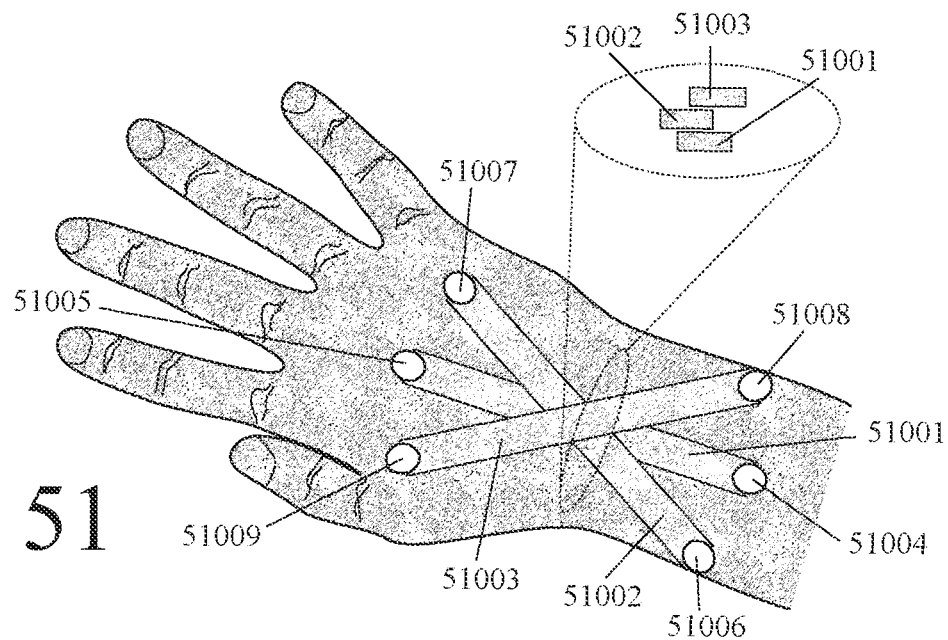
FIG. 51 shows resistive EM strips which intersect centrally for measuring changes in joint configuration.

FIG. 51 shows another example of a wearable deformable sensor for measuring and/or modeling changes in body joint configuration. In this example, there are three conductive structures (e.g. strips or bands) which cross each other as they span a body joint at different angles. The left and lower-right portions of FIG. 51 show a top-down (dorsal) view of the sensor being worn on a person's hand. The upper-right portion of FIG. 51 shows a dotted-line ellipse which contains a cross-sectional view of the sensor.

The wearable deformable sensor in FIG. 51 comprises: a first deformable elongate electrically-conductive structure (e.g. strip or band) 51002 with a central longitudinal axis which is configured to cross the central proximal-to-distal axis of a body joint at an acute angle; a second deformable elongate electrically-conductive structure (e.g. strip or band) 51001 with a central longitudinal axis which is substantially parallel to the central proximal-to-distal axis of the body joint; a third deformable elongate electrically-conductive structure (e.g. strip or band) 51003 with a central longitudinal axis which is configured to cross the central proximal-to-distal axis of the body joint at an acute angle; a first electromagnetic energy emitter 51006 and first electromagnetic energy receiver 51007 which are in electromagnetic communication with the first structure; a second electromagnetic energy emitter 51004 and second electromagnetic energy receiver 51005 which are in electromagnetic communication with the second structure; and a third electromagnetic energy emitter 51008 and third electromagnetic energy receiver 51009 which are in electromagnetic communication with the third structure.

Alternatively, the wearable deformable sensor in FIG. 51 can be described as comprising: three deformable elongate electrically-conductive strips (51001, 51002, and 51003) which are configured to cross each other as they span a body joint at different angles relative to the central proximal-to-distal axis of the body joint; and three pairs of electromagnetic energy emitters and receivers (51004 and 51005, 51006 and 51007, and 51008 and 51009) which are in electromagnetic communication with the three electrically-conductive strips, respectively, wherein movement of the body joint causes deformations of one or more of the three strips, wherein these deformations cause changes in the transmission of electromagnetic energy from the electromagnetic energy emitters to the electromagnetic energy receivers, and wherein these changes in the transmission of electromagnetic energy are analyzed in order to measure and/or model changes in body joint configuration.

Alternatively, the wearable deformable sensor in FIG. 51 can be described as comprising: (A) a first deformable elongate electrically-conductive strip 51002 which is configured to span a body joint in a proximal to distal manner, a first electromagnetic energy emitter 51006 which is in electromagnetic communication with the first strip, and a first electromagnetic energy sensor 51007 which is in electromagnetic communication with the first strip; (B) a second deformable elongate electrically-conductive strip 51001 which is configured to span a body joint in a proximal to distal manner, a second electromagnetic energy emitter 51004 which is in electromagnetic communication with the second strip, and a second electromagnetic energy sensor 51005 which is in electromagnetic communication with the second strip; and a (C) third deformable elongate electrically-conductive strip 51003 which is configured to span a body joint in a proximal to distal manner, a third electromagnetic energy emitter 51008 which is in electromagnetic communication with the third strip, and a third electromagnetic energy sensor 51009 which is in electromagnetic communication with the third strip, wherein the three deformable elongate electrically-conductive strips cross (intersect) each other, and wherein the longitudinal axes of the three deformable elongate electrically-conductive strips cross the proximal-to-distal axis of the body joint (when projected onto a common two-dimensional plane) at different angles.

In an example, a wearable deformable sensor can also include one or more components selected from the group consisting of: data processor; power source (e.g. battery); data transmitter (e.g. wireless transmitter); and data receiver. In an example, changes in the transmission of electromagnetic energy can be due to changes in the resistance, impedance, and/or conductivity of electrically-conductive structures.

In an example, a central longitudinal axis of one of the plurality of elongate structures in this device can be substantially parallel to the proximal-to-distal axis of the body joint which it spans. In an example, the central longitudinal axes of other elongate structures in this device can intersect the proximal-to-distal axis of the body joint, forming (distal facing) acute angles (when these axes are projected onto the same two-dimensional plan as the axis of the body joint). In an example, these acute angles can be within the range of 20 to 70 degrees. In an example, these acute angles can be within the range of 30 to 60 degrees. In an example, the central longitudinal axis of a structure which is parallel to the axis of the body joint can be between the central longitudinal axes of other structures in the device. In an example, the central longitudinal axes of other structures in the device can be symmetric with respect to lateral reflection across the central longitudinal axis of the structure which is parallel to the axis of the body joint.

In an example, when projected onto a common two-dimensional plane, a first deformable elongate electrically-conductive structure can cross the central proximal-to-distal axis of a body joint in a left-to-right diagonal manner, a second deformable elongate electrically-conductive structure can be substantially parallel to the central proximal-to-distal axis of the body joint, and a third deformable elongate electrically-conductive structure can cross the central proximal-to-distal axis of a body joint in a right-to-left diagonal manner. In an example, a plurality of deformable elongate electrically-conductive structures can intersect at the same location. In an example, if the third structure were to be (virtually) laterally reflected across the longitudinal axis of the second structure, it would overlap the first structure. In an example, the longitudinal axes of first and third structures can be symmetric with respect to the longitudinal axis of a second structure.

In this example, there are three deformable elongate conductive structures (e.g. strips or bands) which intersect as they span a body joint in a proximal-to-distal manner. In an example, there can be four or more intersecting deformable elongate structures which intersect as they span a body joint in a proximal-to-distal manner. In this example, a plurality of deformable elongate conductive structures can intersect at their longitudinal mid-points. In an example, a plurality of deformable elongate conductive structures can intersect at a location which is distal relative to their longitudinal mid-points. In an example, a plurality of deformable elongate conductive structures can intersect at a location which is proximal relative to their longitudinal mid-points. In an example, three intersecting structures can combine to form an "*" shape. In an example, first and second intersecting structures can combine to form an "x" shape, with the second structure between them.

In an example, deformable elongate electrically-conductive structures can overlap each other. In an example, one of these structures can be closest to the person's body and another one of these structures can be farthest from the person's body where the structures intersect. Alternatively, deformable elongate electrically-conductive structures can be coplanar as they intersect. In an example, the distal portions of deformable elongate structures can diverge as they extend in a distal direction from a point of intersection. In an example, the proximal portions of deformable elongate structures can diverge as they extend in a proximal direction from a point of intersection. In an example, deformable elongate structures can be substantially straight. In an example, deformable elongate structures can be arcuate. In an example, deformable elongate structures can be convex or concave. In an example, the central longitudinal axis of one or more deformable elongate structures can have a conic section shape.

In an example, a deformable elongate electrically-conductive structure can be an elastomeric strip, strap, or band. In an example, a deformable elongate electrically-conductive structure can comprise silicone and/or polydimethylsiloxane (PDMS) which has been impregnated and/or doped with electrically-conductive material. In an example, a deformable elongate electrically-conductive structure can comprise silicone and/or polydimethylsiloxane (PDMS) which has been impregnated and/or doped with aluminum, carbon, copper, gold, nickel, or silver particles or fibers. In an example, a deformable elongate electrically-conductive structure can comprise electrically-conductive threads, yarns, wires, or fibers which are embedded within silicone and/or polydimethylsiloxane (PDMS). In an example, a deformable elongate electrically-conductive structure can comprise a woven array of electrically-conductive threads, yarns, wires, or fibers. In an example, a deformable elongate electrically-conductive structure can comprise an elastic electrically-conductive fabric and/or textile. Relevant example variations discussed elsewhere in this disclosure or in priority-linked disclosures can also be applied to the example shown in this figure, but are not repeated here in order to reduce narrative redundancy.

Figure 52:
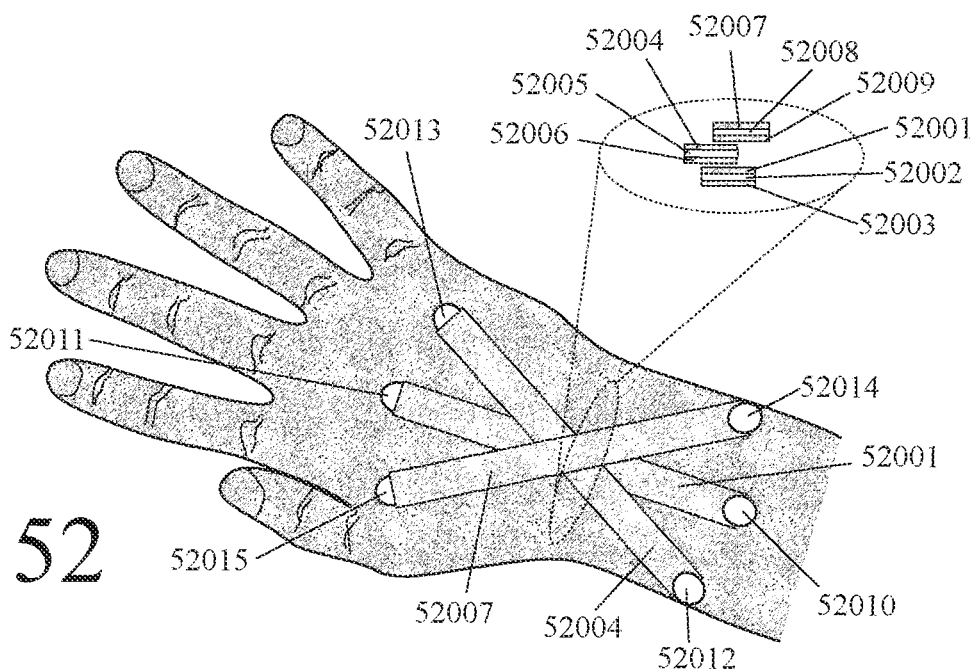
FIG. 52 shows capacitive EM strips which intersect centrally for measuring changes in joint configuration.

FIG. 52 shows another example of a wearable deformable sensor for measuring and/or modeling changes in body joint configuration. This example is similar to the one shown in FIG. 51, except that it comprises three intersecting multi-layer capacitive sensors instead of three intersecting single-layer resistive sensors. The left and lower-right portions of FIG. 52 show a top-down (dorsal) view of the sensor being worn on a person's hand. The upper-right portion of FIG. 52 shows a dotted-line ellipse which contains a cross-sectional view of the sensor.

The wearable deformable sensor in FIG. 52 comprises: (A) a first deformable elongate capacitive structure; wherein this first deformable elongate capacitive structure has a central longitudinal axis which is configured to cross the central proximal-to-distal axis of a body joint at a distal-facing acute angle (when both axes are projected onto a common two-dimensional plane); and wherein this first deformable elongate capacitive structure further comprises a dielectric layer (52005) between first and second electrically-conductive layers (52004 and 52006), a first electromagnetic energy emitter (52012) in electromagnetic communication with one of the first or second electrically-conductive layers, and a first electromagnetic energy receiver (52013) in electromagnetic communication with the other of the first or second electrically-conductive layers; (B) a second deformable elongate capacitive structure; wherein this second deformable elongate capacitive structure has a central longitudinal axis which is configured to be substantially parallel to the central proximal-to-distal axis of the body joint; and wherein this second deformable elongate capacitive structure further comprises a dielectric layer (52002) between third and fourth electrically-conductive layers (52001 and 52003), a second electromagnetic energy emitter (52010) in electromagnetic communication with one of the third or fourth electrically-conductive layers, and a second electromagnetic energy receiver (52011) in electromagnetic communication with the other of the third or fourth electrically-conductive layers; and (C) a third deformable elongate capacitive structure; wherein this third deformable elongate capacitive structure has a central longitudinal axis which is configured to cross the central proximal-to-distal axis of a body joint at a distal-facing acute angle (when both axes are projected onto a common two-dimensional plane); and wherein this third deformable elongate capacitive structure further comprises a dielectric layer (52008) between fifth and sixth electrically-conductive layers (52007 and 52009), a third electromagnetic energy emitter (52014) in electromagnetic communication with one of the fifth or sixth electrically-conductive layers, and a third electromagnetic energy receiver (52015) in electromagnetic communication with the other of the fifth or sixth electrically-conductive layers.

In this example, changes in the capacitance of one or more of the capacitive structures are analyzed in order to measure and/or model changes in body joint configuration. In an example, the sensor can also include one or more components selected from the group consisting of: power source (e.g. battery); data processor; data transmitter (e.g. wireless transmitter); and data receiver. In an example, the sensor can also include a data processor in which changes in capacitance are analyzed. In an example, the sensor can also include a data transmitter which sends data to a remote data processor in which capacitance changes are analyzed.

The deformable capacitive structures shown in FIG. 52 each have three layers: an outer (more) conductive layer; a middle dielectric (non-conductive or less-conductive) layer; and an inner (more) conductive layer. In an example, a deformable capacitive structure can have more than three layers, alternating between conductive and non-conductive layers. In an example, a deformable capacitive structure can comprise three conductive layers and two non-conductive layers. In an example, a deformable capacitive structure can have three or more conductive layers with different orientations which are separated by two or more non-conductive layers. In an example, electrically-conductive layers can all have substantially the same thickness. In an example, electrically-conductive layers can be thinner than dielectric layers. In an example, electrically-conductive layers can be thicker than dielectric layers.

In an example, layers of a deformable capacitive structure can have non-uniform thickness. In an example, there can be longitudinal variation in layer thickness. In an example, distal portions of sensor layers can be thicker than proximal portions of sensor layers, or vice versa. In an example, central portions of sensor layers can be thicker than peripheral portions of sensor layers, or vice versa. In an example, there can be longitudinal variation in the cross-sectional shape of a layer. In an example, distal portions of sensor layers can have a different cross-sectional shape than proximal portions of sensor layers. In an example, central portions of sensor layers can have a different cross-sectional shape than peripheral portions of sensor layers.

In an example, an electrically-conductive layer can comprise silicone and/or polydimethylsiloxane (PDMS) which has been impregnated and/or doped with electrically-conductive material. In an example, an electrically-conductive layer can comprise silicone and/or polydimethylsiloxane (PDMS) which has been impregnated and/or doped with aluminum, carbon, copper, gold, nickel, or silver particles or fibers. In an example, an electrically-conductive layer can comprise electrically-conductive threads, yarns, wires, or fibers which are embedded within silicone and/or polydimethylsiloxane (PDMS). In an example, an electrically-conductive layer can comprise a woven array of electrically-conductive threads, yarns, wires, or fibers. In an example, a deformable dielectric layer can comprise silicone and/or polydimethylsiloxane (PDMS). Relevant example variations discussed elsewhere in this disclosure or in priority-linked disclosures can also be applied to the example shown in this figure, but are not repeated here in order to reduce narrative redundancy.

Figure 53:
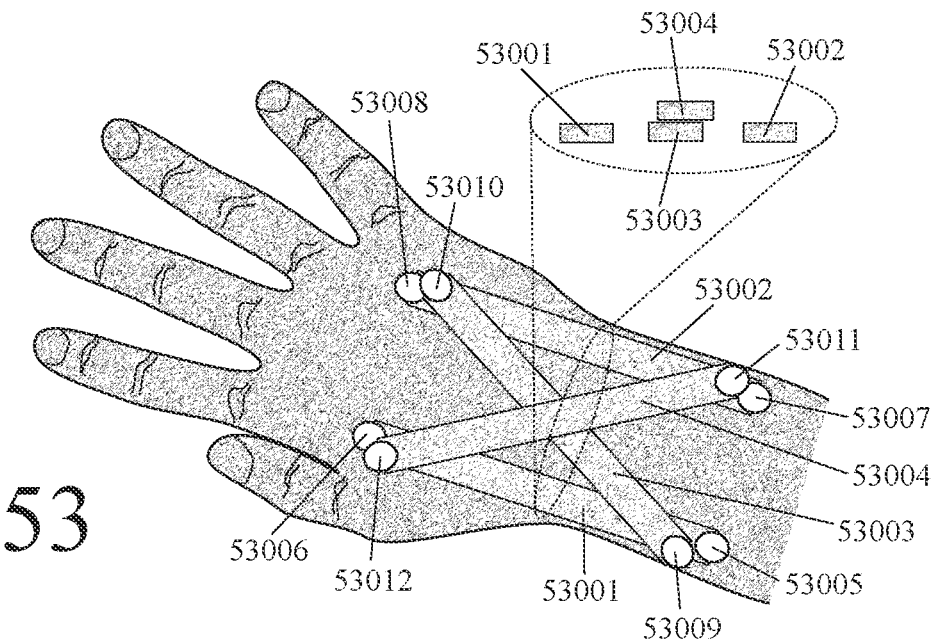
FIG. 53 shows parallel and intersecting resistive EM strips for measuring changes in joint configuration.

FIG. 53 shows another example of a wearable deformable sensor for measuring and/or modeling changes in body joint configuration. The left and lower-right portions of FIG. 53 show a top-down (dorsal) view of the sensor being worn on a person's hand. Similar to the example shown in FIG. 51, this example comprises a plurality of single-layer resistive deformable structures (e.g. strips) which span a body joint. However, in this example there are four deformable structures (e.g. strips), two of which are parallel and two of which intersect. The upper-right portion of FIG. 53 shows a dotted-line ellipse which contains a cross-sectional view of the sensor.

The wearable deformable sensor in FIG. 53 comprises: (A) a first deformable elongate electrically-conductive structure (e.g. strip) 53001 with a central longitudinal axis which is configured to be substantially parallel to the central proximal-to-distal axis of a body joint which it spans, a first electromagnetic energy emitter 53005 in electromagnetic communication with the first structure, and a first electromagnetic energy receiver 53006 in electromagnetic communication with the first structure; (B) a second deformable elongate electrically-conductive structure (e.g. strip) 53002 with a central longitudinal axis which is configured to be substantially parallel to the central proximal-to-distal axis of the body joint, a second electromagnetic energy emitter 53007 in electromagnetic communication with the second structure, and a second electromagnetic energy receiver 53008 in electromagnetic communication with the second structure; (C) a third deformable elongate electrically-conductive structure (e.g. strip) 53003 with a central longitudinal axis which is configured to cross the central proximal-to-distal axis of the body joint at a distal-facing acute angle (when the axes are projected onto a common two-dimensional plane), a third electromagnetic energy emitter 53009 in electromagnetic communication with the third structure, and a third electromagnetic energy receiver 53010 in electromagnetic communication with the third structure; and (D) a fourth deformable elongate electrically-conductive structure (e.g. strip) 53004 with a central longitudinal axis which is configured to cross the central proximal-to-distal axis of the body joint at a distal-facing acute angle and also cross the central longitudinal axis of the third structure (when the axes are projected onto a common two-dimensional plane), a fourth electromagnetic energy emitter 53011 in electromagnetic communication with the fourth structure, and a fourth electromagnetic energy receiver 53012 in electromagnetic communication with the fourth structure.

In an example, a wearable deformable sensor can also include one or more components selected from the group consisting of: data processor; power source (e.g. battery); data transmitter (e.g. wireless transmitter); and data receiver. In an example, changes in the transmission of electromagnetic energy can be due to changes in the resistance, impedance, and/or conductivity of the electrically-conductive structure.

In an example, the central longitudinal axes of two of a plurality of elongate structures in a device can be substantially parallel to the proximal-to-distal axis of the body joint which it spans. In an example, the central longitudinal axes of other elongate structures in a device can intersect the proximal-to-distal axis of the body joint, forming (distal facing) acute angles (when these axes are projected onto the same two-dimensional plan as the axis of the body joint). In an example, these acute angles can be within the range of 20 to 70 degrees. In an example, these acute angles can be within the range of 30 to 60 degrees. In an example, this sensor can be shaped like the Roman numeral ten including parallel top and bottom lines.

In an example, deformable elongate electrically-conductive structures can overlap each other. In an example, one of these structures can be closest to the person's body and another one of these structures can be farthest from the person's body where the structures intersect. Alternatively, deformable elongate electrically-conductive structures can be coplanar as they intersect. In an example deformable elongate structures can be substantially straight. In an example, deformable elongate structures can be arcuate. In an example, deformable elongate structures can be convex or concave. In an example, the central longitudinal axis of a deformable elongate structure can have a conic section shape.

In an example, a deformable elongate electrically-conductive structure can be an elastomeric strip, strap, or band. In an example, a deformable elongate electrically-conductive structure can comprise silicone and/or polydimethylsiloxane (PDMS) which has been impregnated and/or doped with electrically-conductive material. In an example, a deformable elongate electrically-conductive structure can comprise silicone and/or polydimethylsiloxane (PDMS) which has been impregnated and/or doped with aluminum, carbon, copper, gold, nickel, or silver particles or fibers. In an example, a deformable elongate electrically-conductive structure can comprise electrically-conductive threads, yarns, wires, or fibers which are embedded within silicone and/or polydimethylsiloxane (PDMS). In an example, a deformable elongate electrically-conductive structure can comprise a woven array of electrically-conductive threads, yarns, wires, or fibers. In an example, a deformable elongate electrically-conductive structure can comprise an elastic electrically-conductive fabric and/or textile. Relevant example variations discussed elsewhere in this disclosure or in priority-linked disclosures can also be applied to the example shown in this figure, but are not repeated here in order to reduce narrative redundancy.

Figure 54:
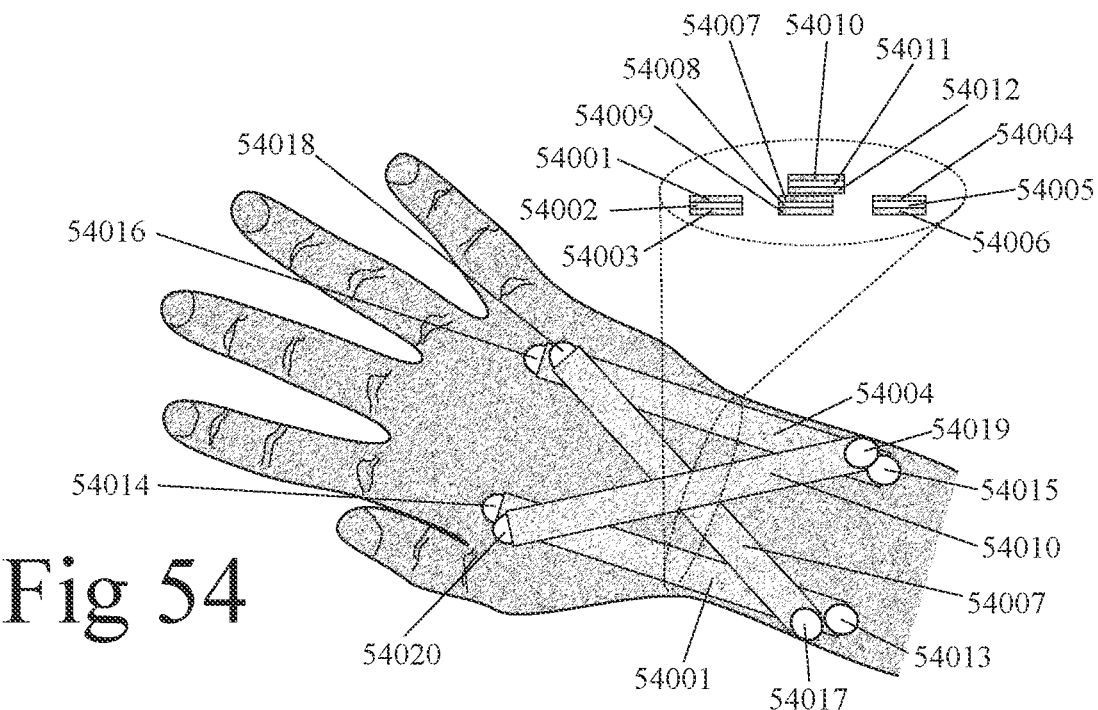
FIG. 54 shows parallel and intersecting capacitive EM strips for measuring changes in joint configuration.

FIG. 54 shows another example of a wearable deformable sensor for measuring and/or modeling changes in body joint configuration. The left and lower-right portions of FIG. 54 show a top-down (dorsal) view of the sensor being worn on a person's hand. This example is similar to the one shown in FIG. 53, except that it comprises multi-layer capacitive sensors instead of single-layer resistive sensors. The upper-right portion of FIG. 54 shows a dotted-line ellipse which contains a cross-sectional view of the sensor.

The wearable deformable sensor in FIG. 54 comprises: (A) a first deformable elongate structure (e.g. strip) with a central longitudinal axis which is configured to be substantially parallel to the central proximal-to-distal axis of a body joint which it spans, wherein this first structure further comprises—inner and outer conductive layers (54003 and 54001) separated by a dielectric layer (54002), a first electromagnetic energy emitter (54013) in electromagnetic communication with the outer conductive layer, and a first electromagnetic energy receiver (54014) in electromagnetic communication with the inner conductive layer; (B) a second deformable elongate structure (e.g. strip) with a central longitudinal axis which is configured to be substantially parallel to the central proximal-to-distal axis of the body joint, wherein this second structure further comprises—inner and outer conductive layers (54006 and 54004) separated by a dielectric layer (54005), a second electromagnetic energy emitter (54015) in electromagnetic communication with the outer conductive layer, and a second electromagnetic energy receiver (54016) in electromagnetic communication with the inner conductive layer; (C) a third deformable elongate structure (e.g. strip) with a central longitudinal axis which is configured to cross the central proximal-to-distal axis of the body joint at a distal-facing acute angle (when the axes are projected onto a common two-dimensional plane), wherein this third structure further comprises—inner and outer conductive layers (54009 and 54007) separated by a dielectric layer (54008), a third electromagnetic energy emitter (54017) in electromagnetic communication with the outer conductive layer, and a third electromagnetic energy receiver (54018) in electromagnetic communication with the inner conductive layer; and (D) a fourth deformable elongate structure (e.g. strip) with a central longitudinal axis which is configured to cross the central proximal-to-distal axis of the body joint at a distal-facing acute angle (when the axes are projected onto a common two-dimensional plane), wherein this fourth structure further comprises—inner and outer conductive layers (54012 and 54010) separated by a dielectric layer (54011), a fourth electromagnetic energy emitter (54019) in electromagnetic communication with the outer conductive layer, and a fourth electromagnetic energy receiver (54020) in electromagnetic communication with the inner conductive layer.

In an example, this sensor can also include one or more components selected from the group consisting of: data processor; power source (e.g. battery); data transmitter (e.g. wireless transmitter); and data receiver. In an example, the central longitudinal axes of two deformable elongate structures in a device can be substantially parallel to each other. In an example, the central longitudinal axes of other elongate structures in the device can intersect each other at an acute distal-facing angle in the range of 20 to 70 degrees. In an example, deformable elongate structures can be substantially straight. In an example, deformable elongate structures can be arcuate. In an example, deformable elongate structures can be convex or concave.

In an example, an electrically-conductive layer can comprise silicone and/or polydimethylsiloxane (PDMS) which has been impregnated and/or doped with electrically-conductive material. In an example, an electrically-conductive layer can comprise silicone and/or polydimethylsiloxane (PDMS) which has been impregnated and/or doped with aluminum, carbon, copper, gold, nickel, or silver particles or fibers. In an example, an electrically-conductive layer can comprise electrically-conductive threads, yarns, wires, or fibers which are embedded within silicone and/or polydimethylsiloxane (PDMS). In an example, an electrically-conductive layer can comprise a woven array of electrically-conductive threads, yarns, wires, or fibers. In an example, a deformable dielectric layer can comprise silicone and/or polydimethylsiloxane (PDMS). Relevant example variations discussed elsewhere in this disclosure or in priority-linked disclosures can also be applied to the example shown in this figure, but are not repeated here in order to reduce narrative redundancy.

Figure 55:
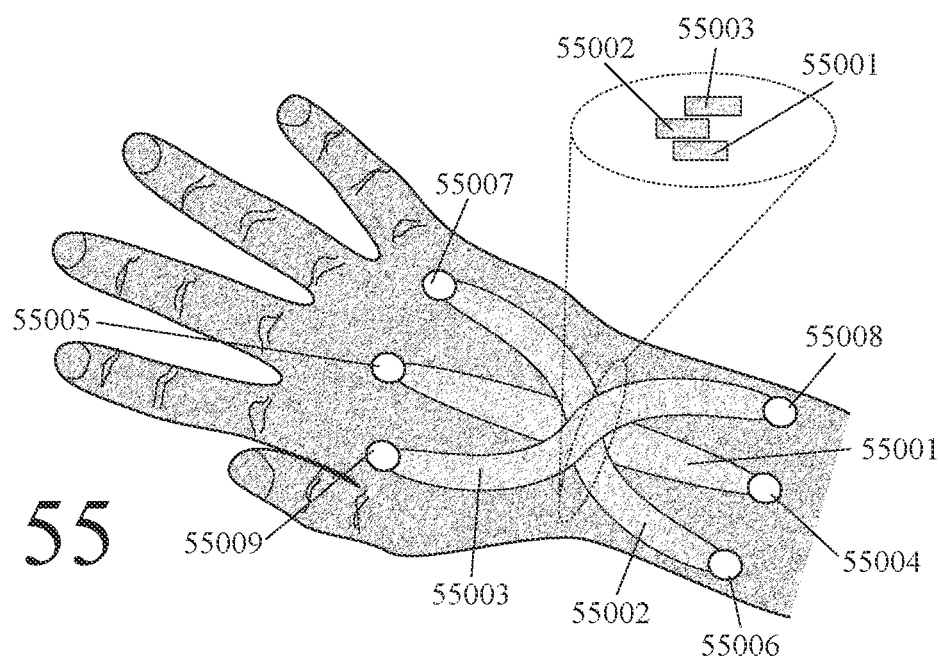
FIG. 55 shows central and (partially) sinusoidal intersecting resistive EM strips for measuring changes in joint configuration.

FIG. 55 shows another example of a wearable deformable sensor for measuring and/or modeling changes in body joint configuration. The left and lower-right portions of FIG. 55 show a top-down (dorsal) view of the sensor being worn on a person's hand. Similar to the example shown in FIG. 53, this example comprises a plurality of single-layer resistive deformable structures which span a body joint. However, in this example two of the deformable structures are arcuate (with a partial sinusoidal wave shape). The upper-right portion of FIG. 55 shows a dotted-line ellipse which contains a cross-sectional view of the sensor.

The wearable deformable sensor in FIG. 55 comprises: (A) a first deformable elongate electrically-conductive structure (e.g. strip) 55002 which spans a body joint, wherein the first structure has an arcuate (partial sinusoidal wave) shape, a first electromagnetic energy emitter 55006 in electromagnetic communication with the first structure, and a first electromagnetic energy receiver 55007 in electromagnetic communication with the first structure; (B) a second deformable elongate electrically-conductive structure (e.g. strip) 55001 which spans a body joint, wherein the second structure has a central longitudinal axis which is substantially parallel to the proximal-to-distal axis of the body joint, a second electromagnetic energy emitter 55004 in electromagnetic communication with the second structure, and a second electromagnetic energy receiver 55005 in electromagnetic communication with the second structure; and (C) a third deformable elongate electrically-conductive structure (e.g. strip) 55003 which spans a body joint, wherein the third structure has an arcuate (partial sinusoidal wave) shape, a third electromagnetic energy emitter 55008 in electromagnetic communication with the third structure, and a third electromagnetic energy receiver 55009 in electromagnetic communication with the third structure.

In an example, a wearable deformable sensor can also include one or more components selected from the group consisting of: data processor; power source (e.g. battery); data transmitter (e.g. wireless transmitter); and data receiver. In an example, changes in the transmission of electromagnetic energy can be due to changes in the resistance, impedance, and/or conductivity of electrically-conductive structures. In an example, the central longitudinal axes of the first and third deformable elongate structures can intersect, forming a (distal facing) acute angle within the range of 20 to 70 degrees. In an example, the distal portion of this sensor can be shaped like the distal end of a fork or trident—facing in a distal direction. In an example, the proximal portion of this sensor can be shaped like the distal end of a fork or trident—facing in a proximal direction.

In an example, a deformable elongate electrically-conductive structure can be an elastomeric strip, strap, or band. In an example, a deformable elongate electrically-conductive structure can comprise silicone and/or polydimethylsiloxane (PDMS) which has been impregnated and/or doped with electrically-conductive material. In an example, a deformable elongate electrically-conductive structure can comprise silicone and/or polydimethylsiloxane (PDMS) which has been impregnated and/or doped with aluminum, carbon, copper, gold, nickel, or silver particles or fibers. In an example, a deformable elongate electrically-conductive structure can comprise electrically-conductive threads, yarns, wires, or fibers which are embedded within silicone and/or polydimethylsiloxane (PDMS). In an example, a deformable elongate electrically-conductive structure can comprise a woven array of electrically-conductive threads, yarns, wires, or fibers. In an example, a deformable elongate electrically-conductive structure can comprise an elastic electrically-conductive fabric and/or textile. Relevant example variations discussed elsewhere in this disclosure or in priority-linked disclosures can also be applied to the example shown in this figure, but are not repeated here in order to reduce narrative redundancy.

Figure 56:
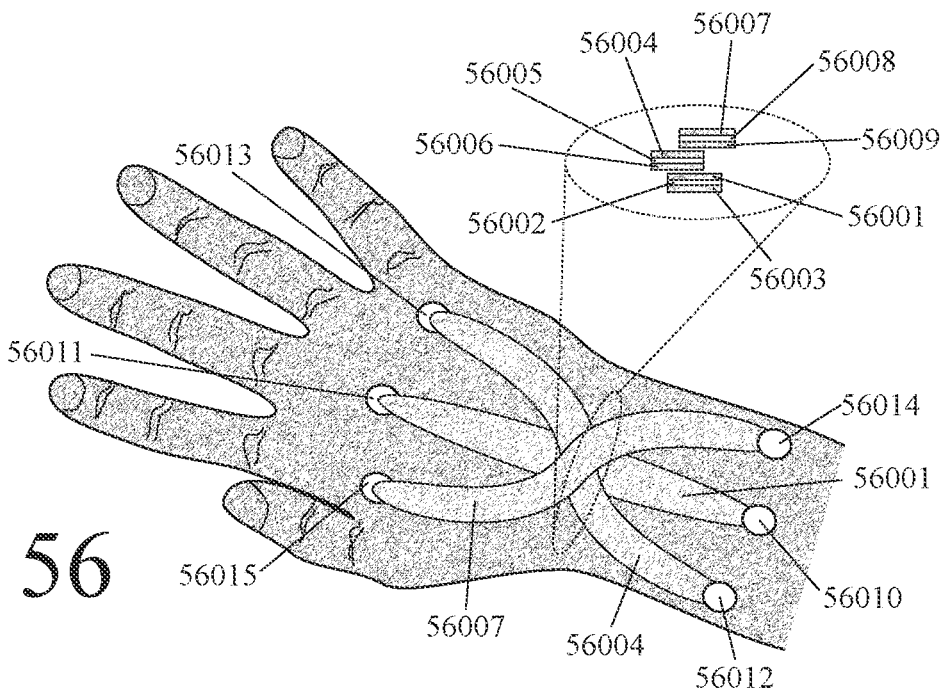
FIG. 56 shows central and (partially) sinusoidal intersecting capacitive EM strips for measuring changes in joint configuration.

FIG. 56 shows another example of a wearable deformable sensor for measuring and/or modeling changes in body joint configuration. The left and lower-right portions of FIG. 56 show a top-down (dorsal) view of the sensor being worn on a person's hand. This example is similar to the one shown in FIG. 55, except that it has multi-layer capacitive sensors instead of single-layer resistive sensors. The upper-right portion of FIG. 56 shows a dotted-line ellipse which contains a cross-sectional view of the sensor.

The wearable deformable sensor in FIG. 56 comprises: (A) a first deformable elongate structure which spans a body joint, wherein the first structure has an arcuate (partial sinusoidal wave) shape, and wherein this first structure further comprises inner and outer conductive layers (56006 and 56004) separated by a dielectric layer (56005), a first electromagnetic energy emitter (56012) in electromagnetic communication with the outer conductive layer, and a first electromagnetic energy receiver (56013) in electromagnetic communication with the inner conductive layer; (B) a second deformable elongate structure which spans the body joint, wherein the second structure has a central longitudinal axis which is substantially parallel to the proximal-to-distal axis of the body joint, and wherein this second structure further comprises inner and outer conductive layers (56003 and 56001) separated by a dielectric layer (56002), a second electromagnetic energy emitter (56010) in electromagnetic communication with the outer conductive layer, and a second electromagnetic energy receiver (56011) in electromagnetic communication with the inner conductive layer; and (C) a third deformable elongate structure which spans the body joint, wherein the third structure has an arcuate (partial sinusoidal wave) shape, and wherein this third structure further comprises inner and outer conductive layers (56009 and 56007) separated by a dielectric layer (56008), a third electromagnetic energy emitter (56014) in electromagnetic communication with the outer conductive layer, and a third electromagnetic energy receiver (56015) in electromagnetic communication with the inner conductive layer.

In an example, this sensor can also include one or more components selected from the group consisting of: data processor; power source (e.g. battery); data transmitter (e.g. wireless transmitter); and data receiver. In an example, an electrically-conductive layer can comprise silicone and/or polydimethylsiloxane (PDMS) which has been impregnated and/or doped with electrically-conductive material. In an example, an electrically-conductive layer can comprise silicone and/or polydimethylsiloxane (PDMS) which has been impregnated and/or doped with aluminum, carbon, copper, gold, nickel, or silver particles or fibers. In an example, an electrically-conductive layer can comprise electrically-conductive threads, yarns, wires, or fibers which are embedded within silicone and/or polydimethylsiloxane (PDMS). In an example, an electrically-conductive layer can comprise a woven array of electrically-conductive threads, yarns, wires, or fibers. In an example, a deformable dielectric layer can comprise silicone and/or polydimethylsiloxane (PDMS). Relevant example variations discussed elsewhere in this disclosure or in priority-linked disclosures can also be applied to the example shown in this figure, but are not repeated here in order to reduce narrative redundancy.

Figure 57:
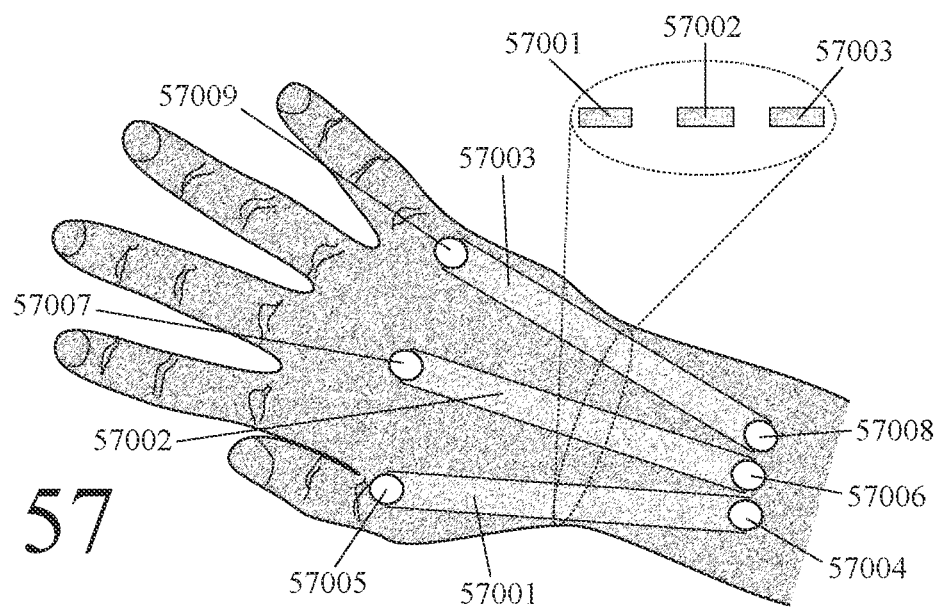
FIG. 57 shows distally-diverging joint-spanning EM strips for measuring changes in joint configuration.

FIG. 57 shows another example of a wearable deformable sensor for measuring and/or modeling changes in body joint configuration. The left and lower-right portions of FIG. 57 show a top-down (dorsal) view of the sensor being worn on a person's hand. This example includes a plurality of (three) relatively-straight single-layer resistive deformable structures which diverge from one another as they span a body joint in a proximal-to-distal direction. The upper-right portion of FIG. 57 shows a dotted-line ellipse which contains a cross-sectional view of the sensor.

The wearable deformable sensor in FIG. 57 comprises: a plurality of deformable elongate electrically-conductive structures (57001, 57002, 57003) which diverge from one another as they span a body joint in a proximal-to-distal manner; and a plurality of pairs of electromagnetic energy emitters and receivers (57004 and 57005, 57006 and 57007, 57008 and 57009), wherein each pair is in electromagnetic communication with one of the deformable elongate electrically-conductive structures.

The wearable deformable sensor in FIG. 57 can also be described as comprising: three deformable elongate electrically-conductive strips (57001, 57002, 57003) which diverge from one another as they span a body joint in a proximal-to-distal manner; and three pairs of electromagnetic energy emitters and receivers (57004 and 57005, 57006 and 57007, 57008 and 57009), wherein each pair is in electromagnetic communication with one of the deformable elongate electrically-conductive strips.

The wearable deformable sensor in FIG. 57 can also be described as comprising: a plurality of deformable elongate electrically-conductive strips (57001, 57002, 57003) which span a body joint in a proximal-to-distal manner and together span an area which is shaped like an isosceles trapezoid; and a plurality of pairs of electromagnetic energy emitters and receivers (57004 and 57005, 57006 and 57007, 57008 and 57009), wherein each pair is in electromagnetic communication with one of the strips.

With the addition of a data processor and power source, the example shown in FIG. 57 can also be described a wearable deformable sensor for human motion capture comprising: a plurality of deformable elongate electrically-conductive strips which are configured to diverge from one another as they span a body joint in a proximal-to-distal manner; and a plurality of pairs of electromagnetic energy emitters and electromagnetic energy receivers, wherein the pairs of electromagnetic energy emitters and electromagnetic energy receivers are in electromagnetic communication with the plurality of deformable elongate electrically-conductive strips, wherein changes in body joint configuration cause deformations of the deformable elongate electrically-conductive strips, wherein the deformations cause changes in the transmission of electromagnetic energy from the electromagnetic energy emitters to the electromagnetic energy receivers, and wherein the changes in the transmission of electromagnetic energy are analyzed in order to measure and/or model changes in body joint configuration; a data processor; and a power source.

In an example, a wearable deformable sensor can also include one or more components selected from the group consisting of: data processor; power source (e.g. battery); data transmitter (e.g. wireless transmitter); and data receiver. In an example, a deformable elongate electrically-conductive structure (e.g. strip) can be relatively straight. In an example, changes in the configuration of the body joint spanned by the sensor cause changes in the transmission of electromagnetic energy through one or more of the plurality of conductive structures. Changes in the transmission of electromagnetic energy are then analyzed to measure and/or model changes in body joint configuration. In an example, changes in electromagnetic energy can comprise changes in resistance, impedance, conductivity, or capacitance.

In an example, energy emitters can be in electromagnetic communication with the proximal ends of conductive structures (e.g. strips) and energy receivers can be in electromagnetic communication with the distal ends of these structure (e.g. strips). In an example, energy emitters can be in electromagnetic communication with the distal ends of conductive structures (e.g. strips) and energy receivers can be in electromagnetic communication with the proximal ends of these structure (e.g. strips). In an example, the distal ends of conductive structures can be farther apart than the proximal ends of these structures. In an example, the distal ends of conductive structures can be at least twice as far apart than the proximal ends of these structures.

In an example, a middle conductive structure can have a longitudinal axis which is substantially parallel to the proximal-to-distal axis of the body joint which it spans. In an example, conductive structures to the right and left of a middle conductive structure (e.g. strip) can be symmetric with respect to reflection across the longitudinal axis of the middle conductive structure (e.g. strip). In an example, a sensor can comprise deformable elongate electrically-conductive structures which diverge as they span a body join in a proximal-to-distal manner. In an example, a sensor can comprise six deformable elongate electrically-conductive structures which diverge as they span a body join in a proximal-to-distal manner.

In an example, a deformable elongate electrically-conductive structure can be an elastomeric strip, strap, or band. In an example, a deformable elongate electrically-conductive structure can comprise silicone and/or polydimethylsiloxane (PDMS) which has been impregnated and/or doped with electrically-conductive material. In an example, a deformable elongate electrically-conductive structure can comprise silicone and/or polydimethylsiloxane (PDMS) which has been impregnated and/or doped with aluminum, carbon, copper, gold, nickel, or silver particles or fibers. In an example, a deformable elongate electrically-conductive structure can comprise electrically-conductive threads, yarns, wires, or fibers which are embedded within silicone and/or polydimethylsiloxane (PDMS). In an example, a deformable elongate electrically-conductive structure can comprise a woven array of electrically-conductive threads, yarns, wires, or fibers. In an example, a deformable elongate electrically-conductive structure can comprise an elastic electrically-conductive fabric and/or textile.

In an example, deformable elongate structures (e.g. strips) in this example can be multi-layer capacitive structures instead of single-layer resistive structures. In an example, each multi-layer capacitive structure (e.g. strip) can further comprise two conductive layers, a dielectric layer between the conductive layers, an electromagnetic energy emitter, and an electromagnetic energy receiver. In an example, the electromagnetic energy emitter can be in electromagnetic communication with the inner layer of the multi-layer capacitive structure (e.g. strip) and the electromagnetic energy receiver can be in electromagnetic communication with the outer layer of the multi-layer capacitive structure (e.g. strip), or vice versa. In an example, a multi-layer capacitive structure (e.g. strip) can have five or more layers, alternating between conductive and a non-conductive layers.

In an example, an electrically-conductive layer can comprise silicone and/or polydimethylsiloxane (PDMS) which has been impregnated and/or doped with electrically-conductive material. In an example, an electrically-conductive layer can comprise silicone and/or polydimethylsiloxane (PDMS) which has been impregnated and/or doped with aluminum, carbon, copper, gold, nickel, or silver particles or fibers. In an example, an electrically-conductive layer can comprise electrically-conductive threads, yarns, wires, or fibers which are embedded within silicone and/or polydimethylsiloxane (PDMS). In an example, an electrically-conductive layer can comprise a woven array of electrically-conductive threads, yarns, wires, or fibers. In an example, a deformable dielectric layer can comprise silicone and/or polydimethylsiloxane (PDMS). Relevant example variations discussed elsewhere in this disclosure or in priority-linked disclosures can also be applied to the example shown in this figure, but are not repeated here in order to reduce narrative redundancy.

Figure 58:
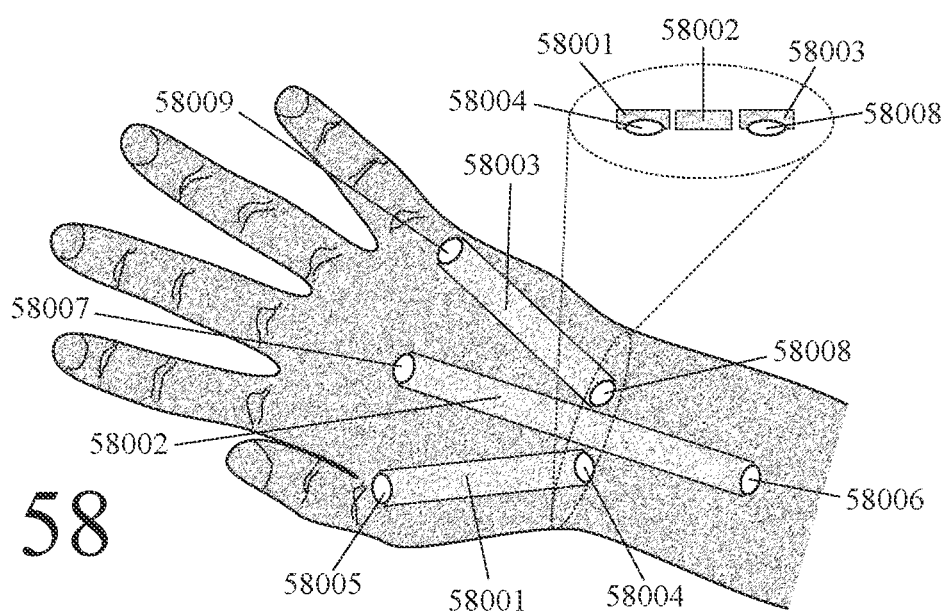
FIG. 58 shows central and central-to-distal-diverging joint-spanning EM strips for measuring changes in joint configuration.

FIG. 58 shows another example of a wearable deformable sensor for measuring and/or modeling changes in body joint configuration. The left and lower-right portions of FIG. 58 show a top-down (dorsal) view of the sensor being worn on a person's hand. The upper-right portion of FIG. 58 shows a dotted-line ellipse which contains a cross-sectional view of the sensor. This example comprises a middle conductive strip which is substantially parallel to the proximal-to-distal axis of a body joint which it spans and two lateral conductive strips which branch out from the center of the middle strip and diverge from each other in a proximal-to-distal direction. This example can be colorfully described as a "chicken foot" design.

The wearable deformable sensor in FIG. 58 comprises: a middle deformable elongate electrically-conductive structure (e.g. strip) 58002 with a longitudinal axis which is configured to be substantially parallel to the proximal-to-distal axis of a body joint which the middle structure spans; a middle electromagnetic energy emitter 58006 which is in electromagnetic communication with the middle structure; a middle electromagnetic energy receiver 58007 which is in electromagnetic communication with the middle structure; a left deformable elongate electrically-conductive structure (e.g. strip) 58001 which extends out from the left side of the middle structure and is shorter than the middle structure; a left electromagnetic energy emitter 58004 which is in electromagnetic communication with the left structure; a left electromagnetic energy receiver 58005 which is in electromagnetic communication with the left structure; a right deformable elongate electrically-conductive structure (e.g. strip) 58003 which extends out from the right side of the middle structure and is shorter than the middle structure, wherein the left and right structures diverge from each other in a proximal-to-distal direction; a right electromagnetic energy emitter 58008 which is in electromagnetic communication with the right structure; and a right electromagnetic energy receiver 58009 which is in electromagnetic communication with the right structure.

In an example, a wearable deformable sensor can also include one or more components selected from the group consisting of: data processor; power source (e.g. battery); data transmitter (e.g. wireless transmitter); and data receiver. In an example, changes in the configuration of the body joint spanned by the sensor cause changes in resistance, impedance, conductivity, and/or capacitance. These changes are then analyzed to measure and/or model changes in body joint configuration. In an example, the relative locations of the energy emitters and receivers (in pairs of such emitters and receivers) can be reversed. In an example, right and left strips can be symmetrically located on the right and left sides of a middle strip.

In an example, a conductive structure (e.g. strip) can comprise silicone and/or polydimethylsiloxane (PDMS) which has been impregnated and/or doped with electrically-conductive material. In an example, a strip can comprise silicone and/or polydimethylsiloxane (PDMS) which has been impregnated and/or doped with aluminum, carbon, copper, gold, nickel, or silver particles or fibers. In an example, a strip can comprise electrically-conductive threads, yarns, wires, or fibers which are embedded within silicone and/or polydimethylsiloxane (PDMS). In an example, a strip can comprise a woven array of electrically-conductive threads, yarns, wires, or fibers. In an example, a strip can comprise an elastic electrically-conductive fabric and/or textile.

In an example, strips in this example can be multi-layer capacitive strips instead of single-layer resistive strips. In an example, each multi-layer capacitive strip can further comprise two conductive layers, a dielectric layer between the conductive layers, an electromagnetic energy emitter, and an electromagnetic energy receiver. In an example, the electromagnetic energy emitter can be in electromagnetic communication with the inner layer of the multi-layer capacitive strip and the electromagnetic energy receiver can be in electromagnetic communication with the outer layer of the multi-layer capacitive strip, or vice versa. In an example, a multi-layer capacitive strip can have three layers, two conductive layers and a non-conductive (dielectric) layer between them.

In an example, an electrically-conductive layer can comprise silicone and/or polydimethylsiloxane (PDMS) which has been impregnated and/or doped with electrically-conductive material. In an example, an electrically-conductive layer can comprise silicone and/or polydimethylsiloxane (PDMS) which has been impregnated and/or doped with aluminum, carbon, copper, gold, nickel, or silver particles or fibers. In an example, an electrically-conductive layer can comprise electrically-conductive threads, yarns, wires, or fibers which are embedded within silicone and/or polydimethylsiloxane (PDMS). In an example, an electrically-conductive layer can comprise a woven array of electrically-conductive threads, yarns, wires, or fibers. In an example, a deformable dielectric layer can comprise silicone and/or polydimethylsiloxane (PDMS). Relevant example variations discussed elsewhere in this disclosure or in priority-linked disclosures can also be applied to the example shown in this figure, but are not repeated here in order to reduce narrative redundancy.

Figure 59:
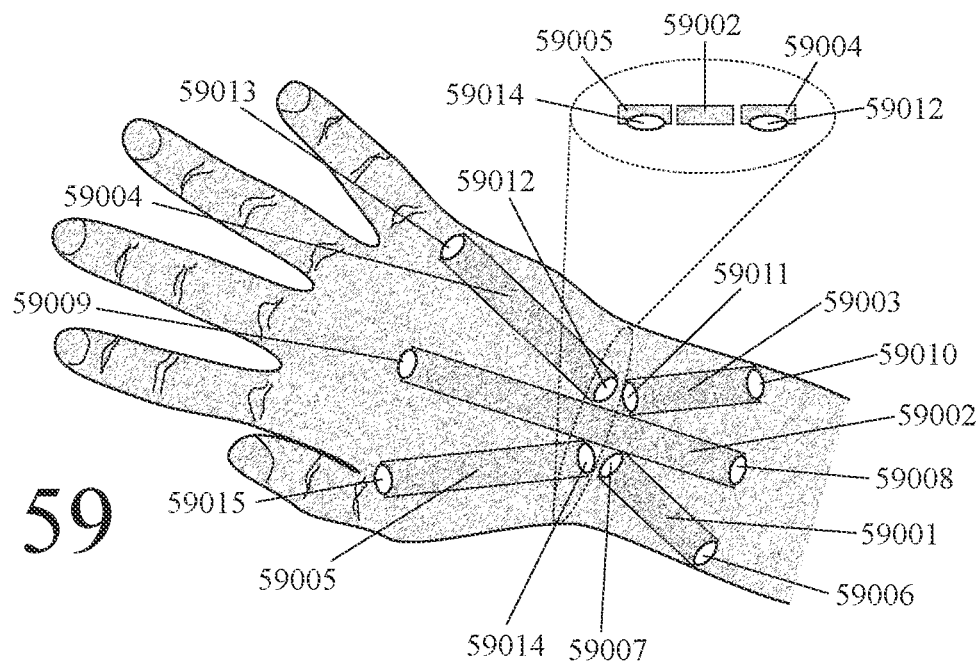
FIG. 59 shows central, central-to-proximal diverging, and central-to-distal diverging joint-spanning EM strips for measuring changes in joint configuration.

FIG. 59 shows another example of a wearable deformable sensor for measuring and/or modeling changes in body joint configuration. The left and lower-right portions of FIG. 59 show a top-down (dorsal) view of the sensor being worn on a person's hand. The upper-right portion of FIG. 59 shows a dotted-line ellipse which contains a cross-sectional view of the sensor. This example comprises a middle conductive strip which is substantially parallel to the proximal-to-distal axis of a body joint and a plurality of conductive strips (e.g. "spokes" or "branches") which radiate outward (some in a distal direction and some in a proximal direction) from a central portion of the middle conductive strip. In this example, there are four radiating conductive strips (e.g. "spokes" or "branches") which radiate outward (two in a distal direction and two in a proximal direction) from a central portion of the middle conductive strip.

The wearable deformable sensor in FIG. 59 comprises: a middle conductive strip (59002) with a longitudinal axis which is configured to be substantially parallel to the proximal-to-distal axis of a body joint; a middle electromagnetic energy emitter (59008) which is in electromagnetic communication with the middle structure; a middle electromagnetic energy receiver (59009) which is in electromagnetic communication with the middle structure; a plurality of proximal conductive strips (59001 and 59003) which extend outward in a proximal manner from a central portion of the middle conductive strip, wherein each proximal conductive strip is in electromagnetic communication with an electromagnetic energy emitter (59006, 59010) and an electromagnetic energy receiver (59007, 59011); and a plurality of distal conductive strips (59005 and 59004) which extend outward in a distal manner from a central portion of the middle conductive strip, wherein each distal conductive strip is in electromagnetic communication with an electromagnetic energy emitter (59014, 59012) and an electromagnetic energy receiver (59015, 59013).

The wearable deformable sensor in FIG. 59 can also be described as comprising: a middle conductive strip (59002) with a longitudinal axis which is configured to be substantially parallel to the proximal-to-distal axis of a body joint; a middle electromagnetic energy emitter (59008) which is in electromagnetic communication with the middle structure; a middle electromagnetic energy receiver (59009) which is in electromagnetic communication with the middle structure; a plurality of proximal conductive strips (59001 and 59003) which radiate outward in a proximal direction from a central portion of the middle conductive strip, wherein each proximal conductive strip is in electromagnetic communication with an electromagnetic energy emitter (59006, 59010) and an electromagnetic energy receiver (59007, 59011); and a plurality of distal conductive strips (59005 and 59004) which radiate outward in a distal direction from a central portion of the middle conductive strip, wherein each distal conductive strip is in electromagnetic communication with an electromagnetic energy emitter (59014, 59012) and an electromagnetic energy receiver (59015, 59013).

The wearable deformable sensor in FIG. 59 can also be described as comprising: a middle conductive strip (59002) with a longitudinal axis which is configured to be substantially parallel to the proximal-to-distal axis of a body joint; a middle electromagnetic energy emitter (59008) which is in electromagnetic communication with the middle structure; a middle electromagnetic energy receiver (59009) which is in electromagnetic communication with the middle structure; a plurality of conductive spokes (59001, 59003, 59004, 59005) which radiate outward in proximal or distal directions from a central portion of the middle conductive strip, wherein each conductive spoke is in electromagnetic communication with an electromagnetic energy emitter (59006, 59010, 59012, 59014) and an electromagnetic energy receiver (59007, 59011, 59013, 59015). In an example, there can be symmetry with respect to the configuration of conductive spokes which are located to the right vs. to the left of the middle conductive strip. In an example, there can be symmetry with respect to the configuration of conductive spokes which radiate in a proximal direction vs. in a distal direction from the central portion of the middle conductive strip.

In an example, a wearable deformable sensor can also include one or more components selected from the group consisting of: data processor; power source (e.g. battery); data transmitter (e.g. wireless transmitter); and data receiver. In an example, changes in the configuration of the body joint spanned by the sensor cause changes in resistance, impedance, conductivity, and/or capacitance, which are analyzed to measure and/or model changes in body joint configuration. In an example, the locations of the energy emitters and receivers can be reversed. In this example, there are four spokes, two of which radiate in outward/proximal directions and two of which radiate in outward/distal directions. In this example, there are four spokes radiating outward in the following directions: right/proximal, left/proximal, right/distal, and left/distal.

In an example, a strip or spoke can comprise silicone and/or polydimethylsiloxane (PDMS) which has been impregnated and/or doped with electrically-conductive material. In an example, a strip or spoke can comprise silicone and/or polydimethylsiloxane (PDMS) which has been impregnated and/or doped with aluminum, carbon, copper, gold, nickel, or silver particles or fibers. In an example, a strip or spoke can comprise electrically-conductive threads, yarns, wires, or fibers which are embedded within silicone and/or polydimethylsiloxane (PDMS). In an example, a strip or spoke can comprise a woven array of electrically-conductive threads, yarns, wires, or fibers. In an example, a strip or spoke can comprise an elastic electrically-conductive fabric and/or textile.

In an example, strips or spokes in this example can be multi-layer capacitive strips or spokes instead of single-layer resistive strips or spokes. In an example, each multi-layer capacitive strip or spoke can further comprise two conductive layers, a dielectric layer between the conductive layers, an electromagnetic energy emitter, and an electromagnetic energy receiver. In an example, the electromagnetic energy emitter can be in electromagnetic communication with the inner layer of the multi-layer capacitive strip or spoke and the electromagnetic energy receiver can be in electromagnetic communication with the outer layer of the multi-layer capacitive strip, or vice versa. In an example, a multi-layer capacitive strip or spoke can have three layers, two conductive layers and a non-conductive (dielectric) layer between them.

In an example, an electrically-conductive layer can comprise silicone and/or polydimethylsiloxane (PDMS) which has been impregnated and/or doped with electrically-conductive material. In an example, an electrically-conductive layer can comprise silicone and/or polydimethylsiloxane (PDMS) which has been impregnated and/or doped with aluminum, carbon, copper, gold, nickel, or silver particles or fibers. In an example, an electrically-conductive layer can comprise electrically-conductive threads, yarns, wires, or fibers which are embedded within silicone and/or polydimethylsiloxane (PDMS). In an example, an electrically-conductive layer can comprise a woven array of electrically-conductive threads, yarns, wires, or fibers. In an example, a deformable dielectric layer can comprise silicone and/or polydimethylsiloxane (PDMS). Relevant example variations discussed elsewhere in this disclosure or in priority-linked disclosures can also be applied to the example shown in this figure, but are not repeated here in order to reduce narrative redundancy.

Figure 60:
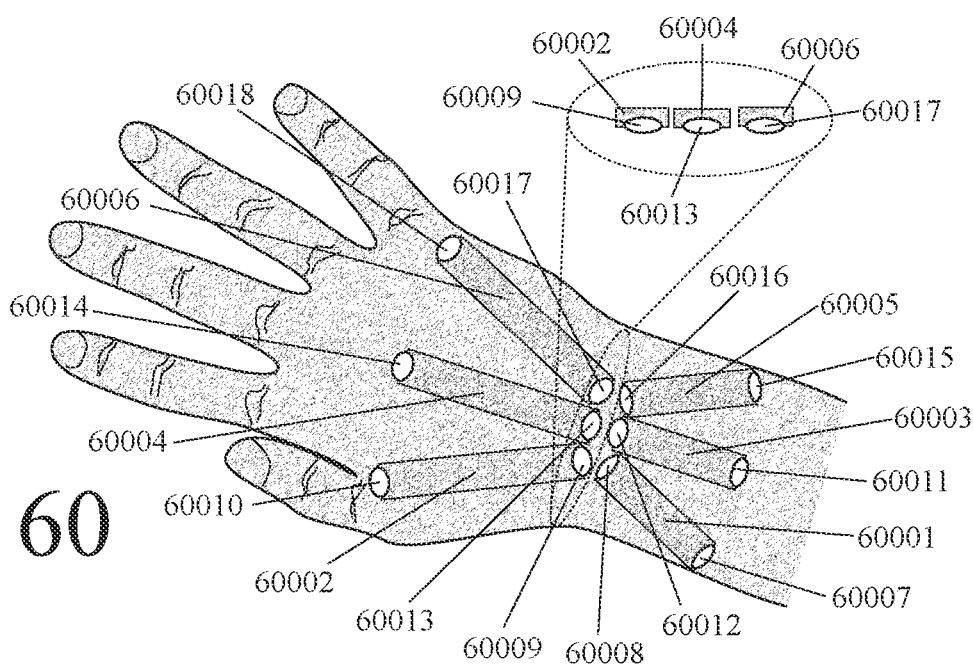
FIG. 60 shows central-to-proximal diverging and central-to-distal diverging joint-spanning EM strips for measuring changes in joint configuration.

FIG. 60 shows another example of a wearable deformable sensor for measuring and/or modeling changes in body joint configuration. The left and lower-right portions of FIG. 60 show a top-down (dorsal) view of the sensor being worn on a person's hand. The upper-right portion of FIG. 60 shows a dotted-line ellipse which contains a cross-sectional view of the sensor. This example comprises a radial (e.g. "starburst") array of electrically-conductive strips (e.g. "spokes") which extend outward in a radial manner from a central area over a body joint. In this example, a plurality of (three) conductive strips (e.g. "spokes") extend outward in a radial and proximal manner from the central area and a plurality of (three) conductive strips (e.g. "spokes") extend outward in a radial and distal manner from the central area.

The wearable deformable sensor in FIG. 60 comprises: a plurality of deformable elongate electrically-conductive structures (e.g. conductive strips or spokes) (60001, 60002, 60003, 60004, 60005, 60006) which are configured to extend outward in a radial manner from a central area over a body joint; and a plurality of pairs of electromagnetic energy emitters (60007, 60009, 60011, 60013, 60015, 60017) and receivers (60008, 60010, 60012, 60014, 60016, 60018), wherein each deformable elongate electrically-conductive structure (e.g. conductive strip or spoke) is in electromagnetic communication with a pair comprising an electromagnetic energy emitter and receiver.

The wearable deformable sensor in FIG. 60 can also be described as comprising: a plurality of deformable elongate electrically-conductive structures spokes (60001, 60002, 60003, 60004, 60005, 60006) which are configured to extend outward in a radial manner from a central area over a body joint in a partial or full star-burst configuration; and a plurality of pairs of electromagnetic energy emitters (60007, 60009, 60011, 60013, 60015, 60017) and receivers (60008, 60010, 60012, 60014, 60016, 60018), wherein each deformable elongate electrically-conductive spoke is in electromagnetic communication with a pair comprising an electromagnetic energy emitter and receiver.

The wearable deformable sensor in FIG. 60 can also be described as comprising: a plurality of deformable elongate electrically-conductive spokes (60001, 60003, 60005) which are configured to extend outward in a radial and proximal manner from a central area over a body joint; a plurality of deformable elongate electrically-conductive spokes (60002, 60004, 60006) which are configured to extend outward in a radial and distal manner from the central area; and a plurality of pairs of electromagnetic energy emitters (60007, 60009, 60011, 60013, 60015, 60017) and receivers (60008, 60010, 60012, 60014, 60016, 60018), wherein each deformable elongate electrically-conductive spoke is in electromagnetic communication with a pair comprising an electromagnetic energy emitter and receiver.

In an example, a wearable deformable sensor can also include one or more components selected from the group consisting of: data processor; power source (e.g. battery); data transmitter (e.g. wireless transmitter); and data receiver. In an example, changes in the configuration of the body joint cause changes in resistance, impedance, conductivity, and/or capacitance, which are then analyzed to measure and/or model changes in body joint configuration. In an example, the locations of the energy emitters and receivers can be reversed.

In this example, there are six strips or spokes, three of which radiate in outward/proximal directions and three of which radiate in outward/distal directions. In an example, there can be left-vs.-right symmetry with respect to the configuration of conductive strips or spokes. In an example, there can be proximal-vs.-distal symmetry with respect to the configuration of conductive strips or spokes. In this example, conductive strips or spokes do not intersect each other. In an alternative example, conductive strips or spokes can intersect each other at a central area over a body joint. In an alternative example, conductive strips or spokes can merge at a central area over a body joint.

In an example, a plurality of radial strips or spokes can collectively comprise a full star-burst pattern. In an example, radial strips or spokes can be evenly distributed around clock or compass positions in a full circle. In an example, a plurality of radial strips or spokes can collectively comprise a partial star-burst pattern. In an example, radial strips or spokes may span only a portion of clock or compass positions. In an example, radial strips or spokes may extend onto a portion of the perimeter of a clock or compass circle, wherein this portion comprises between ⅙ and ½ of the full circular perimeter. In an example, radial strips or spokes may collectively span in a radial manner only between 2 and 6 hours of clock positions of a star-burst pattern over a body joint. In an example, radial strips or spokes in a partial starburst configuration may collectively span a bow-tie shaped area.

In an example, a strip or spoke can comprise silicone and/or polydimethylsiloxane (PDMS) which has been impregnated and/or doped with electrically-conductive material. In an example, a strip or spoke can comprise silicone and/or polydimethylsiloxane (PDMS) which has been impregnated and/or doped with aluminum, carbon, copper, gold, nickel, or silver particles or fibers. In an example, a strip or spoke can comprise electrically-conductive threads, yarns, wires, or fibers which are embedded within silicone and/or polydimethylsiloxane (PDMS). In an example, a strip or spoke can comprise a woven array of electrically-conductive threads, yarns, wires, or fibers. In an example, a strip or spoke can comprise an elastic electrically-conductive fabric and/or textile.

In an example, strips or spokes in this example can be multi-layer capacitive strips or spokes instead of single-layer resistive strips or spokes. In an example, each multi-layer capacitive strip or spoke can further comprise two conductive layers, a dielectric layer between the conductive layers, an electromagnetic energy emitter, and an electromagnetic energy receiver. In an example, the electromagnetic energy emitter can be in electromagnetic communication with the inner layer of the multi-layer capacitive strip or spoke and the electromagnetic energy receiver can be in electromagnetic communication with the outer layer of the multi-layer capacitive strip, or vice versa. In an example, a multi-layer capacitive strip or spoke can have three layers, two conductive layers and a non-conductive (dielectric) layer between them.

In an example, an electrically-conductive layer can comprise silicone and/or polydimethylsiloxane (PDMS) which has been impregnated and/or doped with electrically-conductive material. In an example, an electrically-conductive layer can comprise silicone and/or polydimethylsiloxane (PDMS) which has been impregnated and/or doped with aluminum, carbon, copper, gold, nickel, or silver particles or fibers. In an example, an electrically-conductive layer can comprise electrically-conductive threads, yarns, wires, or fibers which are embedded within silicone and/or polydimethylsiloxane (PDMS). In an example, an electrically-conductive layer can comprise a woven array of electrically-conductive threads, yarns, wires, or fibers. In an example, a deformable dielectric layer can comprise silicone and/or polydimethylsiloxane (PDMS). Relevant example variations discussed elsewhere in this disclosure or in priority-linked disclosures can also be applied to the example shown in this figure, but are not repeated here in order to reduce narrative redundancy.

Figure 61:
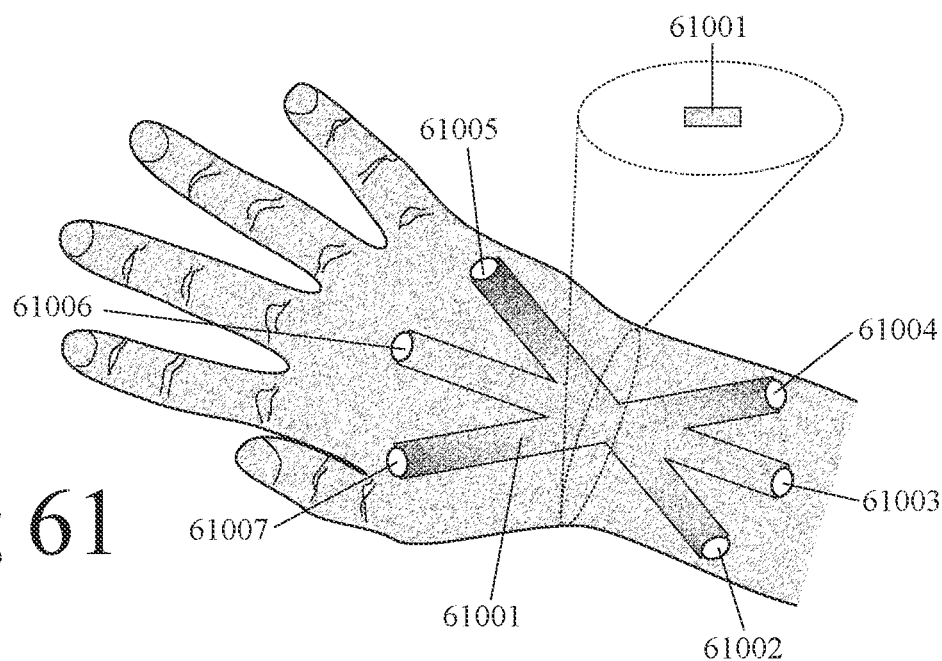
FIG. 61 shows an asterisk-shaped EM-conductive structure for measuring changes in joint configuration.

FIG. 61 shows another example of a wearable deformable sensor for measuring and/or modeling changes in body joint configuration. The left and lower-right portions of FIG. 61 show a top-down (dorsal) view of the sensor on a person's hand and upper-right portion shows a dotted-line ellipse containing a cross-sectional view of the sensor. This example comprises an asterisk-shaped combination of six centrally-connected electrically-conductive spokes which extend outward (in a radial manner) from a central location over a body joint.

The wearable deformable sensor in FIG. 61 comprises: an asterisk-shaped deformable electrically-conductive structure (61001) which further comprises six spokes extending radially outward from a central location over a body joint; a plurality of electromagnetic energy emitters (61002, 61003, 61004) in electromagnetic communication with a first set of selected spokes of the asterisk-shaped structure; and a plurality of electromagnetic energy receivers (61005, 61006, 61007) in electromagnetic communication with a second set of selected spokes of the asterisk-shaped structure.

The wearable deformable sensor in FIG. 61 can also be described as comprising: an asterisk-shaped deformable electrically-conductive combination (61001) of six connected spokes extending radially outward from a central location over a body joint; a plurality of electromagnetic energy emitters (61002, 61003, 61004) in electromagnetic communication with a first set of selected spokes of the asterisk-shaped structure; and a plurality of electromagnetic energy receivers (61005, 61006, 61007) in electromagnetic communication with a second set of selected spokes of the asterisk-shaped structure.

In an example, a wearable deformable sensor can also include one or more components selected from the group consisting of: data processor; power source (e.g. battery); data transmitter (e.g. wireless transmitter); and data receiver. In an example, changes in body joint configuration cause changes in resistance, impedance, conductivity, and/or capacitance which are analyzed to measure and/or model the changes in body joint configuration.

In this example, there are six radial spokes extending outward from a central location over a body joint. In an example, there can be eight or more radial spokes extending outward from a central location over a body joint. In an example, half of the spokes can extend in a distal direction and half of the spokes can extend in a proximal direction. In an example, there can be distal vs. proximal symmetry in the configurations of distally-extending spokes vs. proximally-extending spokes. In an example, energy emitters can be in electromagnetic communication with proximally-extending spokes and energy receivers can be in electromagnetic communication with distally-extending spokes, or vice versa. In an example, electromagnetic energy emission can be time multiplexed. In an example, different electromagnetic energy emitters can emit energy at different times and/or in different sequences. In an example, radial spokes can collectively span a height-compressed asterisk shape and/or a bow-tie shape.

In an example, a spoke can comprise silicone and/or polydimethylsiloxane (PDMS) which has been impregnated and/or doped with electrically-conductive material such as aluminum, carbon, copper, gold, nickel, or silver particles or fibers. In an example, a spoke can comprise electrically-conductive threads, yarns, wires, or fibers which are embedded within silicone and/or polydimethylsiloxane (PDMS). In an example, a spoke can comprise a woven array of electrically-conductive threads, yarns, wires, or fibers. In an example, a spoke can comprise an elastic electrically-conductive fabric and/or textile.

In an example, spokes can be multi-layer capacitive spokes instead of single-layer resistive spokes. In an example, each multi-layer capacitive spoke can further comprise two conductive layers, a dielectric layer between the conductive layers, an electromagnetic energy emitter, and an electromagnetic energy receiver. In an example, an electromagnetic energy emitter can be in electromagnetic communication with an inner layer of a multi-layer capacitive spoke and an electromagnetic energy receiver can be in electromagnetic communication with an outer layer of a multi-layer capacitive spoke, or vice versa. In an example, a multi-layer capacitive spoke can have three layers, two conductive layers and a non-conductive (dielectric) layer between them.

In an example, an electrically-conductive layer can comprise silicone and/or polydimethylsiloxane (PDMS) which has been impregnated and/or doped with electrically-conductive material such as aluminum, carbon, copper, gold, nickel, or silver particles or fibers. In an example, an electrically-conductive layer can comprise electrically-conductive threads, yarns, wires, or fibers which are embedded within silicone and/or polydimethylsiloxane (PDMS). In an example, an electrically-conductive layer can comprise a woven array of electrically-conductive threads, yarns, wires, or fibers. In an example, a deformable dielectric layer can comprise silicone and/or polydimethylsiloxane (PDMS). Relevant example variations discussed elsewhere in this disclosure or in priority-linked disclosures can also be applied to the example shown in this figure, but are not repeated here in order to reduce narrative redundancy.

Figure 62:
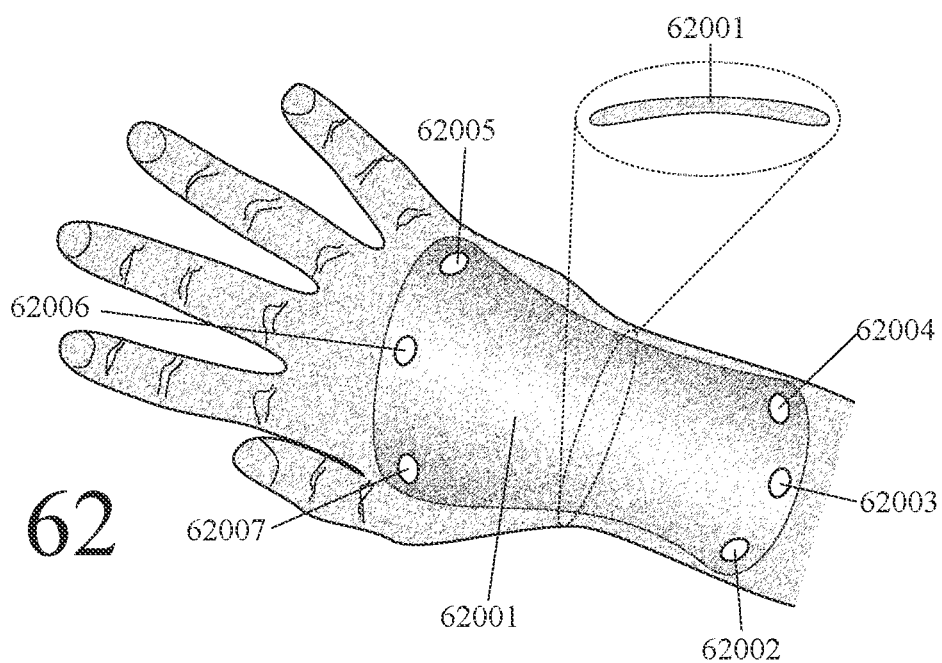
FIG. 62 shows an EM-conductive partial-circumference gauntlet or sleeve for measuring changes in joint configuration.

FIG. 62 shows another sensor for measuring and/or modeling changes in body joint configuration. The left and lower-right portions of FIG. 62 show a top-down (dorsal) view of the sensor on a hand and the upper-right portion shows a dotted-line ellipse containing a cross-sectional view. This example comprises a deformable electrically-conductive partial (e.g. half circumference) gauntlet or sleeve which spans a body joint.

The wearable deformable sensor in FIG. 62 comprises: a deformable electrically-conductive partial gauntlet (62001) which longitudinally spans a body joint, wherein the partial gauntlet covers between 25% and 75% of the circumference of a body member containing the body joint; a plurality of electromagnetic energy emitters (62002, 62003, 62004) in electromagnetic communication with the partial gauntlet; and a plurality of electromagnetic energy receivers (62005, 62006, 62007) in electromagnetic communication with the partial gauntlet.

The wearable deformable sensor in FIG. 62 can also be described as comprising: a deformable electrically-conductive partial sleeve (62001) which longitudinally spans a body joint, wherein the partial sleeve covers between 25% and 75% of the circumference of a body member containing the body joint; a plurality of electromagnetic energy emitters (62002, 62003, 62004) in electromagnetic communication with the partial sleeve; and a plurality of electromagnetic energy receivers (62005, 62006, 62007) in electromagnetic communication with the partial sleeve.

The wearable deformable sensor in FIG. 62 can also be described as comprising: a deformable electrically-conductive convex structure (62001) which longitudinally spans a body joint, wherein the convex structure covers between 25% and 75% of the circumference of a body member containing the body joint; a plurality of electromagnetic energy emitters (62002, 62003, 62004) in electromagnetic communication with the convex structure; and a plurality of electromagnetic energy receivers (62005, 62006, 62007) in electromagnetic communication with the convex structure.

In an example, a wearable deformable sensor can also include one or more components selected from the group consisting of: data processor; power source (e.g. battery); data transmitter (e.g. wireless transmitter); and data receiver. In an example, changes in body joint configuration cause changes in resistance, impedance, conductivity, and/or capacitance which are analyzed to measure and/or model the changes in body joint configuration.

In an example, a partial gauntlet or sleeve can comprise silicone and/or polydimethylsiloxane (PDMS) which has been impregnated and/or doped with electrically-conductive material such as aluminum, carbon, copper, gold, nickel, or silver particles or fibers. In an example, a partial gauntlet or sleeve can comprise electrically-conductive threads, yarns, wires, or fibers which are embedded within silicone and/or polydimethylsiloxane (PDMS). In an example, a partial gauntlet or sleeve can comprise a woven array of electrically-conductive threads, yarns, wires, or fibers. In an example, a partial gauntlet or sleeve can comprise an elastic electrically-conductive fabric and/or textile.

In an example, partial gauntlet or sleeve can be a multi-layer capacitive partial gauntlet or sleeve instead of single-layer resistive partial gauntlet or sleeve. In an example, each multi-layer capacitive partial gauntlet or sleeve can further comprise two conductive layers, a dielectric layer between the conductive layers, an electromagnetic energy emitter, and an electromagnetic energy receiver. In an example, the electromagnetic energy emitter can be in electromagnetic communication with the inner layer of the multi-layer capacitive partial gauntlet or sleeve and the electromagnetic energy receiver can be in electromagnetic communication with the outer layer of the multi-layer capacitive partial gauntlet or sleeve, or vice versa. Relevant example variations discussed elsewhere in this disclosure or in priority-linked disclosures can also be applied to the example shown in this figure, but are not repeated here in order to reduce narrative redundancy.

Figure 63:
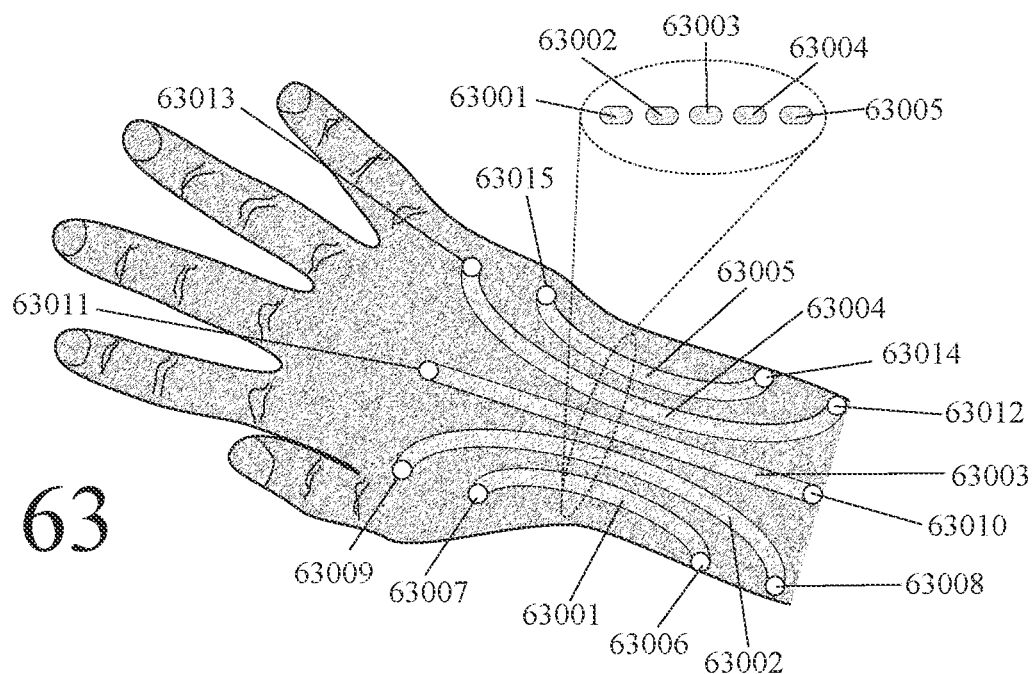
FIG. 63 shows a central EM strip and right-side and left-side nested arrays of concave EM strips for measuring changes in joint configuration.

FIG. 63 shows another sensor for measuring and/or modeling changes in body joint configuration. The left and lower-right portions of FIG. 63 show a top-down (dorsal) view of the sensor on a hand and the upper-right portion shows a dotted-line ellipse containing a cross-sectional view. The example comprises: a deformable electrically-conductive central strip which spans a body joint in a proximal-to-distal manner; and two (right-side and left-side) nested arrays of concave deformable electrically-conductive strips which are symmetrically configured on the right and left sides of the central strip.

The wearable deformable sensor in FIG. 63 comprises: a deformable elongate electrically-conductive central strip (63003) which spans a body joint in a proximal-to-distal manner; a left-side nested array of elongate electrically-conductive concave strips (63001, 63002) to the left of the central strip; a right-side nested array of elongate electrically-conductive concave strips (63004, 63005) to the right of the central strip; a plurality of electromagnetic energy emitters (63006, 63008, 63010, 63012, 63014) in electromagnetic communication with the central strip and/or the concave strips; and a plurality of electromagnetic energy receivers (63007, 63009, 63011, 63013, 63015) in electromagnetic communication with the central strip and/or the concave strips.

The wearable deformable sensor in FIG. 63 can also be described as comprising: a deformable elongate electrically-conductive central strip (63003) with a longitudinal axis which is configured to be substantially parallel to the proximal-to-distal axis of a body joint which the strip spans; a central electromagnetic energy emitter (63010) and a central electromagnetic energy receiver (63011) which are in electromagnetic communication with the central strip; a left-side nested array of elongate electrically-conductive strips (63001, 63002) to the left of the central strip, wherein these left-side strips are bowed inward toward the central strip; left-side electromagnetic energy emitters (63006, 63008) and receivers (63007, 63009) which are in electromagnetic communication with the left-side strips; a right-side nested array of elongate electrically-conductive strips (63004, 63005) to the right of the central strip, wherein these right-side strips are bowed inward toward the central strip; and right-side electromagnetic energy emitters (63012, 63014) and receivers (63013, 63015) which are in electromagnetic communication with the right-side strips.

The wearable deformable sensor in FIG. 63 can also be described as comprising: a deformable elongate electrically-conductive central strip (63003) which is configured to be parallel to the proximal-to-distal axis of a body joint; a central electromagnetic energy emitter (63010) and a central electromagnetic energy receiver (63011) which are in electromagnetic communication with the central strip; a plurality of left-side elongate electrically-conductive strips (63001, 63002) to the left of the central strip, wherein the centers of these left-side strips are curved inward toward the central strip; left-side electromagnetic energy emitters (63006, 63008) and receivers (63007, 63009) which are in electromagnetic communication with the left-side strips; a plurality of right-side elongate electrically-conductive strips (63004, 63005) to the right of the central strip, wherein the centers of these right-side strips are curved inward toward the central strip; and right-side electromagnetic energy emitters (63012, 63014) and receivers (63013, 63015) which are in electromagnetic communication with the right-side strips.

In an example, a wearable deformable sensor can also include one or more components selected from the group consisting of: data processor; power source (e.g. battery); data transmitter (e.g. wireless transmitter); and data receiver. In an example, changes in body joint configuration cause changes in resistance, impedance, conductivity, and/or capacitance which are analyzed to measure and/or model the changes in body joint configuration. In an example, a strip can comprise silicone and/or polydimethylsiloxane (PDMS) which has been impregnated and/or doped with electrically-conductive material such as aluminum, carbon, copper, gold, nickel, or silver particles or fibers. In an example, a strip can comprise electrically-conductive threads, yarns, wires, or fibers which are embedded within silicone and/or polydimethylsiloxane (PDMS). In an example, a strip can comprise a woven array of electrically-conductive threads, yarns, wires, or fibers. In an example, a strip can comprise an elastic electrically-conductive fabric and/or textile.

In an example, a strip can be a multi-layer capacitive strip instead of single-layer resistive strip. In an example, each multi-layer capacitive strip can further comprise two conductive layers, a dielectric layer between the conductive layers, an electromagnetic energy emitter, and an electromagnetic energy receiver. In an example, the electromagnetic energy emitter can be in electromagnetic communication with the inner layer of the multi-layer capacitive strip and the electromagnetic energy receiver can be in electromagnetic communication with the outer layer of the multi-layer capacitive strip, or vice versa. Relevant example variations discussed elsewhere in this disclosure or in priority-linked disclosures can also be applied to the example shown in this figure, but are not repeated here in order to reduce narrative redundancy.

Figure 64:
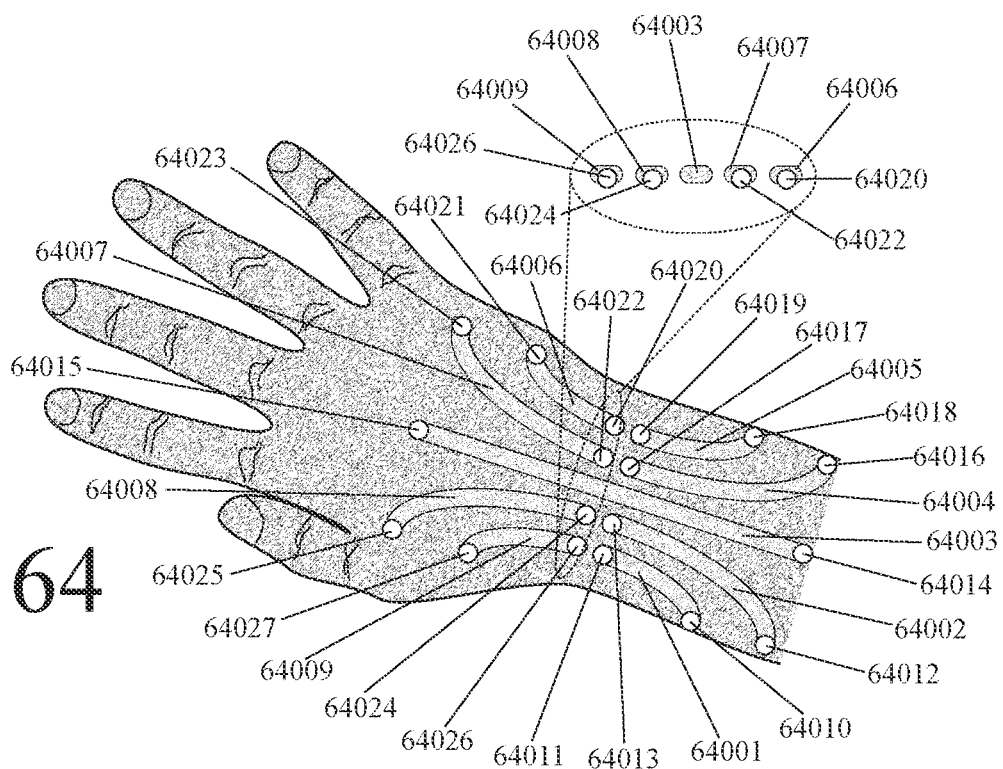
FIG. 64 shows a central EM strip and right-side and left-side, distal and proximal, diverging arrays of EM strips for measuring changes in joint configuration.

FIG. 64 shows another sensor for measuring and/or modeling changes in body joint configuration. The left and lower-right portions of FIG. 64 show a top-down (dorsal) view of the sensor on a hand and the upper-right portion shows a dotted-line ellipse containing a cross-sectional view. The example comprises: a deformable electrically-conductive central strip which spans a body joint in a proximal-to-distal manner; a proximal array of diverging arcuate deformable electrically-conductive strips; and a distal array of diverging arcuate deformable electrically-conductive strips.

The wearable deformable sensor in FIG. 64 comprises: a deformable elongate electrically-conductive central strip (64003) which spans a body joint in a proximal-to-distal manner; a proximal array of arcuate deformable electrically-conductive strips (64001, 64002, 64004, 64005), wherein some of these strips are to the right of the central strip and some of these strips are to the left of the central strip, wherein these strips are proximal relative to the middle of the central strip, and wherein these strips diverge from each other as they extend in a proximal direction; a distal array of arcuate deformable electrically-conductive strips (64006, 64007, 64008, 64009), wherein some of these strips are to the right of the central strip and some of these strips are to the left of the central strip, wherein these strips are distal relative to the middle of the central strip, and wherein these strips diverge from each other as they extend in a distal direction; a central electromagnetic energy emitter (64014) and a central electromagnetic energy receiver (64015) which are in electromagnetic communication with the central strip; a proximal array of electromagnetic energy emitters (64020, 64022, 64024, 64026) and receivers (64021, 64023, 64025, 64027) which are in electromagnetic communication with the proximal array of strips; and a distal array of electromagnetic energy emitters (64010, 64012, 64016, 64018) and receivers (64011, 64013, 64017, 64019) which are in electromagnetic communication with the distal array of strips.

In an example, a wearable deformable sensor can also include one or more components selected from the group consisting of: data processor; power source (e.g. battery); data transmitter (e.g. wireless transmitter); and data receiver. In an example, changes in body joint configuration cause changes in resistance, impedance, conductivity, and/or capacitance which are analyzed to measure and/or model the changes in body joint configuration. In an example, a strip can comprise silicone and/or polydimethylsiloxane (PDMS) which has been impregnated and/or doped with electrically-conductive material such as aluminum, carbon, copper, gold, nickel, or silver particles or fibers. In an example, a strip can comprise electrically-conductive threads, yarns, wires, or fibers which are embedded within silicone and/or polydimethylsiloxane (PDMS). In an example, a strip can comprise a woven array of electrically-conductive threads, yarns, wires, or fibers. In an example, a strip can comprise an elastic electrically-conductive fabric and/or textile.

With the addition of a data processor and power source, the example shown in FIG. 64 can also be described as a wearable deformable sensor for human motion capture comprising: a deformable elongate electrically-conductive central strip which is configured to span a body joint in a proximal-to-distal manner; a central electromagnetic energy emitter and a central electromagnetic energy receiver which are in electromagnetic communication with the deformable elongate electrically-conductive central strip; a proximal array of arcuate deformable electrically-conductive strips, wherein a right set of the strips in the proximal array of arcuate deformable electrically-conductive strips are to the right of the deformable elongate electrically-conductive central strip and a left subset of the strips in the proximal array of arcuate deformable electrically-conductive strips are to the left of the deformable elongate electrically-conductive central strip, wherein strips in the proximal array of arcuate deformable electrically-conductive strips are proximal relative to the middle of the deformable elongate electrically-conductive central strip, and wherein strips in the proximal array of arcuate deformable electrically-conductive strips diverge from each other as they extend in a proximal direction; a proximal array of electromagnetic energy emitters and electromagnetic energy receivers which are in electromagnetic communication with the proximal array of arcuate deformable electrically-conductive strips; a distal array of arcuate deformable electrically-conductive strips, wherein a right set of the strips in the distal array of arcuate deformable electrically-conductive strips are to the right of the deformable elongate electrically-conductive central strip and a left subset of the strips in the distal array of arcuate deformable electrically-conductive strips are to the left of the deformable elongate electrically-conductive central strip, wherein strips in the distal array of arcuate deformable electrically-conductive strips are distal relative to the middle of the deformable elongate electrically-conductive central strip, and wherein strips in the distal array of arcuate deformable electrically-conductive strips diverge from each other as they extend in a distal direction; a distal array of electromagnetic energy emitters and electromagnetic energy receivers which are in electromagnetic communication with the distal array of arcuate deformable electrically-conductive strips; wherein changes in body joint configuration cause deformations of the central, proximal, and distal electrically-conductive strips, wherein the deformations cause changes in the transmission of electromagnetic energy from the electromagnetic energy emitters to the electromagnetic energy receivers, and wherein the changes in the transmission of electromagnetic energy are analyzed in order to measure and/or model changes in body joint configuration; a data processor; and a power source.

In an example, a strip can be a multi-layer capacitive strip instead of single-layer resistive strip. In an example, each multi-layer capacitive strip can further comprise two conductive layers, a dielectric layer between the conductive layers, an electromagnetic energy emitter, and an electromagnetic energy receiver. In an example, the electromagnetic energy emitter can be in electromagnetic communication with the inner layer of the multi-layer capacitive strip and the electromagnetic energy receiver can be in electromagnetic communication with the outer layer of the multi-layer capacitive strip, or vice versa. Relevant example variations discussed elsewhere in this disclosure or in priority-linked disclosures can also be applied to the example shown in this figure, but are not repeated here in order to reduce narrative redundancy.

Figure 65:
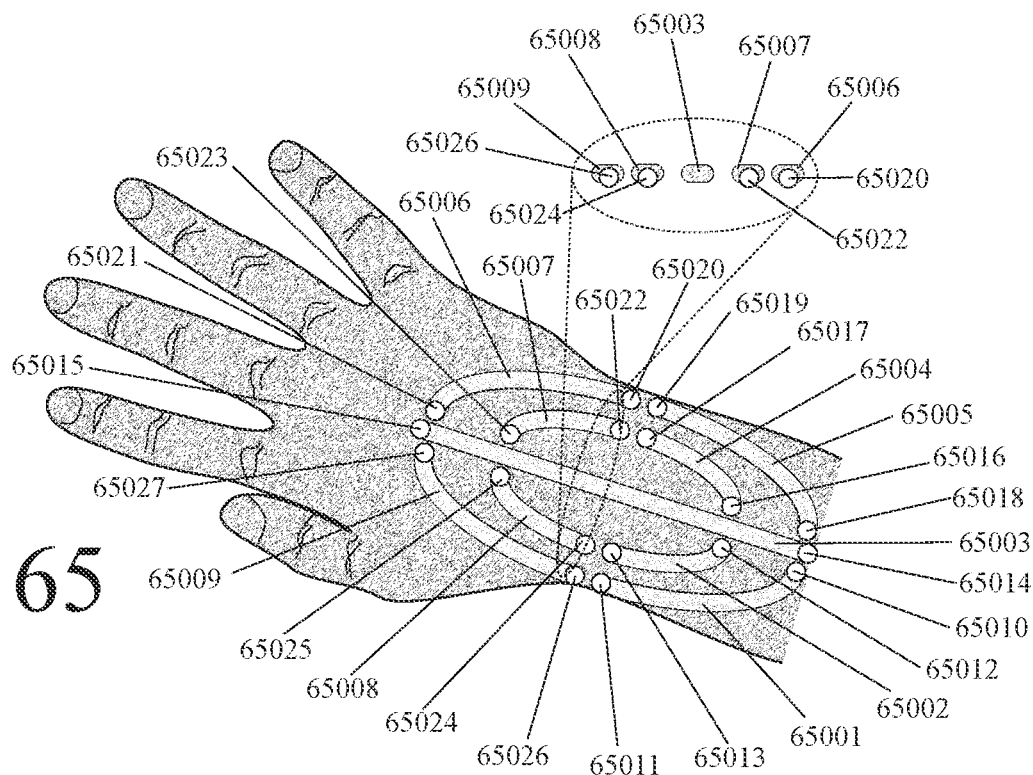
FIG. 65 shows a central EM strip and right-side and left-side, distal and proximal, converging arrays of EM strips for measuring changes in joint configuration.

FIG. 65 shows another sensor for measuring and/or modeling changes in body joint configuration. The left and lower-right portions of FIG. 65 show a top-down (dorsal) view of the sensor on a hand and the upper-right portion shows a dotted-line ellipse containing a cross-sectional view. The example comprises: a deformable electrically-conductive central strip which spans a body joint in a proximal-to-distal manner; a proximal array of converging arcuate deformable electrically-conductive strips; and a distal array of converging arcuate deformable electrically-conductive strips.

The wearable deformable sensor in FIG. 65 comprises: a deformable elongate electrically-conductive central strip (65003) which spans a body joint in a proximal-to-distal manner; a proximal array of arcuate deformable electrically-conductive strips (65001, 65002, 65004, 65005), wherein some of these strips are to the right of the central strip and some of these strips are to the left of the central strip, wherein these strips are proximal relative to the middle of the central strip, and wherein these strips converge toward each other as they extend in a proximal direction; a distal array of arcuate deformable electrically-conductive strips (65006, 65007, 65008, 65009), wherein some of these strips are to the right of the central strip and some of these strips are to the left of the central strip, wherein these strips are distal relative to the middle of the central strip, and wherein these strips converge toward each other as they extend in a distal direction; a central electromagnetic energy emitter (65014) and a central electromagnetic energy receiver (65015) which are in electromagnetic communication with the central strip; a proximal array of electromagnetic energy emitters (65010, 65012, 65016, 65018) and receivers (65011, 65013, 65017, 65019) which are in electromagnetic communication with the proximal array of strips; and a distal array of electromagnetic energy emitters (65020, 65022, 65024, 65026) and receivers (65021, 65023, 65025, 65027) which are in electromagnetic communication with the distal array of strips.

In an example, a wearable deformable sensor can also include one or more components selected from the group consisting of: data processor; power source (e.g. battery); data transmitter (e.g. wireless transmitter); and data receiver. In an example, changes in body joint configuration cause changes in resistance, impedance, conductivity, and/or capacitance which are analyzed to measure and/or model the changes in body joint configuration. In an example, a strip can comprise silicone and/or polydimethylsiloxane (PDMS) which has been impregnated and/or doped with electrically-conductive material such as aluminum, carbon, copper, gold, nickel, or silver particles or fibers. In an example, a strip can comprise electrically-conductive threads, yarns, wires, or fibers which are embedded within silicone and/or polydimethylsiloxane (PDMS). In an example, a strip can comprise a woven array of electrically-conductive threads, yarns, wires, or fibers. In an example, a strip can comprise an elastic electrically-conductive fabric and/or textile.

In an example, a strip can be a multi-layer capacitive strip instead of single-layer resistive strip. In an example, each multi-layer capacitive strip can further comprise two conductive layers, a dielectric layer between the conductive layers, an electromagnetic energy emitter, and an electromagnetic energy receiver. In an example, the electromagnetic energy emitter can be in electromagnetic communication with the inner layer of the multi-layer capacitive strip and the electromagnetic energy receiver can be in electromagnetic communication with the outer layer of the multi-layer capacitive strip, or vice versa. Relevant example variations discussed elsewhere in this disclosure or in priority-linked disclosures can also be applied to the example shown in this figure, but are not repeated here in order to reduce narrative redundancy.

Figure 66:
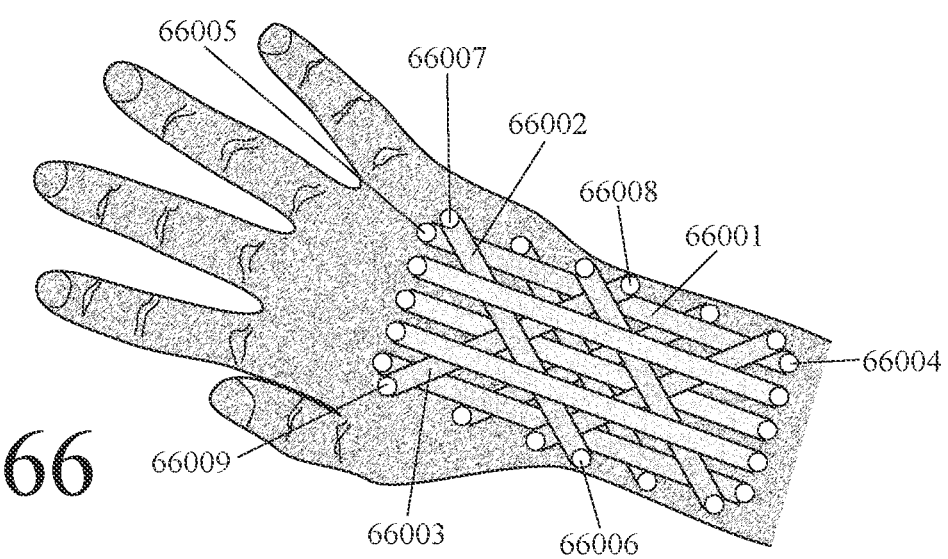
FIG. 66 shows a plurality of EM strips, some parallel to a joint axis and some diagonal to the joint axis, for measuring changes in joint configuration.

FIG. 66 shows another sensor for measuring and/or modeling changes in body joint configuration. The left and lower-right portions of this figure show a top-down (dorsal) view of the sensor and the upper-right portion shows a dotted-line ellipse containing a cross-sectional view. The example comprises a woven or braided array of deformable electrically-conductive central strips which spans a body joint, wherein this array further comprises: a first subset of the strips with longitudinal axes which are substantially parallel to the proximal-to-distal axis of the body joint; a second subset of the strips with longitudinal axes which are diagonal to the proximal-to-distal axis of the body joint; a third subset of the strips with longitudinal axes which are substantially perpendicular to the longitudinal axes of the second subset of the strips; and electromagnetic energy emitters and receivers which are in electro-magnetic communication with the woven array of strips.

The wearable deformable sensor in FIG. 66 comprises: a woven or braided array of deformable electrically-conductive strips which spans a body joint, wherein this array further comprises (A) a first subset of the array of deformable electrically-conductive strips (including 66001), wherein strips in this first subset have longitudinal axes which are substantially parallel to the proximal-to-distal axis of the body joint; (B) a second subset of the array of deformable electrically-conductive strips (including 66002), wherein strips in this second subset have longitudinal axes which are substantially diagonal to the proximal-to-distal axis of the body joint; (C) a third subset of the array of deformable electrically-conductive strips (including 66003), wherein strips in this third subset have longitudinal axes which are substantially perpendicular to the longitudinal axes of strips in the second subset; and (D) electromagnetic energy emitters and receivers (including 66004, 66005, 66006, 66007, 66008, and 66009) which are in electromagnetic communication with the woven array of deformable electrically-conductive strips. In an example, this sensor can also include one or more components selected from the group consisting of: data processor; power source; data transmitter; and data receiver. In an example, changes in body joint configuration cause changes in the resistance, impedance, conductivity, and/or capacitance of the strips which are, in turn, analyzed to measure and/or model the changes in body joint configuration.

In an example, a wearable deformable sensor can also include one or more components selected from the group consisting of: data processor; power source; data transmitter; and data receiver. In an example, changes in body joint configuration cause changes in the resistance, impedance, conductivity, and/or capacitance of the strips—which are, in turn, analyzed to measure and/or model the changes in body joint configuration. In an example, the distal-facing angle between the longitudinal axes of the first and second subsets can be 45 degrees. In an example, the distal-facing angle between the longitudinal axes of the first and second subsets can be in range of 20 to 70 degrees.

The wearable deformable sensor in FIG. 66 can also be described as comprising: a first array of parallel deformable electrically-conductive strips (including 66001) which span a body joint; a first plurality of electromagnetic energy emitters and receivers (including 66004 and 66005) which are in electro-magnetic communication with the first array of parallel deformable electrically-conductive strips; a second array of parallel deformable electrically-conductive strips (including 66002) which span a body joint, wherein the longitudinal axes of strips in the second array intersect the longitudinal axes of strips in the first array at a first distal-facing angle, and wherein the first distal-facing angle is in the range of 20 to 70 degrees; a second plurality of electromagnetic energy emitters and receivers (including 66006 and 66007) which are in electro-magnetic communication with the second array of parallel deformable electrically-conductive strips; a third array of parallel deformable electrically-conductive strips (including 66003) which span a body joint, wherein the longitudinal axes of strips in the third array intersect the longitudinal axes of strips in the second array at a second distal-facing angle, and wherein the second distal-facing angle is in the range of 75 to 105 degrees; and a third plurality of electromagnetic energy emitters and receivers (including 66008 and 66009) which are in electro-magnetic communication with the third array of parallel deformable electrically-conductive strips.

The wearable deformable sensor in FIG. 66 can also be described as comprising: a first array of parallel deformable electrically-conductive yarns or fibers (including 66001) which span a body joint; a first plurality of electromagnetic energy emitters and receivers (including 66004 and 66005) which are in electro-magnetic communication with the first array of parallel deformable electrically-conductive yarns or fibers; a second array of parallel deformable electrically-conductive yarns or fibers (including 66002) which span a body joint, wherein the longitudinal axes of yarns or fibers in the second array intersect the longitudinal axes of yarns or fibers in the first array at a first distal-facing angle, and wherein the first distal-facing angle is in the range of 20 to 70 degrees; a second plurality of electromagnetic energy emitters and receivers (including 66006 and 66007) which are in electro-magnetic communication with the second array of parallel deformable electrically-conductive yarns or fibers; a third array of parallel deformable electrically-conductive yarns or fibers (including 66003) which span a body joint, wherein the longitudinal axes of yarns or fibers in the third array intersect the longitudinal axes of yarns or fibers in the second array at a second distal-facing angle, and wherein the second distal-facing angle is in the range of 75 to 105 degrees; and a third plurality of electromagnetic energy emitters and receivers (including 66008 and 66009) which are in electro-magnetic communication with the third array of parallel deformable electrically-conductive yarns or fibers.

In this example, there are five parallel strips in the first subset of strips. In an example, there can be three strips in the first subset. In an example, there can be more than five strips in the first subset. In this example, there are three parallel strips in the second subset of strips. In an example, there can be more than three strips in the second subset. In this example, there are three parallel strips in the third subset of strips. In an example, there can be more than three strips in the third subset. In an example, a woven strip array can have a weave pattern selected from the group consisting of: plain weave; rib weave; basket weave; twill weave; Satin weave; leno weave; and mock leno weave. In an example, a braided strip array can have a pattern selected from the group consisting of: a one over braid pattern; one over, one under braid (e.g. diamond) braid pattern; one over, three under braid pattern; two over, one under braid pattern; two over, two under braid pattern; two under, two over braid pattern; three over, one under braid pattern; three over, three under braid pattern; four over, one under braid pattern; four over, four under braid pattern; five over, one under braid pattern; six over, one under braid pattern; seven over, one under braid pattern; and eight over, one under braid pattern.

In an example, a strip can comprise silicone and/or polydimethylsiloxane (PDMS) which has been impregnated and/or doped with electrically-conductive material such as aluminum, carbon, copper, gold, nickel, or silver particles or fibers. In an example, a strip can comprise electrically-conductive threads, yarns, wires, or fibers which are embedded within silicone and/or polydimethylsiloxane (PDMS). In an example, a strip can comprise a woven array of electrically-conductive threads, yarns, wires, or fibers. In an example, a strip can comprise an elastic electrically-conductive fabric and/or textile.

In an example, a strip can be a multi-layer capacitive strip instead of single-layer resistive strip. In an example, each multi-layer capacitive strip can further comprise two conductive layers, a dielectric layer between the conductive layers, an electromagnetic energy emitter, and an electromagnetic energy receiver. In an example, the electromagnetic energy emitter can be in electromagnetic communication with the inner layer of the multi-layer capacitive strip and the electromagnetic energy receiver can be in electromagnetic communication with the outer layer of the multi-layer capacitive strip, or vice versa. Relevant example variations discussed elsewhere in this disclosure or in priority-linked disclosures can also be applied to the example shown in this figure, but are not repeated here in order to reduce narrative redundancy.

Figure 67:
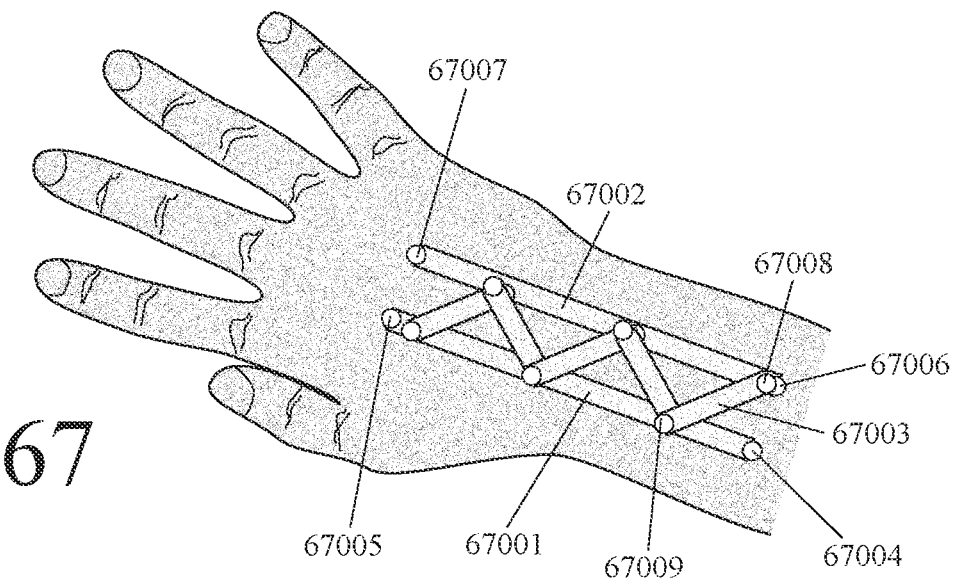
FIG. 67 shows a triangular-truss-shaped configuration of EM strips for measuring changes in joint configuration.

FIG. 67 shows another sensor for measuring and/or modeling changes in body joint configuration. The left and lower-right portions of this figure show a top-down (dorsal) view of the sensor on a hand and the upper-right portion shows a dotted-line ellipse containing a cross-sectional view. This example comprises two parallel conductive strips which are connected by an oscillating (e.g. zigzag or sinusoidal shaped) array of conductive strips.

The wearable deformable sensor in FIG. 67 comprises: a first deformable elongate electrically-conductive strip (67001) which is configured to span a body joint in a proximal-to-distal manner; a second deformable elongate electrically-conductive strip (67002), wherein the longitudinal axis of the second deformable elongate electrically-conductive strip is parallel to the longitudinal axis of the first deformable elongate electrically-conductive strip; a zigzag-shaped array of deformable elongate electrically-conductive strips (including 67003) between the first deformable elongate electrically-conductive strip and the second deformable elongate electrically-conductive strip; and a plurality of electromagnetic energy emitters and receivers (including 67004, 67005, 67006, 67007, 67008, and 67009) which are in electro-magnetic communication with the first deformable elongate electrically-conductive strip, the second deformable elongate electrically-conductive strip, and the zigzag-shaped array of deformable elongate electrically-conductive strips.

The wearable deformable sensor in FIG. 67 can also be described as comprising: a first deformable elongate electrically-conductive strip (67001) which is configured to span a body joint in a proximal-to-distal manner; a first electromagnetic energy emitter (67004) and a first electromagnetic energy receiver (67005) in electromagnetic communication with the first deformable elongate electrically-conductive strip; a second deformable elongate electrically-conductive strip (67002) which is configured to span the body joint, wherein the longitudinal axis of the second deformable elongate electrically-conductive strip is parallel to the longitudinal axis of the first deformable elongate electrically-conductive strip; a second electromagnetic energy emitter (67006) and a first electromagnetic energy receiver (67007) in electromagnetic communication with the second deformable elongate electrically-conductive strip; an oscillating (zigzag or sinusoidal wave shaped) array of deformable elongate electrically-conductive strips (including 67003) connecting the first deformable elongate electrically-conductive strip and the second deformable elongate electrically-conductive strip; and a plurality of electromagnetic energy emitters (including 67008) and receivers (including 67009) which are in electro-magnetic communication with the oscillating (zigzag or sinusoidal wave shaped) array of deformable elongate electrically-conductive strips.

In an example, this sensor can also include one or more components selected from the group consisting of: data processor; power source; data transmitter; and data receiver. In an example, changes in body joint configuration cause changes in the resistance, impedance, conductivity, and/or capacitance of the strips which are, in turn, analyzed to measure and/or model the changes in body joint configuration. In an example, an oscillating array of strips between two parallel strips can have a zigzag shape, forming a proximal-to-distal series of triangles with alternating orientations (similar to a trussed structural beam). In an example, an oscillating array of strips between two parallel strips can have a sinusoidal shape, forming a proximal-to-distal series of sinusoidal-curve-shaped gaps.

In an example, a strip can comprise silicone and/or polydimethylsiloxane (PDMS) which has been impregnated and/or doped with electrically-conductive material such as aluminum, carbon, copper, gold, nickel, or silver particles or fibers. In an example, a strip can comprise electrically-conductive threads, yarns, wires, or fibers which are embedded within silicone and/or polydimethylsiloxane (PDMS). In an example, a strip can comprise a woven array of electrically-conductive threads, yarns, wires, or fibers. In an example, a strip can comprise an elastic electrically-conductive fabric and/or textile.

In an example, a strip can be a multi-layer capacitive strip instead of single-layer resistive strip. In an example, each multi-layer capacitive strip can further comprise two conductive layers, a dielectric layer between the conductive layers, an electromagnetic energy emitter, and an electromagnetic energy receiver. In an example, the electromagnetic energy emitter can be in electromagnetic communication with the inner layer of the multi-layer capacitive strip and the electromagnetic energy receiver can be in electromagnetic communication with the outer layer of the multi-layer capacitive strip, or vice versa. Relevant example variations discussed elsewhere in this disclosure or in priority-linked disclosures can also be applied to the example shown in this figure, but are not repeated here in order to reduce narrative redundancy.

Figure 68:
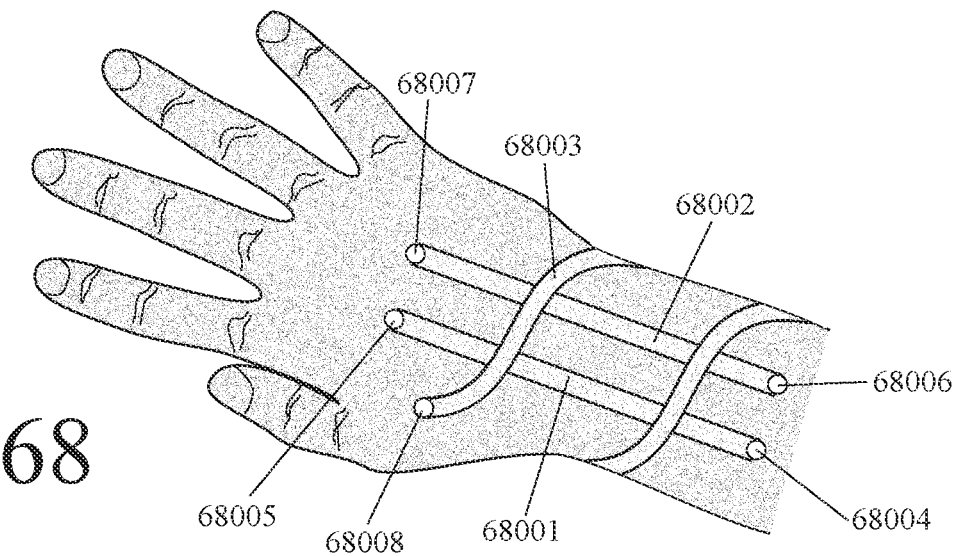
FIG. 68 shows two parallel EM strips and one helical EM strip for measuring changes in joint configuration.

FIG. 68 shows another sensor for measuring and/or modeling changes in body joint configuration. The left and lower-right portions of this figure show a top-down (dorsal) view of the sensor on a hand and the upper-right portion shows a dotted-line ellipse containing a cross-sectional view. This example comprises two parallel conductive strips which span a body joint and a helical conductive strip which encircles the body joint.

The wearable deformable sensor in FIG. 68 comprises: a first deformable elongate electrically-conductive strip (68001) which is configured to span a body joint in a proximal-to-distal manner; a first electromagnetic energy emitter (68004) and a first electromagnetic energy receiver (68005) which are in electromagnetic communication with the first deformable elongate electrically-conductive strip; a second deformable elongate electrically-conductive strip (68002), wherein the longitudinal axis of the second deformable elongate electrically-conductive strip is substantially parallel to the longitudinal axis of the first deformable elongate electrically-conductive strip; a second electromagnetic energy emitter (68006) and a second electromagnetic energy receiver (68007) which are in electromagnetic communication with the second deformable elongate electrically-conductive strip; a third deformable elongate electrically-conductive strip (68003) which has a helical shape and encircles the body joint; and a third electromagnetic energy emitter (not shown here) and a third electromagnetic energy receiver (68008) which are in electromagnetic communication with the third deformable elongate electrically-conductive strip.

In an example, this sensor can also include one or more components selected from the group consisting of: data processor; power source; data transmitter; and data receiver. In an example, changes in body joint configuration cause changes in the resistance, impedance, conductivity, and/or capacitance of the strips which are, in turn, analyzed to measure and/or model the changes in body joint configuration.

In an example, a strip can comprise silicone and/or polydimethylsiloxane (PDMS) which has been impregnated and/or doped with electrically-conductive material such as aluminum, carbon, copper, gold, nickel, or silver particles or fibers. In an example, a strip can comprise electrically-conductive threads, yarns, wires, or fibers which are embedded within silicone and/or polydimethylsiloxane (PDMS). In an example, a strip can comprise a woven array of electrically-conductive threads, yarns, wires, or fibers. In an example, a strip can comprise an elastic electrically-conductive fabric and/or textile.

In an example, a strip can be a multi-layer capacitive strip instead of single-layer resistive strip. In an example, each multi-layer capacitive strip can further comprise two conductive layers, a dielectric layer between the conductive layers, an electromagnetic energy emitter, and an electromagnetic energy receiver. In an example, the electromagnetic energy emitter can be in electromagnetic communication with the inner layer of the multi-layer capacitive strip and the electromagnetic energy receiver can be in electromagnetic communication with the outer layer of the multi-layer capacitive strip, or vice versa. Relevant example variations discussed elsewhere in this disclosure or in priority-linked disclosures can also be applied to the example shown in this figure, but are not repeated here in order to reduce narrative redundancy.

Figure 69:
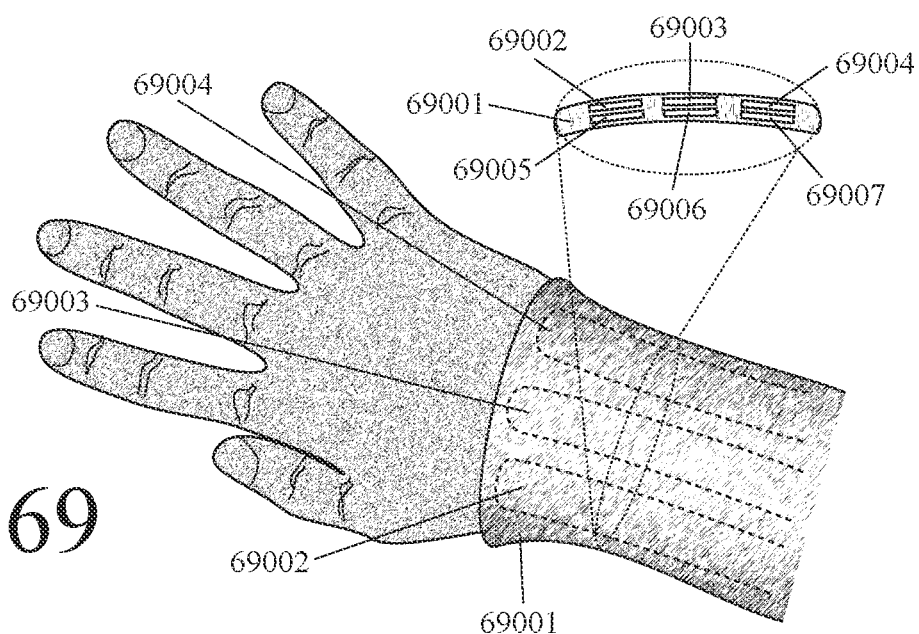
FIG. 69 shows a single-layer sleeve with pairs of inner and outer overlapping EM strips for measuring changes in joint configuration.

FIG. 69 shows another sensor for measuring and/or modeling changes in body joint configuration. The left and lower-right portions of this figure show a top-down (dorsal) view of the sensor and the upper-right portion shows a dotted-line ellipse containing a cross-sectional view. This example is a flexible sleeve or cuff which further comprises a circumferential (or partially-circumferential) array of pairs of inner and outer (overlapping) deformable conductive strips separated by a dielectric layer.

The wearable deformable sensor in FIG. 69 comprises: a flexible sleeve or cuff (69001) which is configured to span a body joint, wherein this flexible sleeve or cuff further comprises a circumferential (or partially circumferential) array of pairs of deformable conductive strips, wherein each pair of deformable conductive strips further comprises an inner deformable conductive strip (such as 69005, 69006, or 69007) which is configured to be first distance from the person's body and an outer deformable conductive strip (such as 69002, 69003, or 69004) which is configured to be a second distance from the person's body, wherein the second distance is greater than the first distance, and wherein the inner deformable conductive strip and the outer deformable conductive strip are separated by a deformable dielectric layer.

The wearable deformable sensor in FIG. 69 can also be described as comprising: a tubular portion of an article of clothing (69001) which is configured to span a body joint; an inner circumferential (or partially circumferential) array of flexible conductive pathways (such as 69005, 69006, and 69007) which are configured to be first distance from the person's body; an outer circumferential (or partially circumferential) array of flexible conductive pathways (such as 69002, 69003, and 69004) which are configured to be second distance from the person's body, wherein the second distance is greater than the first distance; and a deformable dielectric layer between the inner circumferential (or partially circumferential) array and the outer circumferential (or partially circumferential) array. In an example, pathways in the outer array can overlap pathways in the inner array. In an example, pathways in the outer array can be located at the same circumferential positions as pathways in the inner array.

In an example, this sensor can also include one or more components selected from the group consisting of: a plurality of electromagnetic energy emitters and receivers in electromagnetic communication with the strips; a data processor; a power source; a data transmitter; and a data receiver. In an example, changes in body joint configuration cause changes in the resistance, impedance, conductivity of the strips and these changes are, in turn, analyzed to measure and/or model the changes in body joint configuration. In an example, changes in body joint configuration cause changes in the capacitance of pairs of strips and these changes are, in turn, analyzed to measure and/or model the changes in body joint configuration.

FIG. 69 shows an example of this sensor with 3 pairs of strips in a partially circumferential array of pairs of deformable conductive strips. In an example, there can be 4 pairs of strips in a circumferential (or partially circumferential) array of pairs of deformable conductive strips. In an example, there can be 12 pairs of strips in a circumferential (or partially circumferential) array of pairs of deformable conductive strips. In an example, there can be 8 pairs of strips in a circumferential (or partially circumferential) array of pairs of deformable conductive strips. In an example, there can be 6 pairs of strips in a circumferential (or partially circumferential) array of pairs of deformable conductive strips.

In an example, a circumferential array of pairs of deformable strips can collectively span the entire circumference of the part of a person's body which contains a body joint. In an example, there can be twelve pairs of strips, one centered on each clock hour position, which collectively span this circumference. In an example, there can be six pairs of strips, one centered at every two-hour position (e.g. noon, 2 o'clock, 4 o'clock, 6 o'clock, 8 o'clock, and 10 o'clock). In an example, there can be four pairs of strips, one centered at every three-hour position (e.g. noon, 3 o'clock, 6 o'clock, and 9 o'clock). In an example, there can be twelve pairs of strips, one centered on every 30-degree interval (e.g. 0, 30, 60, 90, 120, 150, 180, 210, 240, 270, 300, and 330 degrees) around this circumference. In an example, there can be six pairs of strips, one centered at every 60-degree interval (e.g. 0, 60, 120, 180, 240, and 300 degrees) around the circumference. In an example, there can be four pairs of strips, one centered at every 90-degree interval (e.g. 0, 90, 180, and 270 degrees) around this circumference.

In an example, a partial circumferential array of pairs of deformable strips can collectively span only a portion of the circumference of the part of a person's body which contains a body joint. In an example, a partial circumferential array of pairs of deformable strips can collectively span between ⅛ and ½ of the circumference of the part of a person's body which contains a body joint. In an example, a partial circumferential array of pairs of deformable strips can collectively span between ¼ and ¾ of the circumference of the part of a person's body which contains a body joint. In an example pairs of deformable conductive strips can have longitudinal axes which are substantially parallel to the proximal-to-distal axis of the body joint which they span. In an example, inner and outer conductive strips can be parallel to each other.

In an example, pairs or strips can be separated from each other by a distance in the range of ¼" to 2". In an example, the lateral width of strips can be in the range of ¼" to 2". In an example, the distance between pairs can be at least 50% greater than the lateral width of strips within pairs. In an example, the distance between pairs can be at least twice the lateral width of strips within pairs. In an example, pairs of strips can be evenly-distributed (e.g. evenly-spaced) around the (partial) circumference of a body part. In an example, pairs of strips can be unevenly-distributed (e.g. unevenly-spaced) around the (partial) circumference of a body part. In an example, pairs of strips can be disproportionally clustered on the dorsal surface of a body part. In an example, pairs of strips can be disproportionally clustered on the ventral surface of a body part.

In an example, the main body of a sleeve or cuff can be non-conductive. In an example, the material of the main body of a sleeve or cuff can serve as a dielectric layer between strips. In an example, a strip can comprise silicone and/or polydimethylsiloxane (PDMS) which has been impregnated and/or doped with electrically-conductive material such as aluminum, carbon, copper, gold, nickel, or silver particles or fibers. In an example, a strip can comprise electrically-conductive threads, yarns, wires, or fibers which are embedded within silicone and/or polydimethylsiloxane (PDMS). In an example, a strip can comprise a woven array of electrically-conductive threads, yarns, wires, or fibers. In an example, a strip can comprise an elastic electrically-conductive fabric and/or textile. Relevant example variations discussed elsewhere in this disclosure or in priority-linked disclosures can also be applied to the example shown in this figure, but are not repeated here in order to reduce narrative redundancy.

Figure 70:
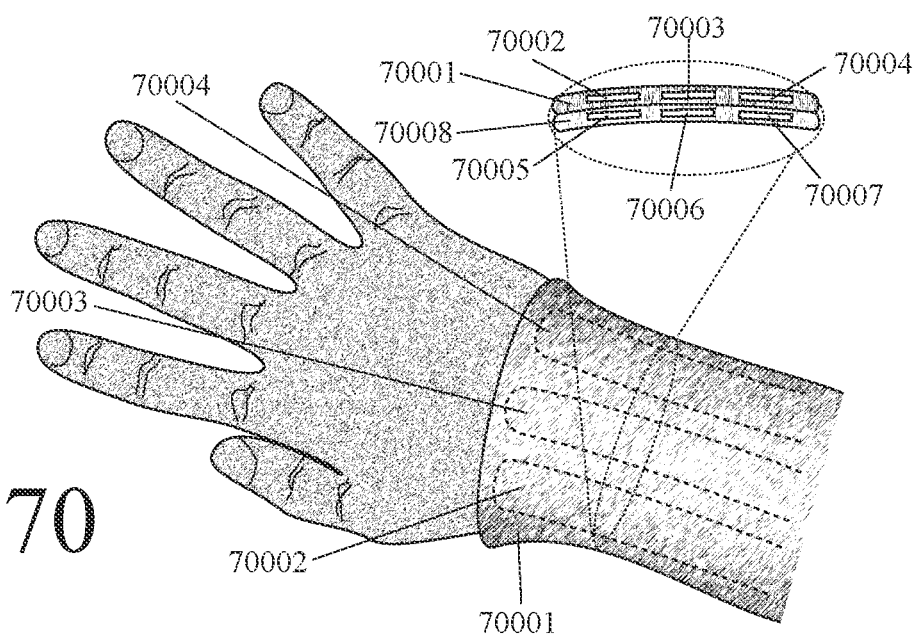
FIG. 70 shows a two-layer sleeve with pairs of inner and outer overlapping EM strips for measuring changes in joint configuration.

FIG. 70 shows another sensor for measuring and/or modeling changes in body joint configuration. The left and lower-right portions of this figure show a top-down (dorsal) view of the sensor and the upper-right portion shows a dotted-line ellipse containing a cross-sectional view. This example is a two-layer flexible sleeve or cuff which further comprises a circumferential (or partially-circumferential) array of pairs of inner and outer overlapping deformable conductive strips.

The wearable deformable sensor in FIG. 70 comprises: a two-layer flexible sleeve or cuff which is configured to span a body joint, where this two-layer sleeve or cuff further comprises an outer layer (70001) made from a first material and an inner layer (70008) made from a second material, wherein this flexible sleeve or cuff further comprises a circumferential (or partially circumferential) array of pairs of deformable conductive strips, wherein each pair of deformable conductive strips further comprises an inner deformable conductive strip (such as 70005, 70006, or 70007) in the inner layer of the sleeve or cuff and an outer deformable conductive strip (such as 70002, 70003, or 70004) contained in the outer layer of the sleeve or cuff. In an example, the first material can have a different level of flexibility or elasticity than the second material. In an example, the first material can have a different level of electromagnetic conductivity than the second material.

The wearable deformable sensor in FIG. 70 can also be described as comprising: a two-layer tubular portion of an article of clothing (70001) which is configured to span a body joint, wherein a first layer of the tubular portion has a first elasticity level and a second layer of the tubular portion has a second elasticity level, and wherein the second level is greater than the first level; an inner circumferential (or partially circumferential) array of flexible conductive pathways (such as 70005, 70006, and 70007) which are configured to be first distance from the person's body; an outer circumferential (or partially circumferential) array of flexible conductive pathways (such as 70002, 70003, and 70004) which are configured to be second distance from the person's body; wherein the second distance is greater than the first distance; and a deformable dielectric layer between the inner circumferential (or partially circumferential) array and the outer circumferential (or partially circumferential) array. In an example, pathways in the outer array can overlap pathways in the inner array. In an example, pathways in the outer array can be located at the same circumferential positions as pathways in the inner array.

In an example, this sensor can also include one or more components selected from the group consisting of: a plurality of electromagnetic energy emitters and receivers in electromagnetic communication with the strips; a data processor; a power source; a data transmitter; and a data receiver. In an example, changes in body joint configuration cause changes in the resistance, impedance, conductivity of the strips and these changes are, in turn, analyzed to measure and/or model the changes in body joint configuration. In an example, changes in body joint configuration cause changes in the capacitance of pairs of strips and these changes are, in turn, analyzed to measure and/or model the changes in body joint configuration. Relevant example variations discussed elsewhere in this disclosure or in priority-linked disclosures can also be applied to the example shown in this figure, but are not repeated here in order to reduce narrative redundancy.

Figure 71:
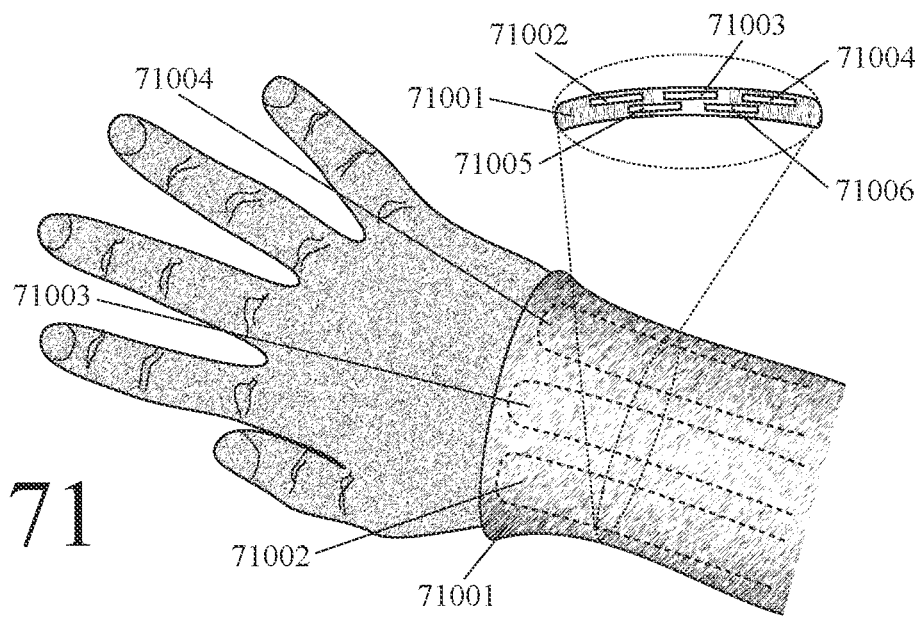
FIG. 71 shows a sleeve with of inner and outer non-overlapping (staggered) EM strips for measuring changes in joint configuration.

FIG. 71 shows another sensor for measuring and/or modeling changes in body joint configuration. The left and lower-right portions of this figure show a top-down (dorsal) view of the sensor and the upper-right portion shows a dotted-line ellipse containing a cross-sectional view. This example is a flexible sleeve or cuff which further comprises staggered circumferential (or partially-circumferential) arrays of inner and outer overlapping deformable conductive strips.

The wearable deformable sensor in FIG. 71 comprises: a flexible sleeve or cuff (71001) which is configured to span a body joint; an inner circumferential (or partially circumferential) array of deformable conductive strips (including 71005 and 71006); an outer circumferential (or partially circumferential) array of deformable conductive strips (including 71002, 71003, and 71004), wherein the inner and outer conductive strips are separated by a dielectric layer, and wherein the inner and outer arrays are staggered relative to each other.

The wearable deformable sensor in FIG. 71 can also be described as comprising: a flexible sleeve or cuff (71001) which is configured to span around body joint; an inner array of deformable conductive strips (including 71005 and 71006) within the flexible sleeve or cuff, wherein strips this inner array are located at a first set of radial locations around the circumference of the body joint; an outer circumferential (or partially circumferential) array of deformable conductive strips (including 71002, 71003, and 71004) within the flexible sleeve or cuff, wherein strips in this outer array are located at a second set of radial locations around the circumference of the body joint, and wherein second set of radial locations is different than the first set of radial locations.

The wearable deformable sensor in FIG. 71 can also be described as comprising: a flexible sleeve or cuff (71001) which is configured to span around body joint; an inner array of deformable conductive strips (including 71005 and 71006) within the flexible sleeve or cuff around (a portion of) the circumference of the body joint; an outer circumferential (or partially circumferential) array of deformable conductive strips (including 71002, 71003, and 71004) within the flexible sleeve or cuff around (a portion of) the circumference of the body joint, and wherein strips in the inner array and strips in the outer array do not completely overlap each other.

The wearable deformable sensor in FIG. 71 can also be described as comprising: a tubular portion of an article of clothing (71001) which is configured to span a body joint; an inner circumferential (or partially circumferential) array of flexible conductive pathways (such as 71005, 71006, and 71007) which are configured to be first distance from the person's body; a outer circumferential (or partially circumferential) array of flexible conductive pathways (such as 71002, 71003, and 71004) which are configured to be second distance from the person's body, wherein the second distance is greater than the first distance; and a deformable dielectric layer between the inner circumferential (or partially circumferential) array and the outer circumferential (or partially circumferential) array. In an example, pathways in the outer array can only partially overlap pathways in the inner array. In an example, pathways in the outer array can be located at different circumferential positions as pathways in the inner array.

In an example, this sensor can also include one or more components selected from the group consisting of: a plurality of electromagnetic energy emitters and receivers in electromagnetic communication with the strips; a data processor; a power source; a data transmitter; and a data receiver. In an example, changes in body joint configuration cause changes in the resistance, impedance, conductivity of the strips and these changes are, in turn, analyzed to measure and/or model the changes in body joint configuration. In an example, changes in body joint configuration cause changes in the capacitance of strips and these changes are, in turn, analyzed to measure and/or model the changes in body joint configuration.

In an example, the main body of a sleeve or cuff can be non-conductive. In an example, the material of the main body of a sleeve or cuff can serve as a dielectric layer between strips. In an example, a strip can comprise silicone and/or polydimethylsiloxane (PDMS) which has been impregnated and/or doped with electrically-conductive material such as aluminum, carbon, copper, gold, nickel, or silver particles or fibers. In an example, a strip can comprise electrically-conductive threads, yarns, wires, or fibers which are embedded within silicone and/or polydimethylsiloxane (PDMS). In an example, a strip can comprise a woven array of electrically-conductive threads, yarns, wires, or fibers. In an example, a strip can comprise an elastic electrically-conductive fabric and/or textile. Relevant example variations discussed elsewhere in this disclosure or in priority-linked disclosures can also be applied to the example shown in this figure, but are not repeated here in order to reduce narrative redundancy.

Figure 72:
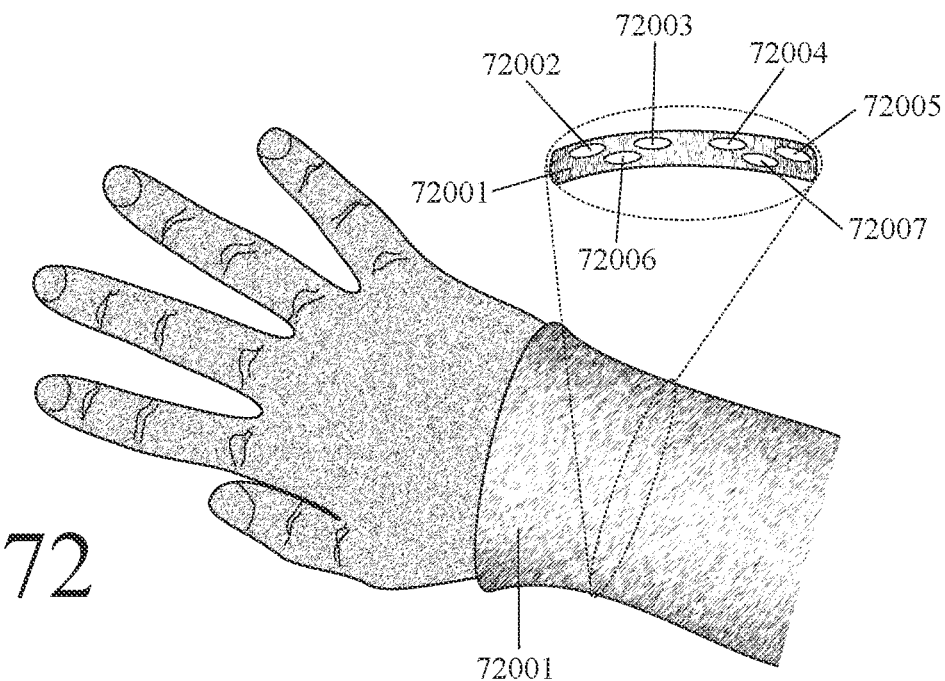
FIG. 72 shows a sleeve with clusters of EM strips for measuring changes in joint configuration.

FIG. 72 shows another sensor for measuring and/or modeling changes in body joint configuration. The left and lower-right portions of this figure show a top-down (dorsal) view of the sensor and the upper-right portion shows a dotted-line ellipse containing a cross-sectional view. This example is a flexible sleeve or cuff containing clusters of deformable elongate conductive strips.

The wearable deformable sensor in FIG. 72 comprises: a flexible dielectric sleeve or cuff (72001) which is configured to span a body joint, wherein this flexible sleeve or cuff further comprises a plurality of clusters of deformable elongate conductive strips (including 72002, 72003, 72004, 72005, 72006, and 72007). In an example, a cluster can comprise three deformable elongate conductive strips. In an example, a cluster can comprise two outer strips and one inner strip. In an example, a cluster can comprise one outer strip and two inner strips. In an example, the distance between strips in a cluster can be less than the distance between clusters. In an example, the distance between strips in a cluster can be less than half of the distance between clusters.

The wearable deformable sensor in FIG. 72 can also be described as comprising: a tubular portion of an article of clothing (72001) which is configured to span a body joint; and a plurality of clusters of flexible conductive pathways (including 72002, 72003, 72004, 72005, 72006, and 72007) which are distributed around the circumference of the tubular portion, wherein the pathways are separated by a deformable dielectric material. In an example, a cluster can comprise three deformable elongate conductive pathways. In an example, a cluster can comprise two outer pathways and one inner pathway. In an example, a cluster can comprise one outer pathway and two inner pathways. In an example, the distance between pathways in a cluster can be less than the distance between clusters. In an example, the distance between pathways in a cluster can be less than half of the distance between clusters.

In an example, this sensor can also include one or more components selected from the group consisting of: a plurality of electromagnetic energy emitters and receivers in electromagnetic communication with the strips or pathways; a data processor; a power source; a data transmitter; and a data receiver. In an example, changes in body joint configuration cause changes in the resistance, impedance, conductivity of the strips or pathways and these changes are, in turn, analyzed to measure and/or model the changes in body joint configuration. In an example, changes in body joint configuration cause changes in the capacitance of strips or pathways and these changes are, in turn, analyzed to measure and/or model the changes in body joint configuration.

In an example, a strip or pathway can comprise silicone and/or polydimethylsiloxane (PDMS) which has been impregnated and/or doped with electrically-conductive material such as aluminum, carbon, copper, gold, nickel, or silver particles or fibers. In an example, a strip or pathway can comprise electrically-conductive threads, yarns, wires, or fibers which are embedded within silicone and/or polydimethylsiloxane (PDMS). In an example, a strip or pathway can comprise a woven array of electrically-conductive threads, yarns, wires, or fibers. In an example, a strip or pathway can comprise an elastic electrically-conductive fabric and/or textile. Relevant example variations discussed elsewhere in this disclosure or in priority-linked disclosures can also be applied to the example shown in this figure, but are not repeated here in order to reduce narrative redundancy.

Figure 73:
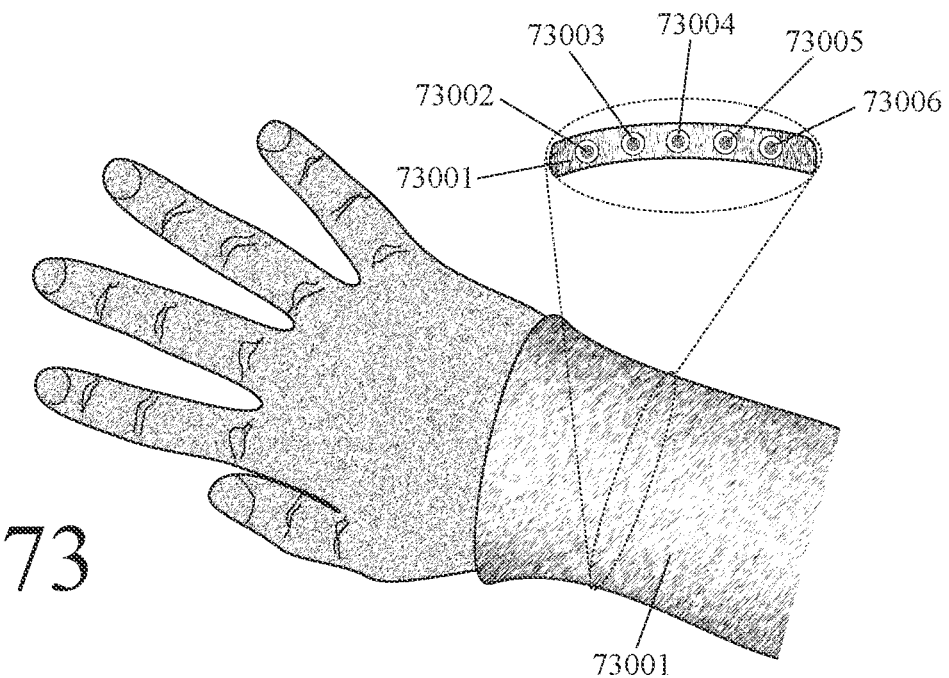
FIG. 73 shows a sleeve with a circumferential array of conductive-fluid-filled lumens for measuring changes in joint configuration.

FIG. 73 shows another sensor for measuring and/or modeling changes in body joint configuration. The left and lower-right portions of this figure show a top-down (dorsal) view of the sensor and the upper-right portion shows a dotted-line ellipse containing a cross-sectional view. This example is a flexible sleeve or cuff containing a circumferential (or partially-circumferential) array of deformable lumens filled with an electrically-conductive flowable substance.

The wearable deformable sensor in FIG. 73 comprises: a flexible sleeve or cuff (73001) which is configured to span a body joint, wherein this flexible sleeve or cuff further comprises a circumferential (or partially-circumferential) array of deformable non-conductive lumens (including 73002, 73003, 73004, 73005, and 73006) which are filled with an electromagnetically conductive flowable substance. The wearable deformable sensor in FIG. 73 can also be described as comprising: a tubular portion of an article of clothing (73001) which is configured to span a body joint; and a circumferential (or partially-circumferential) array of deformable non-conductive lumens (including 73002, 73003, 73004, 73005, and 73006) which are filled with an electromagnetically conductive flowable substance.

In an example, this sensor can also include one or more components selected from the group consisting of: electromagnetic energy emitters and receivers in electromagnetic communication with the flowable substance; a data processor; a power source; a data transmitter; and a data receiver. In an example, changes in body joint configuration can bend, compress, kink, or twist the lumens and change the configuration of the flowable substance inside the lumens. In an example, changes in body joint configuration cause changes in the resistance, impedance, conductivity of the flowable substance in the lumens and these changes are, in turn, analyzed to measure and/or model the changes in body joint configuration.

In an example, there can be between 4 and 12 lumens in a circumferential (or partially circumferential) array. In an example, a circumferential array of lumens can collectively span the entire circumference of the part of a person's body which contains a body joint. In an example, there can be twelve lumens, one centered on each clock hour position, which collectively span this circumference. In an example, there can be six lumens, one centered at every two-hour position (e.g. noon, 2 o'clock, 4 o'clock, 6 o'clock, 8 o'clock, and 10 o'clock). In an example, there can be four lumens, one centered at every three-hour position (e.g. noon, 3 o'clock, 6 o'clock, and 9 o'clock). In an example, there can be twelve lumens, one centered on every 30-degree interval (e.g. 0, 30, 60, 90, 120, 150, 180, 210, 240, 270, 300, and 330 degrees) around this circumference. In an example, there can be six lumens, one centered at every 60-degree interval (e.g. 0, 60, 120, 180, 240, and 300 degrees) around the circumference. In an example, there can be four lumens, one centered at every 90-degree interval (e.g. 0, 90, 180, and 270 degrees) around this circumference.

In an example, a partial circumferential array of lumens can collectively span only a portion of the circumference of the part of a person's body which contains a body joint. In an example, a partial circumferential array of lumens can collectively span between ⅛ and ¾ of the circumference of the part of a person's body which contains a body joint. In an example lumens can have longitudinal axes which are substantially parallel to the proximal-to-distal axis of the body joint which they span. In an example, lumens can be evenly-distributed (e.g. evenly-spaced) around the (partial) circumference of a body part. In an example, lumens can be unevenly-distributed (e.g. unevenly-spaced) around the (partial) circumference of a body part. In an example, lumens can be disproportionally clustered on the dorsal or ventral surface of a body part. Relevant example variations discussed elsewhere in this disclosure or in priority-linked disclosures can also be applied to the example shown in this figure, but are not repeated here in order to reduce narrative redundancy.

Figure 74:
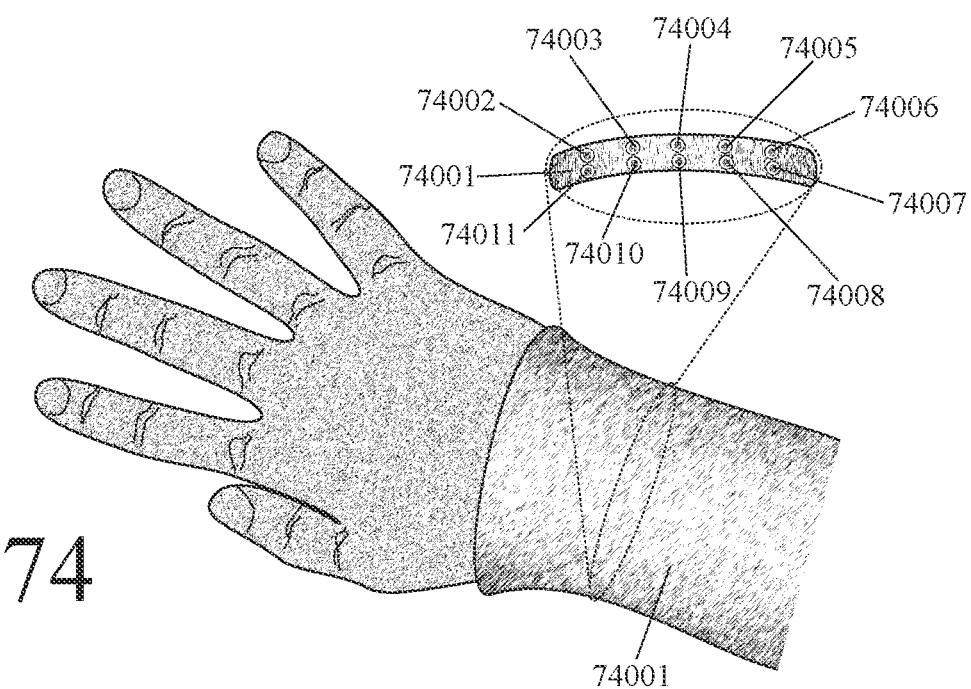
FIG. 74 shows a two-layer sleeve with of pairs of inner and outer conductive-fluid-filled lumens for measuring changes in joint configuration.

FIG. 74 shows another sensor for measuring and/or modeling changes in body joint configuration. The left and lower-right portions of this figure show a top-down (dorsal) view of the sensor and the upper-right portion shows a dotted-line ellipse containing a cross-sectional view. This example is a flexible sleeve or cuff containing inner and outer circumferential (or partially-circumferential) arrays of deformable lumens filled with an electrically-conductive flowable substance.

The wearable deformable sensor in FIG. 74 comprises: a flexible sleeve or cuff (74001) which is configured to span a body joint, wherein flexible sleeve or cuff further comprises (A) an inner circumferential (or partially-circumferential) array of deformable non-conductive lumens (including 74007, 74008, 74009, 74010, and 74011) which are filled with an electromagnetically conductive flowable substance and configured to be a first distance from the person's body and (B) an outer circumferential (or partially-circumferential) array of deformable non-conductive lumens (including 74002, 74003, 74004, 74005, and 74006) which are filled with an electromagnetically conductive flowable substance and configured to be a second distance from the person's body, wherein the second distance is greater than the first distance.

The wearable deformable sensor in FIG. 74 can also be described as comprising: a tubular portion of an article of clothing (74001) which is configured to span a body joint; an inner circumferential (or partially-circumferential) array of deformable non-conductive lumens (including 74007, 74008, 74009, 74010, and 74011) which are filled with an electromagnetically conductive flowable substance and configured to be a first distance from the person's body; and an outer circumferential (or partially-circumferential) array of deformable non-conductive lumens (including 74002, 74003, 74004, 74005, and 74006) which are filled with an electromagnetically conductive flowable substance and configured to be a second distance from the person's body, wherein the second distance is greater than the first distance.

In an example, this sensor can also include one or more components selected from the group consisting of: electromagnetic energy emitters and receivers in electromagnetic communication with the flowable substance; a data processor; a power source; a data transmitter; and a data receiver. In an example, changes in body joint configuration can bend, compress, kink, or twist the lumens and change the configuration of the flowable substance inside the lumens. In an example, changes in body joint configuration cause changes in the resistance, impedance, and/or conductivity of the flowable substance in the lumens and these changes are, in turn, analyzed to measure and/or model the changes in body joint configuration. In an example, lumens in the outer array can be located at the same circumferential positions as lumens in the inner array. Relevant example variations discussed elsewhere in this disclosure or in priority-linked disclosures can also be applied to the example shown in this figure, but are not repeated here in order to reduce narrative redundancy.

Figure 75:
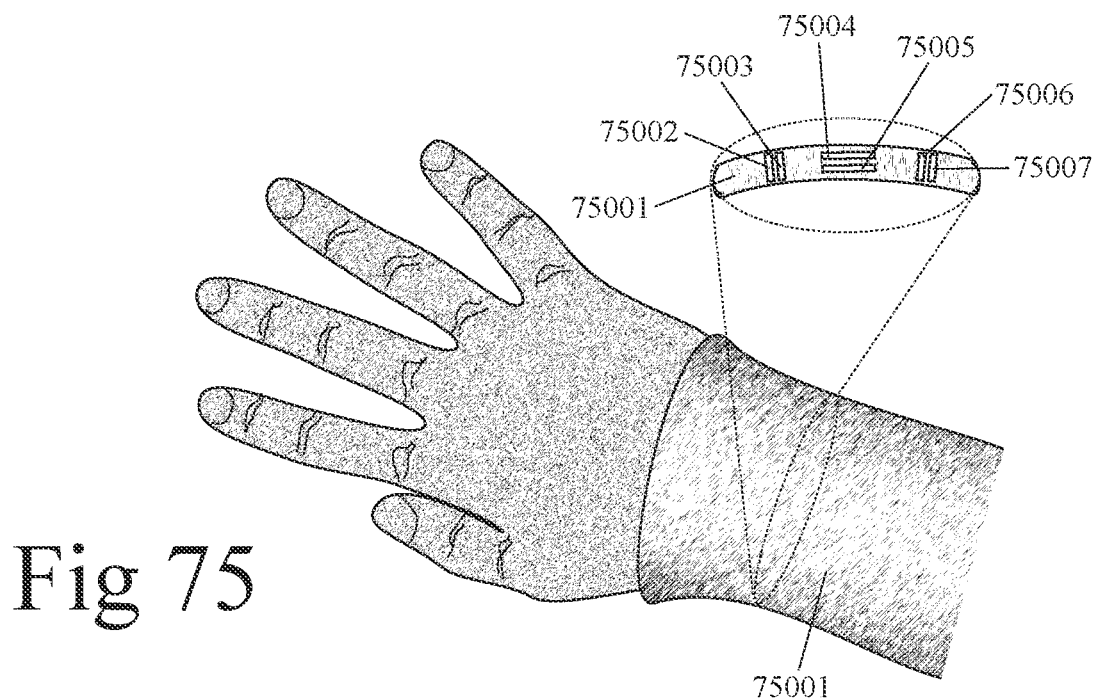
FIG. 75 shows a sleeve with clusters of EM strips with inter-cluster differences in cross-sectional orientation for measuring changes in joint configuration.

FIG. 75 shows another sensor for measuring and/or modeling changes in body joint configuration. The left and lower-right portions of this figure show a top-down (dorsal) view of the sensor and the upper-right portion shows a dotted-line ellipse containing a cross-sectional view. This example is a flexible tubular portion (such as a sleeve or cuff) of an article of clothing which includes one or more clusters of conductive pathways (or strips) with a first cross-sectional orientation and one or more clusters of conductive pathways (or strips) with a second cross-sectional orientation.

The wearable deformable sensor in FIG. 75 comprises: a flexible tubular portion (75001) of an article of clothing which is configured to span a body joint; a first cluster of electrically-conductive pathways (75002 and 75003, or 75006 and 75007) with cross-sections with a first orientation; a second cluster of electrically-conductive pathways (75004 and 75005) with cross-sections with a second orientation, wherein the second orientation is different than the first orientation. In an example, this sensor can also include one or more components selected from the group consisting of: electromagnetic energy emitters and receivers in electromagnetic communication with the flowable substance; a data processor; a power source; a data transmitter; and a data receiver. In an example, changes in body joint configuration cause changes in the resistance, impedance, conductivity, and/or capacitance of the pathways and these changes are, in turn, analyzed to measure and/or model the changes in body joint configuration In an example, the cross-sectional orientation of pathways in a first cluster can be substantially perpendicular to the closest surface of a person's body and the cross-sectional orientation of pathways in a second cluster can be substantially parallel to the closest surface of a person's body. In an example, the second orientation can be perpendicular to the first orientation. In an example, the second orientation can differ from the first orientation by a number of degrees in the range of 60 to 120 degrees. In an example, there can be two pathways in a cluster. In an example, there can be three or more pathways in a cluster. In an example, pathways within a cluster can be parallel to each other. In an example, the distance between clusters can be at least 50% more than the distance between pathways within a cluster. In an example, the distance between clusters can be at least twice the distance between pathways within a cluster. In an example, pathways can be separated by a layer of deformable dielectric material. Relevant example variations discussed elsewhere in this disclosure or in priority-linked disclosures can also be applied to the example shown in this figure, but are not repeated here in order to reduce narrative redundancy.

Figure 76:
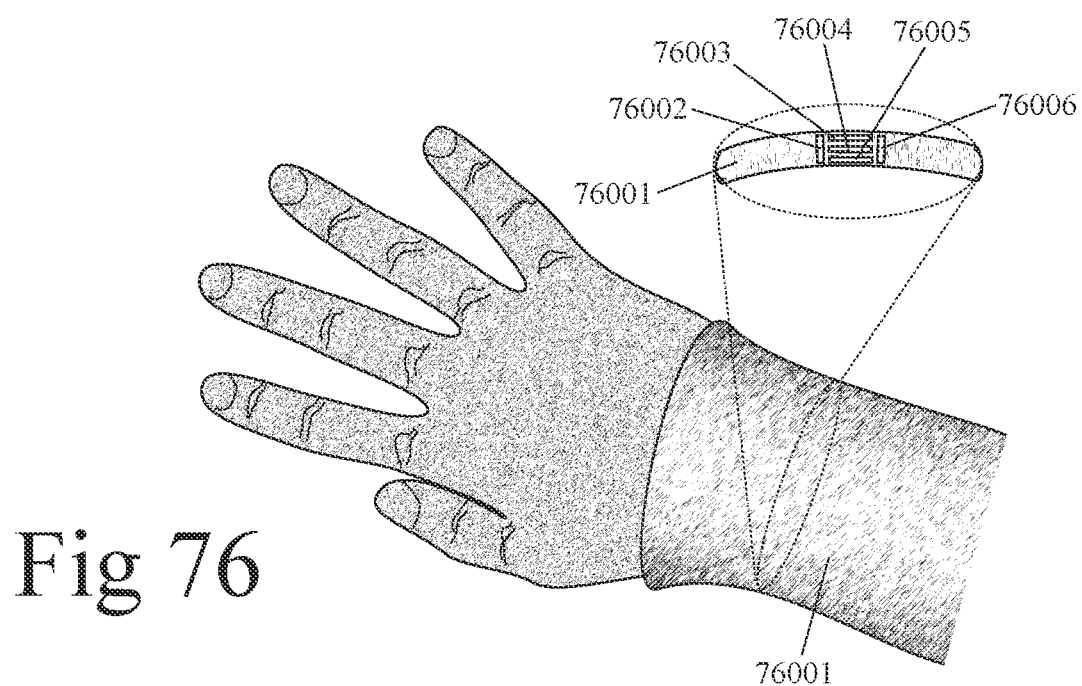
FIG. 76 shows a sleeve with clusters of EM strips with intra-cluster differences in cross-sectional orientation for measuring changes in joint configuration.

FIG. 76 shows another sensor for measuring and/or modeling changes in body joint configuration. The left and lower-right portions of this figure show a top-down (dorsal) view of the sensor and the upper-right portion shows a dotted-line ellipse containing a cross-sectional view. This example is a flexible tubular portion (such as a sleeve or cuff) of an article of clothing which includes one or clusters of a plurality of conductive pathways with perpendicular cross-sectional orientations.

The wearable deformable sensor in FIG. 76 comprises: a flexible tubular portion (76001) of an article of clothing which is configured to span a body joint; one or more clusters of electrically-conductive pathways, wherein a cluster further comprises—(A) a first set of electrically-conductive pathways (76002 and 76006) within the cluster with a first cross-sectional orientation and (B) a second set of electrically-conductive pathways (76003, 76004, and 76005) within the cluster with a second cross-sectional orientation, wherein the second orientation is different than the first orientation. In an example, this sensor can also include one or more components selected from the group consisting of: electromagnetic energy emitters and receivers in electromagnetic communication with the flowable substance; a data processor; a power source; a data transmitter; and a data receiver. In an example, changes in body joint configuration cause changes in the resistance, impedance, conductivity, and/or capacitance of the pathways and these changes are, in turn, analyzed to measure and/or model the changes in body joint configuration In an example, the first orientation can be substantially perpendicular to the closest surface of a person's body and the second orientation can be substantially parallel to the closest surface of a person's body. In an example, the second orientation can be perpendicular to the first orientation. In an example, the second orientation can differ from the first orientation by a number of degrees in the range of 60 to 120 degrees. In an example, there can be two or three pathways in a set. In an example, there can be four or more pathways in a set. In an example, there can be two or three pathways in a cluster. In an example, there can be four or more pathways in a cluster. In an example, the distance between clusters can be at least 50% more than the distance between pathways within a cluster. In an example, the distance between clusters can be at least twice the distance between pathways within a cluster. In an example, pathways can be separated by a layer of deformable dielectric material. Relevant example variations discussed elsewhere in this disclosure or in priority-linked disclosures can also be applied to the example shown in this figure, but are not repeated here in order to reduce narrative redundancy.

Figure 77:
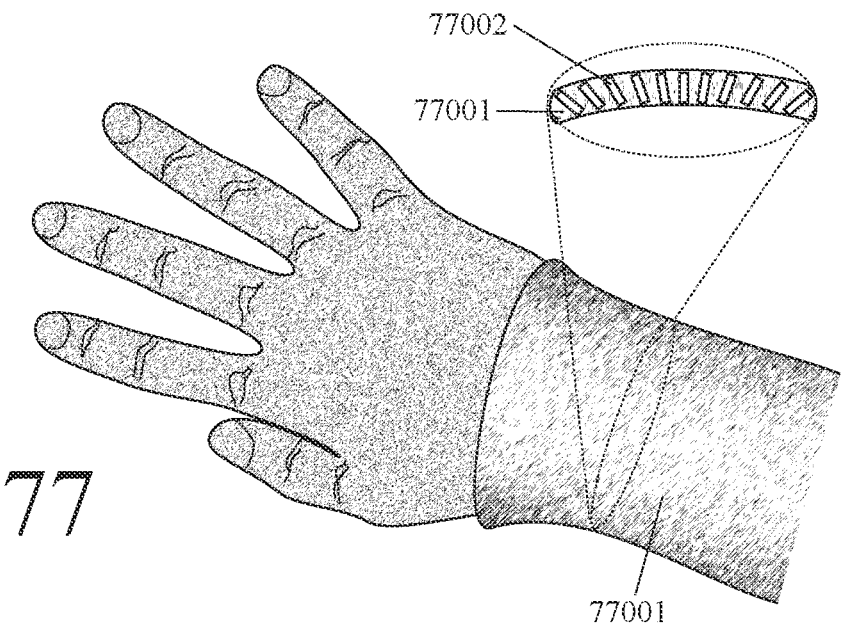
FIG. 77 shows a sleeve with EM strips with spoke-aligned cross-sections for measuring changes in joint configuration.

FIG. 77 shows another sensor for measuring and/or modeling changes in body joint configuration. The left and lower-right portions of this figure show a top-down (dorsal) view of the sensor and the upper-right portion shows a dotted-line ellipse containing a cross-sectional view. This example is a flexible tubular portion (such as a sleeve or cuff) of an article of clothing which includes a circumferential (or partially-circumferential) array of electrically-conductive pathways with different cross-sectional orientations.

The wearable deformable sensor in FIG. 77 comprises: a flexible tubular portion (77001) of an article of clothing which is configured to span a body joint; a circumferential (or partially-circumferential) array of electrically-conductive flexible pathways (including 77002) distributed around the circumference (or a portion of the circumference) of the flexible tubular portion, wherein a first set of one or more electrically-conductive flexible pathways in the circumferential (or partially circumferential) array have cross-sections with a first orientation, wherein a second set of one or more electrically-conductive flexible pathways in the circumferential (or partially circumferential) array have cross-sections with a second orientation, wherein a third set of one or more electrically-conductive flexible pathways in the circumferential (or partially circumferential) array have cross-sections with a third orientation, wherein the first orientation and the second orientation differ by at least 20 degrees, and wherein the first orientation and the third orientation differ by at least 20 degrees.

The wearable deformable sensor in FIG. 77 can also be described as comprising: a flexible tubular portion (77001) of an article of clothing which is configured to span a body joint; a circumferential (or partially-circumferential) array of electrically-conductive flexible pathways (including 77002) distributed around the circumference (or a portion of the circumference) of the flexible tubular portion, wherein each electrically-conductive flexible pathway in the circumferential (or partially circumferential) array has an elongated cross-sectional perimeter, wherein the cross-sectional axis of a pathway spans the cross-sectional perimeter of the pathway in its elongated direction, and wherein different pathways in the circumferential (or partially-circumferential) array of flexible pathways have cross-sectional axes with different orientations. In an example, the orientations of adjacent pathways can differ by at least 10 degrees. In an example, the orientations of non-adjacent pathways can differ by at least 80 degrees.

The wearable deformable sensor in FIG. 77 can also be described as comprising: a flexible tubular portion (77001) of an article of clothing which is configured to span a body joint; a circumferential (or partially-circumferential) array of electrically-conductive flexible pathways (including 77002) distributed around the circumference (or a portion of the circumference) of the flexible tubular portion, wherein each flexible pathway has a cross-sectional orientation which is configured to be substantially perpendicular to the closest surface of the person's body.

With the addition of a data processor and power source, the example shown in FIG. 77 can also be described as a wearable deformable sensor for human motion capture comprising: a flexible tubular portion of an article of clothing which is configured to span a body joint in a proximal-to-distal manner; and a partially-circumferential array of electrically-conductive flexible pathways distributed around part of the circumference of the flexible tubular portion, wherein a first set of one or more electrically-conductive flexible pathways in the partially-circumferential array have aspherical cross-sectional perimeters with a first orientation, wherein a second set of one or more electrically-conductive flexible pathways in the partially-circumferential array have aspherical cross-sectional perimeters with a second orientation, wherein a third set of one or more electrically-conductive flexible pathways in the partially-circumferential array have aspherical cross-sectional perimeters with a third orientation, wherein the first orientation and the second orientation differ by at least 20 degrees, wherein the first orientation and the third orientation differ by at least 20 degrees, wherein changes in body joint configuration cause deformations of the electrically-conductive flexible pathways, wherein the deformations cause changes in the transmission of electromagnetic energy from the electromagnetic energy emitters to the electromagnetic energy receivers, and wherein the changes in the transmission of electromagnetic energy are analyzed in order to measure and/or model changes in body joint configuration; a data processor; and a power source.

In an example, this sensor can also include one or more components selected from the group consisting of: electromagnetic energy emitters and receivers in electromagnetic communication with the flowable substance; a data processor; a power source; a data transmitter; and a data receiver. In an example, changes in body joint configuration cause changes in the resistance, impedance, conductivity, and/or capacitance of the pathways and these changes are, in turn, analyzed to measure and/or model the changes in body joint configuration. In an example, pathways can be separated by a layer of deformable dielectric material. Relevant example variations discussed elsewhere in this disclosure or in priority-linked disclosures can also be applied to the example shown in this figure, but are not repeated here in order to reduce narrative redundancy.

Figure 78:
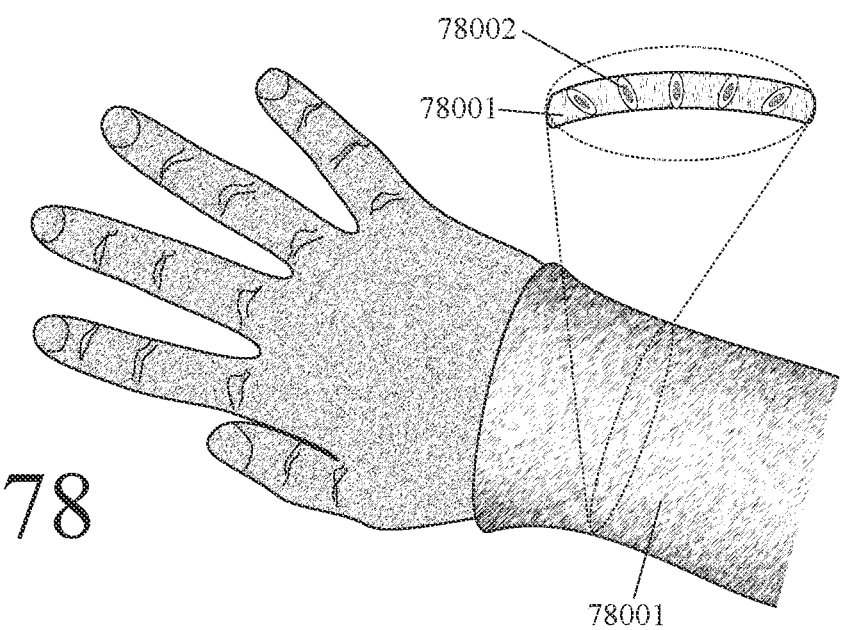
FIG. 78 shows a sleeve with conductive-fluid-filled lumens with spoke-aligned cross-sections for measuring changes in joint configuration.

FIG. 78 shows another sensor for measuring and/or modeling changes in body joint configuration. The left and lower-right portions of this figure show a top-down (dorsal) view of the sensor and the upper-right portion shows a dotted-line ellipse containing a cross-sectional view. This example is a flexible tubular portion (such as a sleeve or cuff) of an article of clothing which includes a circumferential (or partially-circumferential) array of conductive-fluid-containing lumens with different cross-sectional orientations.

The wearable deformable sensor in FIG. 78 comprises: a flexible tubular portion (78001) of an article of clothing which is configured to span a body joint; a circumferential (or partially-circumferential) array of conductive-fluid-filled lumens (including 78002) distributed around the circumference (or a portion of the circumference) of the flexible tubular portion, wherein a first set of one or more conductive-fluid-filled lumens in the circumferential (or partially circumferential) array have cross-sections with a first orientation, wherein a second set of one or more conductive-fluid-filled lumens in the circumferential (or partially circumferential) array have cross-sections with a second orientation, wherein a third set of one or more conductive-fluid-filled lumens in the circumferential (or partially circumferential) array have cross-sections with a third orientation, wherein the first orientation and the second orientation differ by at least 20 degrees, and wherein the first orientation and the third orientation differ by at least 20 degrees.

The wearable deformable sensor in FIG. 78 can also be described as comprising: a flexible tubular portion (78001) of an article of clothing which is configured to span a body joint; a circumferential (or partially-circumferential) array of conductive-fluid-filled lumens (including 78002) distributed around the circumference (or a portion of the circumference) of the flexible tubular portion, wherein each conductive-fluid-filled lumen in the circumferential (or partially circumferential) array has an elongated cross-sectional perimeter, wherein the cross-sectional axis of a lumen spans the cross-sectional perimeter of the lumen in its elongated direction, and wherein different lumens in the circumferential (or partially-circumferential) array of flexible lumens have cross-sectional axes with different orientations. In an example, the orientations of adjacent lumens can differ by at least 10 degrees. In an example, the orientations of non-adjacent lumens can differ by at least 80 degrees.

The wearable deformable sensor in FIG. 78 can also be described as comprising: a flexible tubular portion (78001) of an article of clothing which is configured to span a body joint; a circumferential (or partially-circumferential) array of conductive-fluid-filled lumens (including 78002) distributed around the circumference (or a portion of the circumference) of the flexible tubular portion, wherein each flexible lumen has a cross-sectional orientation which is configured to be substantially perpendicular to the closest surface of the person's body.

In an example, this sensor can also include one or more components selected from the group consisting of: electromagnetic energy emitters and receivers in electromagnetic communication with the flowable substance; a data processor; a power source; a data transmitter; and a data receiver. In an example, changes in body joint configuration cause changes in the resistance, impedance, conductivity, and/or capacitance of the conductive-fluid-filled lumens and these changes are, in turn, analyzed to measure and/or model the changes in body joint configuration. In an example, lumens can be separated by a layer of deformable dielectric material. Relevant example variations discussed elsewhere in this disclosure or in priority-linked disclosures can also be applied to the example shown in this figure, but are not repeated here in order to reduce narrative redundancy.

Figure 79:
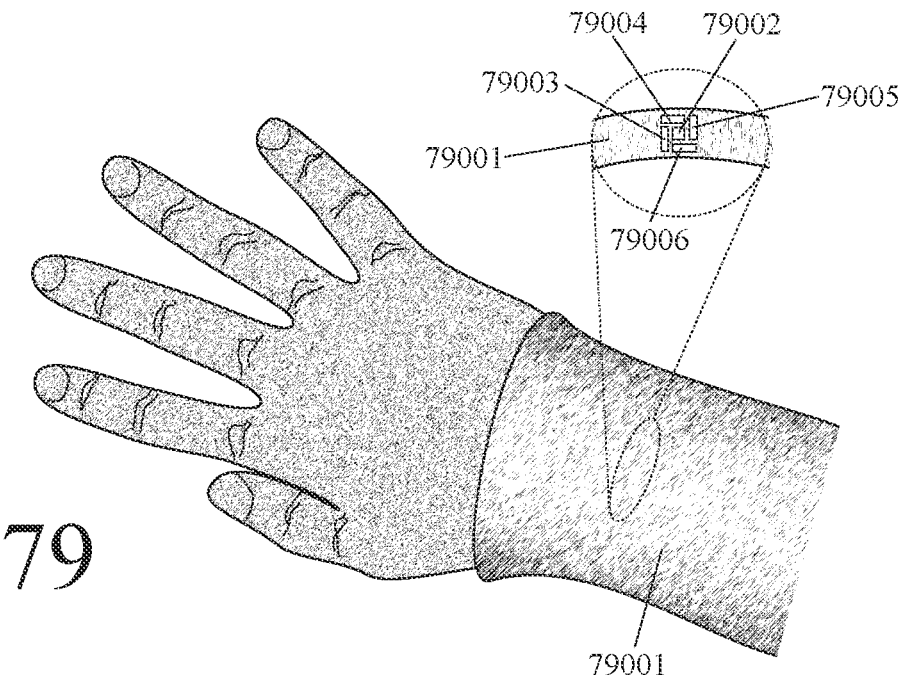
FIG. 79 shows a sleeve with a quadrilateral cluster of EM pathways for measuring changes in joint configuration.

FIG. 79 shows another sensor for measuring and/or modeling changes in body joint configuration. The left and lower-right portions of this figure show a top-down (dorsal) view of the sensor and the upper-right portion shows a dotted-line ellipse containing a cross-sectional view. This example is a flexible tubular portion (such as a sleeve or cuff) of an article of clothing which includes at least one circular or polygonal cluster of conductive pathways, wherein this cluster further comprises four or more peripheral conductive pathways around a core conductive pathway.

The wearable deformable sensor in FIG. 79 comprises: a flexible tubular portion (79001) of an article of clothing which is configured to span a body joint, wherein this tubular portion further comprises at least one circular or polygonal cluster of electrically-conductive pathways, and wherein a circular or polygonal cluster of electrically-conductive pathways further comprises a core electrically-conductive pathway (79002) and at least four peripheral electrically-conductive pathways (79003, 79004, 79005, and 79006) around the core electrically-conductive pathway. In an example, this sensor can also include one or more components selected from the group consisting of: electromagnetic energy emitters and receivers in electromagnetic communication with the flowable substance; a data processor; a power source; a data transmitter; and a data receiver. In an example, changes in body joint configuration cause changes in the resistance, impedance, conductivity, and/or capacitance of the pathways and these changes are, in turn, analyzed to measure and/or model the changes in body joint configuration In an example, the peripheral conductive pathways can be evenly distributed around the circumference of the core conductive pathway. In an example, the peripheral conductive pathways can comprise a first set of two parallel pathways with a first orientation and a second set of parallel pathways with a second orientation, wherein the second orientation is perpendicular to the first orientation. In an example, changes in the capacitances between the core conductive pathway and each of the peripheral conductive pathways can be analyzed to measure and/or model changes in body joint configuration. In an example, there can be a plurality of circular or polygonal clusters at different locations around the circumference of the flexible tubular portion of an article of clothing. In an example, the distance between clusters can be at least 50% more than the distance between pathways within a cluster. In an example, the distance between clusters can be at least twice the distance between pathways within a cluster. In an example, pathways can be separated by a layer of deformable dielectric material. Relevant example variations discussed elsewhere in this disclosure or in priority-linked disclosures can also be applied to the example shown in this figure, but are not repeated here in order to reduce narrative redundancy.

Figure 80:
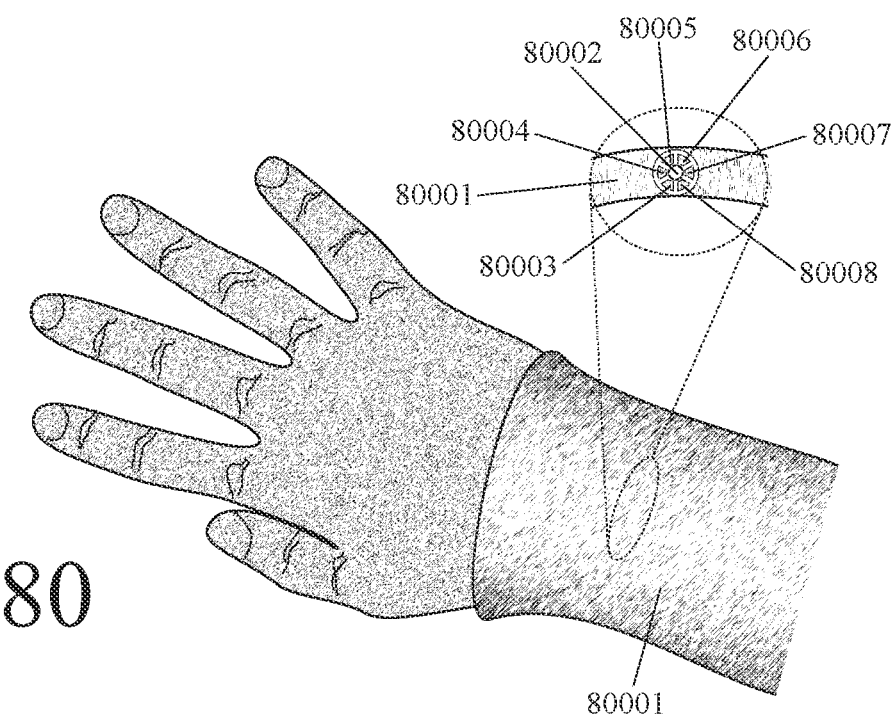
FIG. 80 shows a sleeve with a "wagon-wheel" cluster of EM pathways for measuring changes in joint configuration.

FIG. 80 shows another sensor for measuring and/or modeling changes in body joint configuration. The left and lower-right portions of this figure show a top-down (dorsal) view of the sensor and the upper-right portion shows a dotted-line ellipse containing a cross-sectional view. This example is a flexible tubular portion (such as a sleeve or cuff) of an article of clothing which includes at least one wagon-wheel cluster of conductive pathways with a dielectric core.

The wearable deformable sensor in FIG. 80 comprises: a flexible tubular portion (80001) of an article of clothing which is configured to span a body joint, wherein this tubular portion further comprises at least one wagon-wheel cluster of electrically-conductive pathways, and wherein a wagon-wheel cluster of electrically-conductive pathways comprises a ring of triangular or pie-slice-shaped electrically-conductive pathways (80003, 80004, 80005, 80006, 80007, and 80008) whose vertexes point toward a common center. This example also includes a dielectric core (80002) in the middle of the ring of triangular or pie-slice-shaped electrically-conductive pathways. In an example, this sensor can also include one or more components selected from the group consisting of: electromagnetic energy emitters and receivers in electromagnetic communication with the flowable substance; a data processor; a power source; a data transmitter; and a data receiver. In an example, pathways can be separated by a layer of deformable dielectric material. In an example, changes in body joint configuration cause changes in the resistance, impedance, conductivity, and/or capacitance of the pathways and these changes are, in turn, analyzed to measure and/or model the changes in body joint configuration.

The wearable deformable sensor in FIG. 80 can also be described as comprising: a flexible tubular portion (80001) of an article of clothing which is configured to span a body joint, wherein this tubular portion further comprises at least one wagon-wheel cluster of conductive-fluid-filled lumens, and wherein a wagon-wheel cluster of conductive-fluid-filled lumens comprises a ring of triangular or pie-slice-shaped conductive-fluid-filled lumens (80003, 80004, 80005, 80006, 80007, and 80008) whose vertexes point toward a common center. This example also includes a dielectric core (80002) in the middle of the ring of triangular or pie-slice-shaped conductive-fluid-filled lumens. In an example, this sensor can also include one or more components selected from the group consisting of: electromagnetic energy emitters and receivers in electromagnetic communication with the flowable substance; a data processor; a power source; a data transmitter; and a data receiver. In an example, pathways can be separated by a layer of deformable dielectric material. In an example, changes in body joint configuration cause changes in the resistance, impedance, conductivity, and/or capacitance of the conductive-fluid-filled lumens and these changes are, in turn, analyzed to measure and/or model the changes in body joint configuration. Relevant example variations discussed elsewhere in this disclosure or in priority-linked disclosures can also be applied to the example shown in this figure, but are not repeated here in order to reduce narrative redundancy.

Figure 81:
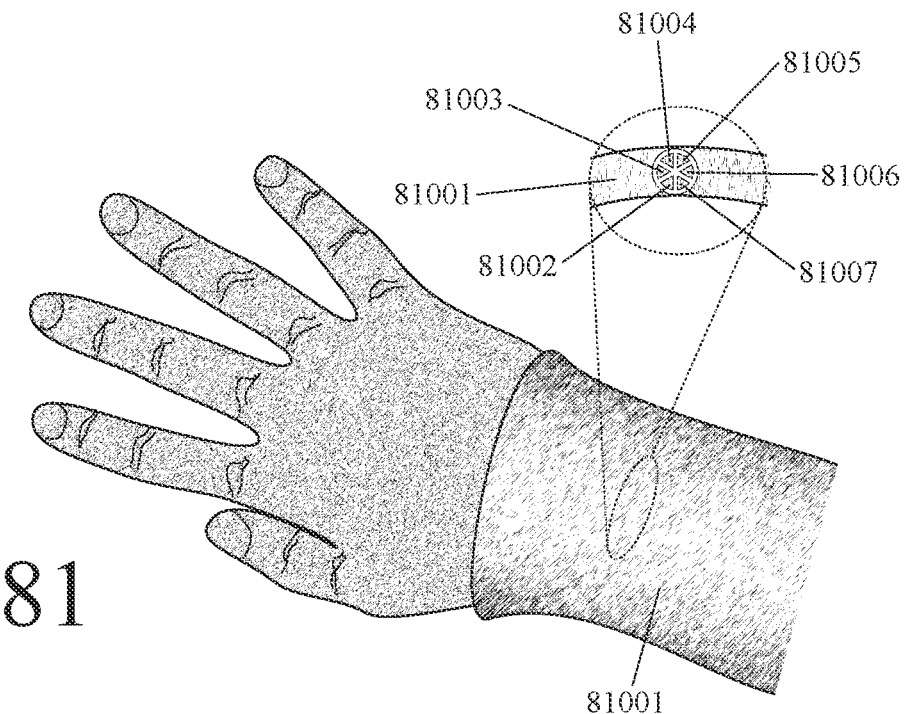
FIG. 81 shows a sleeve with a "pieces-of-pie" (or "citrus cross section") cluster of EM pathways for measuring changes in joint configuration.

FIG. 81 shows another sensor for measuring and/or modeling changes in body joint configuration. The left and lower-right portions of this figure show a top-down (dorsal) view of the sensor and the upper-right portion shows a dotted-line ellipse containing a cross-sectional view. This example is a flexible tubular portion (such as a sleeve or cuff) of an article of clothing which includes at least one wagon-wheel cluster of conductive pathways without a dielectric core.

The wearable deformable sensor in FIG. 81 comprises: a flexible tubular portion (81001) of an article of clothing which is configured to span a body joint, wherein this tubular portion further comprises at least one wagon-wheel cluster of electrically-conductive pathways, and wherein a wagon-wheel cluster of electrically-conductive pathways comprises a ring of triangular or pie-slice-shaped electrically-conductive pathways (81002, 81003, 81004, 81005, 81006, and 81007) whose vertexes point toward a common center. In an example, this sensor can also include one or more components selected from the group consisting of: electromagnetic energy emitters and receivers in electromagnetic communication with the flowable substance; a data processor; a power source; a data transmitter; and a data receiver. In an example, pathways can be separated by a layer of deformable dielectric material. In an example, changes in body joint configuration cause changes in the resistance, impedance, conductivity, and/or capacitance of the pathways and these changes are, in turn, analyzed to measure and/or model the changes in body joint configuration.

The wearable deformable sensor in FIG. 81 can also be described as comprising: a flexible tubular portion (81001) of an article of clothing which is configured to span a body joint, wherein this tubular portion further comprises at least one wagon-wheel cluster of conductive-fluid-filled lumens, and wherein a wagon-wheel cluster of conductive-fluid-filled lumens comprises a ring of triangular or pie-slice-shaped conductive-fluid-filled lumens (81002, 81003, 81004, 81005, 81006, and 81007) whose vertexes point toward a common center. In an example, this sensor can also include one or more components selected from the group consisting of: electromagnetic energy emitters and receivers in electromagnetic communication with the flowable substance; a data processor; a power source; a data transmitter; and a data receiver. In an example, pathways can be separated by a layer of deformable dielectric material. In an example, changes in body joint configuration cause changes in the resistance, impedance, conductivity, and/or capacitance of the conductive-fluid-filled lumens and these changes are, in turn, analyzed to measure and/or model the changes in body joint configuration. Relevant example variations discussed elsewhere in this disclosure or in priority-linked disclosures can also be applied to the example shown in this figure, but are not repeated here in order to reduce narrative redundancy.

Figure 82:
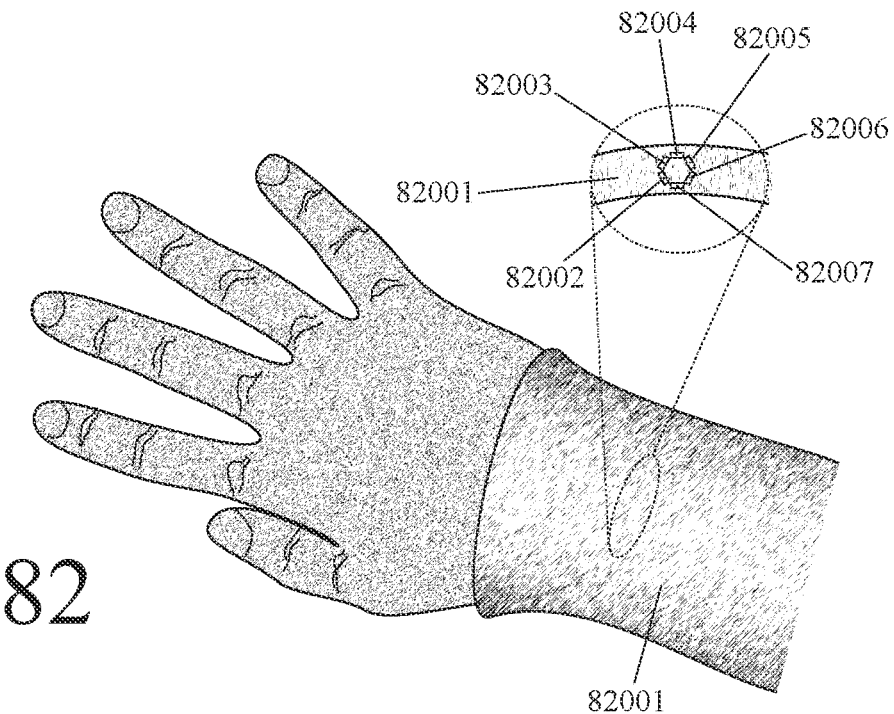
FIG. 82 shows a sleeve with a polygonal cluster of EM pathways for measuring changes in joint configuration.

FIG. 82 shows another sensor for measuring and/or modeling changes in body joint configuration. The left and lower-right portions of this figure show a top-down (dorsal) view of the sensor and the upper-right portion shows a dotted-line ellipse containing a cross-sectional view. This example is a flexible tubular portion (such as a sleeve or cuff) of an article of clothing with at least one polygonal cluster of conductive pathways.

The wearable deformable sensor in FIG. 82 comprises: a flexible tubular portion (82001) of an article of clothing which is configured to span a body joint, wherein this tubular portion further comprises at least one polygonal cluster of deformable electrically-conductive pathways (82002, 82003, 82004, 82005, 82006, and 82007). The wearable deformable sensor in FIG. 82 can also be described as comprising: a flexible tubular portion (82001) of an article of clothing which is configured to span a body joint, wherein this tubular portion further comprises at least one polygonal ring of deformable electrically-conductive pathways (82002, 82003, 82004, 82005, 82006, and 82007).

The wearable deformable sensor in FIG. 82 can also be described as comprising: a cuff or sleeve (82001) which is configured to span a body joint and which further comprises at least one polygonal ring of deformable electrically-conductive strips (82002, 82003, 82004, 82005, 82006, and 82007). The wearable deformable sensor in FIG. 82 can also be described as comprising: a flexible tubular portion (82001) of an article of clothing which is configured to span a body joint; and a cluster of elongate deformable electrically-conductive pathways (82002, 82003, 82004, 82005, 82006, and 82007) whose cross-sections form a polygonal ring.

In an example, this sensor can also include one or more components selected from the group consisting of: electromagnetic energy emitters and receivers in electromagnetic communication with the flowable substance; a data processor; a power source; a data transmitter; and a data receiver. In an example, pathways can be separated by a layer of deformable dielectric material. In an example, changes in body joint configuration cause changes in the resistance, impedance, conductivity, and/or capacitance of the pathways (or strips) and these changes are, in turn, analyzed to measure and/or model the changes in body joint configuration.

In an example a polygonal cluster or ring of deformable electrically-conductive pathways can comprise six deformable electrically-conductive pathways whose cross-sections form a hexagon. In an example a polygonal cluster or ring of deformable electrically-conductive pathways can comprise six deformable electrically-conductive pathways whose cross-sections form an octagon. In an example a polygonal cluster or ring of deformable electrically-conductive pathways can comprise six deformable electrically-conductive pathways whose cross-sections form a square or triangle. Relevant example variations discussed elsewhere in this disclosure or in priority-linked disclosures can also be applied to the example shown in this figure, but are not repeated here in order to reduce narrative redundancy.

Figure 83:
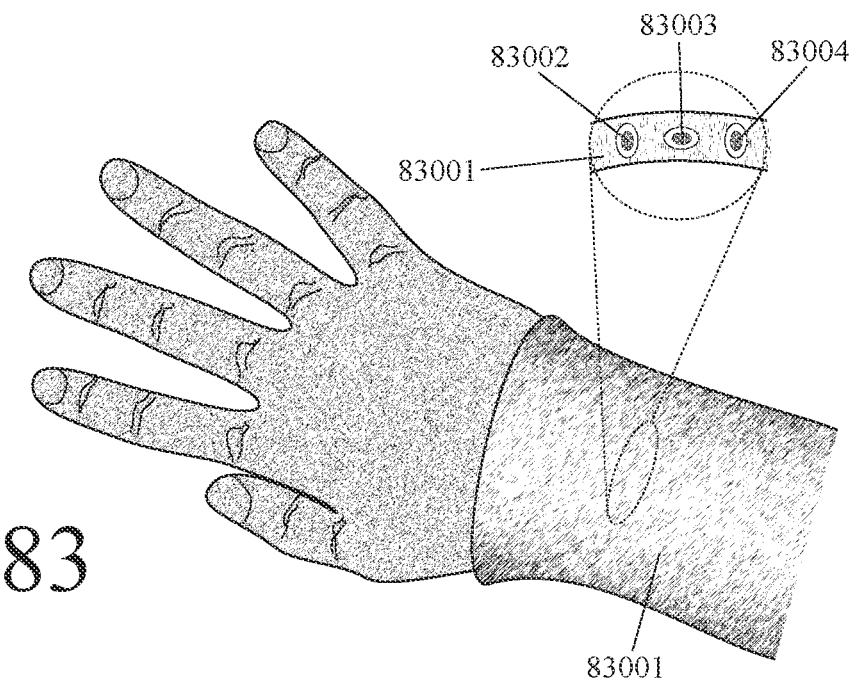
FIG. 83 shows a sleeve with conductive-fluid-filled lumens with alternating cross-sectional orientations for measuring changes in joint configuration.

FIG. 83 shows another sensor for measuring and/or modeling changes in body joint configuration. The left and lower-right portions of this figure show a top-down (dorsal) view of the sensor and the upper-right portion shows a dotted-line ellipse containing a cross-sectional view. This example is a flexible tubular portion (such as a sleeve or cuff) of an article of clothing which further comprises a circumferential (or partially-circumferential) array of conductive-fluid-filled lumens which have elongate cross-sections with different orientations.

The wearable deformable sensor in FIG. 83 comprises: a flexible tubular portion (83001) of an article of clothing which is configured to span a body joint; a first set of lumens filled with a conductive flowable substance, wherein lumens in this first set have elongate cross-sectional perimeters with a first orientation; and a second set of lumens filled with a conductive flowable substance, wherein lumens in this second set have elongate cross-sectional perimeters with a second orientation, and wherein the second orientation differs from the first orientation by at least 20 degrees. In an example, this sensor can also include one or more components selected from the group consisting of: electromagnetic energy emitters and receivers in electromagnetic communication with the flowable substance; a data processor; a power source; a data transmitter; and a data receiver. In an example, changes in body joint configuration cause changes in the resistance, impedance, conductivity, and/or capacitance of the lumens (and/or the flowable substance within them) and these changes are, in turn, analyzed to measure and/or model the changes in body joint configuration. Relevant example variations discussed elsewhere in this disclosure or in priority-linked disclosures can also be applied to the example shown in this figure, but are not repeated here in order to reduce narrative redundancy.

FIG. 84 shows another sensor for measuring and/or modeling changes in body joint configuration. The left and lower-right portions of this figure show a top-down (dorsal) view of the sensor and the upper-right portion shows a dotted-line ellipse containing a cross-sectional view. This example is a flexible tubular portion (such as a sleeve or cuff) of an article of clothing with non-aligned inner and outer circumferential (or partially-circumferential) arrays of flexible conductive pathways separated by deformable dielectric material.

The wearable deformable sensor in FIG. 84 comprises: a flexible tubular portion (84001) of an article of clothing which is configured to span a body joint; an inner circumferential (or partially-circumferential) array of flexible elongate conductive pathways (including 84002, 84004, 84006, and 84008) whose cross-sections are centered on a first set of clock or compass coordinates around the circumference (or partial circumference) of the flexible tubular portion; and an outer circumferential (or partially-circumferential) array of flexible elongate conductive pathways (including 84003, 84005, and 84007) whose cross-sections are centered on a second set of clock or compass coordinates around the circumference (or partial circumference) of the flexible tubular portion, wherein the second set is different than the first set.

The wearable deformable sensor in FIG. 84 can also be described as comprising: a sleeve or cuff (84001) which is configured to span a body joint; an inner circumferential (or partially-circumferential) array of flexible elongate conductive strips (including 84002, 84004, 84006, and 84008) whose cross-sections are centered on a first set of clock or compass coordinates around the circumference (or partial circumference) of the flexible tubular portion; and an outer circumferential (or partially-circumferential) array of flexible elongate conductive strips (including 84003, 84005, and 84007) whose cross-sections are centered on a second set of clock or compass coordinates around the circumference (or partial circumference) of the flexible tubular portion, wherein the second set is different than the first set.

In an example, this sensor can also include one or more components selected from the group consisting of: electromagnetic energy emitters and receivers in electromagnetic communication with the flowable substance; a data processor; a power source; a data transmitter; and a data receiver. In an example, changes in body joint configuration cause changes in the resistance, impedance, conductivity, and/or capacitance of the pathways (or strips) and these changes are, in turn, analyzed to measure and/or model the changes in body joint configuration. In an example, gaps between pathways (or strips) in the inner array can be radially aligned with the centers of pathways (or strips) in the outer array. Relevant example variations discussed elsewhere in this disclosure or in priority-linked disclosures can also be applied to the example shown in this figure, but are not repeated here in order to reduce narrative redundancy

I claim:

1. A wearable deformable sensor for human motion capture comprising:
   a deformable elongate electrically-conductive central strip which is configured to span a body joint in a proximal-to-distal manner;
   a central electromagnetic energy emitter and a central electromagnetic energy receiver which are in electromagnetic communication with the deformable elongate electrically-conductive central strip;
   a proximal array of arcuate deformable electrically-conductive strips, wherein a right set of the strips in the proximal array of arcuate deformable electrically-conductive strips are to the right of the deformable elongate electrically-conductive central strip and a left subset of the strips in the proximal array of arcuate deformable electrically-conductive strips are to the left of the deformable elongate electrically-conductive central strip, wherein strips in the proximal array of arcuate deformable electrically-conductive strips are proximal relative to the middle of the deformable elongate electrically-conductive central strip, and wherein strips in the proximal array of arcuate deformable electrically-conductive strips diverge from each other as they extend in a proximal direction;
   a proximal array of electromagnetic energy emitters and electromagnetic energy receivers which are in electromagnetic communication with the proximal array of arcuate deformable electrically-conductive strips;
   a distal array of arcuate deformable electrically-conductive strips, wherein a right set of the strips in the distal array of arcuate deformable electrically-conductive strips are to the right of the deformable elongate electrically-conductive central strip and a left subset of the strips in the distal array of arcuate deformable electrically-conductive strips are to the left of the deformable elongate electrically-conductive central strip, wherein strips in the distal array of arcuate deformable electrically-conductive strips are distal relative to the middle of the deformable elongate electrically-conductive central strip, and wherein strips in the distal array of arcuate deformable electrically-conductive strips diverge from each other as they extend in a distal direction;

a distal array of electromagnetic energy emitters and electromagnetic energy receivers which are in electromagnetic communication with the distal array of arcuate deformable electrically-conductive strips;

wherein changes in body joint configuration cause deformations of the central, proximal, and distal electrically-conductive strips, wherein the deformations cause changes in the transmission of electromagnetic energy from the electromagnetic energy emitters to the electromagnetic energy receivers, and wherein the changes in the transmission of electromagnetic energy are analyzed in order to measure and/or model changes in body joint configuration;

a data processor; and a power source.

* * * * *